(12) United States Patent
Takada et al.

(10) Patent No.: US 10,720,586 B2
(45) Date of Patent: *Jul. 21, 2020

(54) ORGANIC ELECTROLUMINESCENT DEVICE; A CHARGE TRANSPORTING MATERIAL FOR THE ORGANIC ELECTROLUMINESCENT DEVICE; AND A LUMINESCENT DEVICE, A DISPLAY DEVICE AND A LIGHTING SYSTEM USING THE ORGANIC ELECTROLUMINESCENT DEVICE

(71) Applicant: UDC Ireland Limited, Dublin (IE)

(72) Inventors: Saki Takada, Kanagawa (JP); Yosuke Yamamoto, Kanagawa (JP); Kousuke Watanabe, Kanagawa (JP); Yuichiro Itai, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 210 days.

This patent is subject to a terminal disclaimer.

(21) Appl. No.: 15/874,071

(22) Filed: Jan. 18, 2018

(65) Prior Publication Data

US 2018/0145264 A1 May 24, 2018

Related U.S. Application Data

(62) Division of application No. 15/079,739, filed on Mar. 24, 2016, now Pat. No. 9,887,371, which is a division
(Continued)

(30) Foreign Application Priority Data

Jan. 23, 2012 (JP) .................................. 2012-011349
May 24, 2012 (JP) .................................. 2012-118492

(51) Int. Cl.
*H01L 51/00* (2006.01)
*C07D 487/06* (2006.01)
(Continued)

(52) U.S. Cl.
CPC ........ *H01L 51/0072* (2013.01); *C07D 487/06* (2013.01); *C09K 11/06* (2013.01);
(Continued)

(58) Field of Classification Search
CPC ............. H01L 51/5072; H01L 51/0071; H01L 51/0072; H01L 51/0085; H01L 51/5016;
(Continued)

(56) References Cited

U.S. PATENT DOCUMENTS

2010/0051928 A1 3/2010 Fukuzaki
2012/0075273 A1 3/2012 Abe

FOREIGN PATENT DOCUMENTS

JP 2010050778 A 3/2010
JP 2010087496 A 4/2010
(Continued)

*Primary Examiner* — Ruiyun Zhang
(74) *Attorney, Agent, or Firm* — Riverside Law LLP

(57) ABSTRACT

An organic electroluminescent element comprising a substrate; a pair of electrodes including an anode and a cathode,
(Continued)

disposed on the substrate; and at least one organic layer including a light emitting layer, disposed between the electrodes, wherein the light emitting layer includes a compound represented by the following general formula:

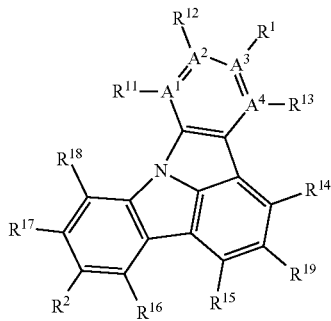

wherein: $R^1$, $R^3$, and $R^{19}$; $R^{11}$ to $R^{18}$; and $A^1$ to $A^4$ are as defined in the specification.

20 Claims, 3 Drawing Sheets

Related U.S. Application Data of application No. 13/747,795, filed on Jan. 23, 2013, now Pat. No. 9,306,176.

(51) Int. Cl.
C09K 11/06 (2006.01)
H05B 33/14 (2006.01)
H01L 51/50 (2006.01)

(52) U.S. Cl.
CPC ...... H01L 51/0085 (2013.01); H01L 51/5016 (2013.01); H05B 33/14 (2013.01); C09K 2211/1011 (2013.01); C09K 2211/1029 (2013.01); C09K 2211/185 (2013.01); H01L 51/006 (2013.01); H01L 51/5024 (2013.01); H01L 51/5056 (2013.01); H01L 51/5072 (2013.01); H01L 51/5088 (2013.01); H01L 51/5092 (2013.01); H01L 51/5096 (2013.01)

(58) Field of Classification Search
CPC ............ H01L 51/5012; H01L 51/5048; C07D 491/048; C07D 487/06; H05B 33/14; C09K 11/06; C09K 2211/1011; C09K 2211/1029; C09K 2211/185
USPC .......... 428/690; 548/419, 304.4, 305.1, 440; 257/40; 546/276.7
See application file for complete search history.

(56) References Cited

FOREIGN PATENT DOCUMENTS

JP 2012072099 4/2012
WO 2007031165 A2 3/2007

[Fig. 1]
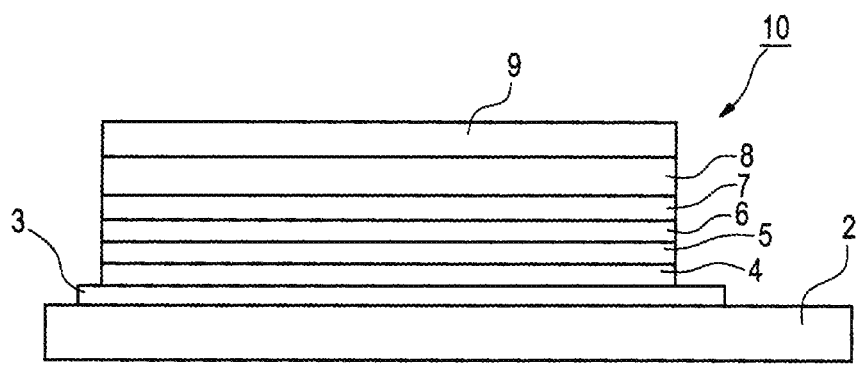
[Fig. 2]
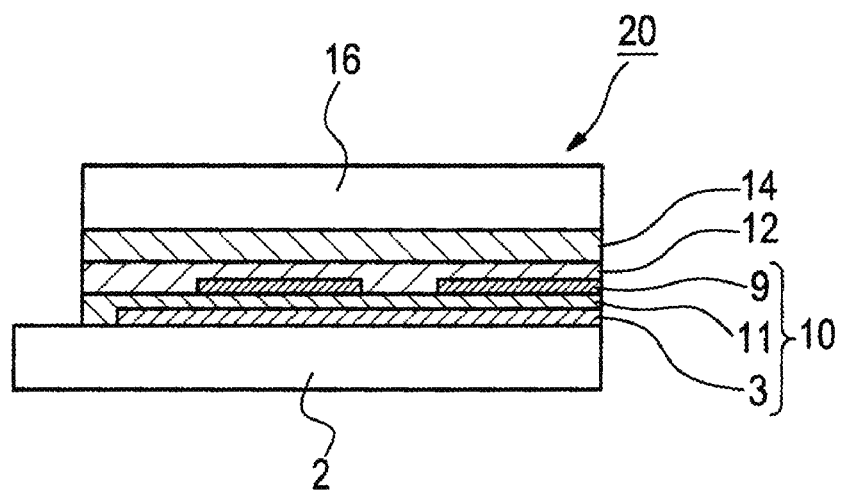

[Fig. 3]
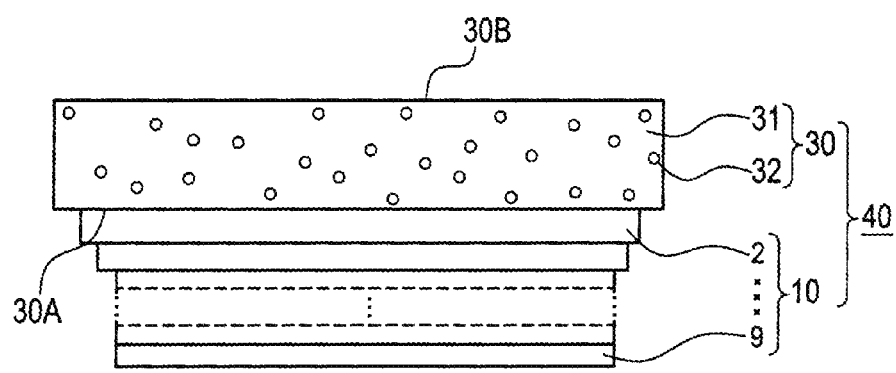

[Fig. 4]
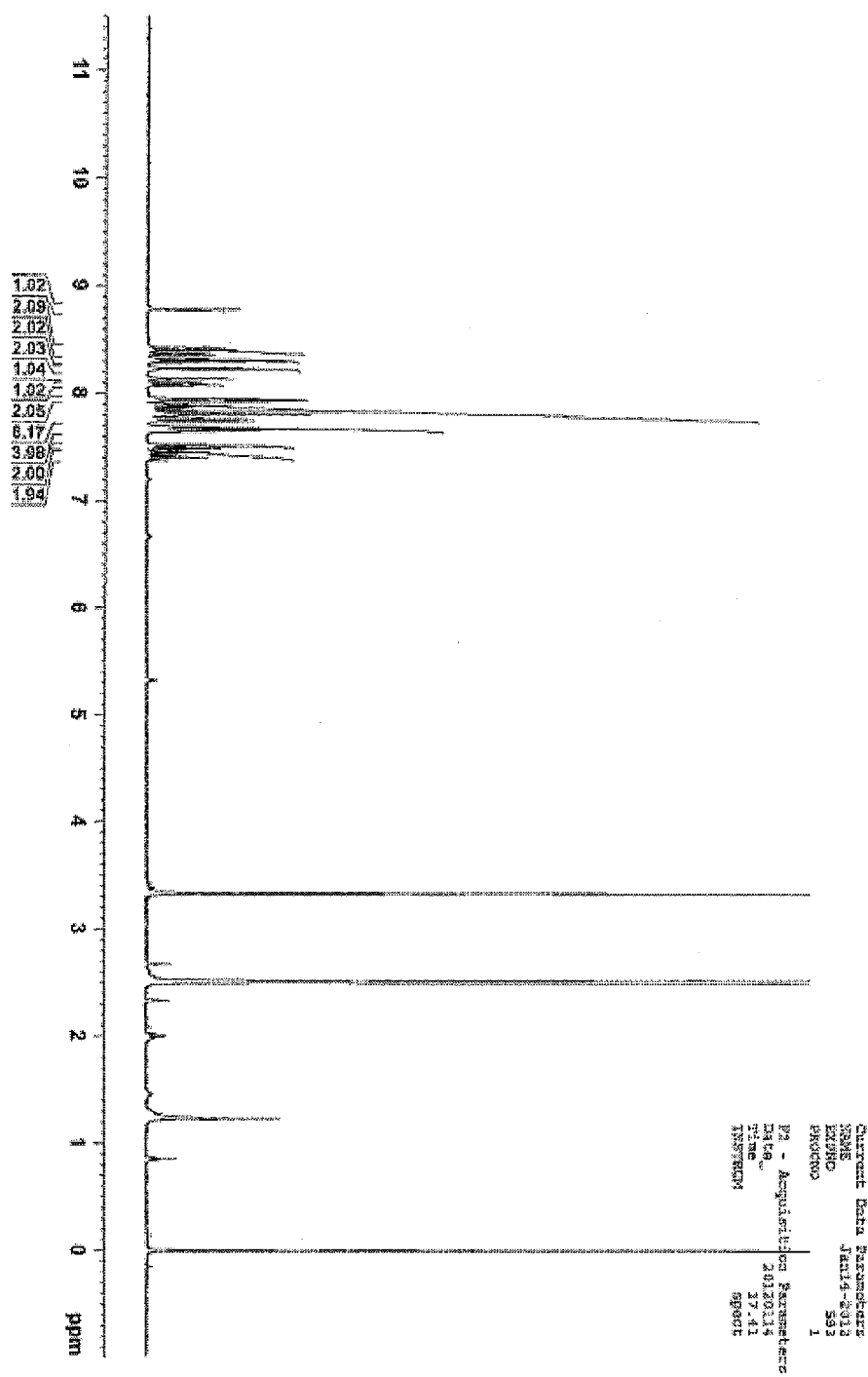

ORGANIC ELECTROLUMINESCENT DEVICE; A CHARGE TRANSPORTING MATERIAL FOR THE ORGANIC ELECTROLUMINESCENT DEVICE; AND A LUMINESCENT DEVICE, A DISPLAY DEVICE AND A LIGHTING SYSTEM USING THE ORGANIC ELECTROLUMINESCENT DEVICE

CROSS-REFERENCE TO RELATED APPLICATIONS

The present application is a divisional application of U.S. patent application Ser. No. 15/079,739, filed on Mar. 24, 2016, now allowed, which is a divisional application of U.S. patent application Ser. No. 13/747,795, filed on Jan. 23, 2013, now U.S. Pat. No. 9,306,176, and claims priority to Japanese Patent Application Nos. 2012-118492, filed on May 24, 2012, and JP 2012-011349, filed on Jan. 23, 2012, the contents of all of which are herein incorporated by reference in their entireties.

FIELD OF THE INVENTION

The present invention relates to an organic electroluminescent element, a charge transporting material for an organic electroluminescent element, and a light emitting device, a display device and an illumination device each using the element.

BACKGROUND OF INVENTION

Since organic electroluminescent elements (which may hereinafter also be referred to as "elements" or "organic EL elements") are capable of high-luminance light emitting using low voltage driving, they have been actively researched and developed. The organic electroluminescent elements have a pair of electrodes and an organic layer between the pair of electrodes, and utilize, for light emitting, energy of the exciton generated as a result of recombination of the electron injected from the cathode and the hole injected from the anode in the organic layer.

In recent years, high efficiency in organic electroluminescent elements is being advanced by using a phosphorescent material. However, in practical implementation, improvements are demanded from the viewpoints of a lowering of driving voltage and durability.

On the other hand, organic electroluminescent elements using, as a host material of the light emitting layer, a compound having a structure in which phenyl groups of triphenylamine are connected to each other and fused to from a carbazole ring or the like are known.

Patent Document 1 describes an organic electroluminescent element using, as a host material of the light emitting layer, a material having a structure in which benzene rings of a triphenylamine are mainly connected to each other via a methylene chain or the like and combining it with a phosphorescent material, and it can be read from Patent Document 1 that high efficiency, low voltage, and element durability are greatly enhanced. As for the means of connecting the benzene rings of a triphenylamine to each other, Patent Document 1 does not describe that a single bond is particularly excellent.

On the other hand, Patent Document 2 describes an organic electroluminescent element using, as a host material of the light emitting layer, a compound having a structure analogous to that in Patent Document 1 and combining it with a phosphorescent material and reports that when formed into an element capable of undergoing red phosphorescence emission, high efficiency and low voltage are achieved. Though Patent Document 2 describes various compounds in which benzene rings of a triphenylamine are connected to each other via a methylene chain or a single bond, it does not describe any compound in which benzene rings of a triphenylamine are connected to each other via two or more single bonds.

Patent Document 3 describes a compound having a structure in which two phenyl groups of triphenylamine are connected to each other and fused and describes that by using this compound as a host material of the light emitting layer, an organic electroluminescent element with good luminous efficiency and low driving voltage can be provided. Though Patent Document 3 describes some compounds having an indolocarbazole skeleton in which benzene rings of a triphenylamine are connected to each other via two single bonds, it does not describe any indolocarbazole having an oligoaromatic hydrocarbon ring as a substituent.

RELATED ART DOCUMENTS

Patent Documents

[Patent Document 1] WO2007/031165
[Patent Document 2] WO2010/050778
[Patent Document 3] JP-A-2010-087496

However, Patent Document 1 reports the element durability regarding only blue-emitting elements. In addition, Patent Documents 1 to 3 inclusive of Patent Document 1 neither disclose nor suggest how the luminance is deteriorated particularly at the initial light time. In this respect, the present inventors investigated characteristics of the organic electroluminescent elements described in Patent Documents 1 to 3. As a result, it was noted that dissatisfaction remains from the viewpoint of a luminance deterioration rate at the initial stage of lighting; and that dissatisfaction also remains on long-term durability until the luminance reduces by half. In particular, the matter that the luminance deterioration of an organic electroluminescent element at the initial stage of lighting is fast is not so problematic in the case of use for simple illumination, the use of which is in general not advanced due to issues of cost. However, it was noted that, for example, when such an element in which the luminance deterioration at the initial stage of lighting is fast is used as a light source of green of a display, a difference in the luminance deterioration rate at the initial stage of lighting from a red or blue light source is generated, resulting in a problem of color shift exceeding a range of assumption at the time of manufacture of a usual display. That is, it was noted that when abrupt luminance deterioration at the initial stage of lighting occurs, although such abrupt luminance deterioration is hardly perceived in the case of a single color, when the color is mixed with other colors as in a display application or the like, it is perceived as a color shift, resulting in a problem.

An object of the present invention is to provide an organic electroluminescent element having a slow luminance deterioration rate at the initial stage of lighting and excellent long-term durability.

BRIEF SUMMARY OF THE INVENTION

As a result of extensive and intensive investigations made by the present inventors, it has been found that by using a material having a specified substituent that is a hydrocarbon aromatic group at a specified position of an indolocarbazole skeleton, it is possible to provide an organic electroluminescent element having a slow luminance deterioration rate at the initial stage of lighting and excellent long-term durability.

Measures for solving the above-described problems are as follows.

[1] An organic electroluminescent element comprising a substrate; a pair of electrodes including an anode and a cathode, disposed on the substrate; and at least one organic layer including a light emitting layer, disposed between the electrodes, wherein the light emitting layer includes a compound represented by the following general formula (1):

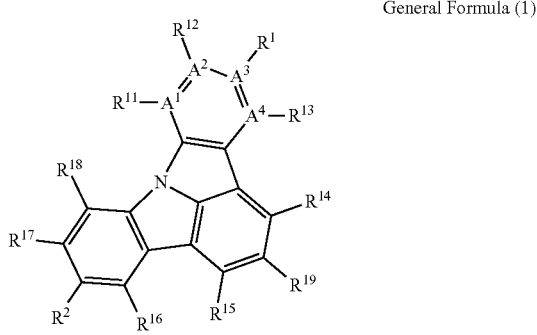

General Formula (1)

(In the general formula (1), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; $R^{11}$ to $R^{18}$ each independently represent a hydrogen atom or a substituent; and $A^1$ to $A^4$ each independently represent a nitrogen atom or a carbon atom, provided that when $A^1$ to $A^4$ are a nitrogen atom, $R^1$ and $R^{11}$ to $R^{13}$ connecting to the nitrogen atom do not exist.)

[2] The organic electroluminescent element as set forth in [1], wherein the compound represented by the general formula (1) is preferably a compound represented by the following general formula (2):

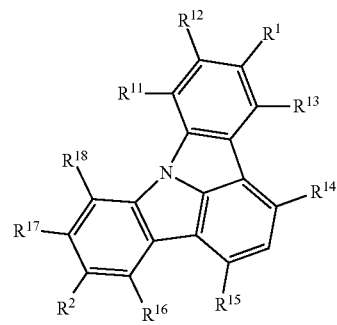

General Formula (2)

(In the general formula (2), $R^1$ and $R^2$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$ and $R^2$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.)

[3] The organic electroluminescent element as set forth in [1], wherein the compound represented by the general formula (1) is preferably a compound represented by the following general formula (3):

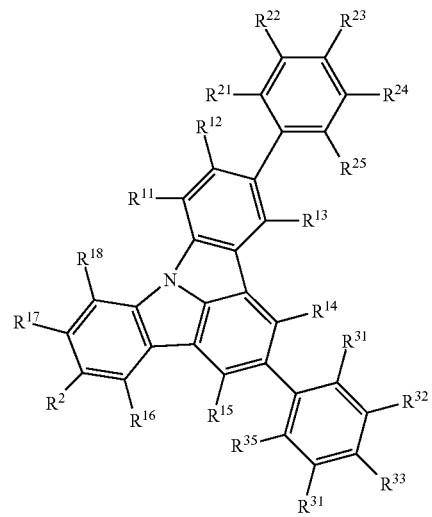

General Formula (3)

(In the general formula (3), $R^2$ represents a hydrogen atom, a phenyl group, a monovalent oligoaryl group having the number of rings of from 2 to 10, or a monovalent fused polycyclic aromatic hydrocarbon group having the number of rings of from 2 to 6, and the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$, $R^{21}$ to $R^{25}$, and $R^{31}$ to $R^{35}$ each independently represent a hydrogen atom or a substituent, provided that $R^2$ represents a monovalent oligoaryl group having the number of rings of from 2 to 10 or a monovalent fused polycyclic aromatic hydrocarbon group having the number of rings of from 2 to 6, at least one of $R^{21}$ to $R^{25}$ and $R^{31}$ to $R^{35}$ represents an aryl group, or two or more of $R^{21}$ to $R^{25}$ or two or more of $R^{31}$ to $R^{35}$ are bound to each other to form a fused polycyclic aromatic hydrocarbon ring having the number of rings of from 2 to 6.)

[4] The organic electroluminescent element as set forth in [1], wherein the compound represented by the general formula (1) is preferably a compound represented by the following general formula (4):

General Formula (4)

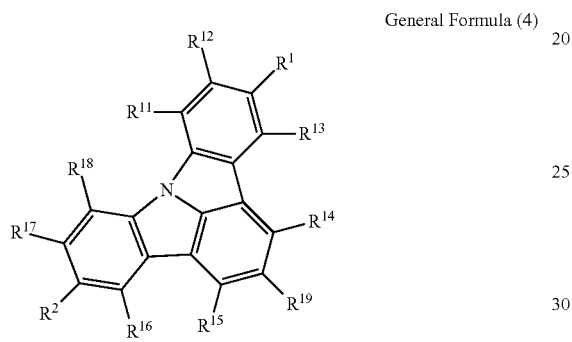

(In the general formula (4), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a group selected from the following general formulae (CH-1) to (CH-11), and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.)

General Formulae (CH-1) to (CH-11)

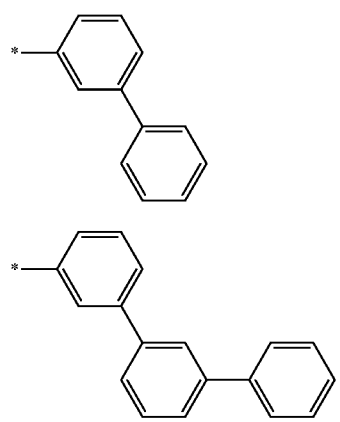

(CH-1)

(CH-2)

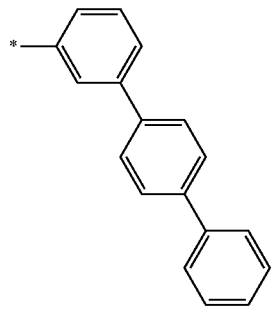

(CH-3)

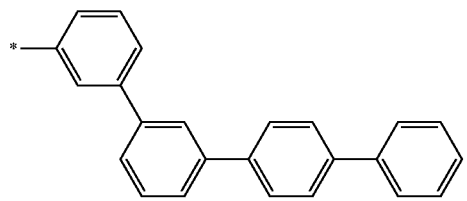

(CH-4)

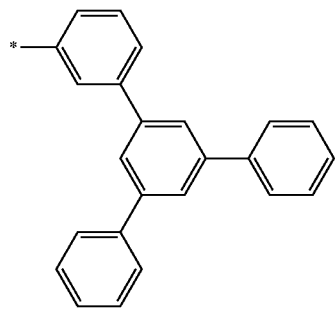

(CH-5)

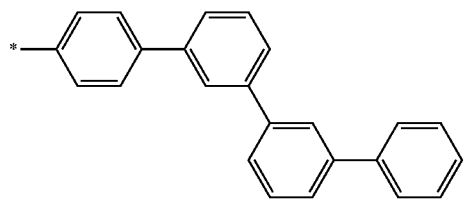

(CH-6)

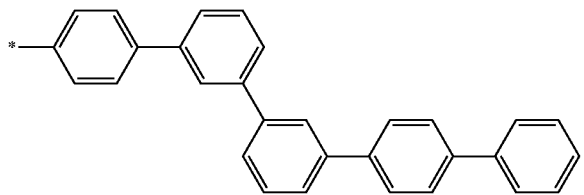

(CH-7)

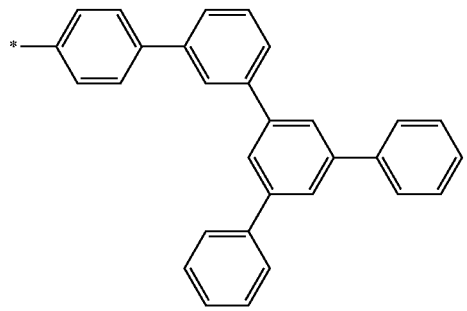

(CH-8)

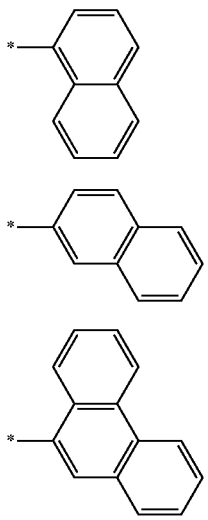

(CH-9)

(CH-10)

(CH-11)

(In the general formulae (CH-1) to (CH-11), * represents a binding site.)

[5] The organic electroluminescent element as set forth in any one of [1] to [4], wherein, in the general formula (1), the group represented by $R^1$ or $R^2$ is preferably a group containing only one p-phenylene group.

[6] The organic electroluminescent element as set forth in any one of [1] to [5], wherein the light emitting layer preferably further contains a phosphorescent material.

[7] The organic electroluminescent element as set forth in [6], wherein the phosphorescent material is preferably an iridium complex.

[8] The organic electroluminescent element as set forth in [7], wherein the iridium complex is preferably represented by the following general formula (E-1):

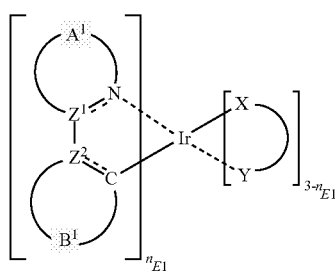

(E-1)

(In the general formula (E-1), $Z^1$ and $Z^2$ each independently represent a carbon atom or a nitrogen atom; $A^1$ represents an atomic group for forming a 5- or 6-membered heterocyclic ring together with $Z^1$ and the nitrogen atom; $B^1$ represents an atomic group for forming a 5- or 6-membered heterocyclic ring together with $Z^2$ and the carbon atom; (X—Y) represents a monoanionic bidentate ligand; and $n_{E1}$ represents an integer of from 1 to 3.)

[9] The organic electroluminescent element as set forth in [8], wherein the iridium complex represented by the general formula (E-1) is preferably represented by the following general formula (E-2):

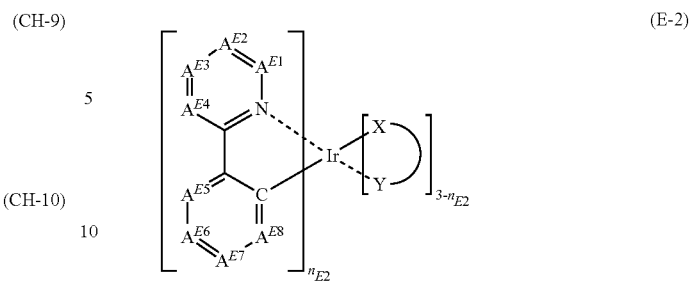

(E-2)

(In the general formula (E-2), $A^{E1}$ to $A^{E8}$ each independently represent a nitrogen atom or C-RE; RE represents a hydrogen atom or a substituent; (X—Y) represents a monoanionic bidentate ligand; and $n_{E2}$ represents an integer of from 1 to 3.)

[10] The organic electroluminescent element as set forth in any one of [7] to [9], wherein the iridium complex represented by the general formula (E-1) is preferably the following compound:

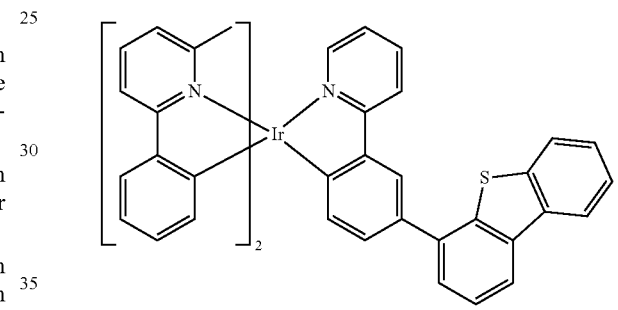

[11] The organic electroluminescent element as set forth in any one of [1] to [10], wherein the compound represented by the general formula (1) preferably has a molecular weight of not more than 800.

[12] The organic electroluminescent element as set forth in any one of [1] to [11], wherein the light emitting layer is preferably formed by a vacuum deposition process.

[13] The organic electroluminescent element as set forth in any one of [1] to [11], wherein the light emitting layer is preferably formed by a wet process.

[14] A charge transporting material for an organic electroluminescent element represented by the following general formula (1):

General Formula (1)

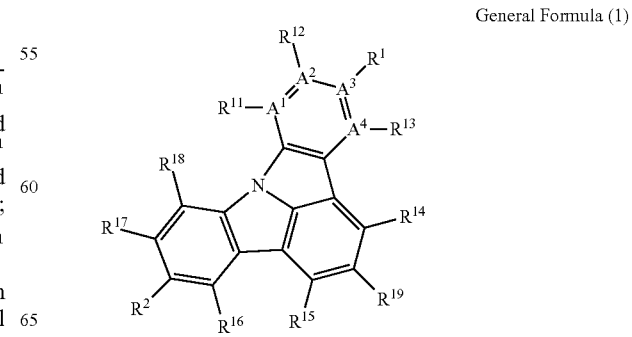

(In the general formula (1), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; $R^{11}$ to $R^{18}$ each independently represent a hydrogen atom or a substituent; and $A^1$ to $A^4$ each independently represent a nitrogen atom or a carbon atom, provided that when $A^1$ to $A^4$ are a nitrogen atom, $R^1$ and $R^{11}$ to $R^{13}$ connecting to the nitrogen atom do not exist.)

[15] The charge transporting material for an organic electroluminescent element as set forth in [14], wherein the compound represented by the general formula (1) is preferably a compound represented by the following general formula (2):

General Formula (2)

[Structure showing carbazole-type fused ring with substituents $R^1$, $R^{11}$, $R^{12}$, $R^{13}$, $R^{14}$, $R^{15}$, $R^{16}$, $R^{17}$, $R^{18}$, $R^{19}$, $R^2$]

(In the general formula (2), $R^1$ and $R^2$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$ and $R^2$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.)

[16] The charge transporting material for an organic electroluminescent element as set forth in [14], wherein the compound represented by the general formula (1) is preferably a compound represented by the following general formula (3):

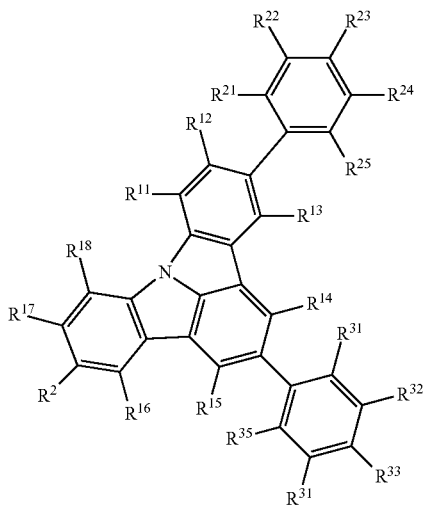

General Formula (3)

(In the general formula (3), $R^2$ represents a hydrogen atom, a phenyl group, a monovalent oligoaryl group having the number of rings of from 2 to 10, or a monovalent fused polycyclic aromatic hydrocarbon group having the number of rings of from 2 to 6, and the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$, $R^{21}$ to $R^{25}$ and $R^{31}$ to $R^{35}$ each independently represent a hydrogen atom or a substituent, provided that $R^2$ represents a monovalent oligoaryl group having the number of rings of from 2 to 10 or a monovalent fused polycyclic aromatic hydrocarbon group having the number of rings of from 2 to 6, at least one of $R^{21}$ to $R^{25}$ and $R^{31}$ to $R^{35}$ represents an aryl group, or two or more of $R^{21}$ to $R^{25}$ or two or more of $R^{31}$ to $R^{35}$ are bound to each other to form a fused polycyclic aromatic hydrocarbon ring having the number of rings of from 2 to 6.)

[17] The charge transporting material for an organic electroluminescent element as set forth in [14], wherein the compound represented by the general formula (1) is preferably a compound represented by the following general formula (4):

General Formula (4)

[Structure showing fused ring system with substituents $R^1$, $R^{11}$, $R^{12}$, $R^{13}$, $R^{14}$, $R^{15}$, $R^{16}$, $R^{17}$, $R^{18}$, $R^{19}$, $R^2$]

(In the general formula (4), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a group selected from the following general formulae (CH-1) to (CH-11), and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.)

General Formulae (CH-1) to (CH-11)

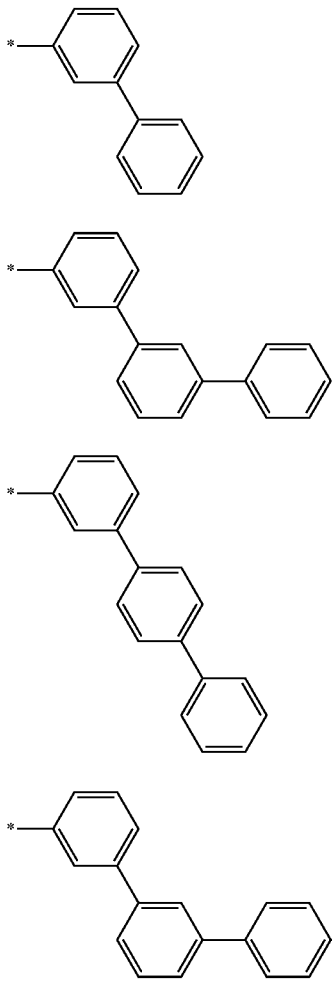

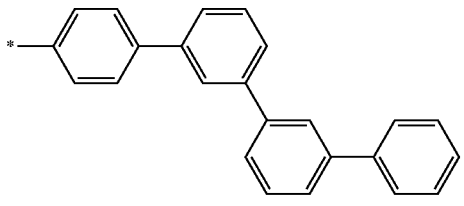

(In the general formulae (CH-1) to (CH-11), * represents a binding site.)

[18] The charge transporting material for an organic electroluminescent element as set forth in any one of [14] to [17], wherein, in the general formula (1), the group represented by $R^1$ or $R^2$ is preferably a group containing only one p-phenylene group.

[19] The charge transporting material for an organic electroluminescent element as set forth in any one of [14] to [18], wherein the compound represented by the general formula (1) preferably has a molecular weight of not more than 800.

[20] A light emitting device using the organic electroluminescent element as set forth in any one of [1] to [13].

[21] A display device using the organic electroluminescent element as set forth in any one of [1] to [13].

[22] An illumination device using the organic electroluminescent element as set forth in any one of [1] to [13].

According to the present invention, it is possible to provide an organic electroluminescent element having a slow luminance deterioration rate at the initial stage of lighting and excellent long-term durability.

In addition, according to the present invention, it is further possible to provide a light emitting device, a display device, and an illumination device each using the element.

BRIEF DESCRIPTION OF THE DRAWINGS

FIG. 1 A schematic view showing one example of a configuration of the organic electroluminescent element according to the present invention.

FIG. 2 A schematic view showing one example of the light emitting device according to the present invention.

FIG. 3 A schematic view showing one example of the illumination device according to the present invention.

FIG. 4 An NMR chart of Illustrative Compound 3.

DETAILED DESCRIPTION OF THE INVENTION

The details of the present invention are hereunder described. The description of the configuration requirements below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Organic Electroluminescent Element and Charge Transporting Material for Organic Electroluminescent Element]

The charge transporting material for an organic electroluminescent element according to the present invention comprises a compound represented by the following general formula (1). By using a material having a hydrocarbon aromatic substituent at a specified position of an indolocarbazole skeleton as a phosphorescent host material, it is possible to provide an organic electroluminescent element capable of making high durability and suppression of deterioration at the initial stage of lighting compatible with each other.

The organic electroluminescent element according to the present invention comprises a substrate; a pair of electrodes including an anode and a cathode, disposed on the substrate; and at least one organic layer including a light emitting layer, disposed between the electrodes, wherein the light emitting layer includes a compound represented by the following general formula (1):

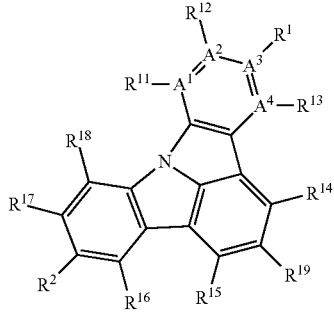

General Formula (1)

(In the general formula (1), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; $R^{11}$ to $R^{18}$ each independently represent a hydrogen atom or a substituent; and $A^1$ to $A^4$ each independently represent a nitrogen atom or a carbon atom, provided that when $A^1$ to $A^4$ are a nitrogen atom, $R^1$ and $R^{11}$ to $R^{13}$ connecting to the nitrogen atom do not exist.)

The configuration of the organic electroluminescent element according to the present invention is not particularly limited. FIG. 1 shows one example of the configuration of the organic electroluminescent element according to the present invention. An organic electroluminescent element 10 of FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed description thereon in this patent document can be applied to the present invention.

Preferred embodiments of the organic electroluminescent element according to the present invention are hereunder described in detail in the order of the substrate, the electrodes, the organic layer, a protective layer, a sealing enclosure, a driving method, a light emitting wavelength, and applications.

<Substrate>

The organic electroluminescent element according to the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferable.

<Electrodes>

The organic electroluminescent element according to the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element according to the present invention has an organic layer disposed between the electrodes.

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

The configuration of the organic layer, the method for forming an organic layer, preferred embodiments of the respective layers constituting the organic layer, and the materials used in the respective layers in the organic electroluminescent element according to the present invention are hereunder described in detail in order.

(Configuration of Organic Layer)

In the organic electroluminescent element according to the present invention, the organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer.

The organic electroluminescent element according to the present invention includes the light emitting layer containing a phosphorescent material and other organic layer, and the light emitting layer includes the compound represented by the general formula (1). The compound represented by the general formula (1) is preferably used as a host compound of the light emitting layer. Furthermore, in the organic electroluminescent element according to the present invention, the organic layer more preferably includes the light emitting layer containing a phosphorescent material and other organic layer. However, in the organic electroluminescent element according to the present invention, even in the case where the organic layer includes the light emitting layer and other organic layer, a space between the both layers may not be always made distinct.

In addition, in the organic electroluminescent element including an electron transporting layer between a pair of electrodes, disposed adjacent to the cathode and further arbitrarily including a hole blocking layer adjacent to the electron transporting layer on the opposite side to the cathode, the charge transporting material for an organic electroluminescent element according to the present invention is also preferably contained in the electron transporting layer or the hole blocking layer.

In each of these organic layers, plural layers may be provided, and in the case where plural layers are provided, the layers may be formed of the same material or may be formed of a different material in every layer.

(Method for Forming Organic Layer)

The respective organic layers in the organic electroluminescent element according to the present invention can be suitably formed by any of dry film forming methods such as a deposition method and a sputtering method, wet type film forming methods (solution coating methods) such as a transfer method, a printing method, a spin coating method, and a bar coating method.

In the organic electroluminescent element according to the present invention, the light emitting layer is preferably formed by a vacuum deposition process. In addition, in the organic electroluminescent element according to the present invention, the light emitting layer is also preferably formed by a wet process.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism. The light emitting layer in the organic electroluminescent element according to the present invention preferably contains, in addition to the compound represented by the general formula (1), at least one phosphorescent material.

The light emitting layer in the organic electroluminescent element according to the present invention may be constituted of only the compound represented by the general formula (1) and the phosphorescent material, or may be constituted as a mixed layer of the phosphorescent material using the compound represented by the general formula (1) as a host material. The phosphorescent material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Furthermore, the light emitting layer may include a material which does not have charge transporting properties and which does not emit light.

In addition, the light emitting layer may be made of a single layer or multiple layers of two or more layers. The respective layers may include the same light emitting material or host material, and may also include a different material in every layer. In the case where plural light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

(I) Compound Represented by the General Formula (1):

In the organic electroluminescent element according to the present invention, the light emitting layer contains the compound represented by the general formula (1), and it is a preferred embodiment to use the compound represented by the general formula (1) as a host material of the light emitting layer. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1% relative to the total amount of light emission in the whole of the element.

As for the materials of the light emitting layer, the compound represented by the general formula (1), the phosphorescent material, and other host material other than the compound represented by the general formula (1) are hereunder described in order. Incidentally, in the organic electroluminescent element according to the present invention, the compound represented by the general formula (1) may be used in other layer than the light emitting layer.

Not wishing to be restricted to any theory, it may be considered that the structure of the compound represented by the general formula (1) is small in a structure strain, and therefore, it has excellent durability.

Furthermore, it may be considered that in view of the fact that the compound represented by the general formula (1) has oligoaromatic substituents at the positions of $R^1$ and $R^2$ corresponding to the para position relative to the central nitrogen atom, a lowering of the luminance seen at the initial stage of lighting can be suppressed. Though a cause of the phenomenon wherein the luminance becomes abruptly small at the initial stage of lighting in this way is not elucidated yet, it may be assumed that such a phenomenon occurs due to rearrangement properties of intramembraneous molecules in the light emitting layer by application of voltage. As compared with the conventionally known compounds having a structure in which phenyl groups of triphenylamine are connected to each other and fused, the compound represented by the general formula (1) is small in a difference between the molecular arrangement at the time of forming a film by deposition or a wet process (in particular, deposition) and the optimum molecular arrangement at the time of applying voltage, and therefore, it may be considered that the matter that the luminance becomes abruptly small at the initial stage of lighting can be suppressed.

Preferred structures of the compound represented by the general formula (1) are hereunder described.

In the present invention, the hydrogen atom in the description of the general formula (1) also includes isotopes (a deuterium atom and the like), and the atoms constituting the substituent are also intended to include isotopes of the atoms.

In the present invention, the "substituent" at each occurrence may be further substituted. For example, in the present invention, the "alkyl group" at each occurrence includes an alkyl group substituted with a fluorine atom (for example, a trifluoromethyl group), an alkyl group substituted with an aryl group (for example, a triphenylmethyl group), and the like, but "an alkyl group having from 1 to 6 carbon atoms" represents one having from 1 to 6 carbon atoms, as any group also including substituted groups thereof.

General Formula (1)

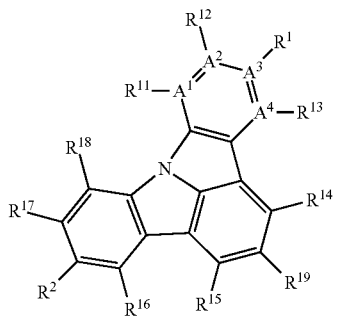

In the general formula (1), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent.

In the present specification, the "monovalent oligoaryl group having the number of rings of from 2 to 10" refers to a group containing from 2 to 10 aryl groups crosslinked by a covalent bond. The monovalent oligoaryl group having the number of rings of from 2 to 10 may have a substituent so far as the gist of the present invention is not deviated. In the present specification, the "monovalent fused polycyclic aromatic hydrocarbon group having the number of rings of from 2 to 6" refers to an aryl group resulting from fusion of from 2 to 6 rings and may have a substituent so far as the gist of the present invention is not deviated.

Examples of the substituent which the phenyl group in $R^1$, $R^2$, and $R^{19}$ may further have include an alkyl group having from 1 to 6 carbon atoms, an alkenyl group having from 2 to 6 carbon atoms, a phenyl group, an aromatic heterocyclic group having from 5 to 10 carbon atoms, an alkoxy group having from 1 to 4 carbon atoms, a phenoxy group, a fluoro group, a silyl group, and a cyano group. Above all, an alkyl group having from 1 to 6 carbon atoms, a phenyl group, an aromatic heterocyclic group having from 5 to 10 carbon atoms, a fluoro group, a silyl group, and a cyano group are preferable, and an alkyl group having from 1 to 3 carbon atoms, a phenyl group, an aromatic heterocyclic group having from 5 to 10 carbon atoms, a fluoro group, and a silyl group are more preferable.

The monovalent oligoaryl group having the number of rings of from 2 to 10 in $R^1$, $R^2$, and $R^{19}$ is preferably a group in which from 2 to 10 phenyl groups are crosslinked by a covalent bond and connected to each other, more preferably a group in which from 2 to 6 phenyl groups are crosslinked by a covalent bond and connected to each other, still more preferably a group in which from 2 to 5 phenyl groups are crosslinked by a covalent bond and connected to each other, and especially preferably a biphenyl group, a p-terphenyl group, an m-terphenyl group, or a quaterphenyl group.

Above all, in the organic electroluminescent element according to the present invention, the monovalent oligoaryl group having the number of rings of from 2 to 10, represented by $R^1$, $R^2$, or $R^{19}$, is preferably a group containing only one p-phenylene group from the viewpoint of luminous efficiency. Incidentally, at that time, a p-terphenyl group is formed in the general formula (1).

In addition, the monovalent oligoaryl group having the number of rings of from 2 to 10, represented by $R^1$, $R^2$, or $R^{19}$, is preferably a group containing at least one m-phenylene group, and more preferably a group containing two m-phenylene groups. Furthermore, the monovalent oligoaryl group having the number of rings of from 2 to 10, represented by $R^1$, $R^2$, or $R^{19}$, is preferably a group containing an m-phenylene group in a portion binding directly to a skeleton of an indolocarbazole analogue represented by the general formula (1).

The number of rings in $R^1$, $R^2$, and $R^{19}$ is preferably from 2 to 5, more preferably from 2 to 4, especially preferably 3 or 4, and more especially preferably 4.

Examples of the monovalent oligoaryl group having the number of rings of from 2 to 10 in $R^1$, $R^2$, and $R^{19}$ may further have include an alkyl group having from 1 to 6 carbon atoms, an alkenyl group having from 2 to 6 carbon atoms, a phenyl group, an aromatic heterocyclic group having from 5 to 10 carbon atoms, an alkoxy group having from 1 to 4 carbon atoms, a phenoxy group, a fluoro group, a silyl group, and a cyano group. Above all, an alkyl group having from 1 to 6 carbon atoms, a phenyl group, an aromatic heterocyclic group having from 5 to 10 carbon atoms, a fluoro group, a silyl group, and a cyano group are preferable, and an alkyl group having from 1 to 3 carbon atoms, a phenyl group, an aromatic heterocyclic group having from 5 to 10 carbon atoms, a fluoro group, and a cyano group are more preferable.

Examples of the monovalent fused polycyclic aromatic hydrocarbon group having the number of rings of from 2 to 6 in $R^1$, $R^2$, and $R^{19}$ include a naphthyl group, an anthracenyl group, a phenanthrenyl group, a pyrenyl group, a triphenylenyl group, a chrysenyl group, a tetracenyl group, a tetraphenyl group, a picenyl group, a perylenyl group, a pentaphenyl group, a pentacenyl group, a benzopyrenyl group, a hexahelicenyl group, a hexaphenyl group, and a hexacenyl group. Above all, a naphthyl group, an anthracenyl group, a phenanthrenyl group, a pyrenyl group, and a triphenylenyl group are preferable, and a naphthyl group, an anthracenyl group, and a phenanthrenyl group are more preferable.

Examples of the monovalent fused polycyclic aromatic hydrocarbon group having the number of rings of from 2 to 6 in $R^1$, $R^2$, and $R^{19}$ may further have include an alkyl group having from 1 to 6 carbon atoms, an alkenyl group having from 2 to 6 carbon atoms, a phenyl group, an aromatic heterocyclic group having from 5 to 10 carbon atoms, an alkoxy group having from 1 to 4 carbon atoms, a phenoxy group, a fluoro group, a silyl group, and a cyano group. Above all, an alkyl group having from 1 to 6 carbon atoms, a phenyl group, an aromatic heterocyclic group having from 5 to 10 carbon atoms, a fluoro group, a silyl group, and a cyano group are preferable, and an alkyl group having from 1 to 3 carbon atoms, a phenyl group, an aromatic heterocyclic group having from 5 to 10 carbon atoms, a fluoro group, and a cyano group are more preferable.

Of these, in the case where a luminous color from the organic electroluminescent element is green (emission peak wavelength: 490 to 580 nm), $R^1$, $R^2$, and $R^{19}$ do not preferably have a fused ring from the viewpoint of luminous efficiency namely $R^1$, $R^2$, and $R^{19}$ are preferably a hydrogen atom, a phenyl group, or a monovalent oligoaryl group having the number of rings of from 2 to 10, and more preferably a hydrogen atom or a monovalent oligoaryl group having the number of rings of from 2 to 10.

Furthermore, it is especially preferable that only one of $R^1$, $R^2$, and $R^{19}$ is a monovalent oligoaryl group having the number of rings of from 2 to 10, and it is more especially preferable that only one of $R^1$, $R^2$, and $R^{19}$ is a monovalent oligoaryl group having the number of rings of from 2 to 10, and the other one of $R^1$, $R^2$, and $R^{19}$ is a hydrogen atom or a phenyl group.

In the general formula (1), $R^{11}$ to $R^{18}$ each independently represent a hydrogen atom or a substituent; and $A^1$ to $A^4$ each independently represent a nitrogen atom or a carbon atom, provided that when $A^1$ to $A^4$ are a nitrogen atom, $R^1$ and $R^{11}$ to $R^{13}$ connecting to the nitrogen atom do not exist.

In the general formula (1), examples of the substituent represented by $R^{11}$ to $R^{18}$ independently include those in Substituent Group A as described below. The substituent may further have a substituent. Examples of the further substituent include groups selected from the Substituent Group A.

<<Substituent Group A>>

An alkyl group (having preferably from 1 to 30 carbon atoms, more preferably from 1 to 20 carbon atoms, and especially preferably from 1 to 10 carbon atoms; for example, methyl, ethyl, n-propyl, isopropyl, t-butyl, n-hexyl, n-octyl, n-decyl, n-hexadecyl, cyclopropyl, cyclopentyl, cyclohexyl, and trifluoromethyl), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl and 3-pentynyl), an aryl group (having preferably from 6 to 30 carbon atoms, more preferably from 6 to 20 carbon atoms, and especially preferably from 6 to 14 carbon atoms; for example, phenyl, p-methylphenyl, 2-fluorophenyl, 3-fluorophenyl, 4-fluorophenyl, naphthyl, anthranyl, and triphenylenyl), an amino group (having preferably from 0 to 30 carbon atoms, more preferably from 0 to 20 carbon atoms, and especially preferably from 0 to 10 carbon atoms; for example, amino, methylamino, dimethylamino, diethylamino, dibenzylamino, phenylamino, diphenylamino, and ditolylamino), an alkoxy group (having preferably from 1 to 30 carbon atoms, more preferably from 1 to 20 carbon atoms, and especially preferably from 1 to 10 carbon atoms; for example, methoxy, ethoxy, butoxy, and 2-ethylhexyloxy), an aryloxy group (having preferably from 6 to 30 carbon atoms, more preferably from 6 to 20 carbon atoms, and especially preferably from 6 to 12 carbon atoms; for example, phenyloxy, 1-naphthyloxy, and 2-naphthyloxy), a heterocyclic oxy group (having preferably from 1 to 30 carbon atoms, more preferably from 1 to 20 carbon atoms, and especially preferably from 1 to 12 carbon atoms; for example, pyridyloxy, pyrazyloxy, pyrimidyloxy, and quinolyloxy), an acyl group (having preferably from 2 to 30 carbon atoms, more preferably from 2 to 20 carbon atoms, and especially preferably from 2 to 12 carbon atoms; for example, acetyl, benzoyl, formyl, and pivaloyl), an alkoxycarbonyl group (having preferably from 2 to 30 carbon atoms, more preferably from 2 to 20 carbon atoms, and especially preferably from 2 to 12 carbon atoms; for example, methoxycarbonyl and ethoxycarbonyl), an aryloxycarbonyl group (having preferably from 7 to 30 carbon atoms, more preferably from 7 to 20 carbon atoms, and especially preferably from 7 to 12 carbon atoms; for example, phenyloxycarbonyl), an acyloxy group (having preferably from 2 to 30 carbon atoms, more preferably from 2 to 20 carbon atoms, and especially preferably from 2 to 10 carbon atoms; for example, acetoxy and benzoyloxy), an acylamino group (having preferably from 2 to 30 carbon atoms, more preferably from 2 to 20 carbon atoms, and especially preferably from 2 to 10 carbon atoms; for example, acetylamino and benzoylamino), an alkoxycarbonylamino group (having preferably from 2 to 30 carbon atoms, more preferably from 2 to 20 carbon atoms, and especially preferably from 2 to 12 carbon atoms; for example, methoxycarbonylamino), an aryloxycarbonylamino group (having preferably from 7 to 30 carbon atoms, more preferably from 7 to 20 carbon atoms, and especially preferably from 7 to 12 carbon atoms; for example, phenyloxycarbonylamino), a sulfonylamino group (having preferably from 1 to 30 carbon atoms, more preferably from 1 to 20 carbon atoms, and especially preferably from 1 to 12 carbon atoms; for example, methanesulfonylamino and benzenesulfonylamino), a sulfamoyl group (having preferably from 0 to 30 carbon atoms, more preferably from 0 to 20 carbon atoms, and especially preferably from 0 to 12 carbon atoms; for example, sulfamoyl, methyl sulfamoyl, dimethyl sulfamoyl, and phenyl sulfamoyl), a carbamoyl group (having preferably from 1 to 30 carbon atoms, more preferably from 1 to 20 carbon atoms, and especially preferably from 1 to 12 carbon atoms; for example, carbamoyl, methyl carbamoyl, diethyl carbamoyl, and phenyl carbamoyl), an alkylthio group (having preferably from 1 to 30 carbon atoms, more preferably from 1 to 20 carbon atoms, and especially preferably from 1 to 12 carbon atoms; for example, methylthio and ethylthio), an arylthio group (having preferably from 6 to 30 carbon atoms, more preferably from 6 to 20 carbon atoms, and especially preferably from 6 to 12 carbon atoms; for example, phenylthio), a heterocyclic thio group (having preferably from 1 to 30 carbon atoms, more preferably from 1 to 20 carbon atoms, and especially preferably from 1 to 12 carbon atoms; for example, pyridylthio, 2-benzimizolylthio, 2-benzoxazolylthio, and 2-benzthiazolylthio), a sulfonyl group (having preferably from 1 to 30 carbon atoms, more preferably from 1 to 20 carbon atoms, and especially preferably from 1 to 12 carbon atoms; for example, mesyl and tosyl), a sulfinyl group (having preferably from 1 to 30 carbon atoms, more preferably from 1 to 20 carbon atoms, and especially preferably from 1 to 12 carbon atoms; for example, methane sulfinyl and benzene sulfinyl), a ureido group (having preferably from 1 to 30 carbon atoms, more preferably from 1 to 20 carbon atoms, and especially preferably from 1 to 12 carbon atoms; for example, ureido, methylureido, and phenylureido), a phosphoramide group (having preferably from 1 to 30 carbon atoms, more preferably from 1 to 20 carbon atoms, and especially preferably from 1 to 12 carbon atoms; for example, diethylphosphoramide and phenylphosphoramide), a hydroxyl group, a mercapto group, a halogen atom (for example, a fluorine atom, a chlorine atom, a bromine atom, and an iodine atom), a sulfo group, a carboxyl group, a nitro group, a hydroxamic group, a sulfino group, a hydrazino group, an imino group, a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, a silolyl group, a dibenzothiophenyl group, and a dibenzofuranyl group), a silyl group (having preferably from 3 to 40 carbon atoms, more preferably from 3 to 30 carbon atoms, and especially preferably from 3 to 24 carbon atoms; for example, trimethylsilyl and triphenylsilyl), a silyloxy group (having preferably from 3 to 40 carbon atoms, more preferably from 3 to 30 carbon atoms, and especially preferably from 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the further substituent include the groups selected from the Substituent Group A as described above.

Among the groups of the above-described Substituent Group A, $R^{11}$ to $R^{18}$ are each independently preferably a hydrogen atom, an aryl group, or a heteroaryl group, and more preferably a hydrogen atom or an aryl group.

The aryl group represented by $R^{11}$ to $R^{18}$ has preferably from 6 to 30 carbon atoms, more preferably from 6 to 20 carbon atoms, and especially preferably from 6 to 18 carbon atoms, and examples thereof include a phenyl group, a xylyl group, a biphenyl group, a terphenyl group, a naphthyl group, an anthranyl group, and a triphenylenyl group.

The heteroaryl group represented by $R^{11}$ to $R^{18}$ has preferably the number of rings of from 5 to 30, more preferably the number of rings of from 5 to 20, and especially preferably the number of rings of from 5 to 15, and examples thereof include a pyridyl group, a pyrimidyl group, a triazyl group, a pyrazyl group, a pyridazyl group, a carbazolyl group, a dibenzothiophenyl group, and a dibenzofuranyl group.

As described above, $R^{11}$ to $R^{18}$ may further have the substituent represented by the Substituent Group A. Examples of the further substituent include an aryl group, a pyridine ring, a pyrimidine ring, a triazine ring, a cyano group, and a carbonyl group.

However, in order to increase the luminous efficiency of green phosphorescence, it is preferable that the substituents which $R^{11}$ to $R^{18}$ may further have are not connected to each other to form a fused ring. In order to increase the luminous efficiency of red phosphorescence, it is also preferable that the substituents which $R^{11}$ to $R^{18}$ may further have are connected to each other to form a fused ring.

Though adjacent two of $R^{11}$ to $R^{18}$ may be bound to each other to form a ring, in order to increase the luminous efficiency of green phosphorescence, it is not preferable that the adjacent two of $R^{11}$ to $R^{18}$ are not bound to each other to form a ring. In order to increase the luminous efficiency of red phosphorescence, it is also preferable that the adjacent two of $R^{11}$ to $R^{18}$ are connected to each other to form a fused ring.

Preferably, from 5 to 8 of $R^{11}$ to $R^{18}$ are a hydrogen atom, more preferably, from 6 to 8 of $R^{11}$ to $R^{18}$ are a hydrogen atom, and especially preferably all of $R^{11}$ to $R^{18}$ are a hydrogen atom.

$A^1$ to $A^4$ each independently represent a nitrogen atom or a carbon atom. Among $A^1$ to $A^4$, the number of carbon atoms is preferably from 2 to 4, more preferably from 3 to 4, and especially preferably 4.

As one of preferred embodiments of the compound represented by the general formula (1), there is exemplified a compound represented by the following general formula (2)

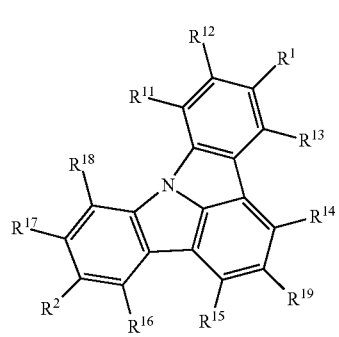

General Formula (2)

In the general formula (2), $R^1$ and $R^2$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$ and $R^2$ represents a monovalent oligoaryl group having the number of rings of from 2 to 10 or a monovalent fused polycyclic aromatic hydrocarbon group having the number of rings of from 2 to 6, and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.

Preferred ranges of $R^1$ and $R^2$ in the general formula (2) are the same as the preferred ranges of $R^1$ and $R^2$ in the general formula (1).

Preferred ranges of $R^{11}$ to $R^{18}$ in the general formula (2) are the same as the preferred ranges of $R^{11}$ to $R^{18}$ in the general formula (1).

As one of preferred embodiments of the compound represented by the general formula (1), there is exemplified a compound represented by the following general formula (3)

General Formula (3)

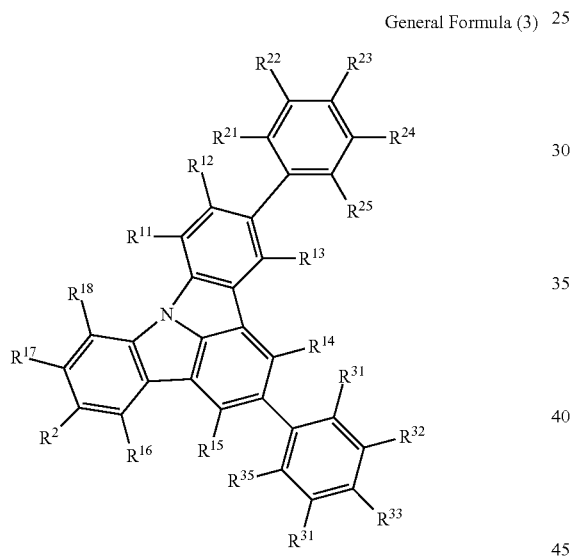

In the general formula (3), R represents a hydrogen atom, a phenyl group, a monovalent oligoaryl group having the number of rings of from 2 to 10, or a monovalent fused polycyclic aromatic hydrocarbon group having the number of rings of from 2 to 6, and the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$, $R^{21}$ to $R^{25}$, and $R^{31}$ to $R^{35}$ each independently represent a hydrogen atom or a substituent, provided that $R^2$ represents a monovalent oligoaryl group having the number of rings of from 2 to 10 or a monovalent fused polycyclic aromatic hydrocarbon group having the number of rings of from 2 to 6, at least one of $R^{21}$ to $R^{25}$ and $R^{31}$ to $R^{35}$ represents an aryl group, or two or more of $R^{21}$ to $R^{25}$ or two or more of $R^{31}$ to $R^{35}$ are bound to each other to form a fused polycyclic aromatic hydrocarbon ring having the number of rings of from 2 to 6.

The compound represented by the general formula (3) is more preferable from the viewpoint of realizing low voltage because the ionization potential is small as compared with the case where $R^1$ of the general formula (2) is a hydrogen atom.

Preferred ranges of $R^{11}$ to $R^{18}$ in the general formula (3) are the same as the preferred ranges of $R^{11}$ to $R^{18}$ in the general formula (1).

Preferred ranges of the phenyl group on which $R^2$ and $R^{21}$ to $R^{25}$ are substituted and the phenyl group on which $R^{31}$ to $R^{35}$ are substituted in the general formula (3) are the same as the preferred ranges of $R^1$, $R^2$, and $R^{19}$ in the general formula (1).

As one of preferred embodiments of the compound represented by the general formula (1), there is exemplified a compound represented by the following general formula (4).

General Formula (4)

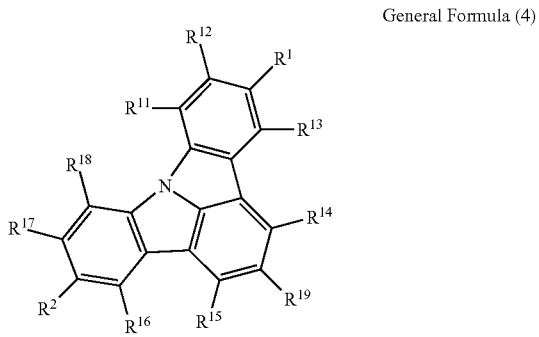

(In the general formula (4), $R^1$, $R^2$, and $R^{19}$ each independently represent a hydrogen atom, a phenyl group, a monovalent oligoaryl group having the number of rings of from 2 to 10, or a monovalent fused polycyclic aromatic hydrocarbon group having the number of rings of from 2 to 6, provided that at least one of $R^1$, $R^2$, and $R^{19}$ represents a group selected from the following general formulae (CH-1) to (CH-11), and that the phenyl group, the monovalent oligoaryl group having the number of rings of from 2 to 10, and the monovalent fused polycyclic aromatic hydrocarbon group having the number of rings of from 2 to 6 do not have an amino group as a substituent; and $R^{11}$ to $R^{18}$ each independently represent a hydrogen atom or a substituent.)

General Formulae (CH-1) to (CH-11)

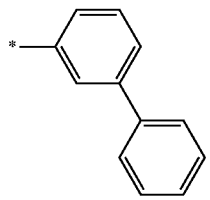

(CH-1)

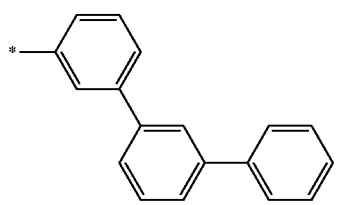

(CH-2)

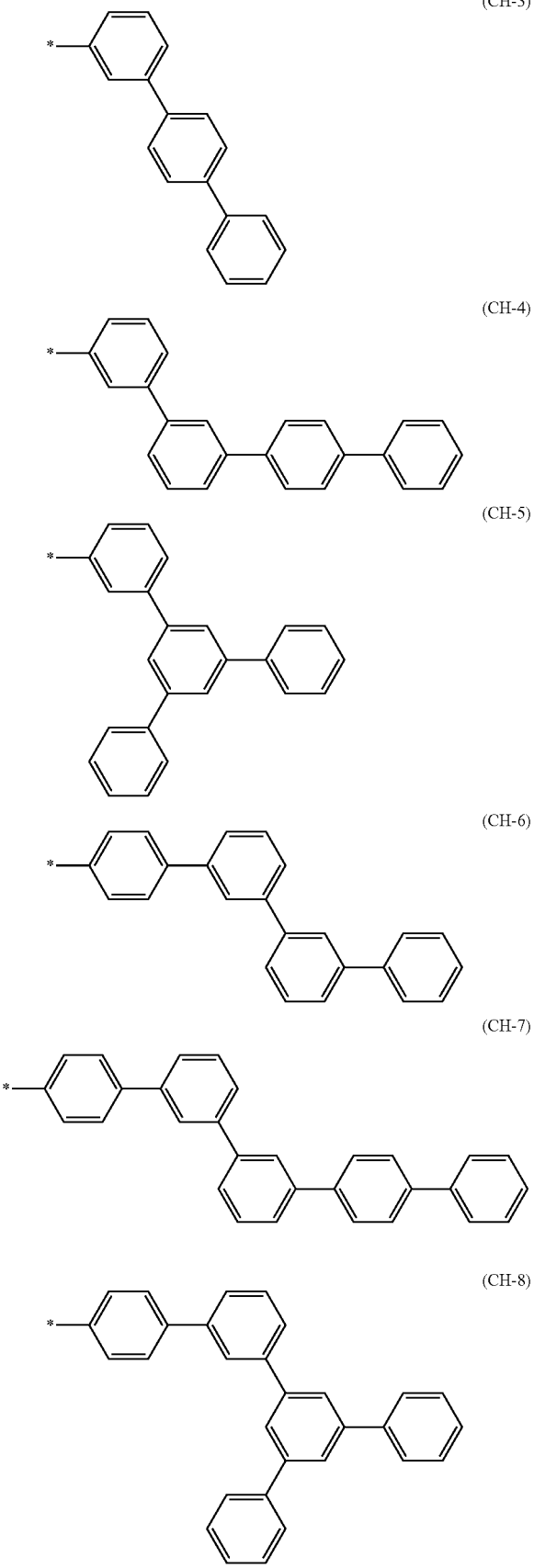

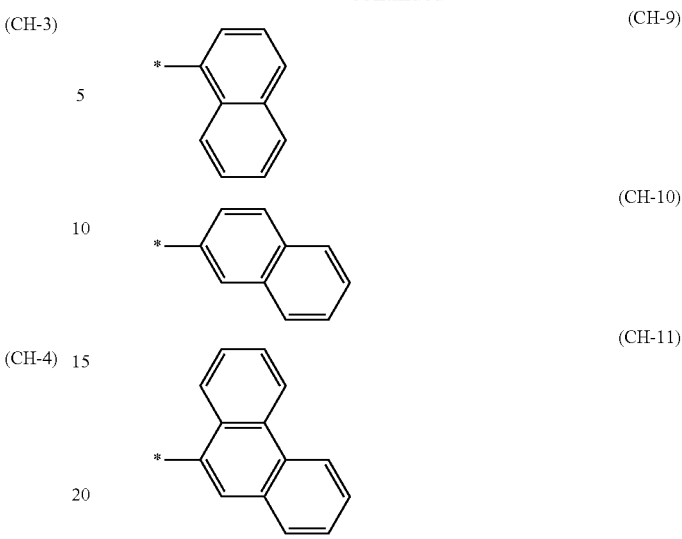

(In the general formulae (CH-1) to (CH-11), * represents a binding site.)

At least one of $R^1$, $R^2$, and $R^{19}$ represents a group selected from the general formulae (CH-1) to (CH-11). In order to increase the luminous efficiency of green phosphorescence, at least one of $R^1$, $R^2$, and $R^{19}$ is preferably a group selected from the general formulae (CH-1) to (CH-8), more preferably a group selected from the general formulae (CH-2) to (CH-8), still more preferably a group selected from the general formulae (CH-3) to (CH-8), and especially preferably a group selected from the general formulae (CH-4) to (CH-8).

In order to increase the luminous efficiency of red phosphorescence, at least one of $R^1$, $R^2$, and $R^{19}$ is preferably a group selected from the general formulae (CH-2) to (CH-11), more preferably a group selected from the general formulae (CH-4) to (CH-11), still more preferably a group selected from the general formulae (CH-9) to (CH-11), and especially preferably a group selected from the general formula (CH-9) or (CH-10).

Preferred ranges of $R^{11}$ to $R^{18}$ in the general formula (4) are the same as the preferred ranges of $R^{11}$ to $R^{18}$ in the general formula (1).

From the viewpoint of deposition adaptability, the molecular weight of the compound represented by the general formula (1) is preferably not more than 800, more preferably 400 or more and not more than 800, still more preferably 450 or more and not more than 750, and especially preferably 500 or more and not more than 700. What the molecular weight is 450 or more is advantageous for forming an amorphous thin film with good quality. When the molecular weight is not more than the above-described upper limit, solubility and sublimation properties are enhanced, and such is advantageous for enhancing the purity of the compound. Such is also preferable from the viewpoint of laminating a composition containing the compound represented by the general formula (1) by means of deposition.

In the case of using the compound represented by the general formula (1) as a host material of the light emitting layer of the organic electroluminescent element or as a charge transporting material of a layer adjacent to the light emitting layer, when an energy gap in a thinner film state than the light emitting material as described later (lowest excited triplet ($T_1$) energy in a thin film state in the case where the light emitting material as described later is a phosphorescent material) is large, quenching of the light emission can be prevented from occurring, and such is advantageous for enhancing the efficiency. On the other hand, from the viewpoint of chemical stability of the compound, it is preferable that the energy gap and the $T_1$ energy are not excessively large.

The $T_1$ energy of the compound represented by the general formula (1) in a thin film state is preferably 1.77 eV (40 kcal/mole) or more and not more than 3.51 eV (81 kcal/mole), and more preferably 2.39 eV (55 kcal/mole) or more and not more than 3.25 eV (75 kcal/mole). In the organic electroluminescent element according to the present invention, from the viewpoint of luminous efficiency, the $T_1$ energy of the compound represented by the general formula (1) is preferably higher than the $T_1$ energy of the phosphorescent material as described later. In particular, in the case where a luminous color from the organic electroluminescent element is green (emission peak wavelength: 490 to 580 nm), from the viewpoint of luminous efficiency, the $T_1$ energy is still more preferably 2.39 eV (55 kcal/mole) or more and not more than 2.82 eV (65 kcal/mole).

The $T_1$ energy can be determined from a short wavelength end obtained by measuring a phosphorescent spectrum of a thin film of the material. For example, the material is subjected to film forming in a film thickness of about 50 nm on a rinsed quartz glass substrate by a vacuum deposition method, and a phosphorescent spectrum of the thin film is measured using a Hitachi's fluorescent spectrophotometer F-7000 (manufactured by Hitachi High-Technologies Corporation). The $T_1$ energy can be determined by reducing a rise-up wavelength on the short wavelength side of the obtained luminous spectrum into an energy unit.

From the viewpoint of stably operating the organic electroluminescent element against the heat generation at the time of high-temperature driving or during the element driving, or the viewpoint of minimizing chromaticity shift at the time of high-temperature storage, in the organic electroluminescent element according to the present invention, the compound represented by the general formula (1) is preferably a compound having a glass transition temperature of 100° C. or higher. The glass transition temperature (Tg) of the compound represented by the general formula (1) is more preferably 100° C. or higher and not higher than 400° C., still more preferably 120° C. or higher and not higher than 400° C., and especially preferably 140° C. or higher and not higher than 400° C.

When the purity of the compound represented by the general formula (1) is low, impurities work as a trap of the charge transportation or promote the deterioration of the element, and therefore, the purity of the compound represented by the general formula (1) is preferably as high as possible. The purity can be measured by means of, for example, high performance liquid chromatography (HPLC), and when detected at a light absorption intensity at 254 nm, an area ratio of the compound represented by the general formula (1) is preferably 95.0% or more, more preferably 97.0% or more, especially preferably 99.0% or more, and most preferably 99.9% or more. Examples of a method for increasing the purity of the compound represented by the general formula (1) include recrystallization and sublimation purification.

Specific examples of the compound represented by the general formula (1) are enumerated below, but it should not be construed that the present invention is limited thereto.

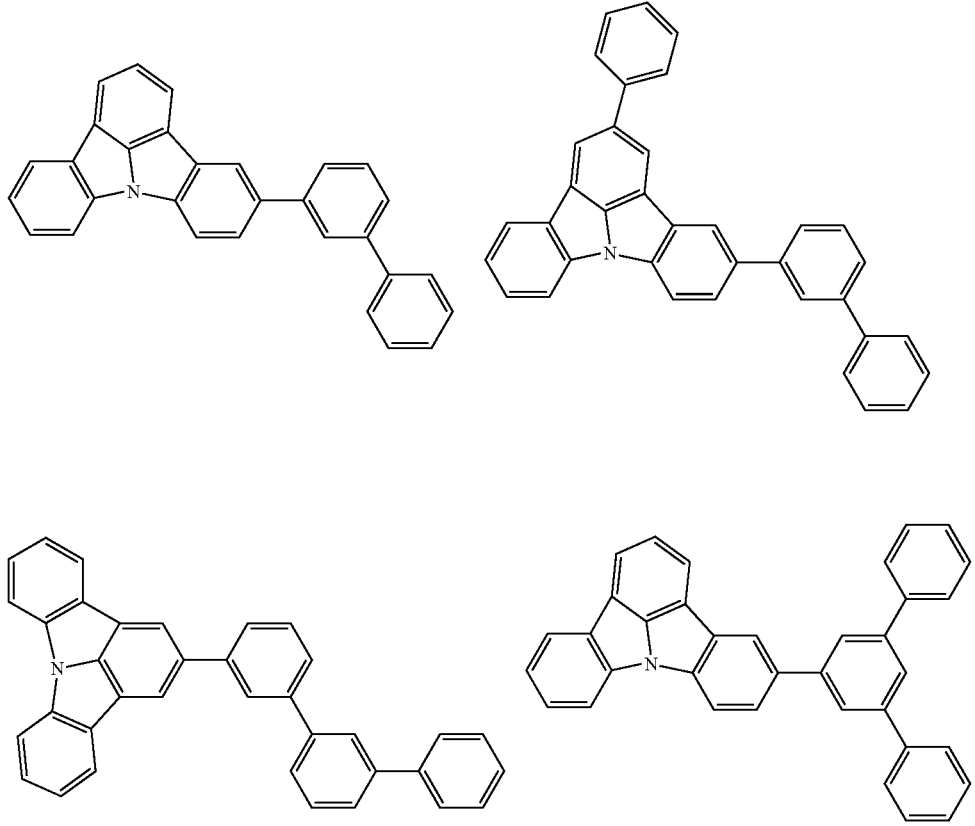

-continued
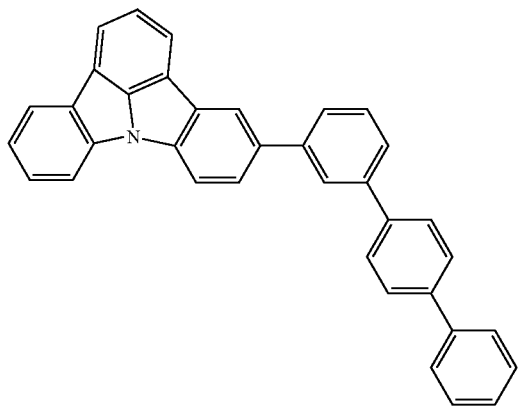
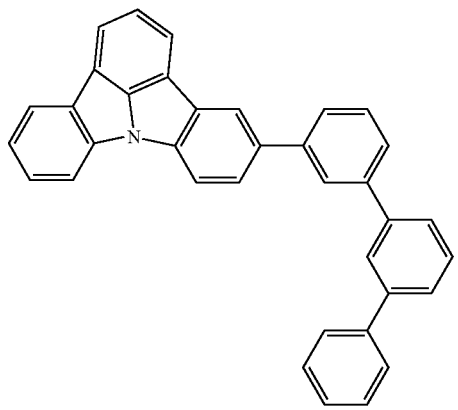
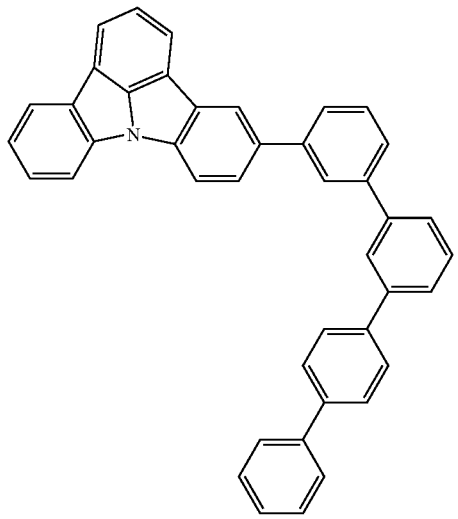
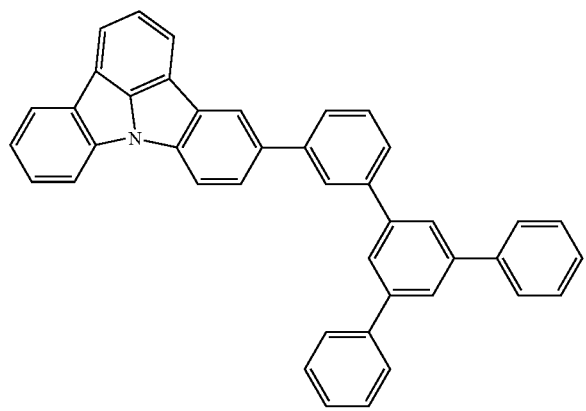
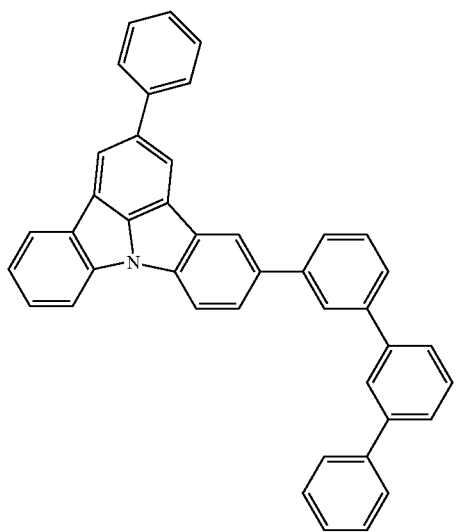
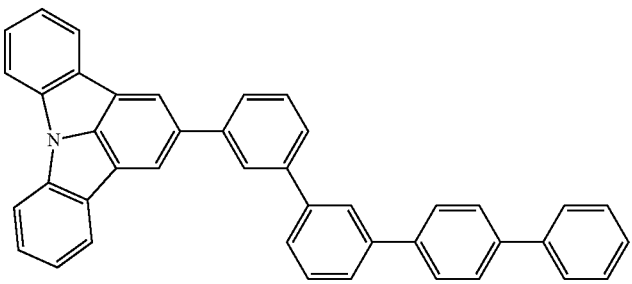

-continued
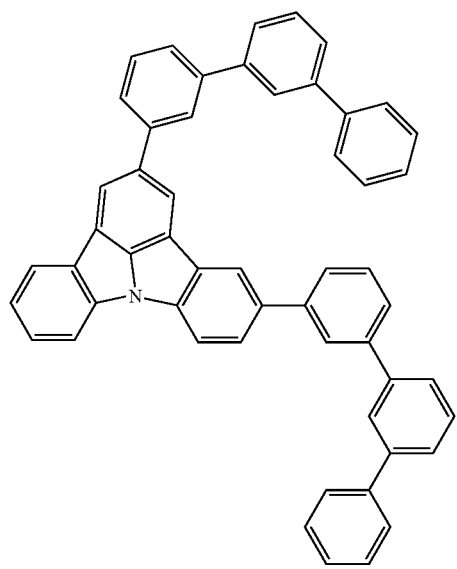
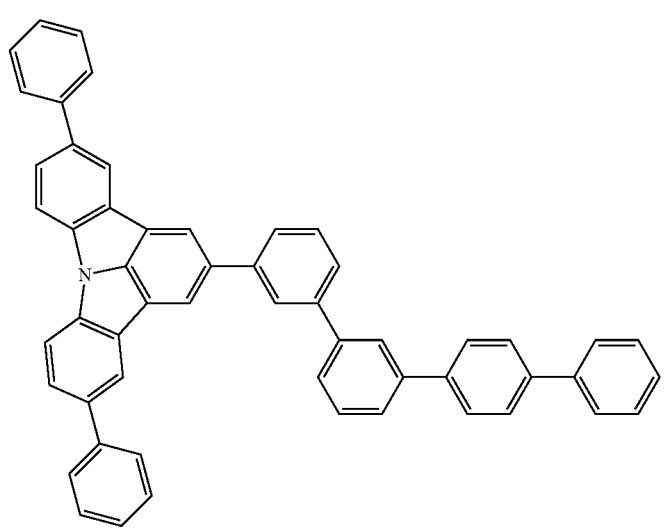
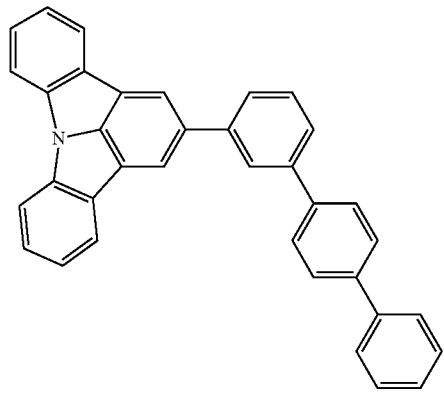
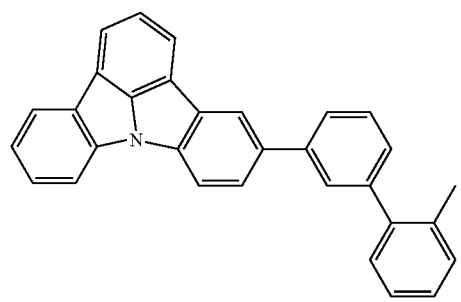
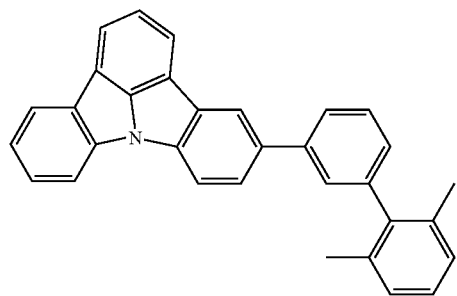
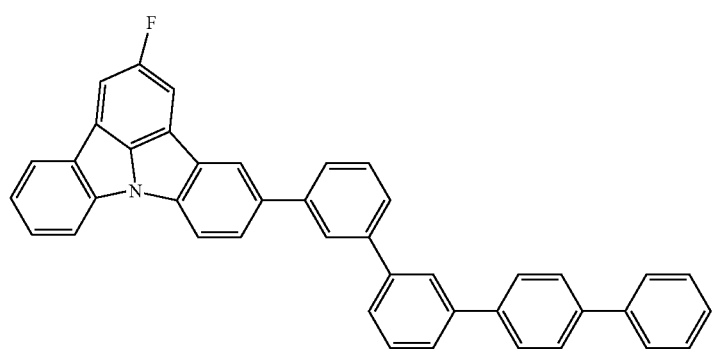

-continued
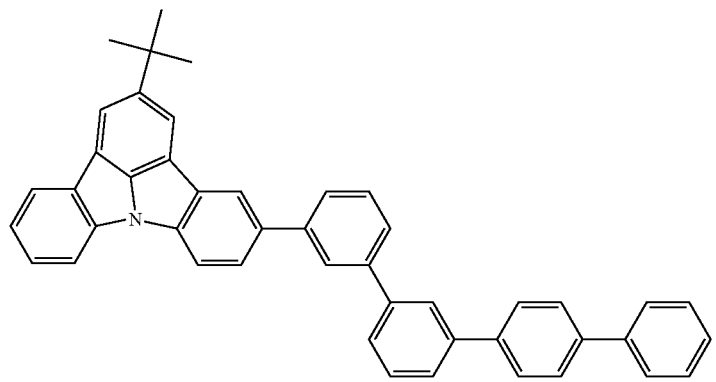
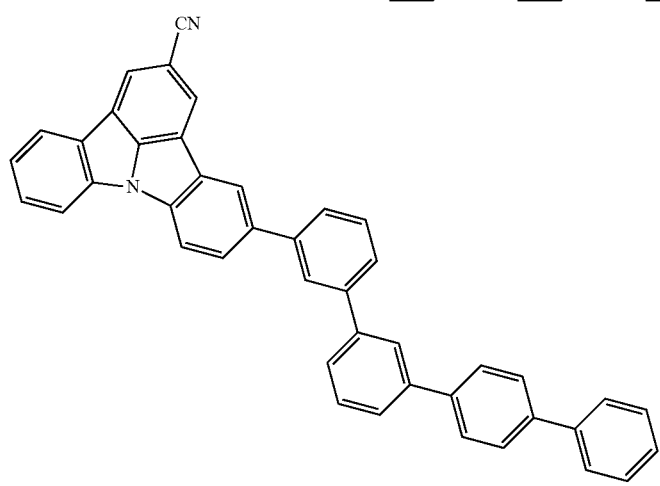
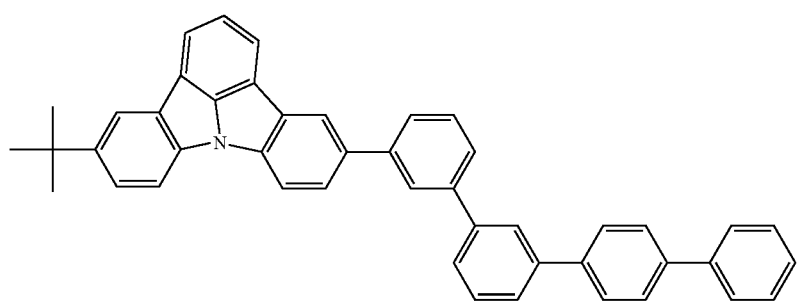
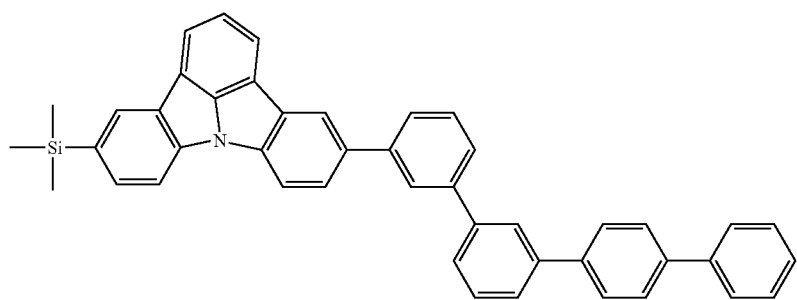

-continued
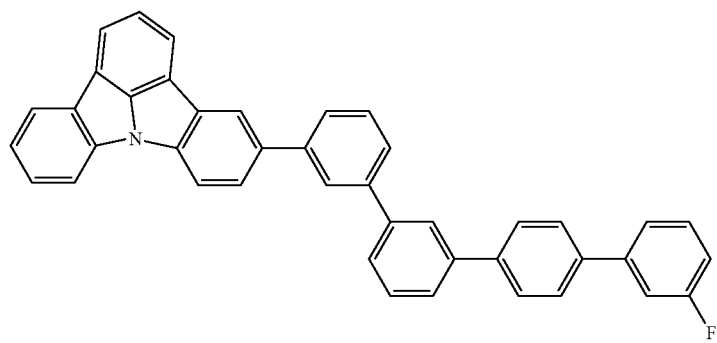
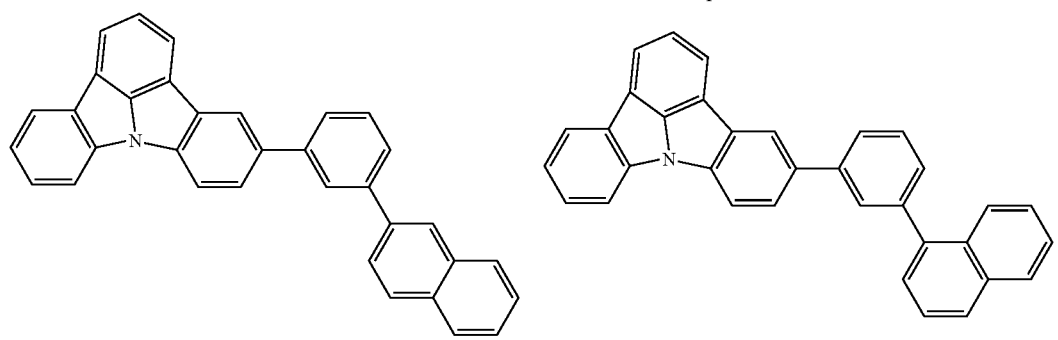
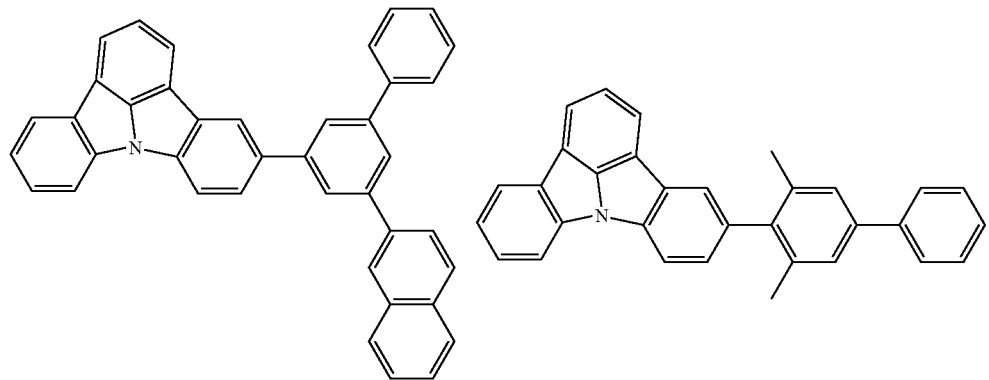
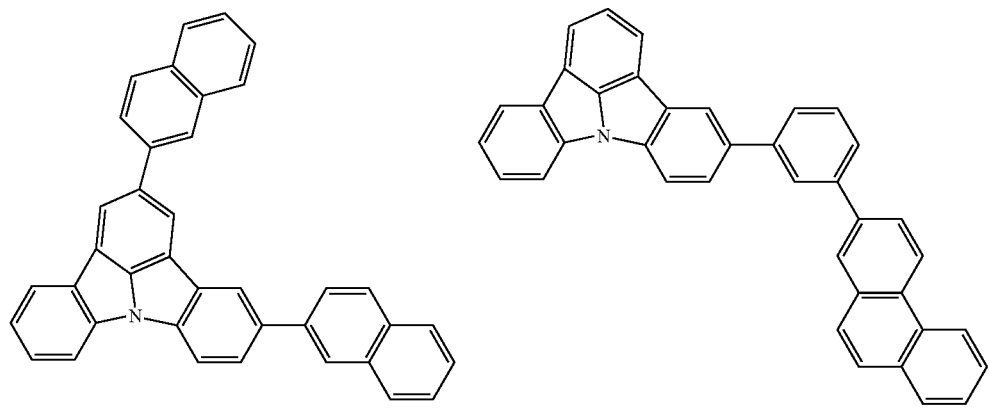

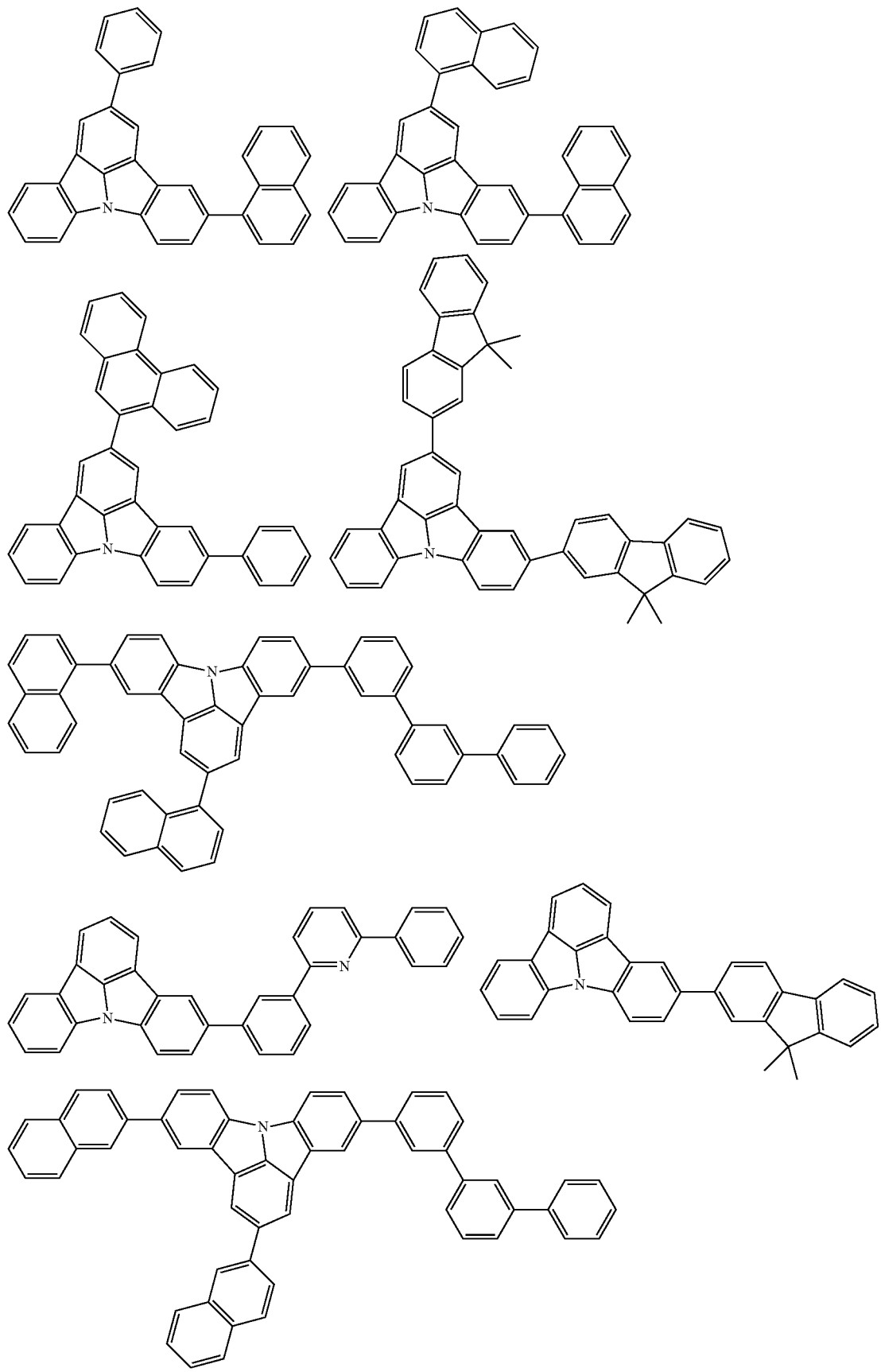

-continued
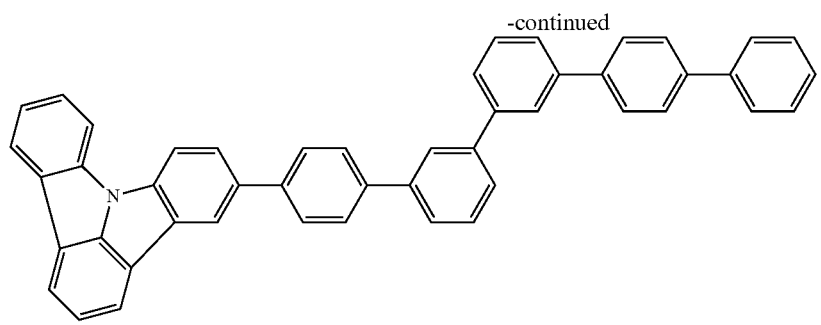
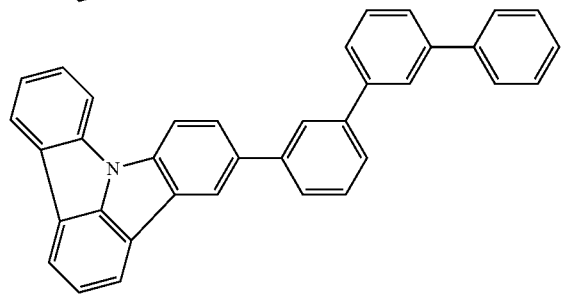
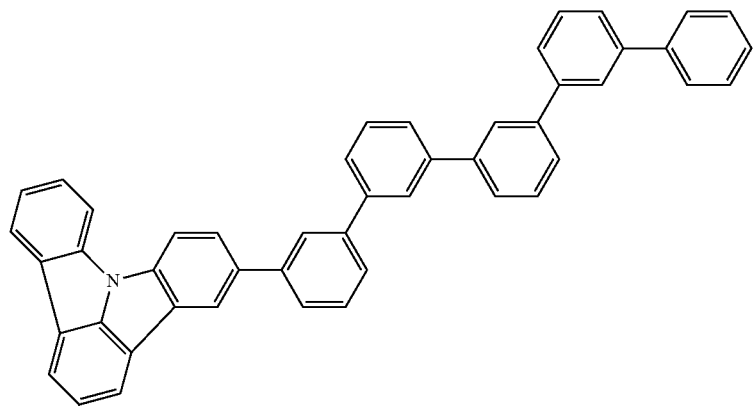
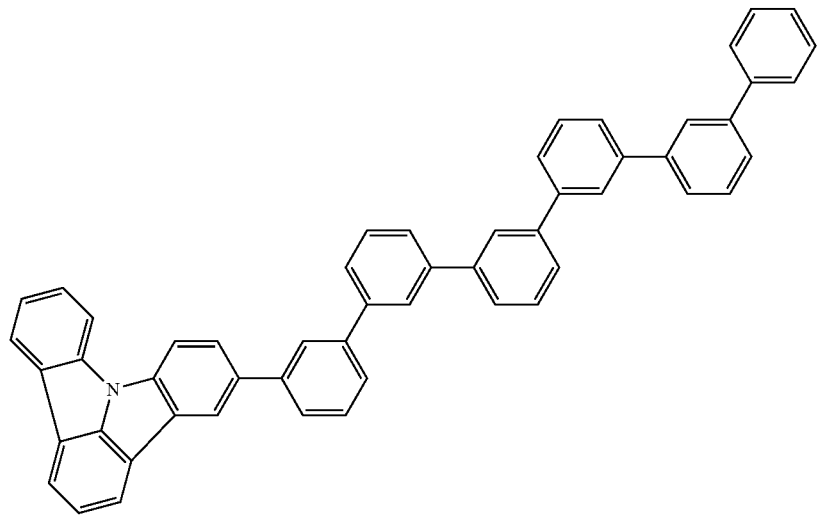

-continued
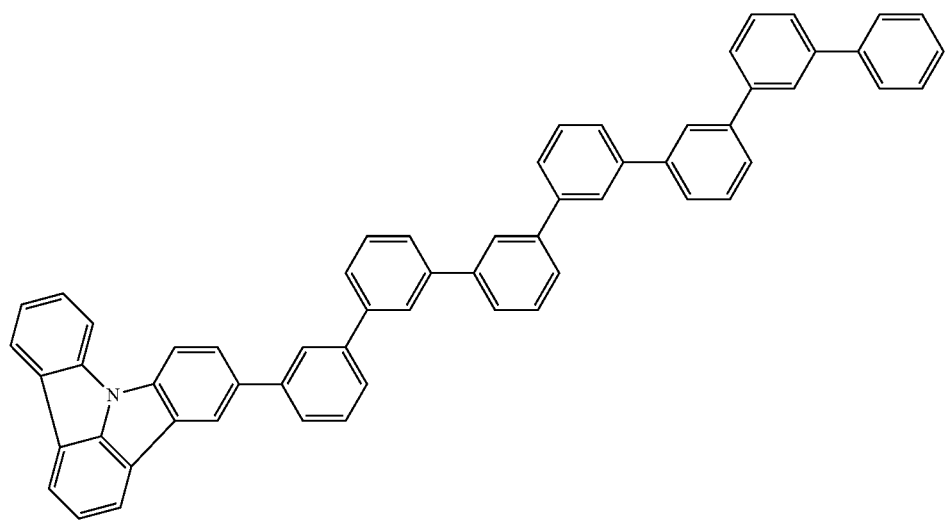
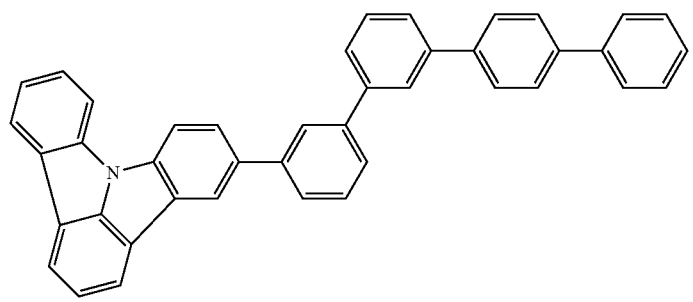
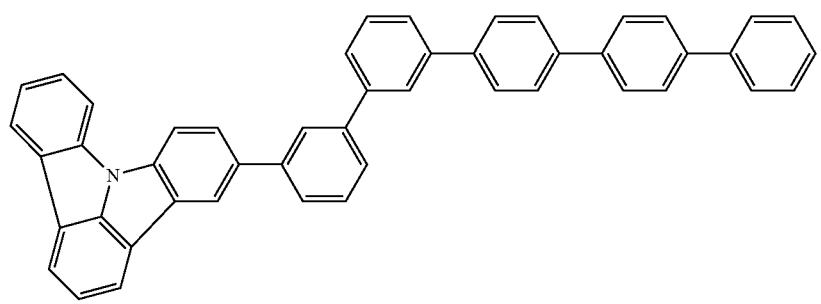
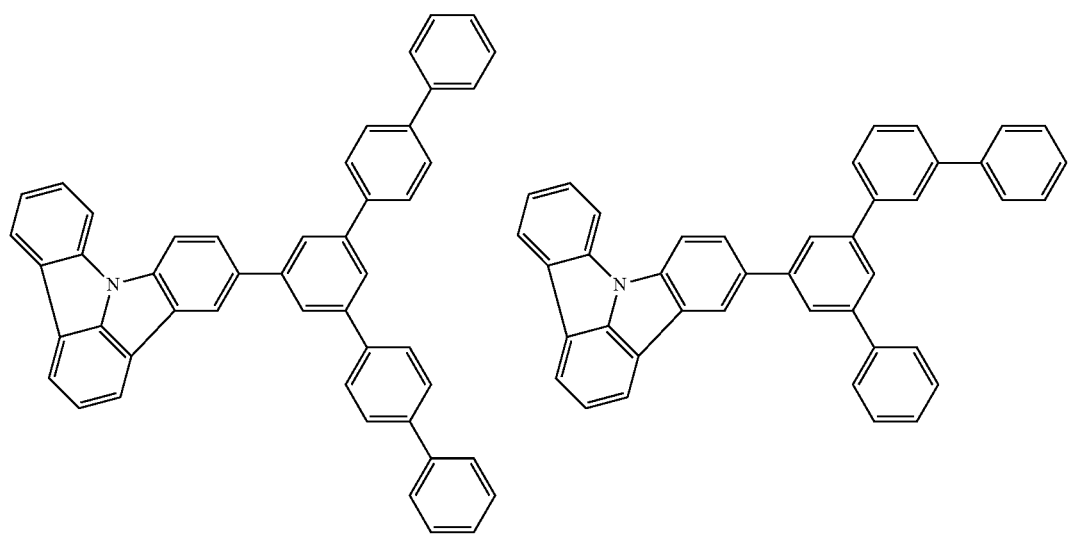

-continued
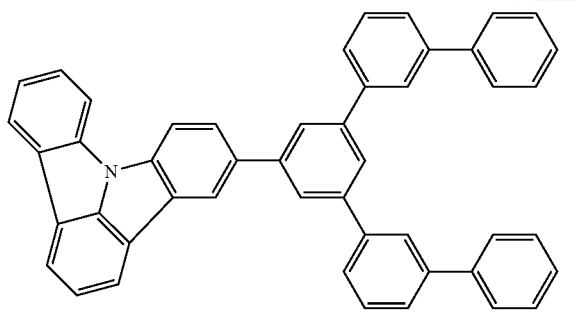
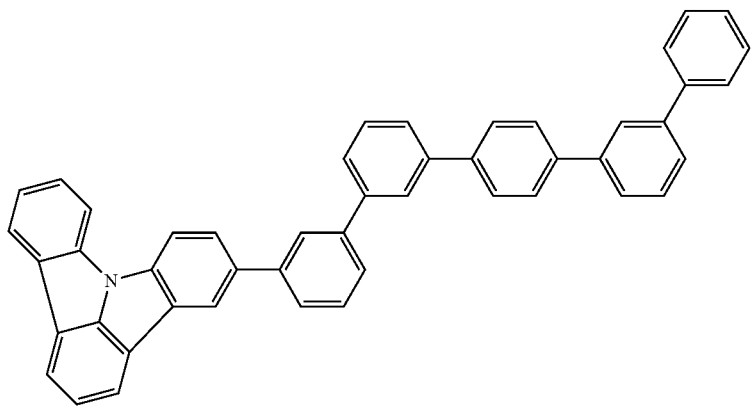
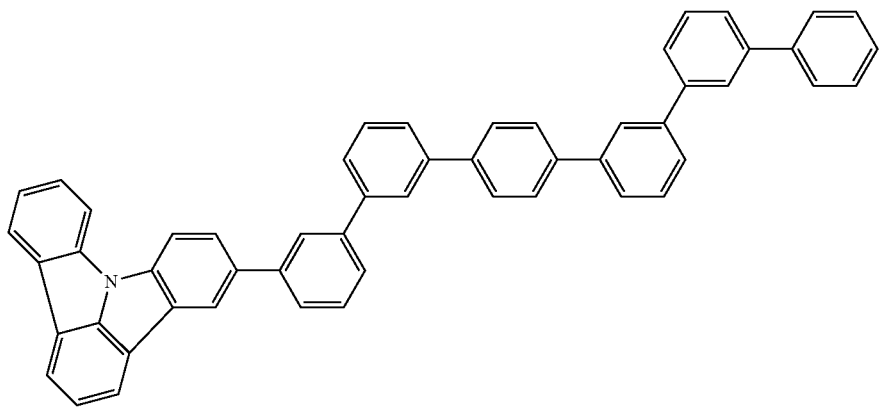
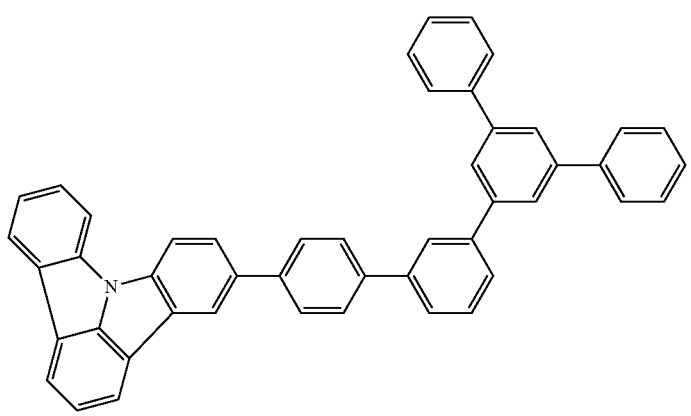

-continued
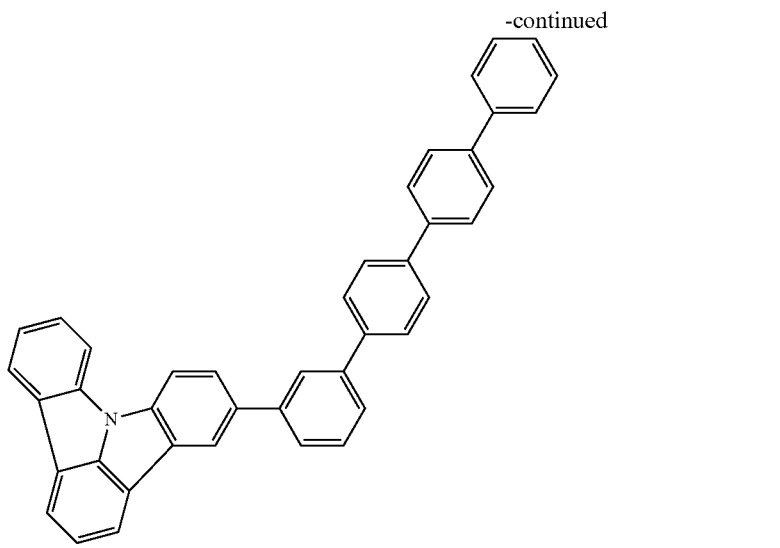
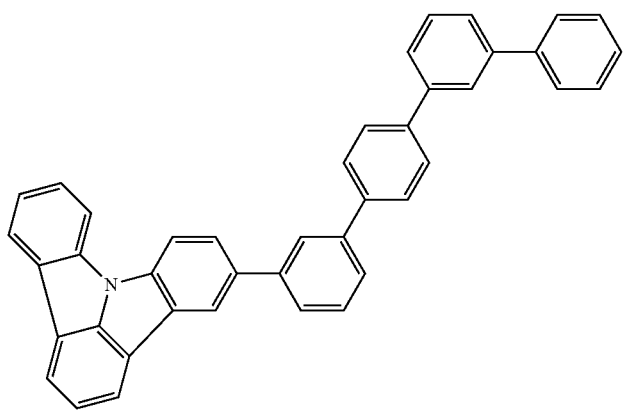
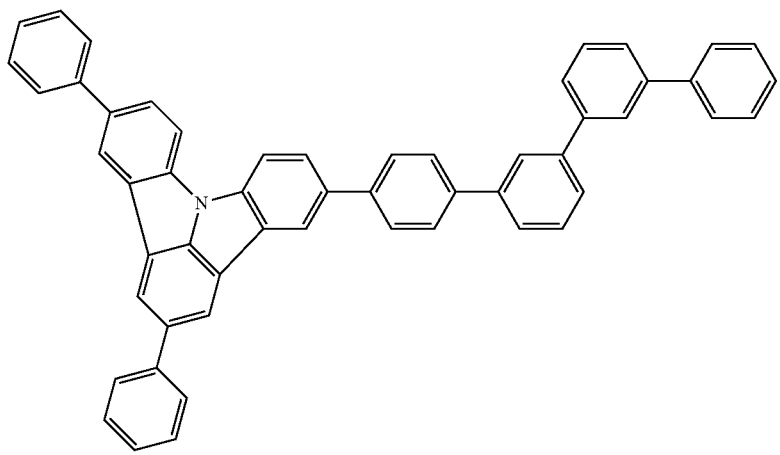

-continued
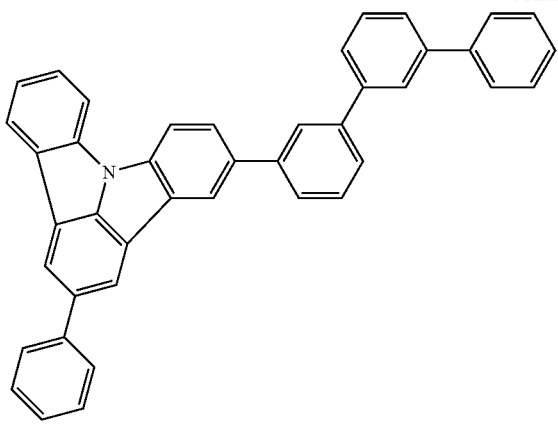
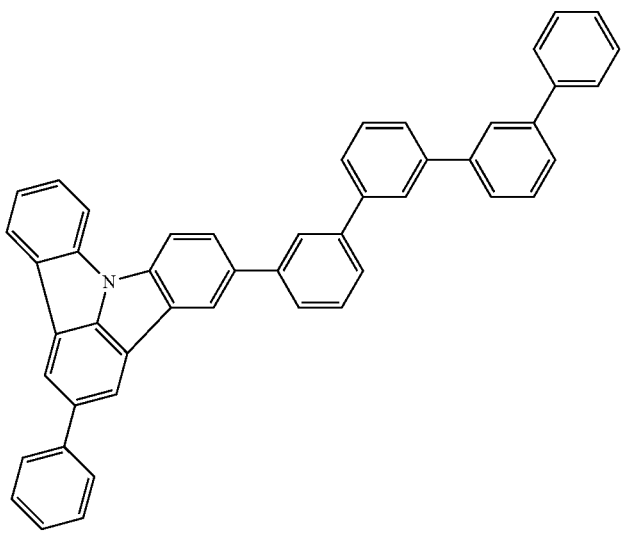
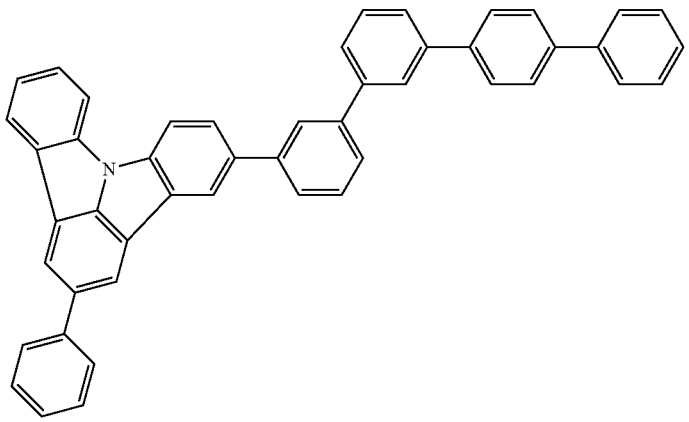
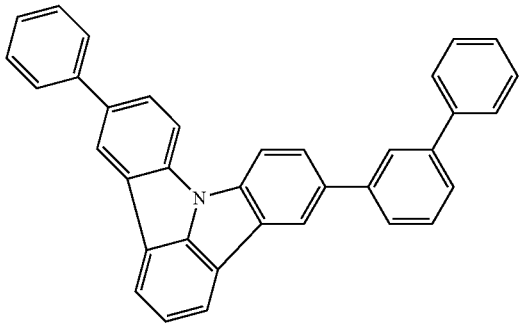

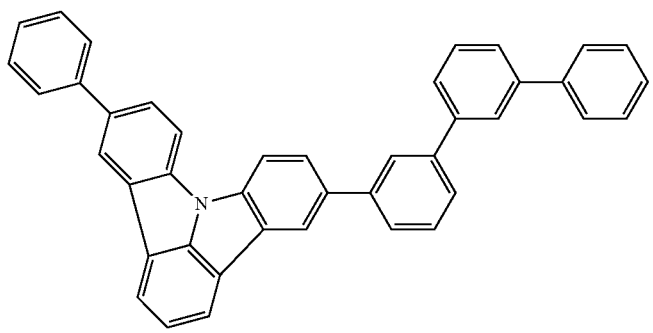
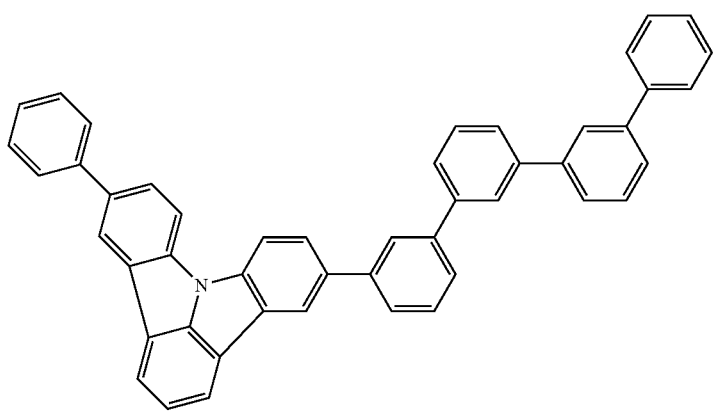
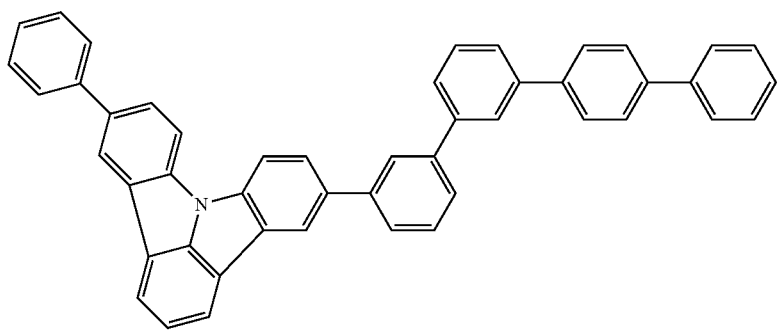
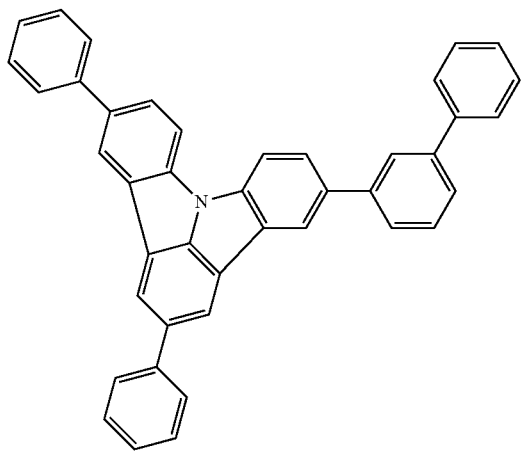

-continued
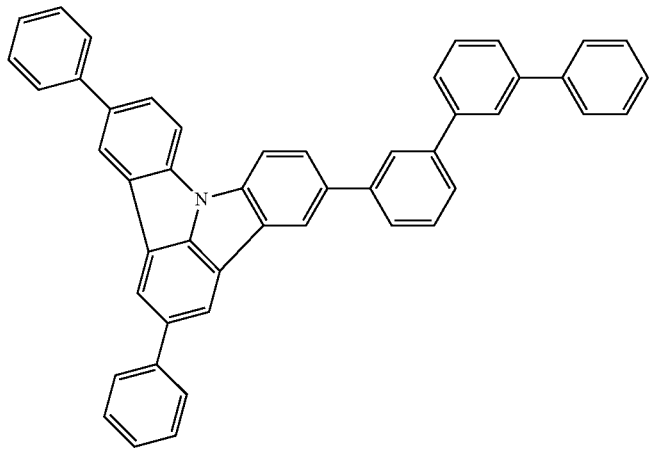
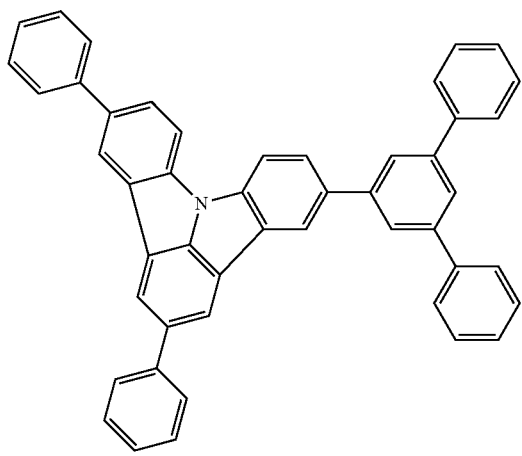
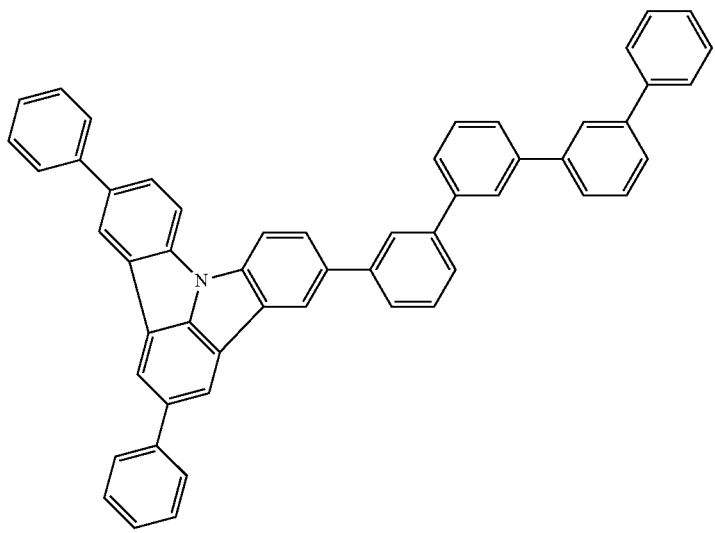

-continued
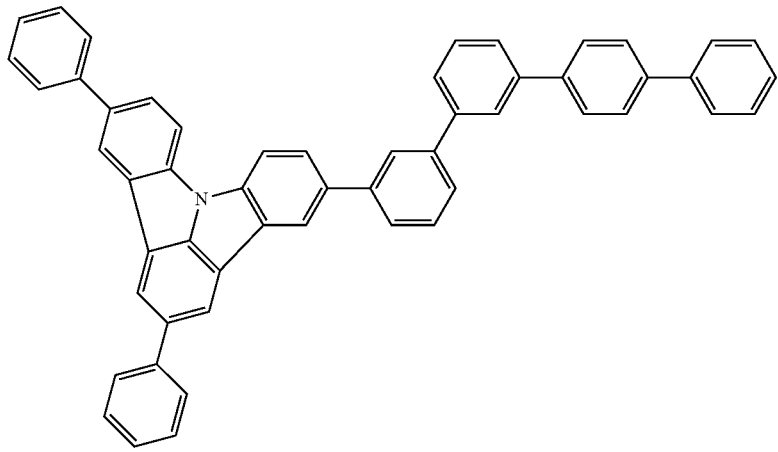
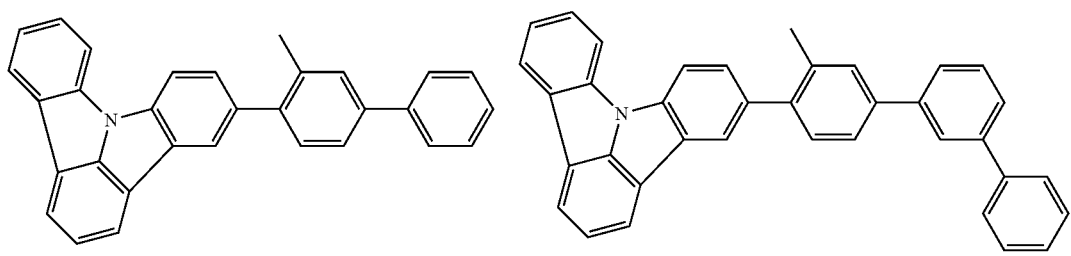
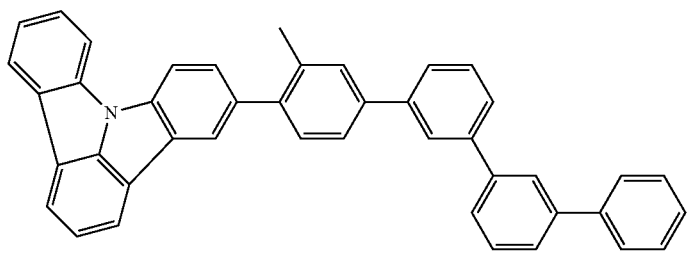
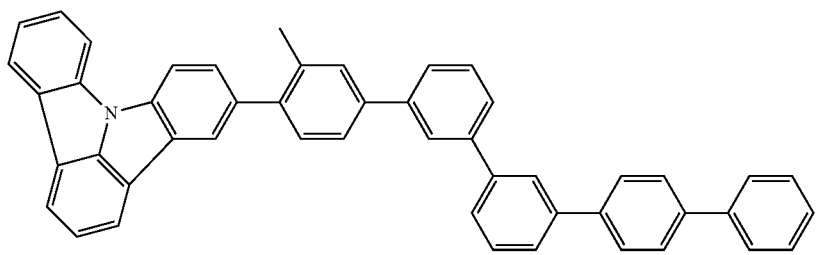
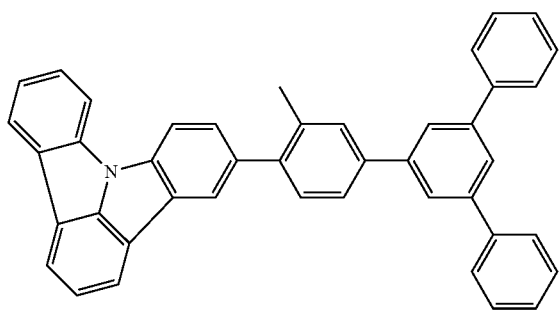

-continued
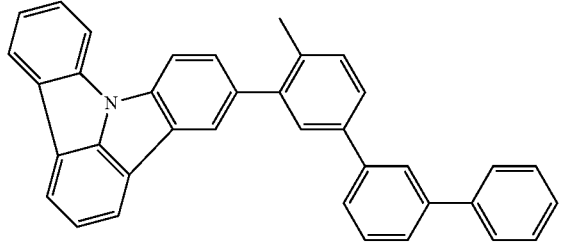
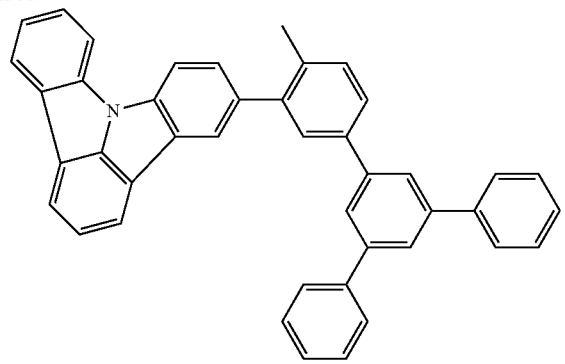
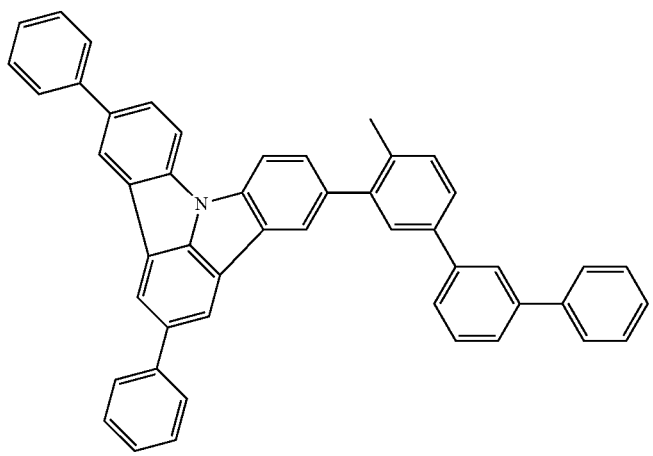
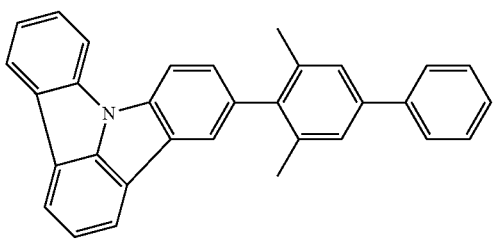
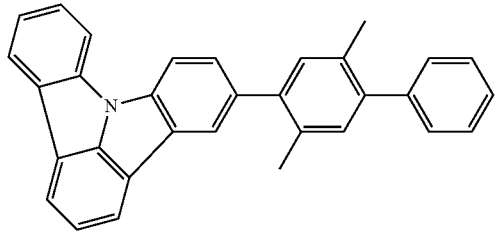
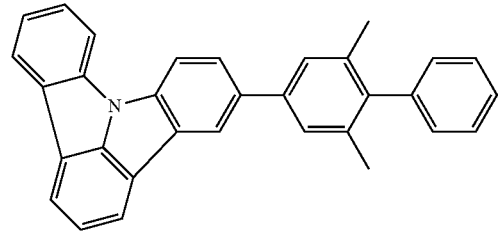
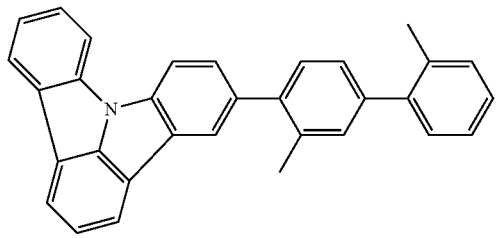
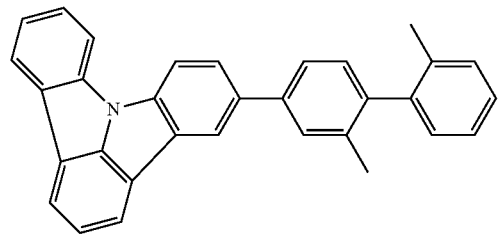
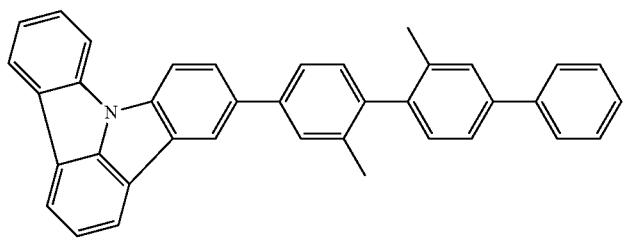
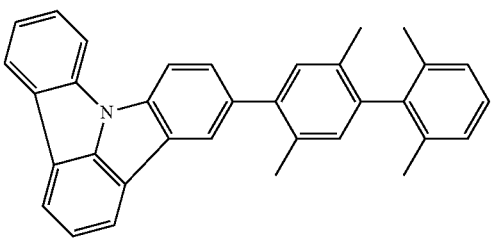

-continued
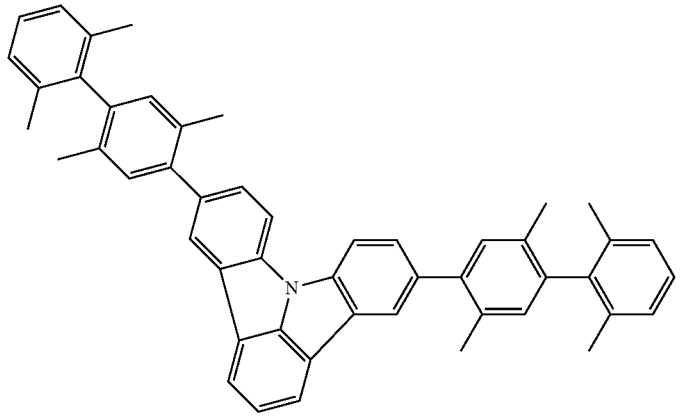
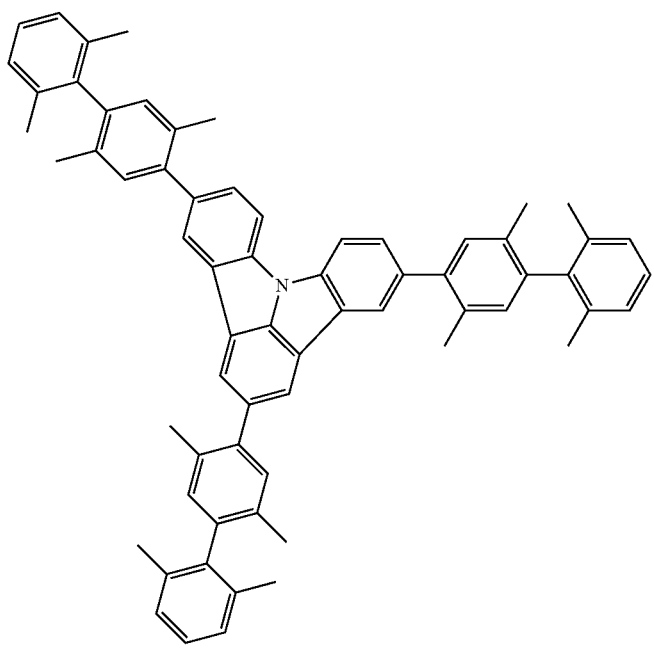
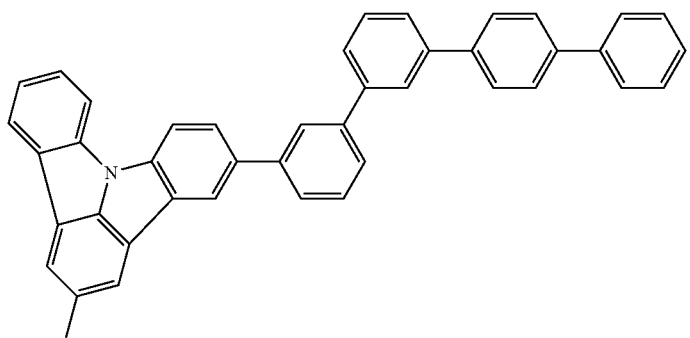

-continued
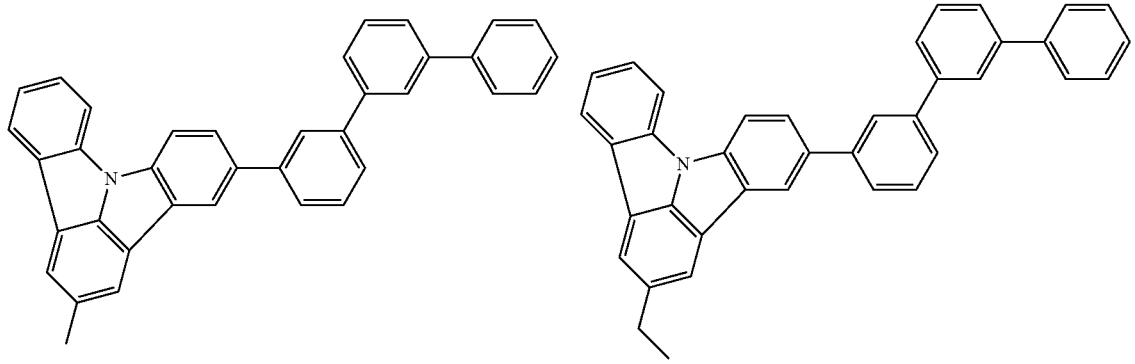
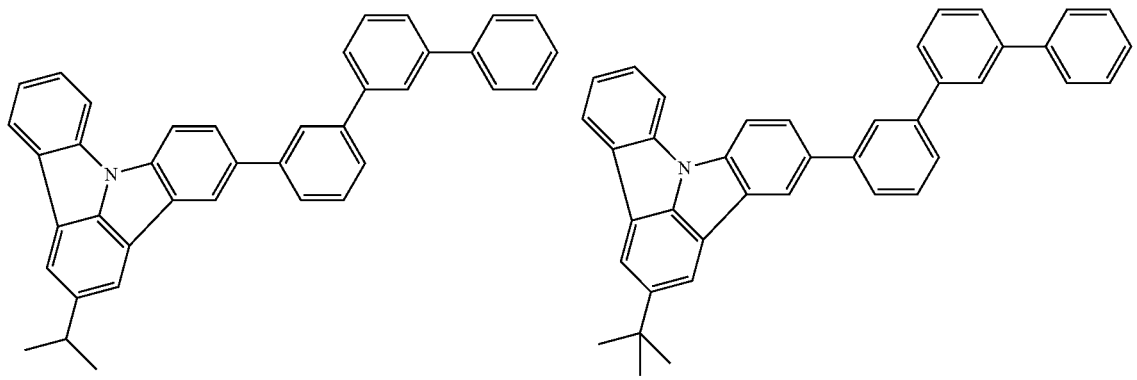
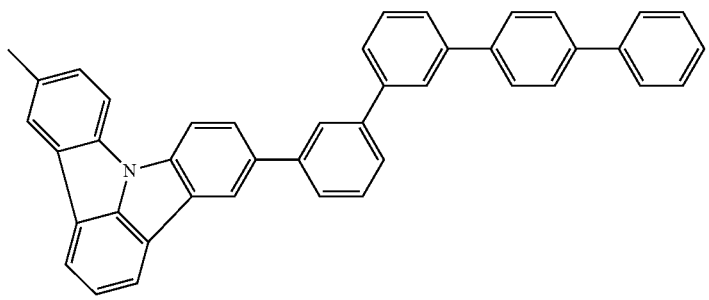
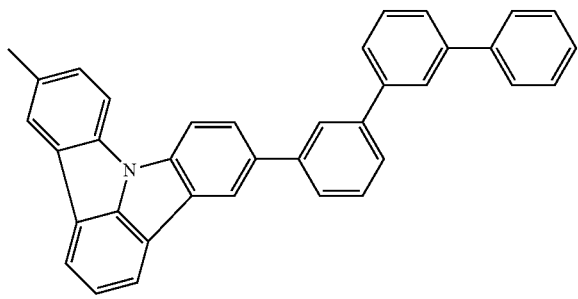
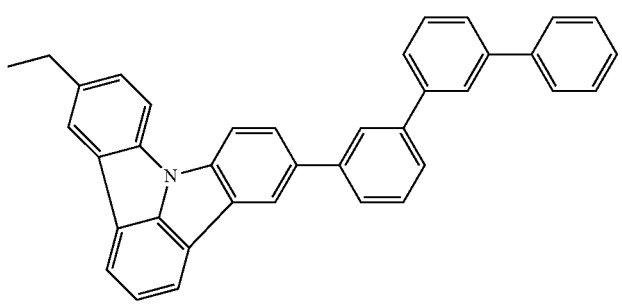

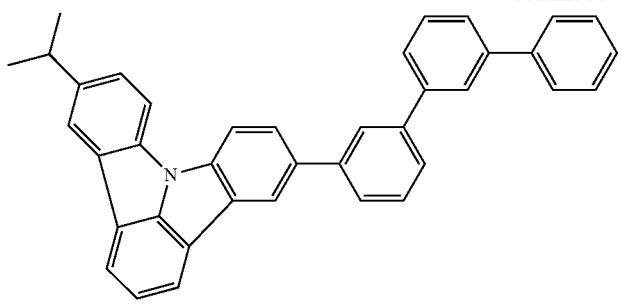
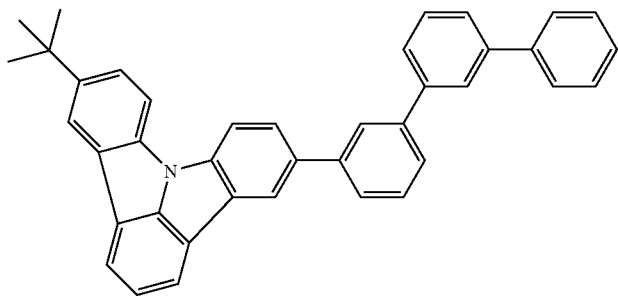
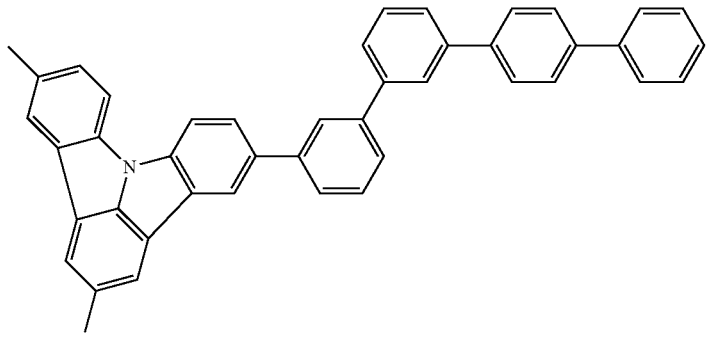
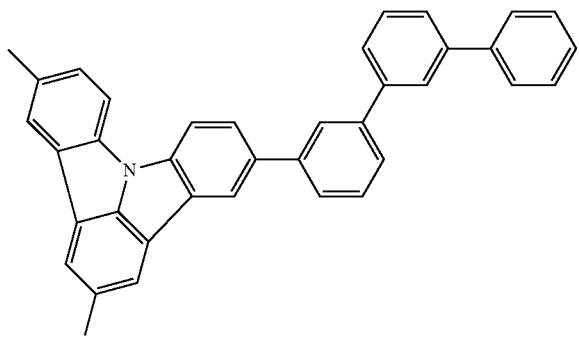
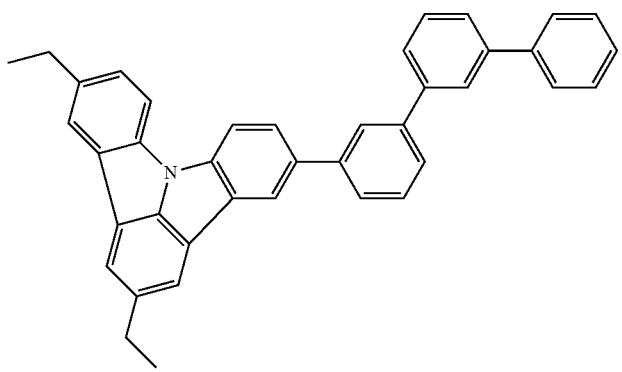

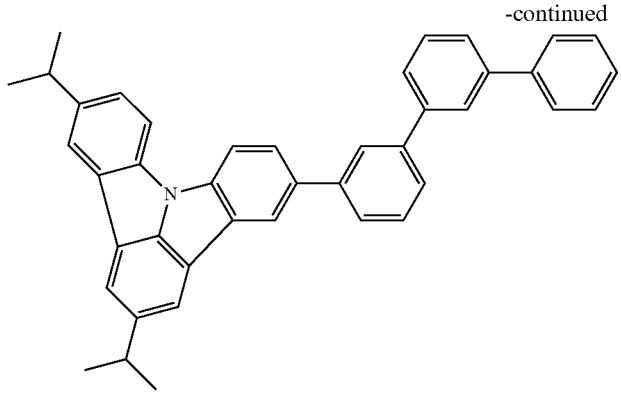
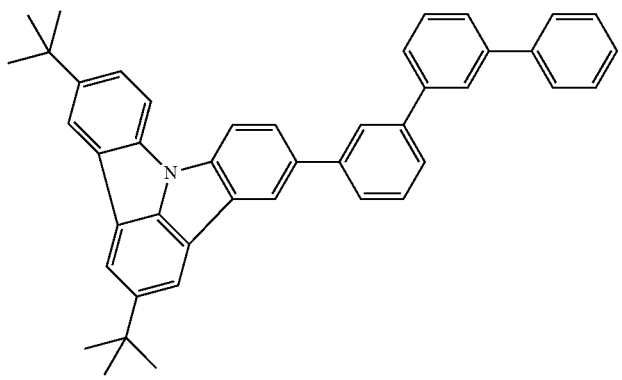
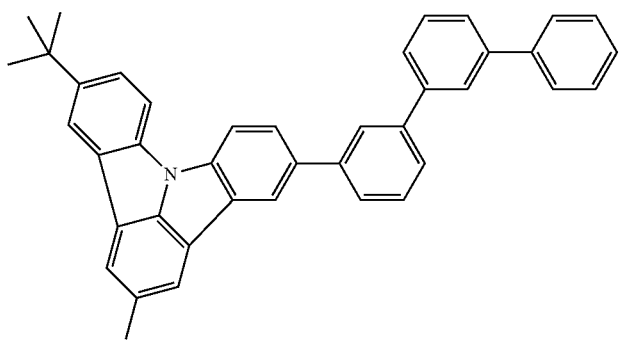
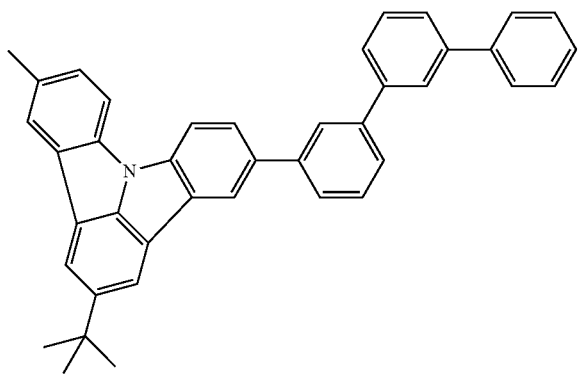

-continued
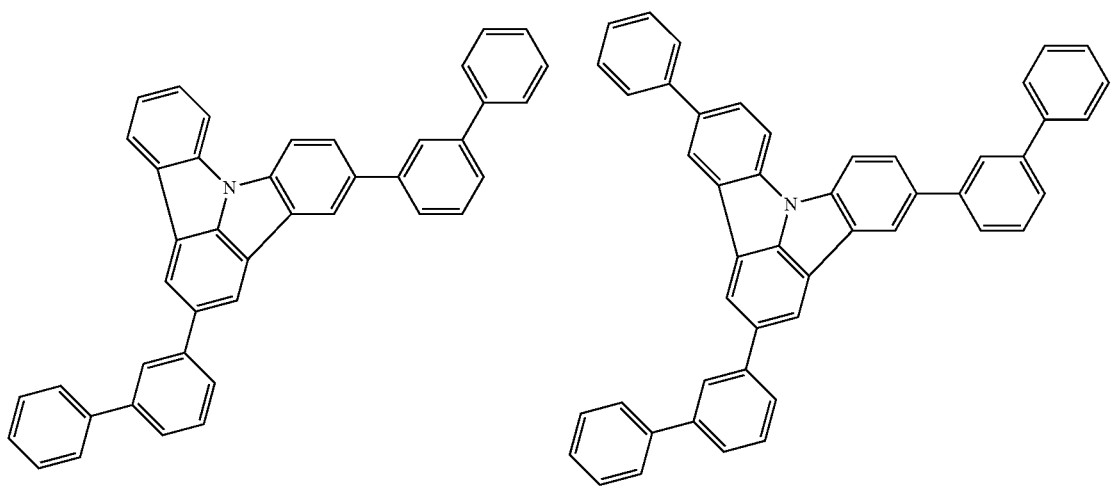
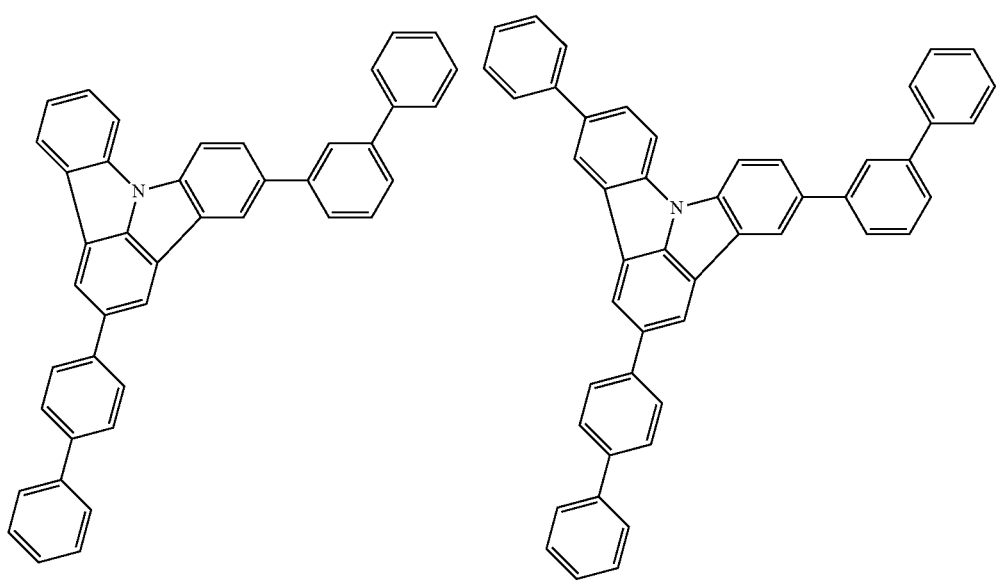
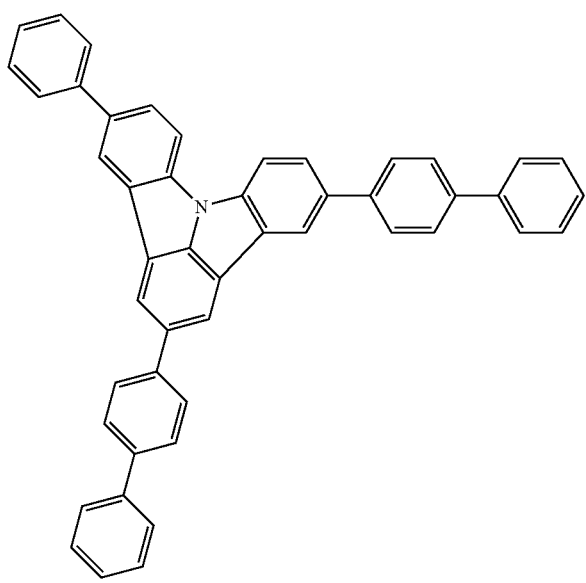

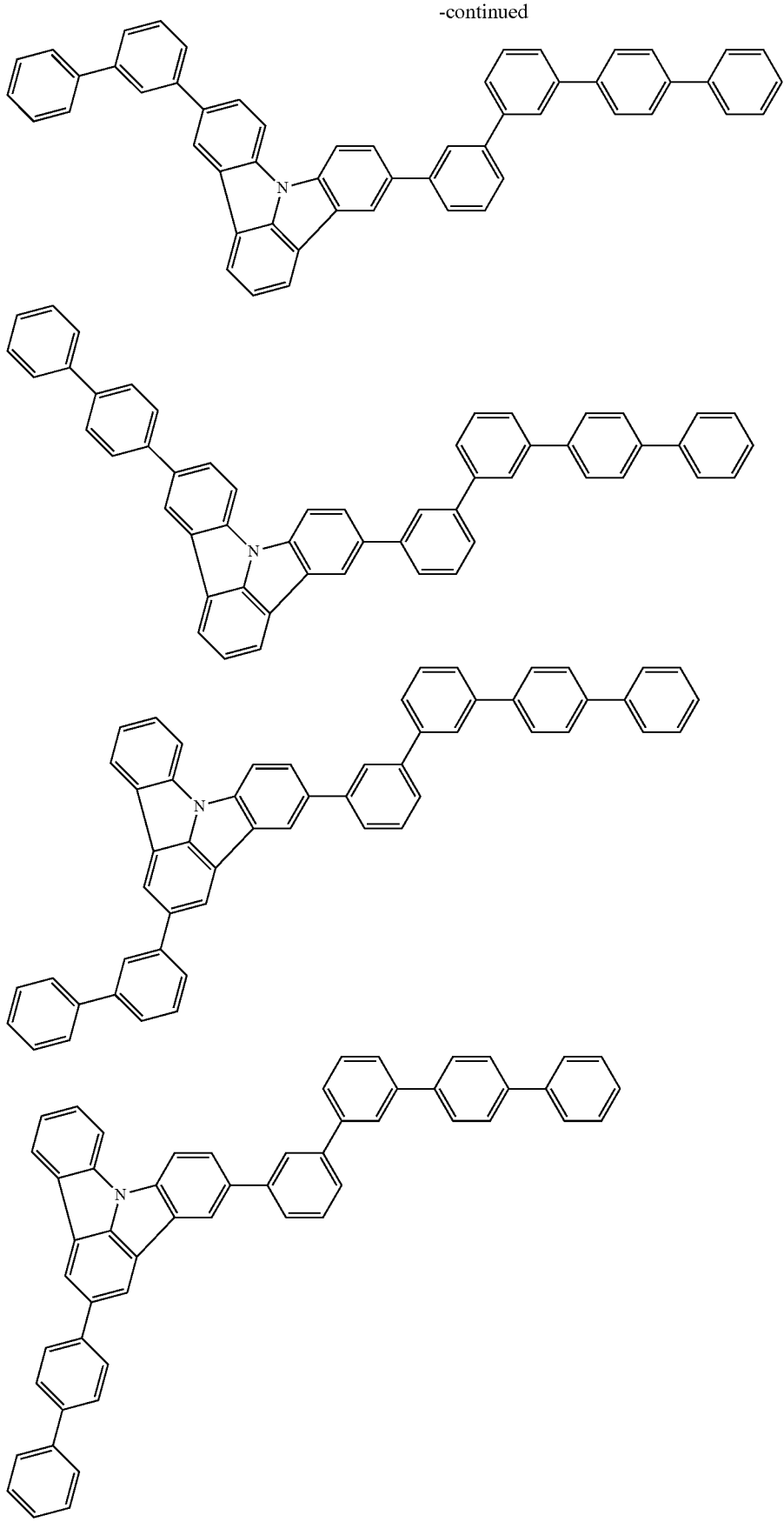

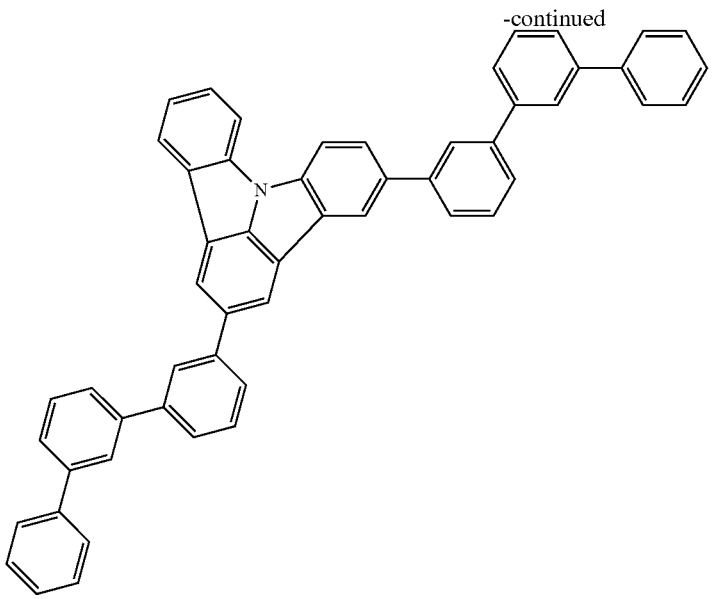

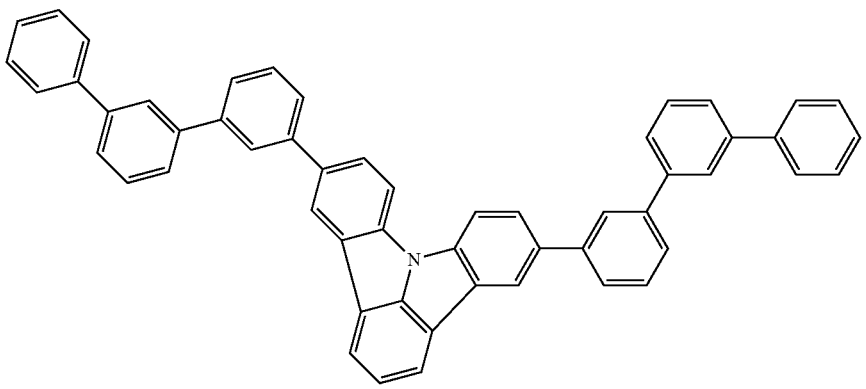

The compounds exemplified as the compound represented by the general formula (1) can be synthesized by, for example, a method described in JP-A-2010-087496.

The compound represented by the general formula (1) can also be preferably synthesized by the following scheme. However, the following synthesis scheme is one example of the synthesis, and the compound represented by the general formula (1) can also be synthesized by another known method.

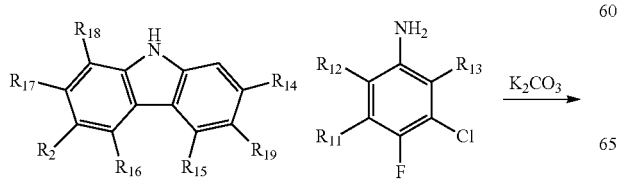

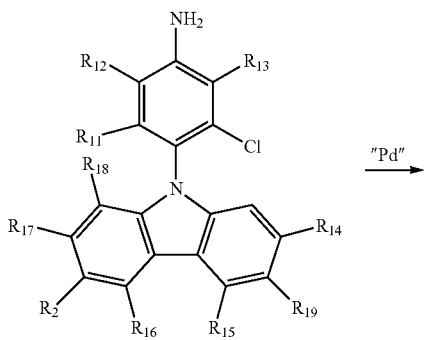

-continued

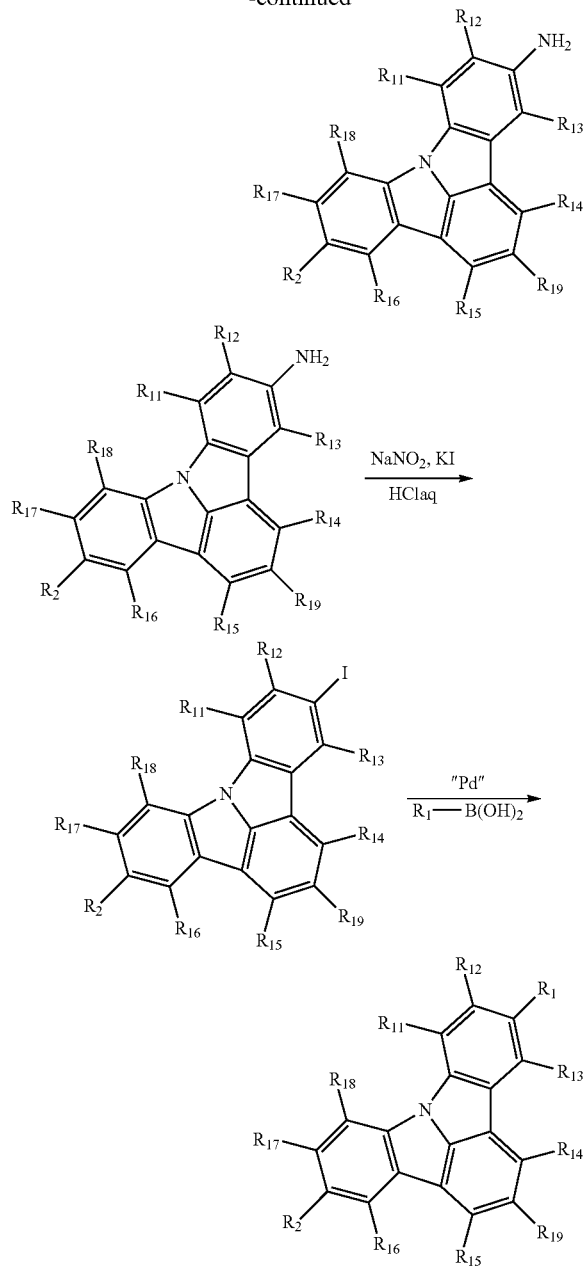

Concerning the carbazole compounds, synthesis by dehydrogenation aromatization after the Aza-Cope arrangement of the condensation product of an aryl hydrazine and a cyclohexane derivative (L. F. Tieze and Th. Eicher, translated by Takano and Ogasawara, *Precision Organic Syntheses*, page 339, published by Nanko-Do) is exemplified. In addition, concerning the coupling reaction of the obtained compound and an aryl halide compound using a palladium catalyst, the methods described in *Tetrahedron Letters*, Vol. 39, page 617 (1998), ibid., Vol. 39, page 2367 (1998), and ibid., Vol. 40, page 6393 (1999) are exemplified. The reaction temperature and the reaction time are not particularly limited, and the conditions in the above-described documents are applicable. In addition, the synthesis can be conducted by the method described in, for example, WO2007/031165, paragraph 47, et seq.

The compound represented by the general formula (1) is a charge transporting material for an organic electroluminescent element and may be contained in any layer other than the light emitting layer in the organic layer. As for the layer into which the compound represented by the general formula (1) is introduced, the compound represented by the general formula (1) is preferably contained in any one of the light emitting layer, a layer between the light emitting layer and a cathode (in particular, a layer adjacent to the light emitting layer), and a layer between the light emitting layer and an anode, more preferably contained in any one or plural layers of the light emitting layer, an electron transporting layer, an electron injecting layer, an exciton blocking layer, a hole blocking layer, and an electron blocking layer, still more preferably contained in any one of the light emitting layer, an electron transporting layer, a hole blocking layer, and a hole transporting layer, and especially preferably contained in the light emitting layer or an electron transporting layer. In addition, the compound represented by the general formula (1) may be used in a plurality of the above-described layers. For example, the compound represented by the general formula (1) may be used in both the light emitting layer and the electron transporting layer.

In the case of containing the compound represented by the general formula (1) in the light emitting layer, the compound represented by the general formula (1) is contained in an amount of preferably from 0.1 to 99% by mass, more preferably from 1 to 97% by mass, and still more preferably from 10 to 96% by mass relative to the total mass of the light emitting layer. In the case where the compound represented by the general formula (1) is further contained in the layer other than the light emitting layer, the compound represented by the general formula (1) is contained in an amount of preferably from 50 to 100% by mass, and more preferably from 85 to 100% by mass relative to the total mass of the layer other than the light emitting layer.

(II) Phosphorescent Material:

In the present invention, the light emitting layer preferably includes at least one phosphorescent material. In the present invention, in addition to the above-described phosphorescent material, a fluorescent light emitting material and a phosphorescent material different from the phosphorescent material contained in the light emitting layer can be used as the light emitting material.

Such fluorescent light emitting material and phosphorescent material are described in detail in, for example, paragraphs [0100] to [0164] of JP-A-2008-270736 and paragraphs [0088] to [0090] of JP-A-2007-266458, the detailed descriptions thereon in these patent documents can be applied to the present invention.

Examples of the phosphorescent material which can be used in the present invention include phosphorescent materials described in patent documents, for example, U.S. Pat. No. 6,303,238B1, U.S. Pat. No. 6,097,147, WO00/57676, WO00/70655, WO01/08230, WO01/39234A2, WO01/41512A1, WO02/02714A2, WO02/15645A1, WO02/44189A1, WO05/19373A2, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-2475859, JP-A-2001-298470, JP-A-2002-173674, JP-A-2002-203678, JP-A-2002-203679, JP-A-2004-357791, JP-A-2006-256999, JP-A-2007-19462, JP-A-2007-94635, and JP-A-2007-96259. Above all, examples of the light emitting material which is more preferable include phosphorescent light emitting metal complex compounds such as iridium (Ir) complexes, platinum (Pt) complexes, Cu complexes, Re complexes, W complexes, Rh complexes, Ru complexes, Pd complexes, Os complexes, Eu complexes, Tb complexes, Gd complexes, Dy complexes, and Ce complexes, with iridium (Ir) complexes, platinum (Pt) complexes, and Re complexes being especially preferable. Above all, iridium (Ir) complexes, platinum (Pt) complexes, and Re complexes each including at least one coordination mode of a metal-carbon bond, a metal-nitrogen bond, a metal-oxygen bond, and a metal-sulfur bond are preferable. Furthermore, from the viewpoints of luminous efficiency, driving durability, and chromaticity, iridium (Ir) complexes and platinum (Pt) complexes are especially preferable, and iridium (IR) complexes are the most preferable.

As the phosphorescent material which is contained in the light emitting layer in the present invention, it is preferable to use an iridium (Ir) complex represented by the following general formula (E-1) or a platinum (Pt) complex as described below.

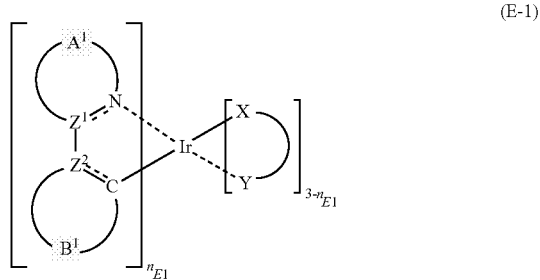

(E-1)

In the general formula (E-1), Z and $Z^2$ each independently represent a carbon atom or a nitrogen atom; $A^1$ represents an atomic group for forming a 5- or 6-membered heterocyclic ring together with $Z^1$ and the nitrogen atom; $B^1$ represents an atomic group for forming a 5- or 6-membered heterocyclic ring together with $Z^2$ and the carbon atom; (X—Y) represents a monoanionic bidentate ligand; and $n_{E1}$ represents an integer of from 1 to 3.

$Z^1$ and $Z^2$ are preferably a carbon atom. $n_{E1}$ is preferably 2 or 3. In that case, two or three ligands containing $Z^1$, $Z^2$, $A^1$, and $B^1$ are present, and these ligands may be the same as or different from each other.

Examples of the 5- or 6-membered heterocyclic ring containing $A^1$, $Z^1$, and a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. The 5- or 6-membered heterocyclic ring formed of $A^1$, $Z^1$, and a nitrogen atom may have a substituent.

Examples of the 5- or 6-membered heterocyclic ring formed of $B^1$, $Z^2$, and a carbon atom include a benzene ring, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, a furan ring, and a pyrrole ring. The 5- or 6-membered heterocyclic ring formed of $B^1$, $Z^2$, and a carbon atom may have a substituent.

Examples of the substituent include the groups selected from the Substituent Group A as described above. The substituents may be connected to each other to form a ring. Examples of the ring which is formed include an unsaturated 4- to 7-membered ring, a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. Such a formed ring may have a substituent, and a ring may be further formed via the substituent on the formed ring. In addition, the substituent of the 5- or 6-membered heterocyclic ring formed of $A^1$, $Z^1$, and a nitrogen atom and the substituent of the 5- or 6-membered ring formed of $B^1$, $Z^2$, and a carbon atom may be connected to each other to form the same fused ring as that described above. A ring may be further formed via the substituent on the formed ring.

As the ligand represented by (X—Y), there are enumerated various known ligands which are used in conventionally known metal complexes. Examples thereof include ligands described in H. Yersin, *Photochemistry and Photophysics of Coordination Compounds*, Springer-Verlag, 1987, nitrogen-containing heteroaryl ligands, and diketone ligands. Above all, ligands represented by the following general formulae (1-1) to (1-39) are preferable, and ligands represented by the general formulae (1-1), (1-4), (1-15), (1-16), (1-17), (1-18), (1-19), (1-22), (1-25), (1-28), (1-29), (1-36), and (1-39) are more preferable. However, it should not be construed that the present invention is limited thereto.

(1-1)

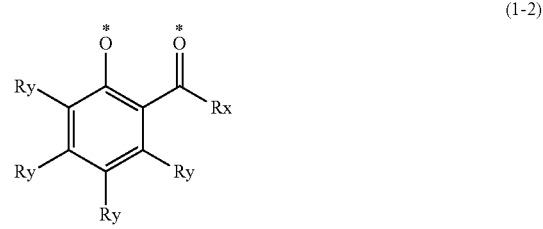

(1-2)

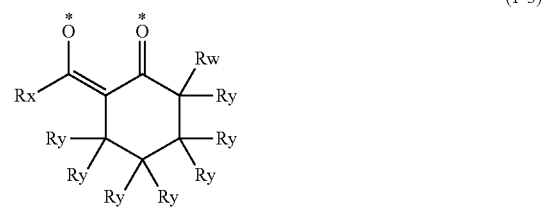

(1-3)

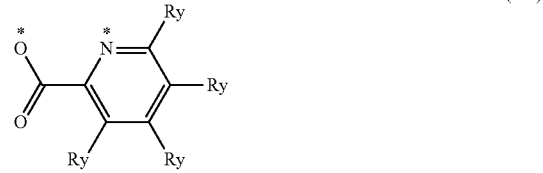

(1-4)

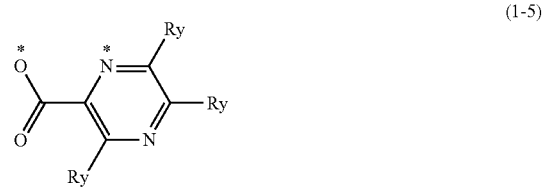

(1-5)

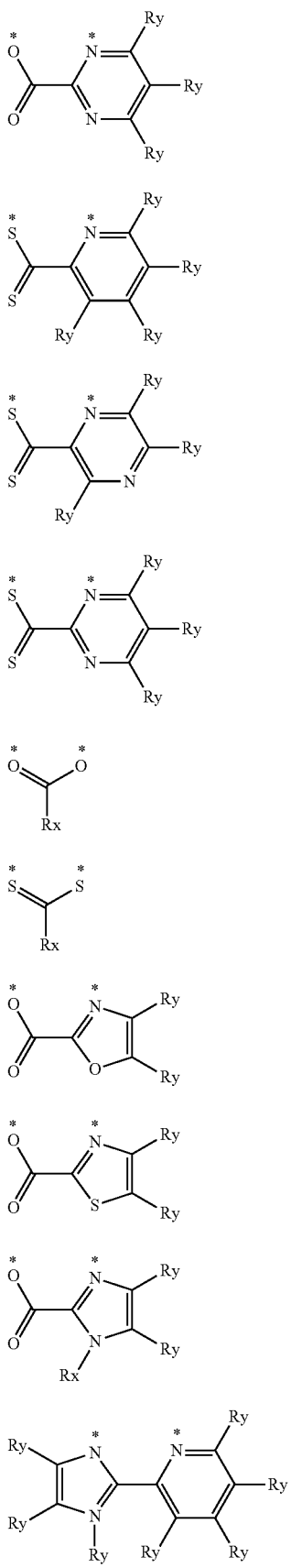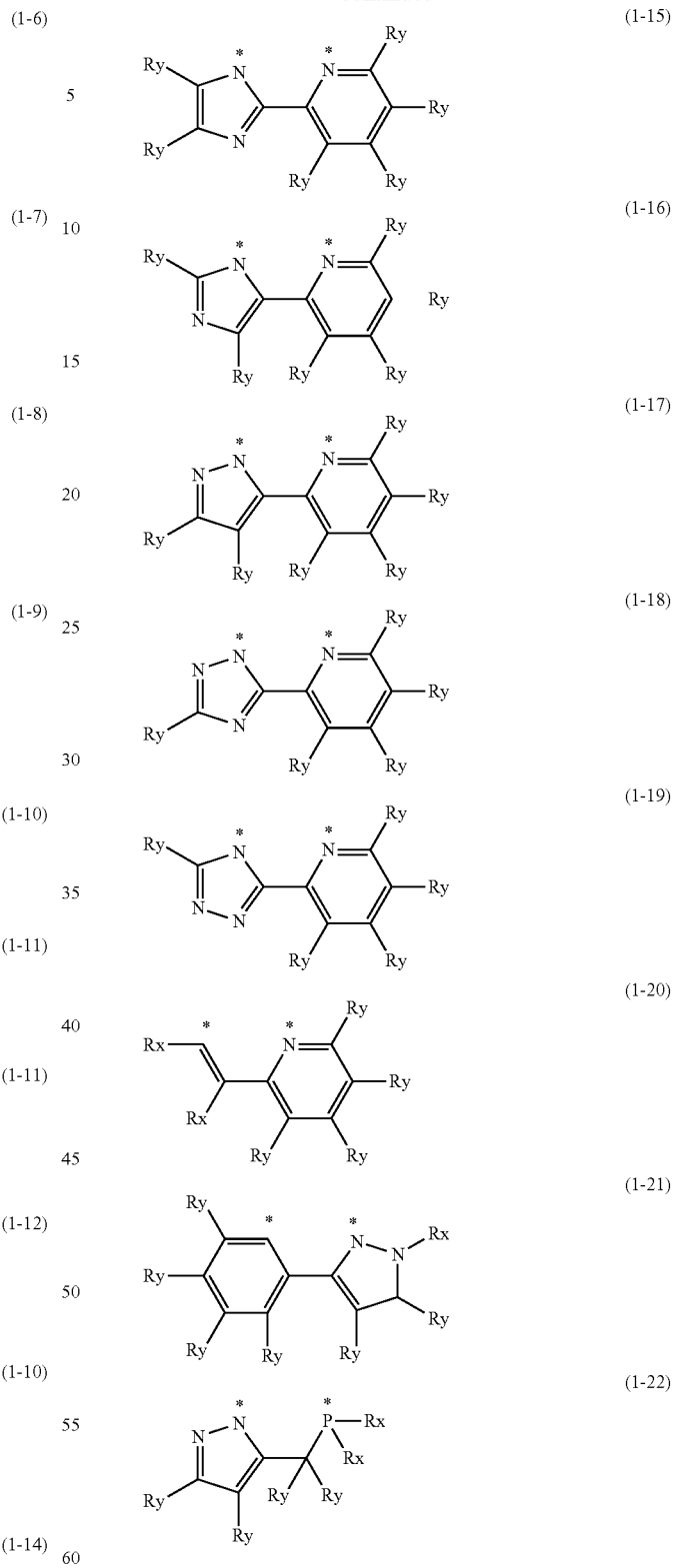
\* represents a coordination position to iridium (Ir) in the general formula (E-1). Rx, Ry, and Rz each independently represent a hydrogen atom or a substituent. Examples of the substituent include the substituents selected from the Substituent Group A as described above. Rx and Ry are each independently preferably an alkyl group, a perfluoroalkyl group, or an aryl group. Ry is preferably any one of a hydrogen atom, an alkyl group, a perfluoroalkyl group, a fluorine atom, a cyano group, and an aryl group. Rx and Ry which are plurally present in one ligand may be the same as or different from each other.

The complex having such a ligand can be synthesized using a corresponding ligand precursor in the same manner as that in known synthesis examples.

A preferred embodiment of the iridium (Ir) complex represented by the general formula (E-1) is an iridium (Ir) complex represented by the following general formula (E-2).

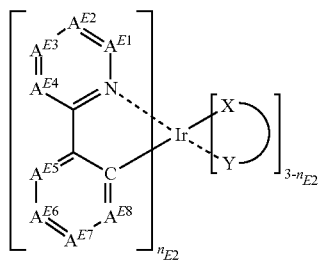

(E-2)

In the general formula (E-2), $A^{E1}$ to $A^{E8}$ each independently represent a nitrogen atom or C-RE; and RE represents a hydrogen atom or a substituent. As the substituent, the substituents exemplified as the Substituent Group A as described above can be applied. $R^E$s may be connected to each other to form a ring. Examples of the ring which is formed include the same rings as the fused rings in the general formula (E-1). (X—Y) and $n_{E2}$ are synonymous with (X—Y) and $n_{E2}$ in the general formula (E-1), respectively, and preferred ranges thereof are also the same. In the case where $n_{E2}$ is 2 or 3, two or three ligands containing $A^{E1}$ to $A^{E8}$ are present. In this respect, the ligands may be the same as or different from each other.

A more preferred embodiment of the compound represented by the general formula (E-2) is a compound represented by the following general formula (E-3).

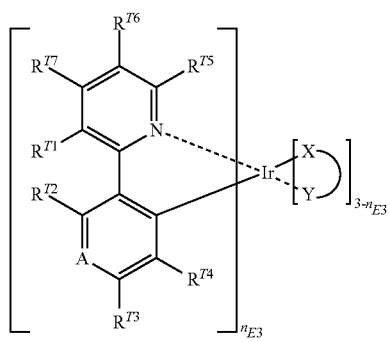

(E-3)

In the general formula (E-3), $R^{T1}, R^{T2}, R^{T3}, R^{T4}, R^{T5}, R^{T6}$, and $R^{T7}$ are synonymous with $R^E$. A represents CR'''' or a nitrogen atom, and R'''' is synonymous with $R^E$. As for $R^{T1}$ to $R^{T7}$ and R'''', arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A. (X—Y) and $n_{E3}$ are synonymous with (X—Y) and $n_{E1}$ in the general formula (E-1), respectively, and preferred ranges thereof are also the same. In the case where $n_{E3}$ is 2 or 3, two or three ligands containing $R^{T1}$, $R^{T2}, R^{T3}, R^{T4}, R^{T5}, R^{T6}, R^{T7}$, and A are present. In this respect, the ligands may be the same as or different from each other.

Preferred ranges of A and $R^{T1}$ to $R^{T7}$ vary depending upon the luminous color required according to an application. They are hereunder described while dividing the aimed luminous color into three regions of a blue to sky blue color, a green to yellow color, and a yellowish orange to red color. However, it should not be construed that the present invention is limited thereto.

In order to obtain a luminous color of yellowish orange to red color, the compound represented by the general formula (E-1) is preferably a compound represented by the following general formula (E-4), general formula (E-5), or general formula (E-6).

General Formula (E-4)

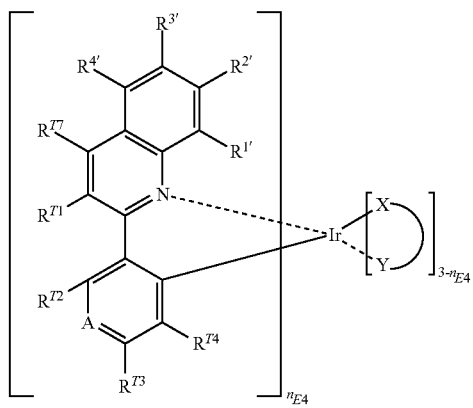

In the general formula (E-4), $R^{T1}$ to $R^{T4}, R^{T7}$, A (CR'''' or a nitrogen atom), (X—Y), and $n_{E4}$ are synonymous with $R^{T1}$ to $R^{T4}, R^{T7}$, A, (X—Y), and $n_{E3}$ in the general formula (E-3), respectively. $R^{T1}$ to $R^{T4}$ are synonymous with $R^E$.

As for $R^{T1}$ to $R^{T4}$, $R^{T7}$, $R_1'$ to $R_4'$, and R'''', arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A.

In the case where $n_{E4}$ is 2 or 3, two or three ligands containing $R^{T1}$ to $R^{T4}$, $R^{T7}$, A, and $R_1'$ to $R_4'$ are present. In this respect, the ligands may be the same as or different from each other.

$R_1'$ to $R_4'$ are preferably a hydrogen atom, a fluorine atom, an alkyl group, or an aryl group. In addition, the case where not only A represents CR'''', but from 0 to 3 of $R^{T1}$ to $R^{T4}$, $R^{T7}$, and R'''' are an alkyl group or a phenyl group, with all of the remainder being a hydrogen atom, is preferable.

Preferred specific examples of the compound represented by the general formula (E-4) are enumerated below, but it should not be construed that the present invention is limited thereto.

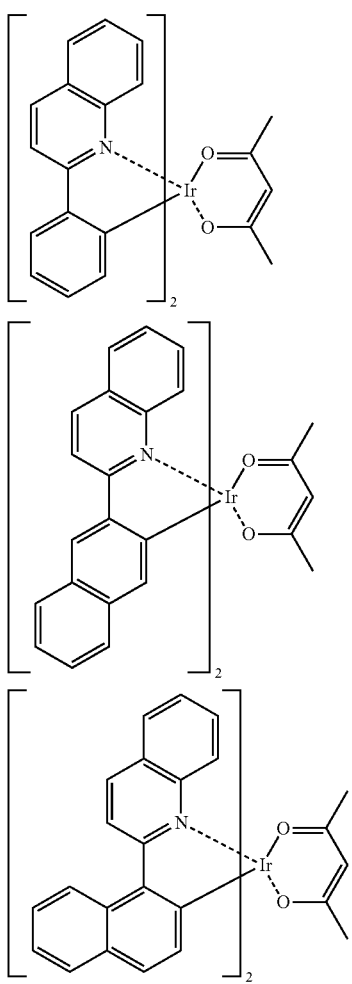
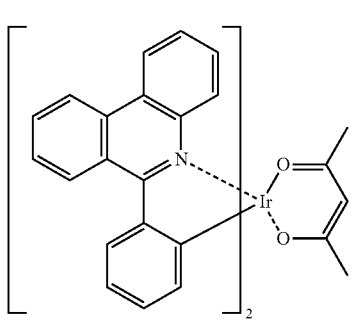
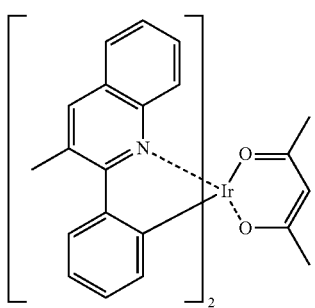
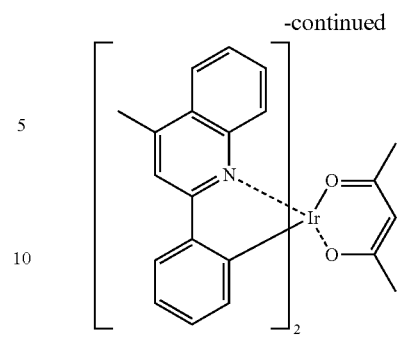
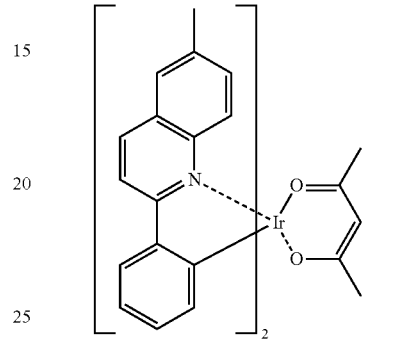
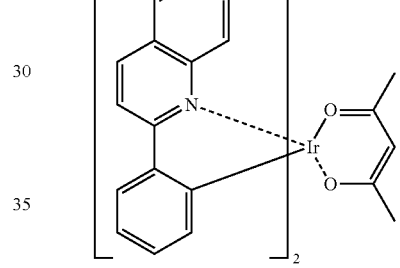
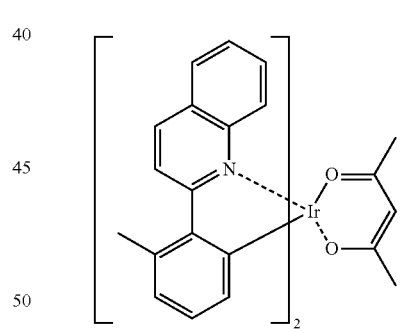
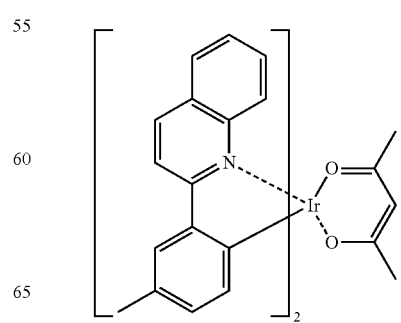

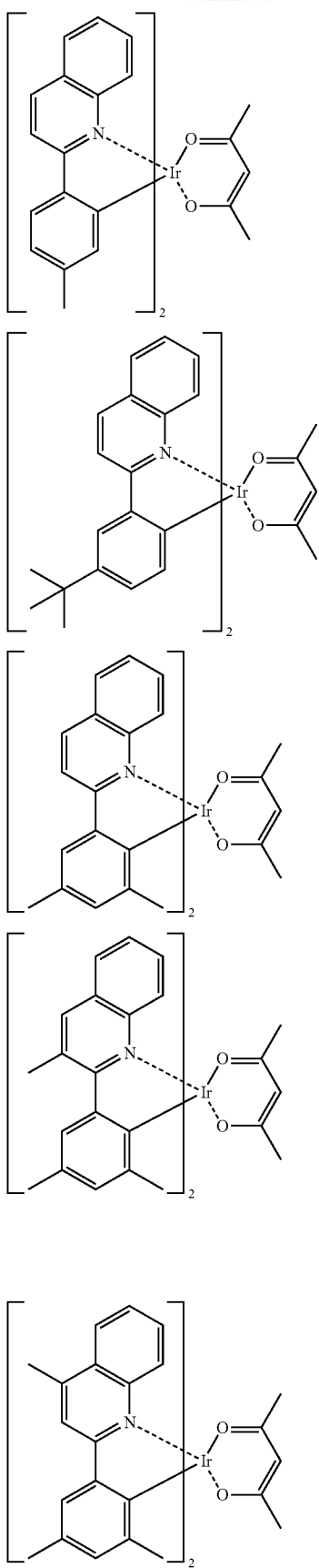

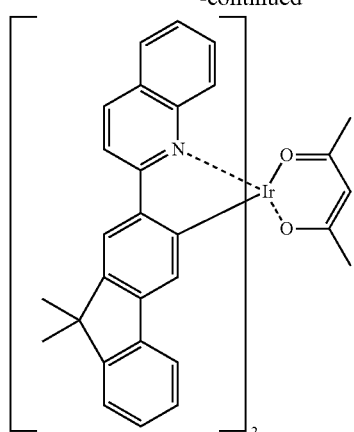
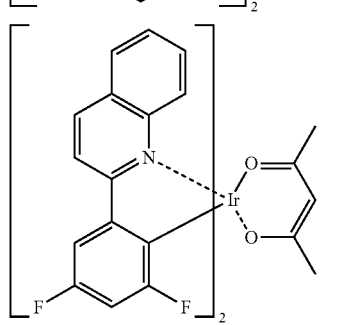
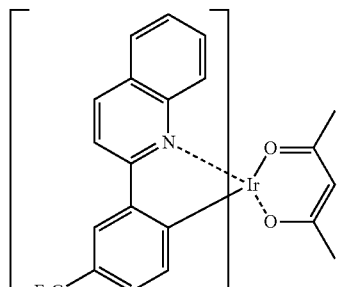
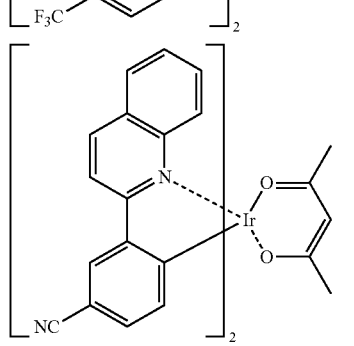
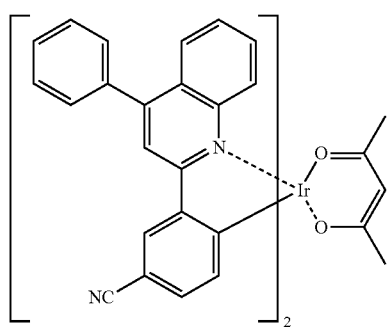
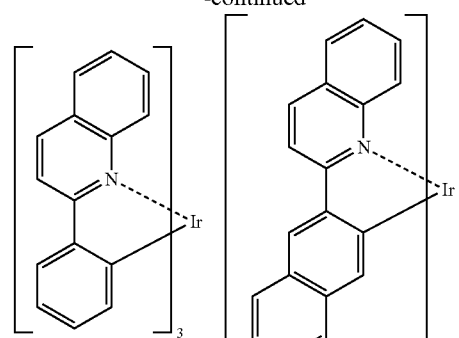
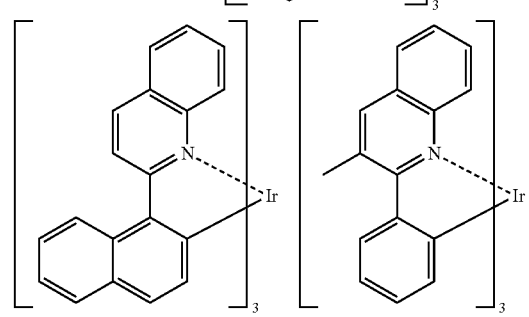
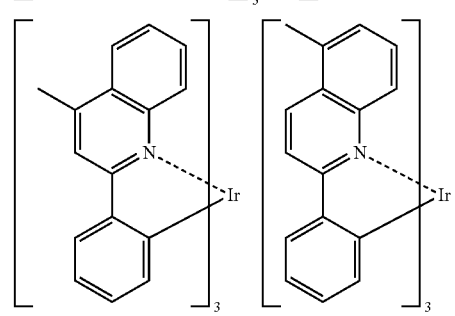
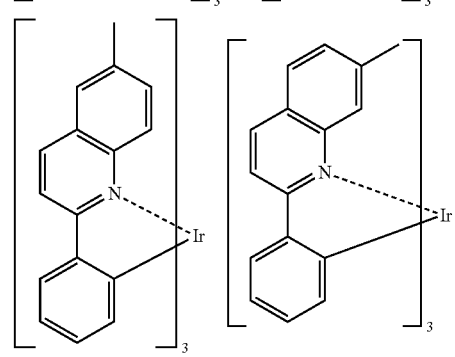
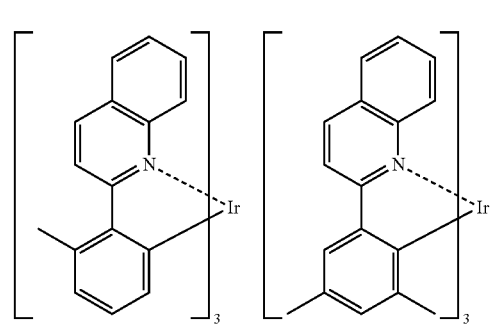

-continued

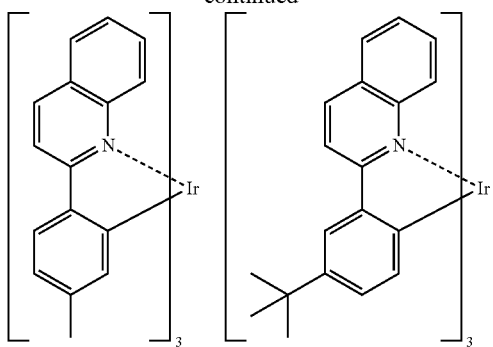

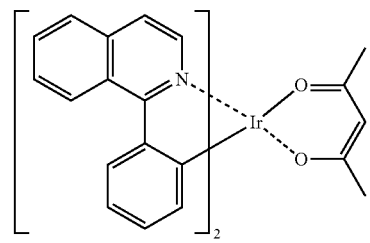

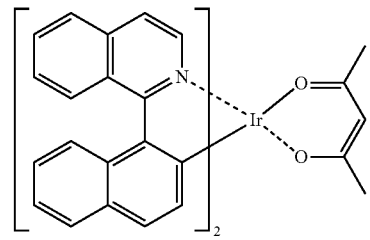

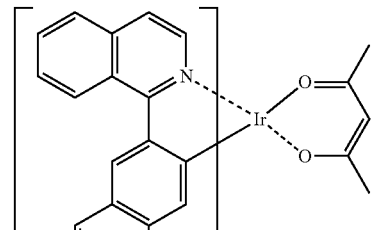

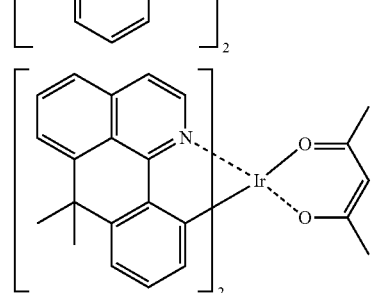

General Formula (E-5)

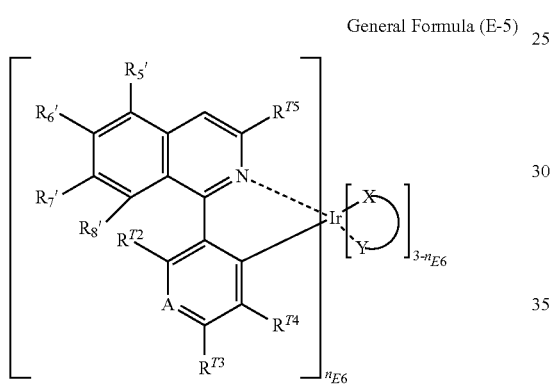

In the general formula (E-5), $R^{T2}$ to $R^{T6}$, A (CR'''' or a nitrogen atom), (X—Y), and $n_{E5}$ are synonymous with $R^{T2}$ to $R^{T6}$, A, (X—Y), and $n_{E3}$ in the general formula (E-3), respectively. $R_5'$ to $R_8'$ are synonymous with $R_1'$ to $R_4'$ in the general formula (E-4), respectively.

As for $R^{T2}$ to $R^{T6}$, $R_5'$ to $R_8'$, and R'''', arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A.

In the case where $n_{E5}$ is 2 or 3, two or three ligands containing $R^{T2}$ to $R^{T6}$, A, and $R_5'$ to $R_8'$ are present. In this respect, the ligands may be the same as or different from each other.

In addition, preferred ranges of $R_5'$ to $R_8'$ are the same as the preferred ranges of $R_1'$ to $R_4'$ in the general formula (E-4). In addition, the case where not only A represents CR'''', but from 0 to 3 of $R^{T2}$ to $R^{T6}$, R'''', and $R_5'$ to $R_8'$ are an alkyl group or a phenyl group, with all of the remainder being a hydrogen atom, is preferable.

Preferred specific examples of the compound represented by the general formula (E-5) are enumerated below, but it should not be construed that the present invention is limited thereto.

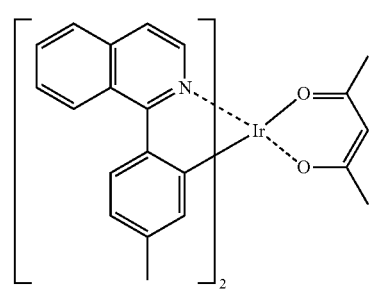

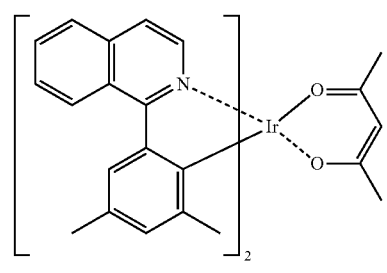

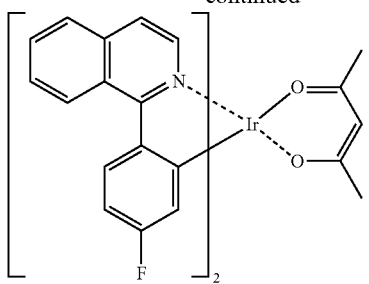
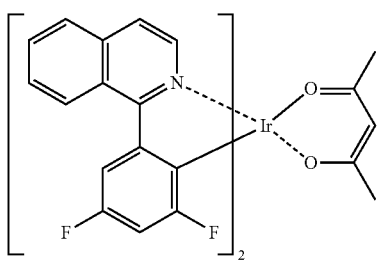
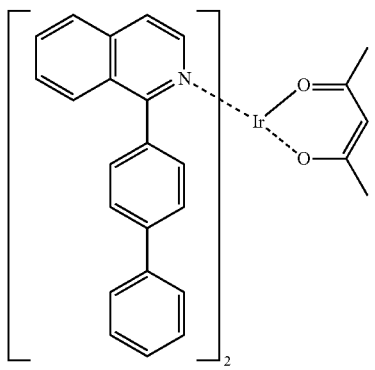
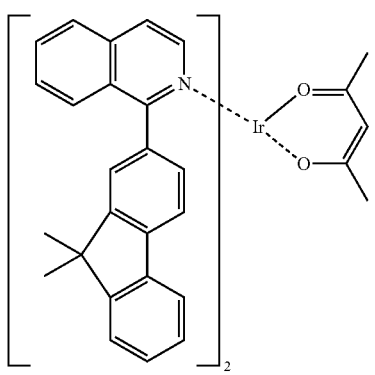
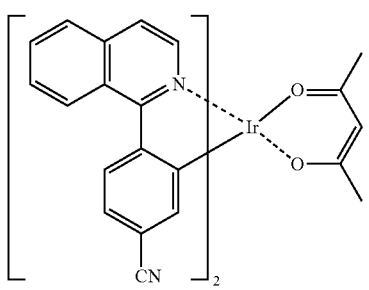
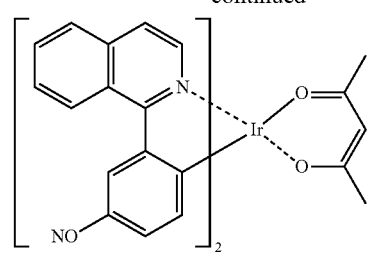
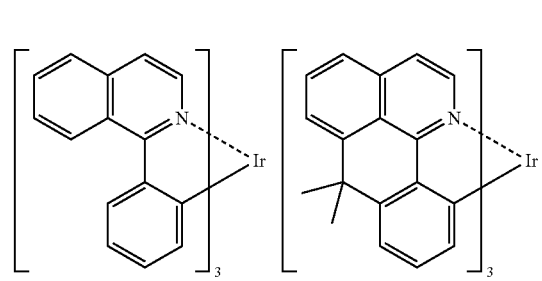
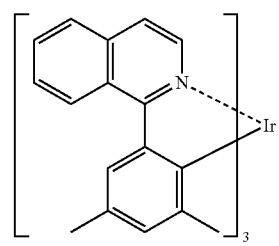
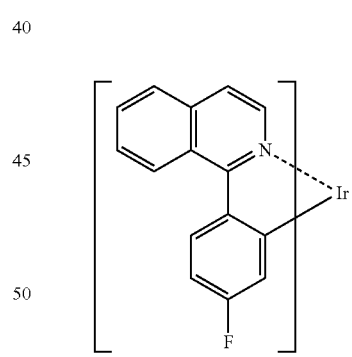
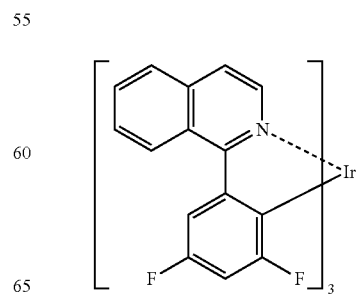

General Formula (E-6)

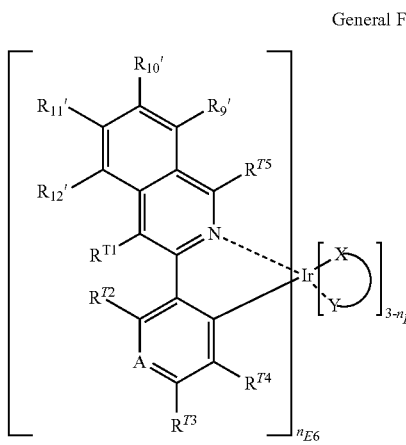

In the general formula (E-6), $R^{T1}$ to $R^{T5}$, A (CR'''' or a nitrogen atom), (X—Y), and $n_{E6}$ are synonymous with $R^{T1}$ to $R^{T5}$, A, (X—Y), and $n_{E3}$ in the general formula (E-3), respectively. $R_9{'}$ to $R_{12}{'}$ are synonymous with $R_1{'}$ to $R_4{'}$ in the general formula (E-4), respectively.

As for $R^{T1}$ to $R^{T5}$, $R_9{'}$ to $R_{12}{'}$, and R'''', arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A.

In the case where $n_{E6}$ is 2 or 3, two or three ligands containing $R^{T1}$ to $R^{T5}$, A, and $R_9{'}$ to $R_{12}{'}$ are present. In this respect, the ligands may be the same as or different from each other.

In addition, preferred ranges of $R_9{'}$ to $R_{12}{'}$ are the same as the preferred ranges of $R_1{'}$ to $R_4{'}$ in the general formula (E-4). In addition, the case where not only A represents CR'''', but from 0 to 3 of $R^{T1}$ to $R^{T5}$, R'''', and $R_9{'}$ to $R_{12}{'}$ are an alkyl group or a phenyl group, with all of the remainder being a hydrogen atom, is preferable.

Preferred specific examples of the compound represented by the general formula (E-6) are enumerated below, but it should not be construed that the present invention is limited thereto.

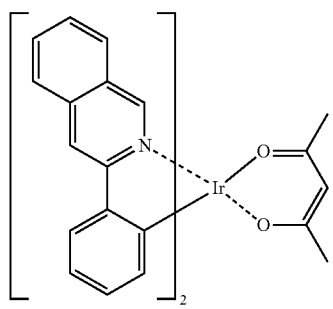

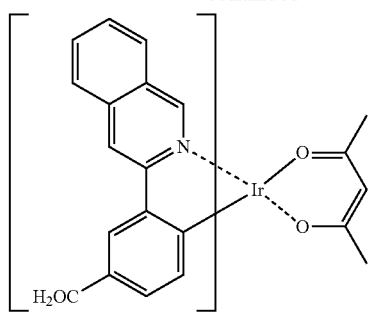

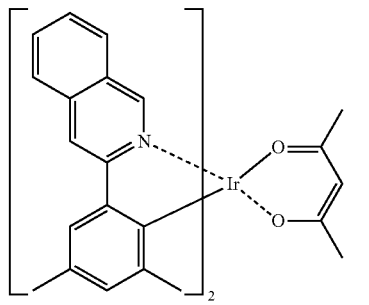

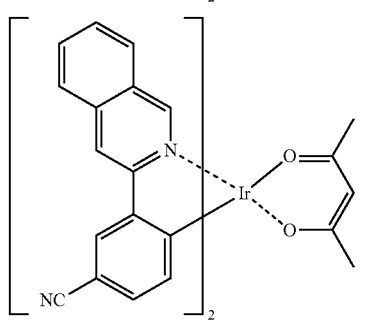

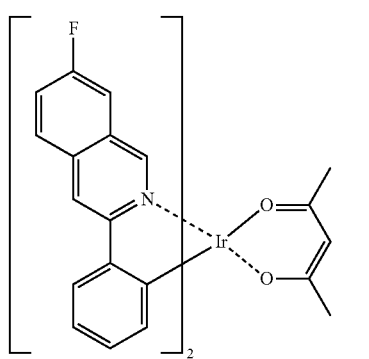

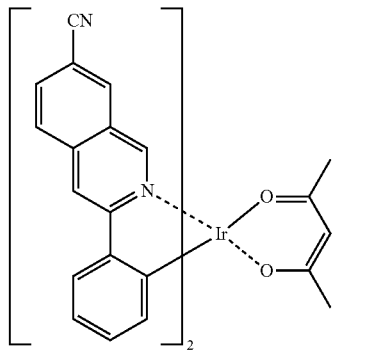

-continued
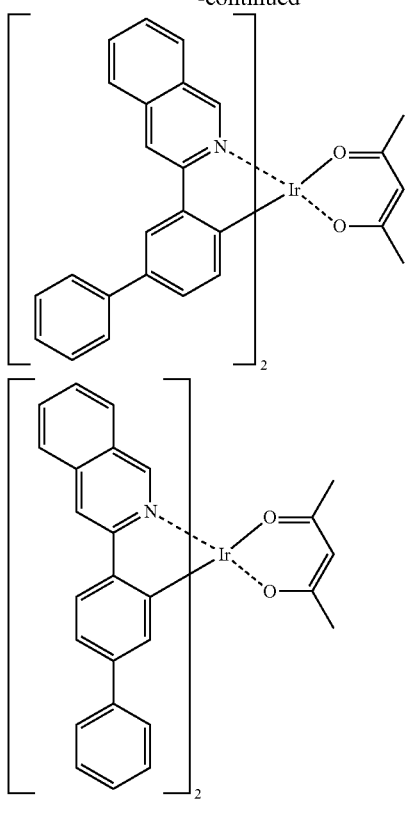
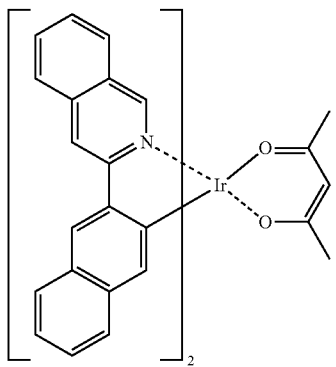
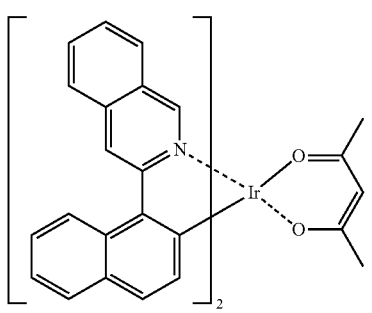
-continued
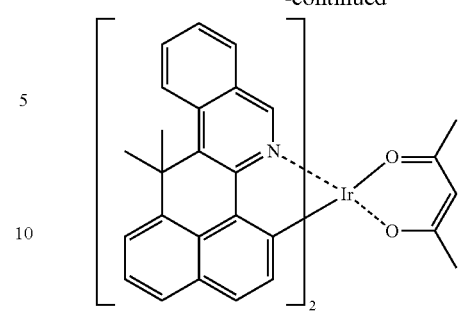
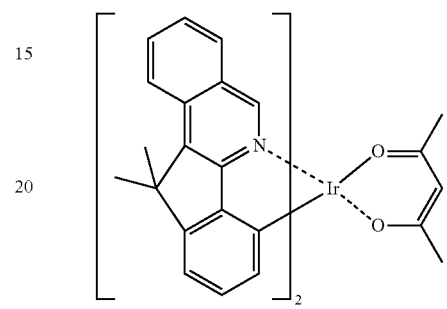
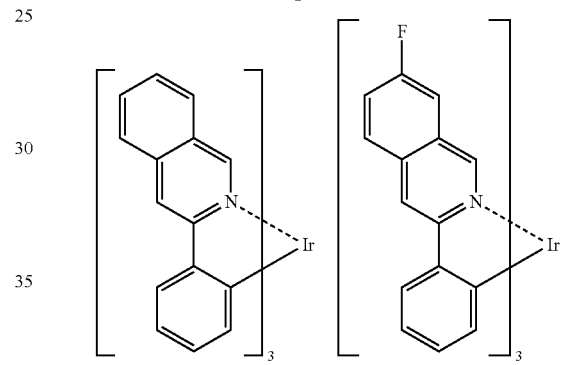
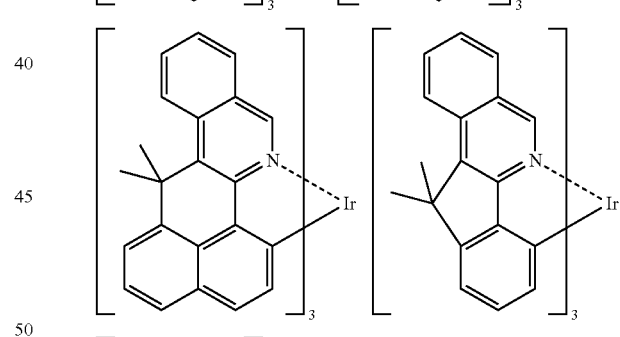
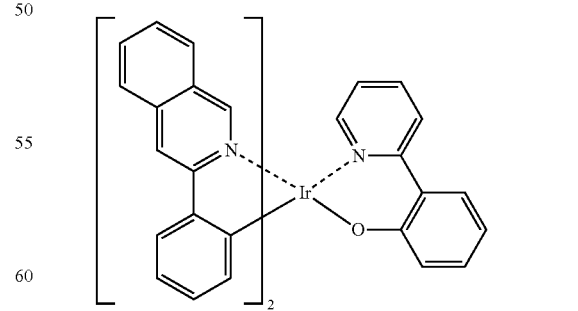
In order to obtain a luminous color of green to yellow color, the compound represented by the general formula (E-1) is preferably a compound represented by the following general formula (E-7).

General Formula (E-7)

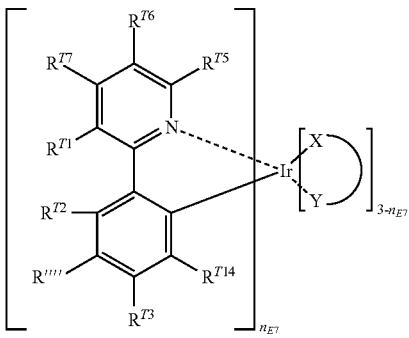

In the general formula (E-7), $R^{T1}$, $R^{T2}$, $R^{T3}$, $R^{T4}$, $R^{T5}$, $R^{T6}$, $R^{T7}$, R"", (X—Y), and $n_{E7}$ are synonymous with $R^{T1}$, $R^{T2}$, $R^{T3}$, $R^{T4}$, $R^{T5}$, $R^{T6}$, $R^{T7}$, R"", (X—Y), and $n_{E3}$ in the general formula (E-3), respectively. As for $R^{T1}$ to $R^{T7}$ and R"", arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A.

In the case where $n_{E7}$ is 2 or 3, two or three ligands containing $R^{T1}$, $R^{T2}$, $R^{T3}$, $R^{T4}$, $R^{T5}$, $R^{T6}$, $R^{T7}$, and R"" are present. In this respect, the ligands may be the same as or different from each other.

$R^{T1}$, $R^{T2}$, $R^{T3}$, $R^{T4}$, $R^{T5}$, $R^{T6}$, $R^{T7}$, and R"" are preferably a hydrogen atom, a fluorine atom, an alkyl group, an aryl group, a heteroaryl group, or a cyano group.

$n_{E7}$ is preferably 3. Furthermore, the compound represented by the general formula (E-7) is preferably a compound represented by the following general formula (E-7-1)

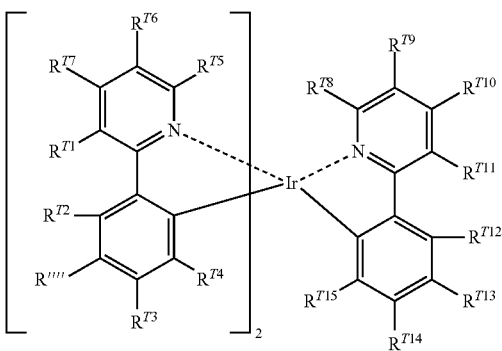

In the general formula (E-7-1), $R^{T1}$, $R^{T2}$, $R^{T3}$, $R^{T4}$, $R^{T5}$, $R^{T6}$, $R^{T7}$, and R"" are synonymous with $R^{T1}$, $R^{T2}$, $R^{T3}$, $R^{T4}$, $R^{T5}$, $R^{T6}$, $R^{T7}$, and R"" in the general formula (E-7), respectively, and preferred ranges thereof are also the same. $R^{T8}$ to $R^{T15}$ are synonymous with $R^{T1}$, $R^{T2}$, $R^{T3}$, $R^{T4}$, $R^{T5}$, $R^{T6}$, $R^{T7}$, and R"", respectively, and preferred ranges thereof are also the same. The phenylpyridine ligand containing $R^{T1}$, $R^{T2}$, $R^{T3}$, $R^{T4}$, $R^{T5}$, $R^{T6}$, $R^{T7}$, and R"" and the phenylpyridine ligand containing $R^{T8}$ to $R^{T15}$ are different from each other.

In the luminous color of green to yellow color, in order to obtain the luminous color close to a green color, $R^{T1}$, $R^{T2}$, $R^{T3}$, $R^{T4}$, $R^{T5}$, $R^{T6}$, $R^{T7}$, and R"" are more preferably a hydrogen atom, a fluorine atom, an alkyl group, or a cyano group, and from 1 to 3 of $R^{T1}$, $R^{T5}$, $R^{T4}$, and R"" are still more preferably an alkyl group. $R^{T8}$ to $R^{T11}$ are more preferably a hydrogen atom or an alkyl group. In addition, $R^{T12}$ to $R^{T15}$ are more preferably a hydrogen atom, an alkyl group, a cyano group, or an aryl group. The substitution position of the alkyl group, the cyano group, or the aryl group is preferably $R^{T13}$ or $R^{T14}$. The aryl group may further have a substituent and may form a fused ring via a substituent.

In the luminous color of green to yellow color, in order to obtain the luminous color close to a yellow color, $R^{T1}$, $R^{T2}$, $R^{T3}$, $R^{T4}$, $R^{T5}$, $R^{T6}$, $R^{T7}$, and R"" are more preferably a hydrogen atom or an alkyl group, and from 1 to 3 of $R^{T1}$, $R^{T5}$, $R^{T4}$, and R"" are still more preferably an alkyl group. At least one of $R^{T8}$ to $R^{T11}$ is more preferably an aryl group, and any one of $R^{T9}$ and $R^{T10}$ is still more preferably an aryl group, with the remainder being a hydrogen atom or an alkyl group. The aryl group may further have a substituent and may form a fused ring via a substituent.

In the general formula (E-7-1), it is also preferable that the general formula (E-7-1) includes a partial structure represented by the following general formula (E-7-2). When the partial structure represented by the following general formula (E-7-2) is included, there may be the case where the effects of low voltage and high durability are conspicuously revealed through a combination with the host material.

General Formula (E-7-2)

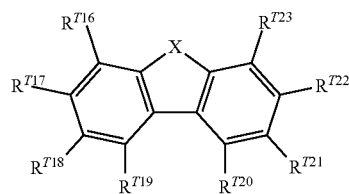

In the general formula (E-7-2), X is —O—, —S—, —$NR^{T24}$—, —$CR^{T25}R^{T26}$—, or —$SiR^{T27}R^{T28}$—; and any one of $R^{T16}$ to $R^{T28}$ is bound to a part of the general formula (E-7-1) via a single bond or a substituent.

In the general formula (E-7-2), any one of $R^{T6}$ to $R^{T28}$ is preferably bound to a part in the general formula (E-7-1) via a single bond or an aryl group. In the case where it is intended to obtain a luminous color close to a green color, any one of $R^{T16}$ to $R^{T28}$ is bound more preferably at $R^{T13}$ or $R^{T14}$, and still more preferably at $R^{T13}$. In the case where it is intended to obtain a luminous color close to a yellow color, any one of $R^{T16}$ to $R^{T28}$ is bound more preferably at $R^{T9}$ or $R^{T10}$.

X is preferably —O—, —S—, —$NR^{T24}$—, or —$CR^{T25}R^{T26}$—, and more preferably —O— or —S—.

When X is —O— or —S—, the partial structure represented by the general formula (E-7-2) is preferably bound to a part in the general formula (E-7-1) at the position of $R^{T16}$ via a single bond; when X is —$NR^{T24}$—, the partial structure represented by the general formula (E-7-2) is preferably bound to a part in the general formula (E-7-1) at the position of $R^{T18}$ or $R^{T24}$ via a single bond; and when X is —$CR^{T25}R^{T26}$—, the partial structure represented by the general formula (E-7-2) is preferably bound to a part in the general formula (E-7-1) at the position of $R^{T17}$ via a single bond.

Preferred specific examples of the compound represented by the general formula (E-7) are enumerated below, but it should not be construed that the present invention is limited thereto.

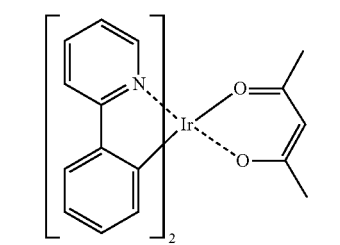
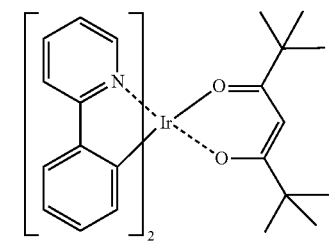
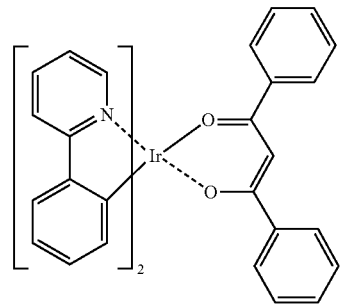
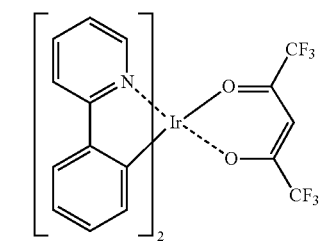
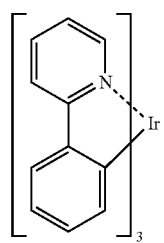
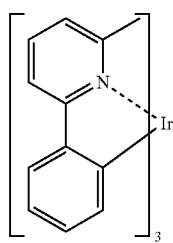
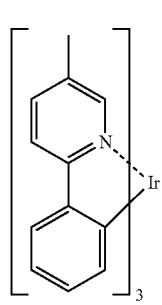
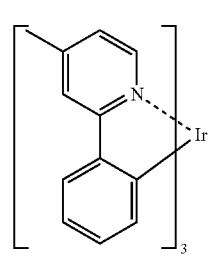
-continued
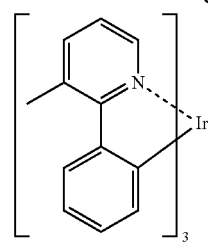
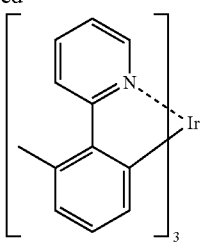
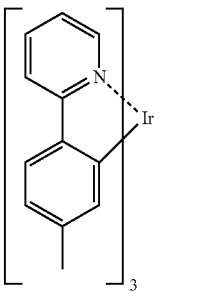
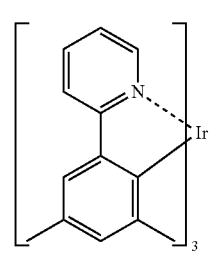
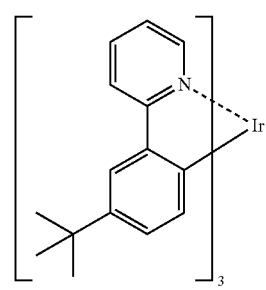
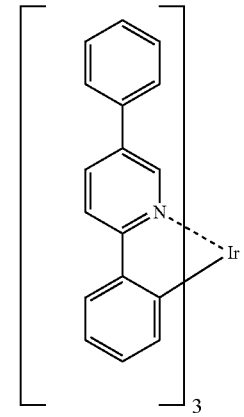
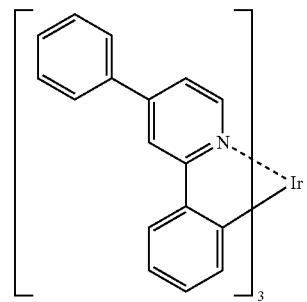
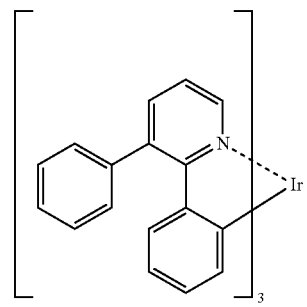

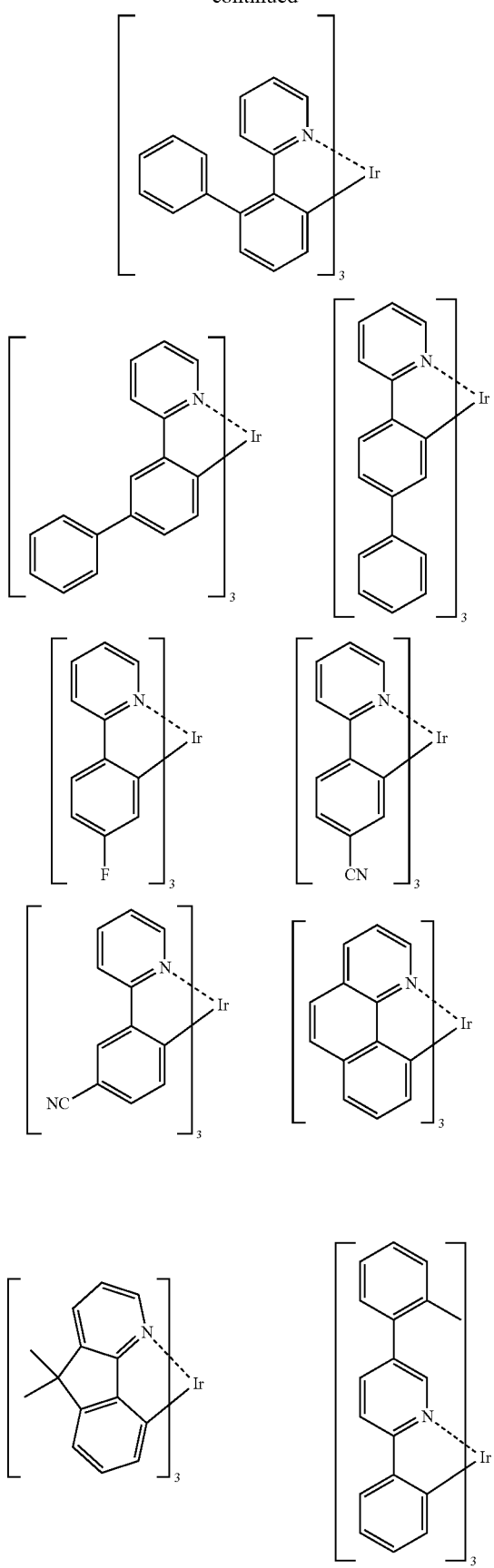
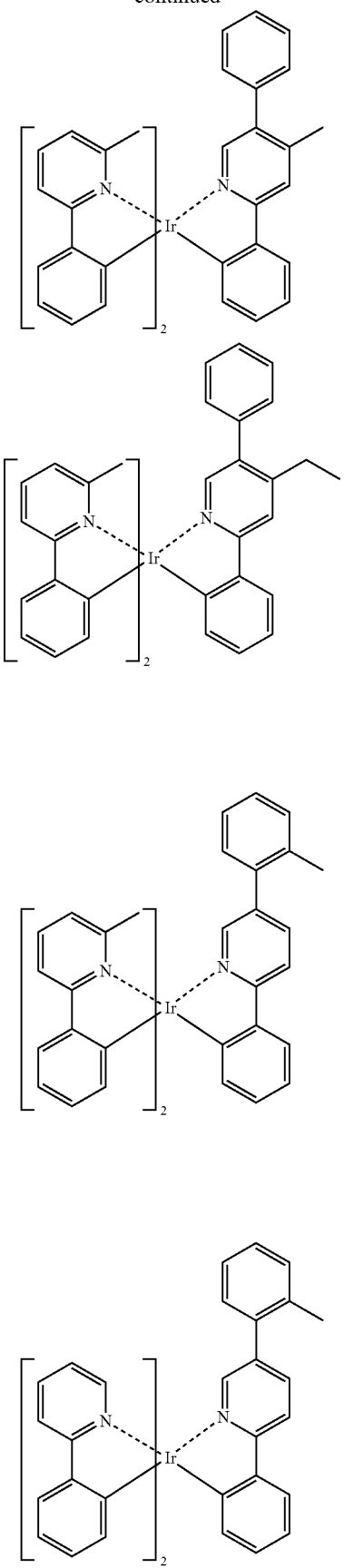

99
-continued
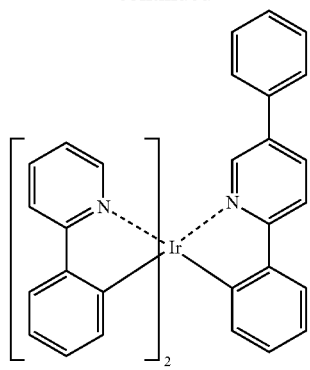
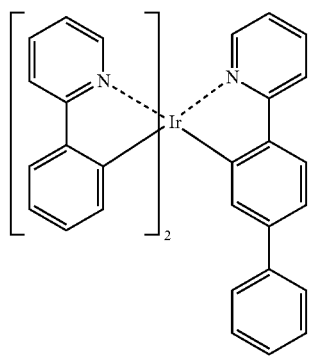
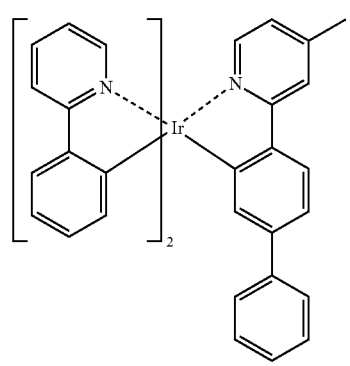
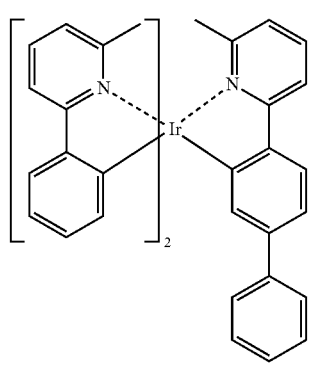
100
-continued
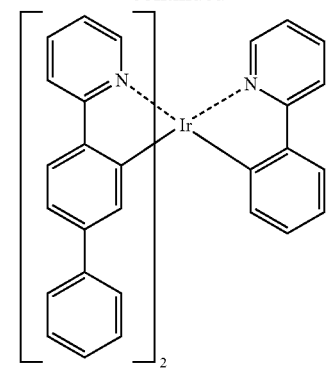
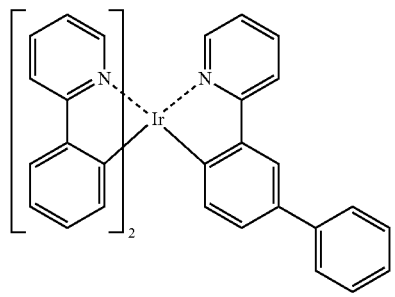
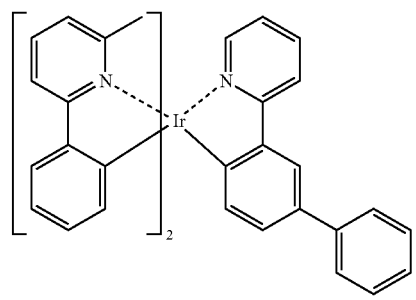
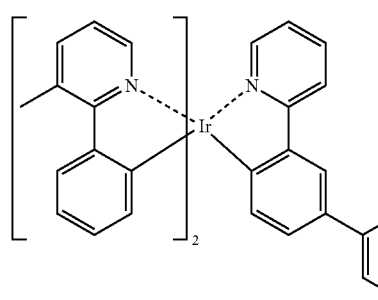
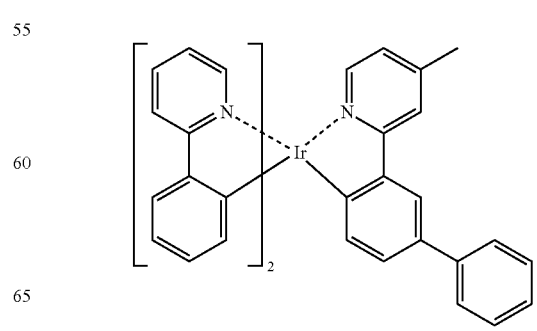

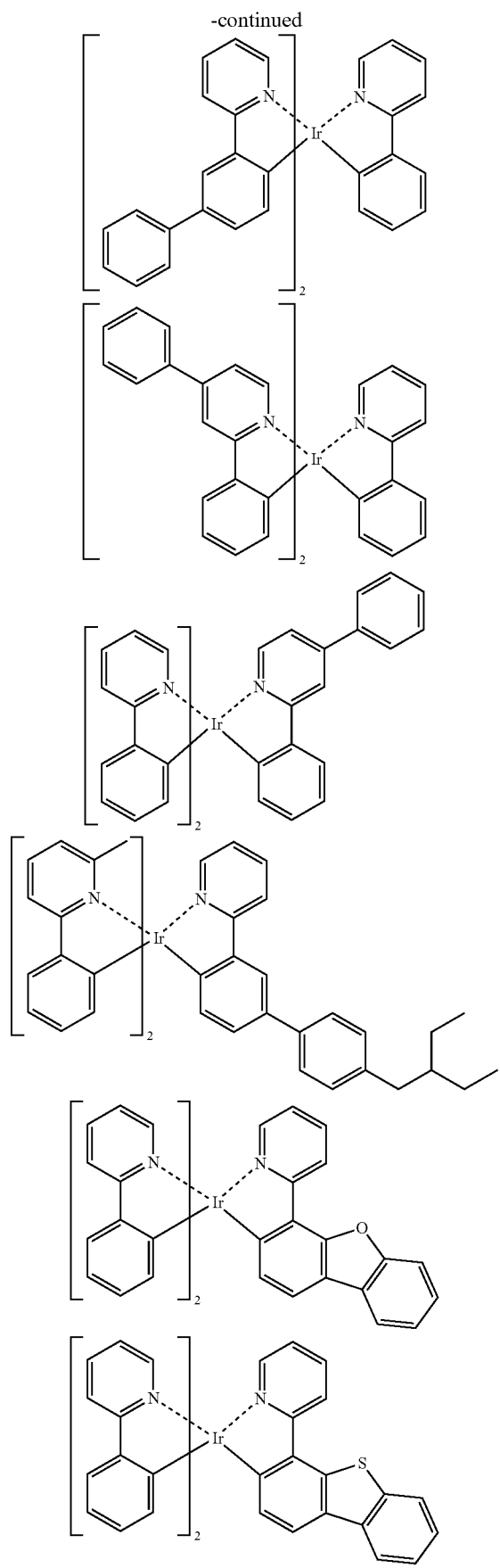

103
-continued
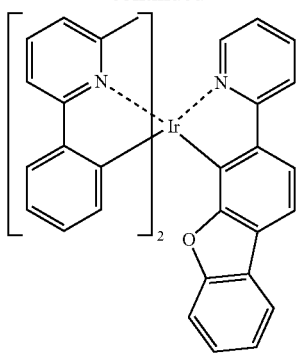
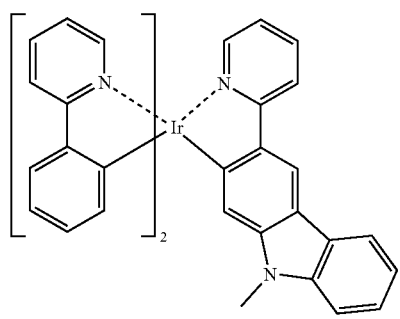
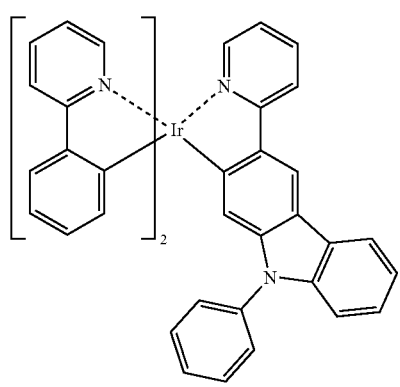
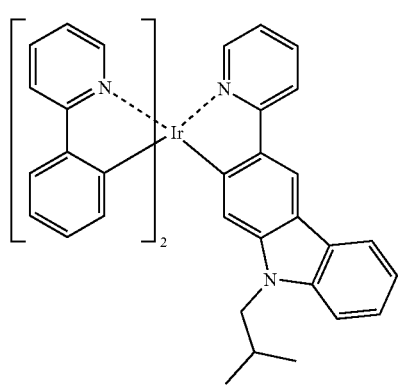
104
-continued
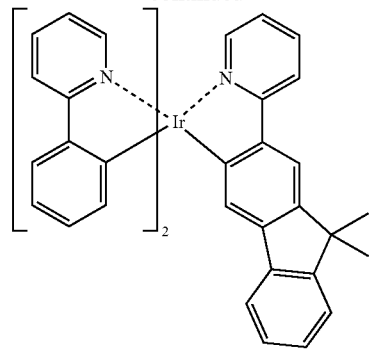
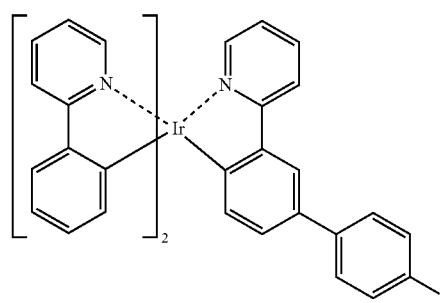
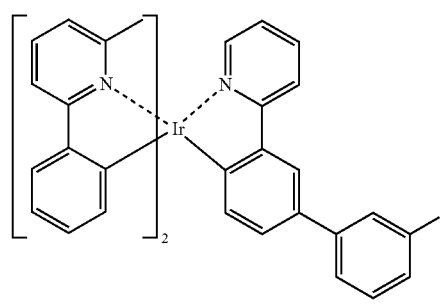
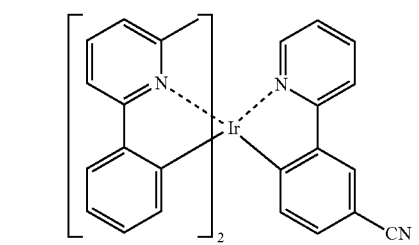

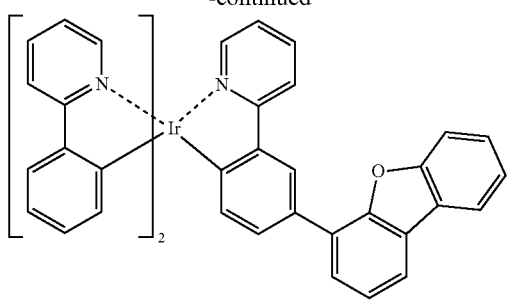
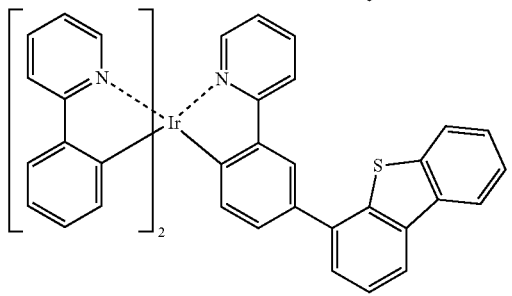
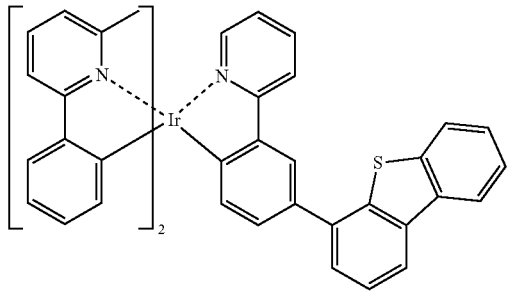
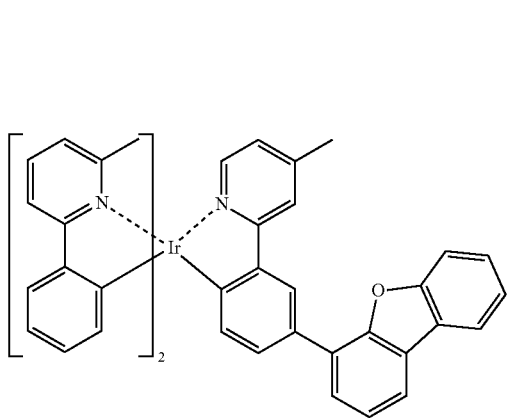
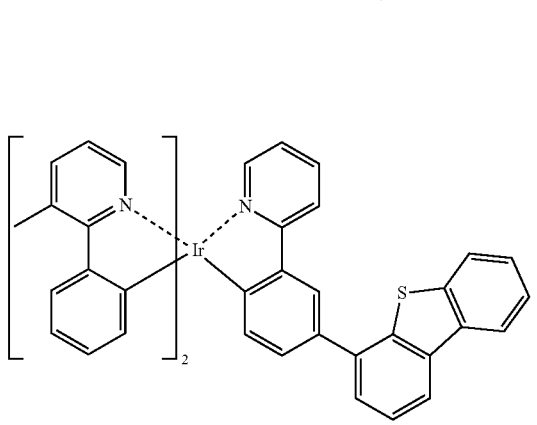
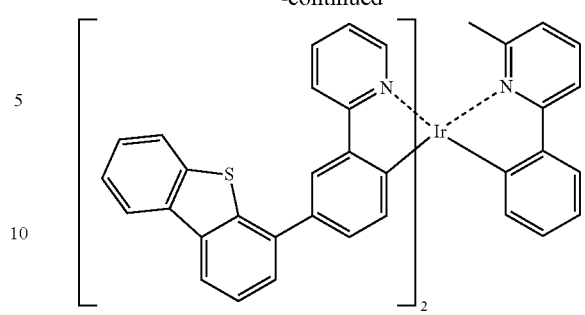
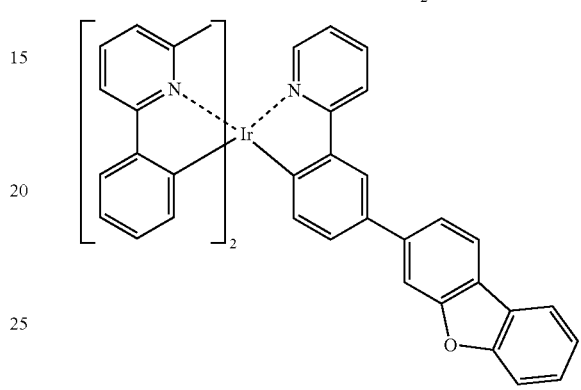
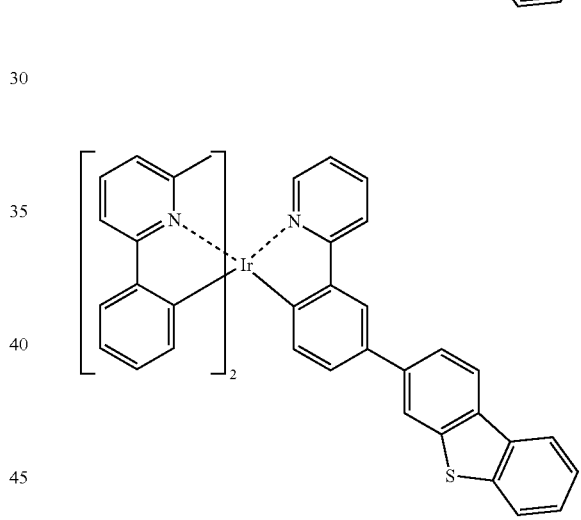
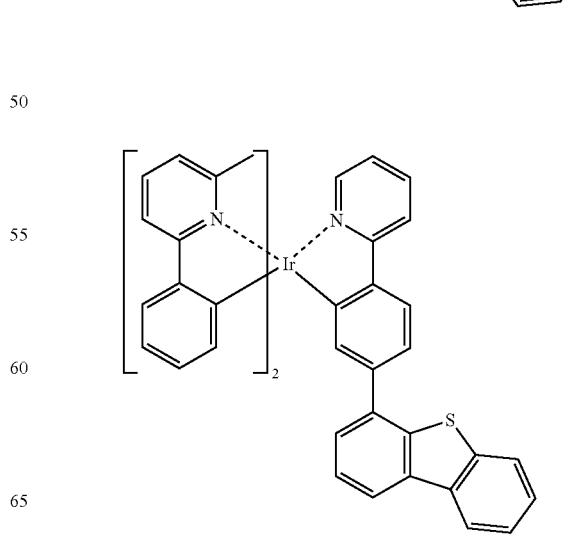

107
-continued
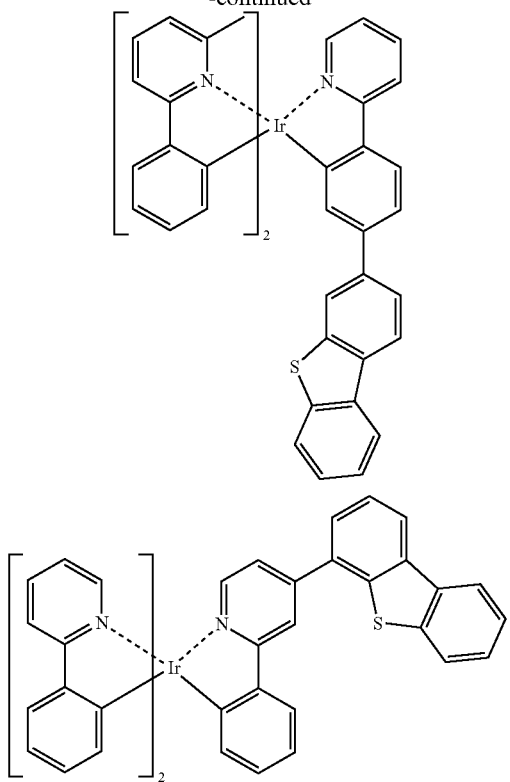
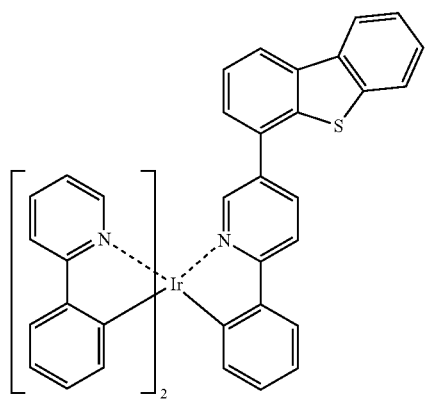
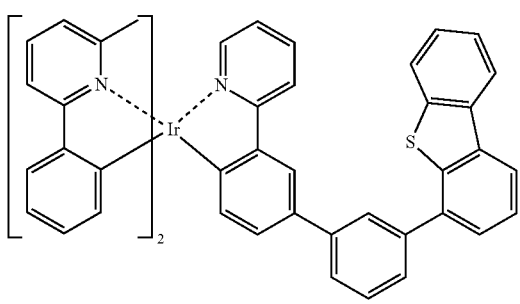
108
-continued
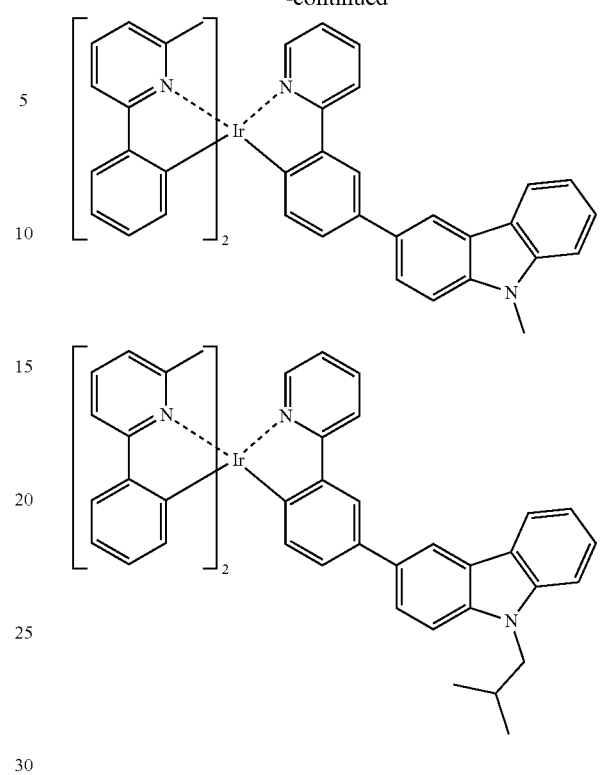
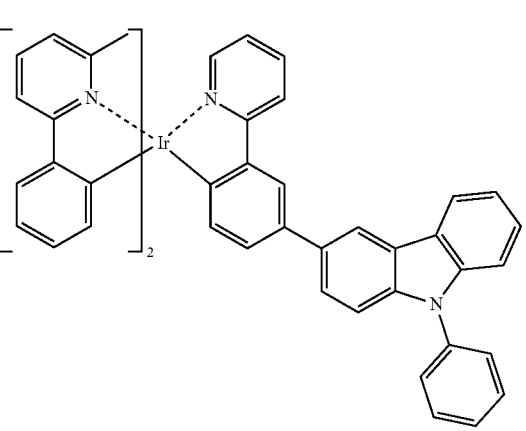

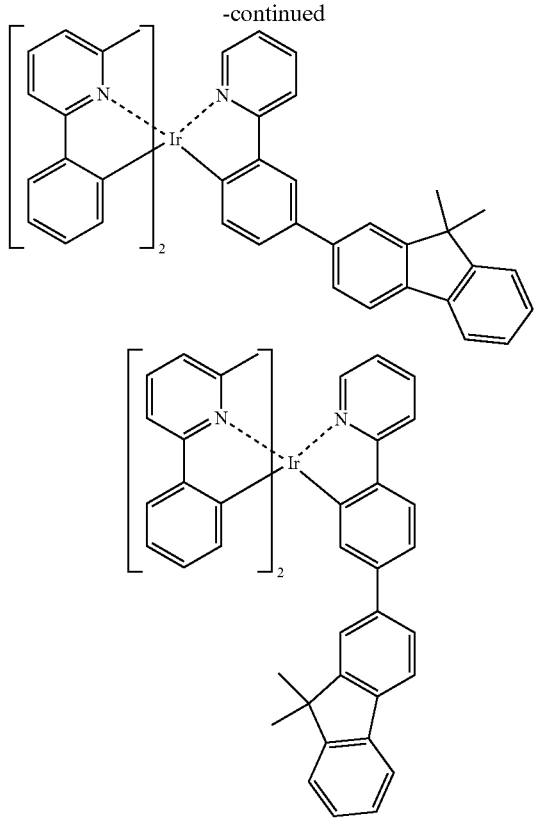

In order to obtain a luminous color of blue to sky blue color, the compound represented by the general formula (E-1) is preferably a compound represented by the following general formula (E-8) or general formula (E-9).

General Formula (E-8)

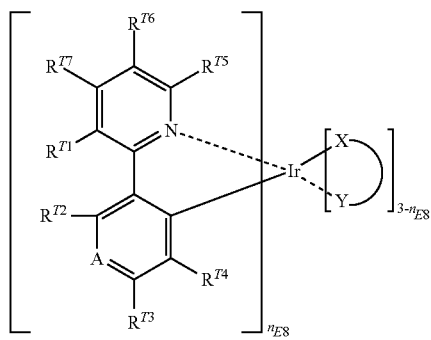

In the general formula (E-8), $R^{T1}$, $R^{T2}$, $R^{T3}$, $R^{T4}$, $R^{T5}$, $R^{T6}R^{T7}$, A (CR"" or a nitrogen atom), (X—Y), and $n_{E8}$ are synonymous with $R^{T1}$, $R^{T2}$, $R^{T3}$, $R^{T4}$, $R^{T5}$, $R^{T6}$, $R^{T7}$, A, (X—Y), and $n_{E3}$ in the general formula (E-3), respectively.

In the general formula (E-8), $R^{T1}$ and $R^{T5}$ to $R^{T7}$ are more preferably a hydrogen atom, an alkyl group, or an aryl group. $R^{T2}$ to $R^{T4}$ are preferably a hydrogen atom, a fluorine atom, or a cyano group. A is preferably any one of a fluorine atom or a cyano group in terms of R"" of CR"", and a nitrogen atom. $n_{E8}$ is preferably 2 or 3. (X—Y) is synonymous with (X—Y) in the general formula (E-1), and a preferred range thereof is also the same.

Preferred specific examples of the compound represented by the general formula (E-8) are enumerated below, but it should not be construed that the present invention is limited thereto.

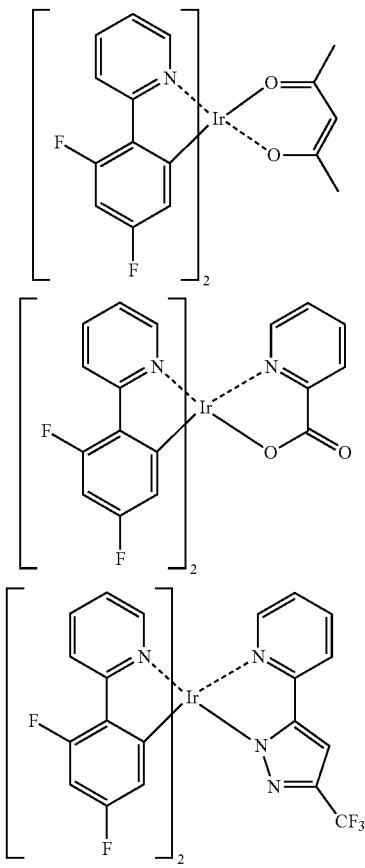

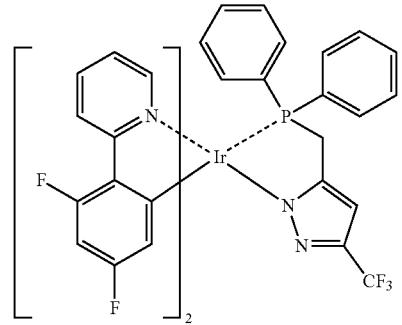

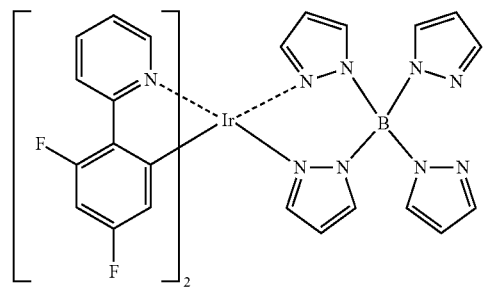

111
-continued
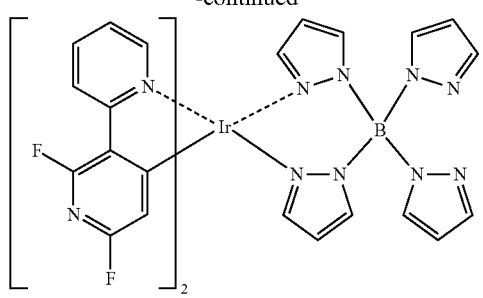
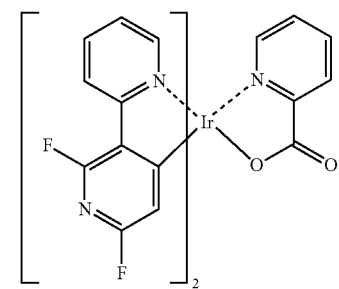
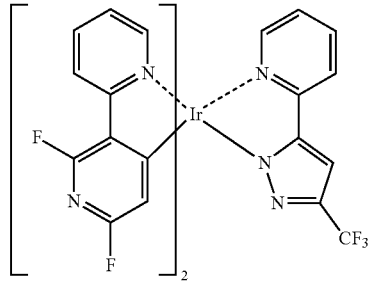
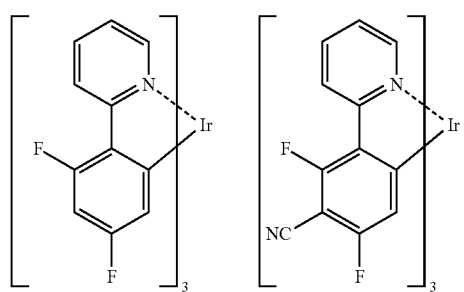
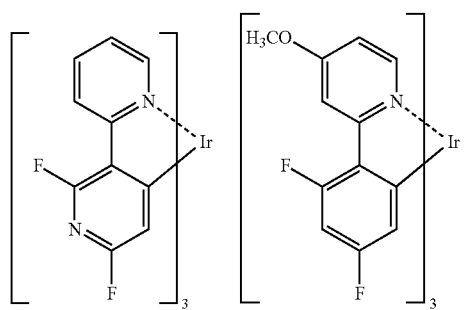
112
-continued
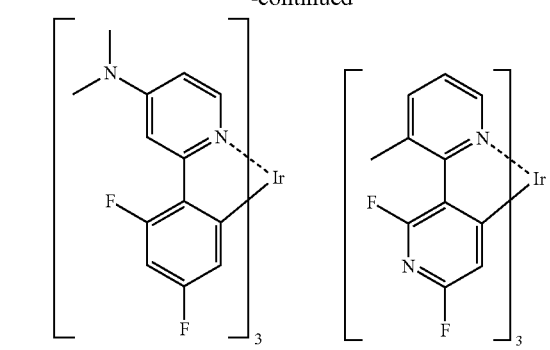
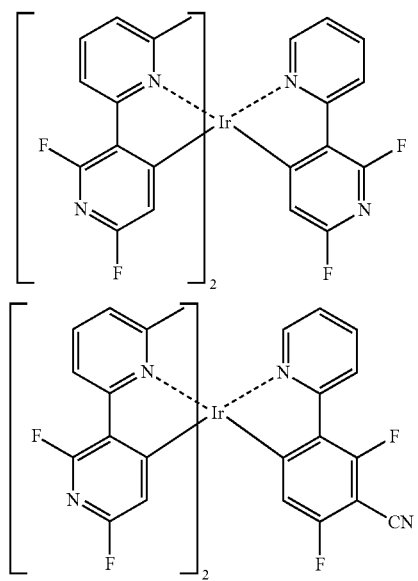
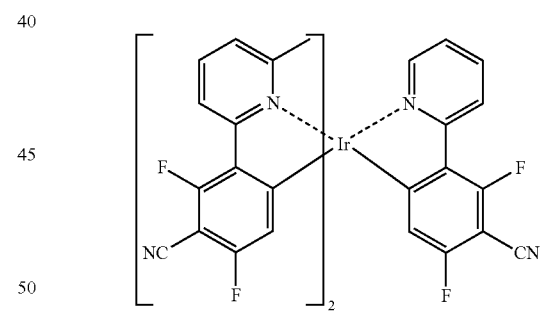
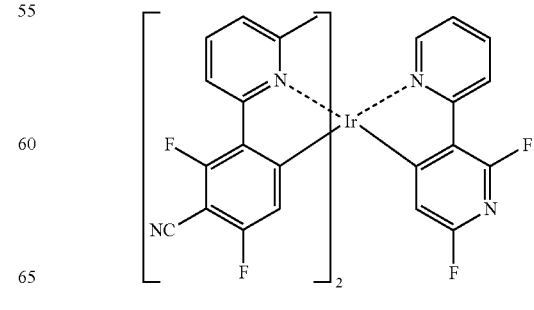

General Formula (E-9)

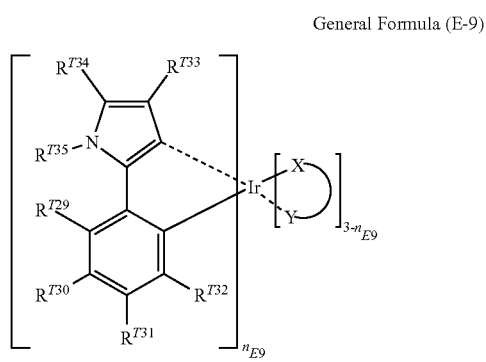

In the general formula (E-9), $R^{T29}$ to $R^{T34}$, (X—Y), and $n_{E9}$ are synonymous with $R^{T1}$ to $R^{T6}$, (X—Y), and $n_{E3}$ in the general formula (E-3), respectively. $R^{T35}$ represents a substituent, and examples of the substituent include those of the Substituent Group A as described above. As for $R^{T29}$ to $R^{T35}$, arbitrary two adjacent groups may be bound to each other to form a fused 4- to 7-membered ring; the fused 4- to 7-membered ring is a cycloalkene, a cycloalkadiene, an aryl, or an heteroaryl; and the fused 4- to 7-membered ring may further have the substituent represented by the Substituent Group A.

In the case where $n_{E9}$ is 2 or 3, two or three ligands containing $R^{T1}$, $R^{T2}$, $R^{T3}$, $R^{T4}$, $R^{T5}$, $R^{T6}$, $R^{T7}$, and R"" are present. In this respect, the ligands may be the same as or different from each other.

$R^{T29}$ to $R^{T34}$ are preferably a hydrogen atom, an alkyl group, an aryl group, or a cyano group. $R^{35}$ is preferably an alkyl group or an aryl group. $R^{T35}$ is preferably connected to $R^{T29}$ to form a ring. It is more preferable that $R^{T35}$ and $R^{T29}$ are bound to each other via an aryl group, resulting in forming a nitrogen-containing 6-membered ring. As for $R^{T35}$, the aryl group resulting from the connection to $R^{T29}$ may further have a substituent, and from the viewpoint of durability, it is still more preferable that the aryl group is substituted with an alkyl group.

Preferred specific examples of the compound represented by the general formula (E-9) are enumerated below, but it should not be construed that the present invention is limited thereto.

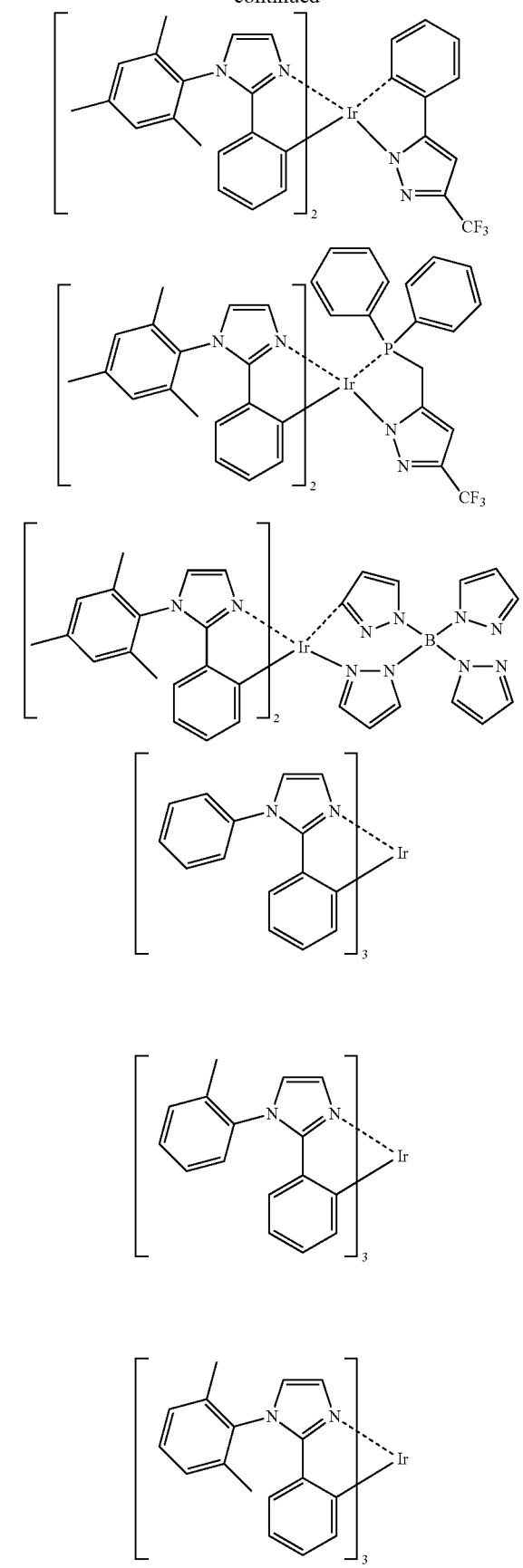

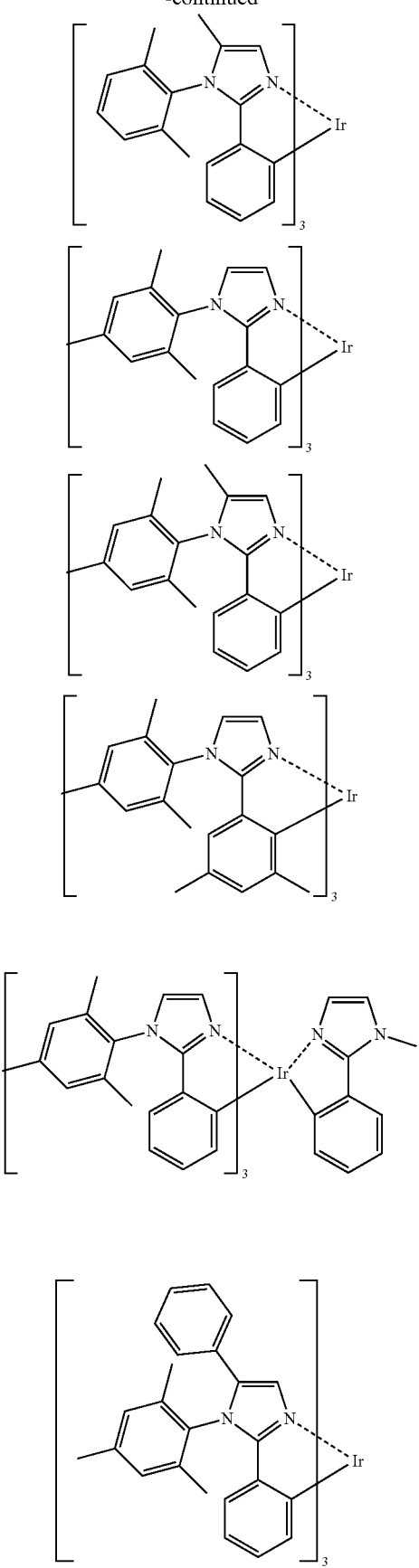
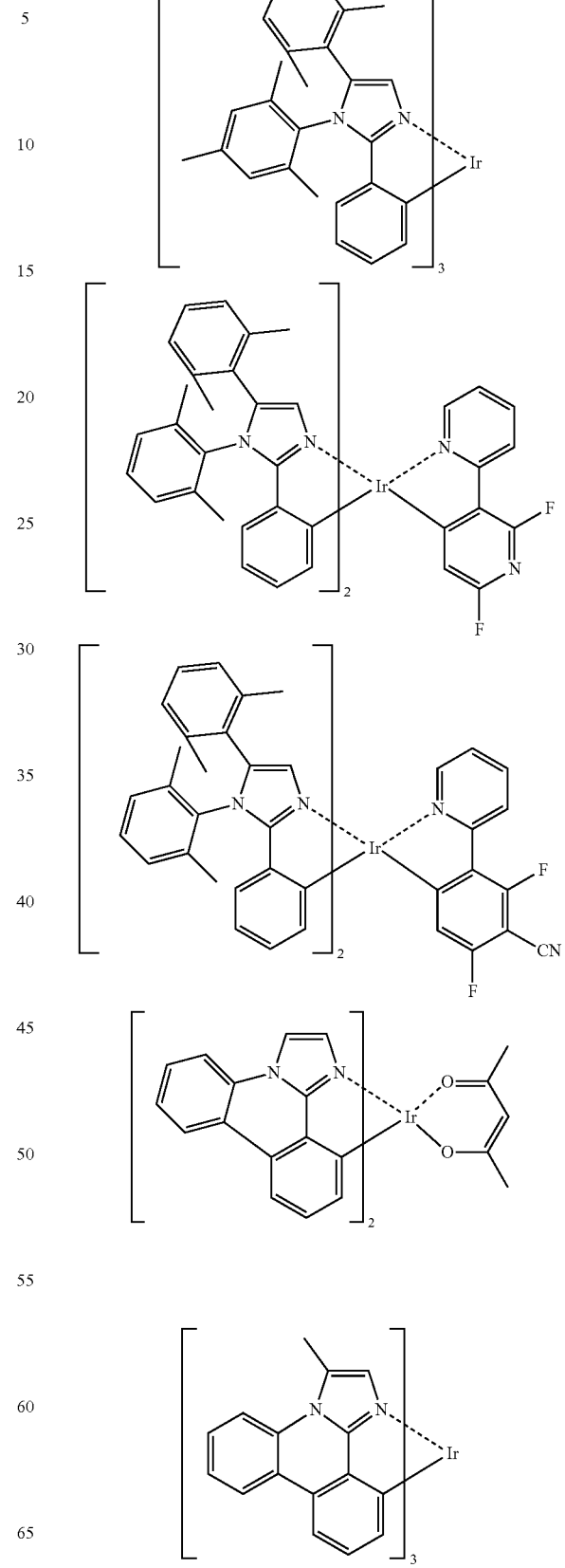

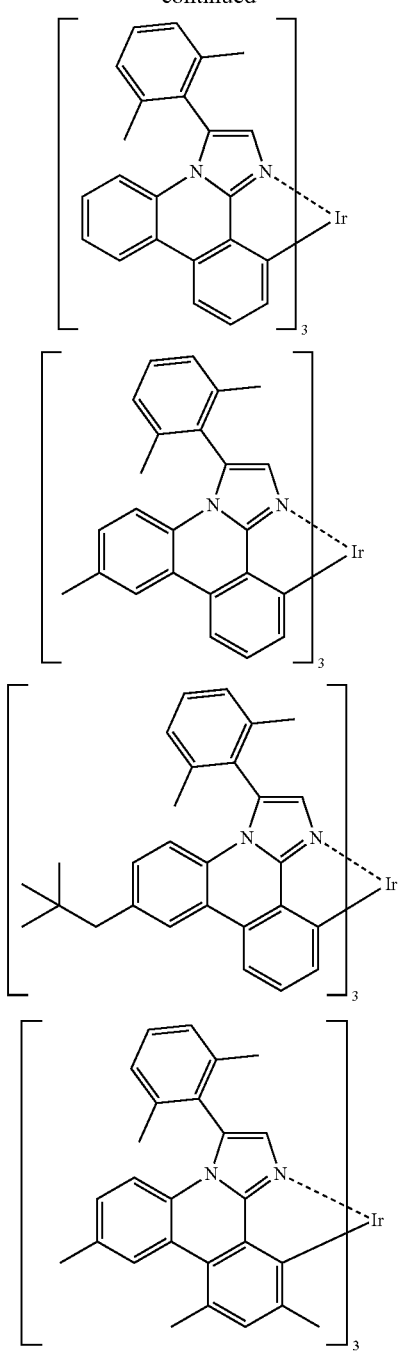
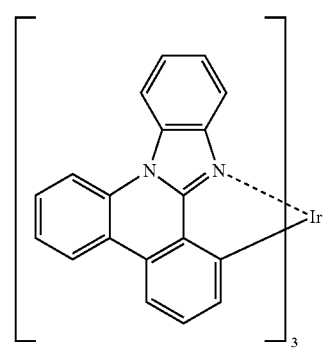
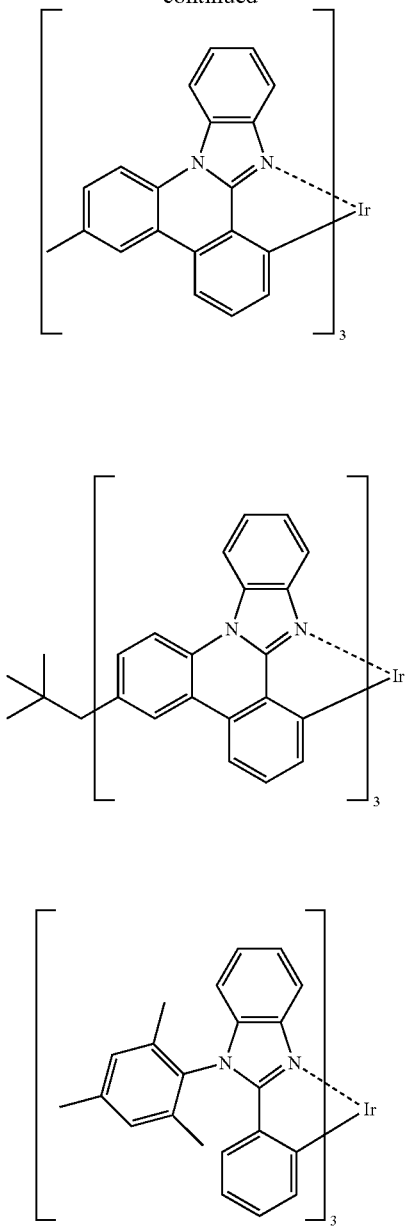
Preferred specific examples of the compound represented by the general formula (E-1) other than those described above are enumerated below, but it should not be construed that the present invention is limited thereof.
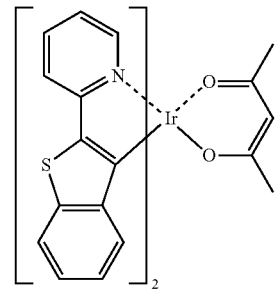

119
-continued
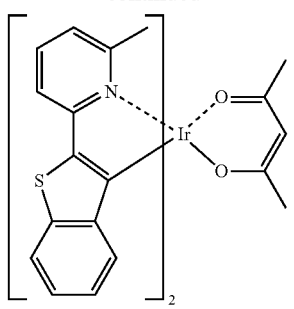
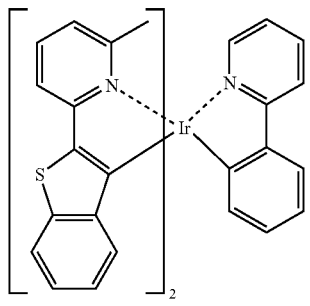
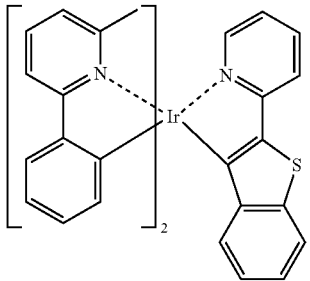
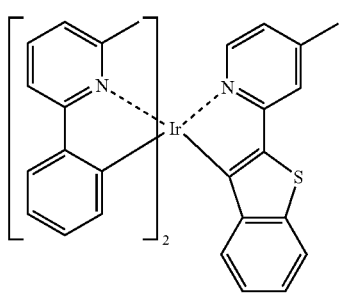
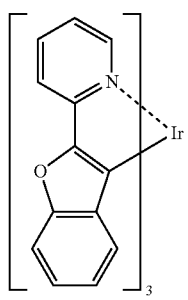
120
-continued
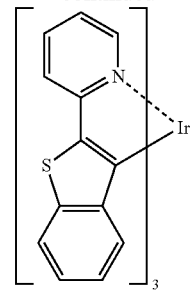
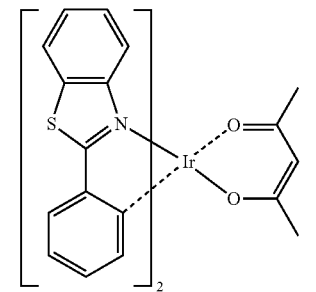
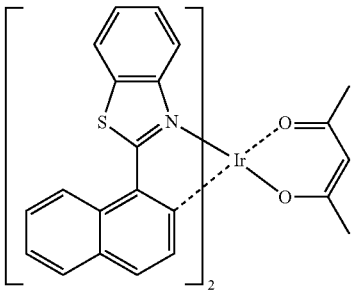
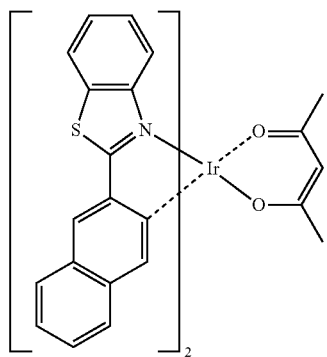
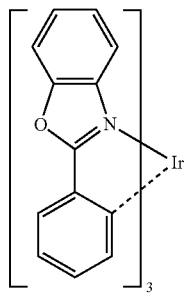

-continued

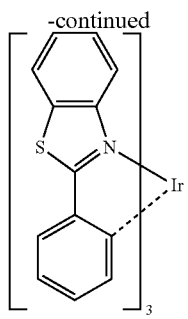

The compounds exemplified as the compound represented by the general formula (E-1) can be synthesized by a method described in JP-A-2009-99783 or various methods described in, for example, U.S. Pat. No. 7,278,232. It is preferable that after the synthesis, the product is purified by means of column chromatography, recrystallization, or the like and then purified by means of sublimation purification. By the sublimation purification, not only organic impurities can be separated, but inorganic salts, a residual solvent, and the like can be effectively removed.

The compound represented by the general formula (E-1) is preferably contained in the light emitting layer. However, its application is not limited, and the compound represented by the general formula (E-1) may be further contained in any one layer in the organic layers.

The compound represented by the general formula (E-1) in the light emitting layer is generally contained in an amount of from 0.1% by mass to 50% by mass relative to the total mass of the compounds forming the light emitting layer. From the viewpoints of durability and external quantum efficiency, the compound represented by the general formula (E-1) is preferably contained in an amount of from 0.2% by mass to 50% by mass, more preferably contained in an amount of from 0.3% by mass to 40% by mass, still more preferably contained in an amount of from 0.4% by mass to 30% by mass, and especially preferably contained in an amount of from 0.5% by mass to 20% by mass.

In the present invention, it is especially preferable to use the compound represented by the general formula (1) in combination of the compound represented by any one of the general formulae (E-1) to (E-9) in the light emitting layer.

The platinum complex which can be used as the phosphorescent material is preferably a platinum complex represented by the following general formula (C-1).

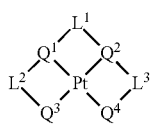

(C-1)

In the general formula (C-1), Q1, $Q^2$, $Q^3$, and $Q^4$ each independently represent a ligand which is coordinated on Pt; and $L^1$, $L^2$, and $L^3$ each independently represent a single bond or a divalent connecting group.

The genera formula (C-1) is described. $Q^1$, $Q^2$, $Q^3$, and $Q^4$ each independently represent a ligand which is coordinated on Pt. At that time, the bond of each of $Q^1$, $Q^2$, $Q^3$, and $Q^4$ to Pt may be any of a covalent bond, an ionic bond, or a coordination bond. As an atom bonding to Pt in each of $Q^1$, $Q^2$, $Q^3$, and $Q^4$, a carbon atom, a nitrogen atom, an oxygen atom, a sulfur atom, and a phosphorus atom are preferable. Among the atoms bonding to Pt in $Q^1$, $Q^2$, $Q^3$, and $Q^4$, it is preferable that at least one of them is a carbon atom; it is more preferable that two of them are a carbon atom; and it is especially preferable that two of them are a carbon atom, with other two being a nitrogen atom.

As $Q^1$, $Q^2$, $Q^3$, and $Q^4$ bonding to Pt with a carbon atom, any of an anionic ligand or a neutral ligand is useful. Examples of the anionic ligand include a vinyl ligand, an aromatic hydrocarbon ring ligand (for example, a benzene ligand, a naphthalene ligand, an anthracene ligand, a phenanthrene ligand, etc.) and a heterocyclic ring ligand (for example, a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand and condensed ring materials including the same (for example, a quinoline ligand, a benzothiazole ligand, etc.), etc.). Examples of the neutral ligand include a carbene ligand.

The group represented by each of $Q^1$, $Q^2$, $Q^3$, and $Q^4$ may have a substituent. As the substituent, those exemplified as the Substituent Group A as described above can be properly applied. In addition, the substituents may be connected to each other (in the case where $Q^3$ and $Q^4$ are connected to each other, a Pt complex of a cyclic tetradentate ligand is formed).

The group represented by $Q^1$, $Q^2$, $Q^3$, and $Q^4$ is preferably an aromatic hydrocarbon ring ligand bonding to Pt with a carbon atom, an aromatic heterocyclic ring ligand bonding to Pt with a carbon atom, a nitrogen-containing aromatic heterocyclic ring ligand bonding to Pt with a nitrogen atom, an acyloxy ligand, an alkyloxy ligand, an aryloxy ligand, a heteroaryloxy ligand, or a silyloxy ligand; more preferably an aromatic hydrocarbon ring ligand bonding to Pt with a carbon atom, an aromatic heterocyclic ring ligand bonding to Pt with a carbon atom, a nitrogen-containing aromatic heterocyclic ring ligand bonding to Pt with a nitrogen atom, an acyloxy ligand, or an aryloxy ligand; and still more preferably an aromatic hydrocarbon ring ligand bonding to Pt with a carbon atom, an aromatic heterocyclic ring ligand bonding to Pt with a carbon atom, a nitrogen-containing aromatic heterocyclic ring ligand bonding to Pt with a nitrogen atom, or an acyloxy ligand.

$L^1$, $L^2$, and $L^3$ each represent a single bond or a divalent connecting group. Examples of the divalent connecting group represented by $L^1$, $L^2$, and $L^3$ include an alkylene group (for example, methylene, ethylene, propylene, etc.), an arylene group (for example, phenylene, naphthalenediyl, etc.), a heteroarylene group (for example, pyridinediyl, thiophenediyl, etc.), an imino group (—NR—) (for example, a phenylimino group, etc.), an oxy group (—O—), a thio group (—S—), a phosphinidene group (—PR—) (for example, a phenylphosphinidene group, etc.), a silylene group (—SiRR'—) (for example, a dimethylsilylene group, a diphenylsilylene group, etc.), and a combination thereof. Here, examples of R and R' independently include an alkyl group and an aryl group. These connecting groups may further have a substituent.

From the viewpoints of stability and light emission quantum yield of the complex, $L^1$, $L^2$, and $L^3$ are preferably a single bond, an alkylene group, an arylene group, a heteroarylene group, an imino group, an oxy group, a thio group, or a silylene group; more preferably a single bond, an alkylene group, an arylene group, or an imino group; still more preferably a single bond, an alkylene group, or an arylene group; yet still more preferably a single bond, a methylene group, or a phenylene group; even yet still more preferably a single bond or a di-substituted methylene group; even yet still more further preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group.

$L^1$ is especially preferably a dimethylmethylene group, a diphenylmethylene group, or a cyclohexanediyl group, and most preferably a dimethylmethylene group.

$L^2$ and $L^3$ are most preferably a single bond.

The platinum complex represented by the general formula (C-1) is more preferably a platinum complex represented by the following general formula (C-2).

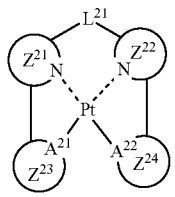

General Formula (C-2)

In the general formula (C-2), $L^{21}$ represents a single bond or a divalent connecting group; $A^{21}$ and $A^{22}$ each independently represent a carbon atom or a nitrogen atom; $Z^{21}$ and $Z^{22}$ each independently represent a nitrogen-containing aromatic heterocyclic ring; and $Z^{23}$ and $Z^{24}$ each independently represent a benzene ring or an aromatic heterocyclic ring.

The general formula (C-2) is described. $L^{21}$ is synonymous with L in the general formula (C-1), and a preferred range thereof is also the same.

$A^{21}$ and $A^{22}$ each independently represent a carbon atom or a nitrogen atom. It is preferable that at least one of $A^{21}$ and $A^{22}$ is a carbon atom. From the viewpoint of stability of the complex and the viewpoint of light emission quantum yield of the complex, it is preferable that both $A^{21}$ and $A^{22}$ are a carbon atom.

$Z^{21}$ and $Z^{22}$ each independently represent a nitrogen-containing aromatic heterocyclic ring. Examples of the nitrogen-containing aromatic heterocyclic ring represented by $Z^{21}$ and $Z^{22}$ include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. From the viewpoints of stability, control of light emitting wavelength, and light emission quantum yield of the complex, the ring represented by $Z^{21}$ and $Z^{22}$ is preferably a pyridine ring, a pyrazine ring, an imidazole ring, or a pyrazole ring, more preferably a pyridine ring, an imidazole ring, or a pyrazole ring, still more preferably a pyridine ring or a pyrazole ring, and especially preferably a pyridine ring.

$Z^{23}$ and $Z^{24}$ each independently represent a benzene ring or an aromatic heterocyclic ring. Examples of the nitrogen-containing aromatic heterocyclic ring represented by $Z^{23}$ and $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring. From the viewpoints of stability, control of light emitting wavelength, and light emission quantum yield of the complex, the ring represented by $Z^{23}$ and $Z^{24}$ is preferably a benzene ring, a pyridine ring, a pyrazine ring, an imidazole ring, a pyrazole ring, or a thiophene ring, more preferably a benzene ring, a pyridine ring, or a pyrazole ring, and still more preferably a benzene ring or a pyridine ring.

Of the platinum complexes represented by the general formula (C-2), one of more preferred embodiments is a platinum complex represented by the following general formula (C-4).

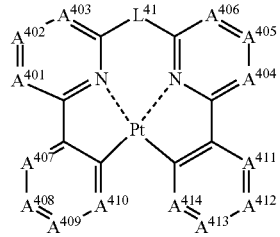

General Formula (C-4)

In the general formula (C-4), $A^{401}$ to $A^{414}$ each independently represent C—R or a nitrogen atom; R represents a hydrogen atom or a substituent; and $L^{41}$ represents a single bond or a divalent connecting group.

The general formula (C-4) is described.

$A^{401}$ to $A^{414}$ each independently represent C—R or a nitrogen atom; and R represents a hydrogen atom or a substituent.

As the substituent represented by R, those exemplified as the Substituent Group A as described above can be applied.

$A^{401}$ to $A^{406}$ are preferably C—R, and Rs may be connected to each other to form a ring. In the case where $A^{401}$ to $A^{406}$ are C—R, R in $A^{402}$ and $A^{405}$ are preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, and especially preferably a hydrogen atom or a fluorine atom. R in $A^{401}$, $A^{403}$, $A^{404}$, and $A^{406}$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, and especially preferably a hydrogen atom.

$L^{41}$ is synonymous with $L^1$ in the general formula (C-1), and a preferred range thereof is also the same.

As $A^{407}$ to $A^{414}$, in each of $A^{407}$ to $A^{410}$ and $A^{411}$ to $A^{414}$, the number of N (nitrogen atom) is preferably from 0 to 2, and more preferably from 0 to 1. In the case of shifting the light emitting wavelength to the short wavelength side, it is preferable that any one of $A^{408}$ and $A^{412}$ is a nitrogen atom; and it is more preferable that both $A^{408}$ and $A^{412}$ are a nitrogen atom.

Of the platinum complexes represented by the general formula (C-2), one of more preferred embodiments is a platinum complex represented by the following general formula (C-5).

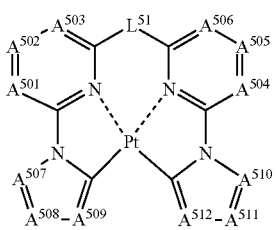

General Formula (C-5)

In the general formula (C-5), $A^{501}$ to $A^{512}$ each independently represent C—R or a nitrogen atom; R represents a hydrogen atom or a substituent; and $L^{51}$ represents a single bond or a divalent connecting group.

The general formula (C-5) is described. $A^{501}$ to $A^{506}$ and $L^{51}$ are synonymous with $A^{401}$ to $A^{406}$ and $L^{41}$ in the general formula (C-4), respectively, and preferred ranges thereof are also the same.

$A^{507}$, $A^{508}$ and $A^{509}$, and $A^{510}$, $A^{511}$ and $A^{512}$ each independently represent C—R or a nitrogen atom; and R represents a hydrogen atom or a substituent. As the substituent represented by R, those exemplified as the Substituent Group A as described above can be applied.

Of the platinum complexes represented by the general formula (C-1), another more preferred embodiment is a platinum complex represented by the following general formula (C-6).

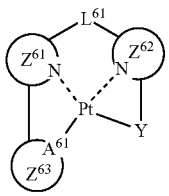

General Formula (C-6)

In the general formula (C-6), $L^{61}$ represents a single bond or a divalent connecting group; $A^{61}$ represents a carbon atom or a nitrogen atom; $Z^{61}$ and $Z^{62}$ each independently represent a nitrogen-containing aromatic heterocyclic ring; $Z^{63}$ represents a benzene ring or an aromatic heterocyclic ring; and Y represents an anionic non-cyclic ligand bonding to Pt.

The general formula (C-6) is described. $L^{61}$ is synonymous with L in the general formula (C-1), and a preferred range thereof is also the same.

$A^{61}$ represents a carbon atom or a nitrogen atom. From the viewpoint of stability of the complex and the viewpoint of light emission quantum yield of the complex, $A^{61}$ is preferably a carbon atom.

$Z^{61}$ and $Z^{62}$ are synonymous with $Z^{21}$ and $Z^{22}$ in the general formula (C-2), respectively, and preferred ranges thereof are also the same. $Z^{63}$ is synonymous with $Z^{23}$ in the general formula (C-2), and a preferred range thereof is also the same.

Y is an anionic non-cyclic ligand bonding to Pt. The non-cyclic ligand as referred to herein is one in which an atom bonding to Pt does not form a ring in a ligand state. The atom bonding to Pt in Y is preferably a carbon atom, a nitrogen atom, an oxygen atom, or a sulfur atom, more preferably a nitrogen atom or an oxygen atom, and most preferably an oxygen atom.

Examples of Y bonding to Pt with a carbon atom include a vinyl ligand. Examples of Y bonding to Pt with a nitrogen atom include an amino ligand and an imino ligand. Examples of Y bonding to Pt with an oxygen atom include an alkoxy ligand, an aryloxy ligand, a heteroaryloxy ligand, an acyloxy ligand, a silyloxy ligand, a carboxyl ligand, a phosphate ligand, or a sulfonate ligand. Examples of Y bonding to Pt with a sulfur atom include an alkyl mercapto ligand, an aryl mercapto ligand, a heteroaryl mercapto ligand, and a thiocarboxylate ligand.

The ligand represented by Y may have a substituent. As the substituent, those exemplified as the Substituent Group A as described above can be properly applied. In addition, the substituents may be connected to each other.

The ligand represented by Y is preferably a ligand bonding to Pt with an oxygen atom, more preferably an acyloxy ligand, an alkyloxy ligand, an aryloxy ligand, a heteroaryloxy ligand, or a silyloxy ligand, and still more preferably an acyloxy ligand.

Of the platinum complexes represented by the general formula (C-6), one of more preferred embodiments is a platinum complex represented by the following general formula (C-7).

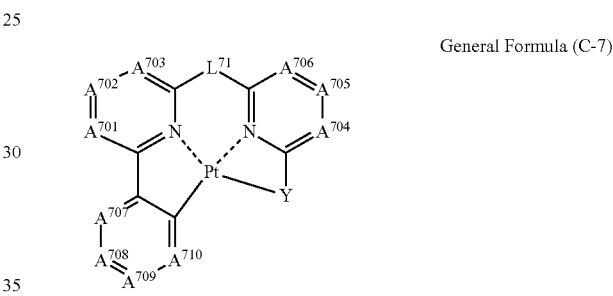

General Formula (C-7)

In the general formula (C-7), $A^{701}$ to $A^{710}$ each independently represent C—R or a nitrogen atom; R represents a hydrogen atom or a substituent; $L^{71}$ represents a single bond or a divalent connecting group; and Y represents an anionic non-cyclic ligand bonding to Pt.

The general formula (C-7) is described. $L^{71}$ is synonymous with $L^{61}$ in the general formula (C-6), and a preferred range thereof is also the same. $A^{701}$ to $A^{710}$ are synonymous with $A^{401}$ to $A^{410}$ in the general formula (C-4), respectively, and preferred ranges thereof are also the same. Y is synonymous with Y in the general formula (C-6), and a preferred range thereof is also the same.

Specific examples of the platinum complex represented by the general formula (C-1) include compounds disclosed in paragraphs [0143] to [0152], [0157] to [0158], and [0162] to [0168] of JP-A-2005-310733, compounds disclosed in paragraphs [0065] to [0083] of JP-A-2006-256999, compounds disclosed in paragraphs [0065] to [0090] of JP-A-2006-93542, compounds disclosed in paragraphs [0063] to [0071] of JP-A-2007-73891, compounds disclosed in paragraphs [0079] to [0083] of JP-A-2007-324309, compounds disclosed in paragraphs [0065] to [0090] of JP-A-2006-93542, compounds disclosed in paragraphs [0055] to [0071] of JP-A-2007-96255, and compounds disclosed in paragraphs [0043] to [0046] of JP-A-2006-313796. Besides, the following platinum complexes can be exemplified.

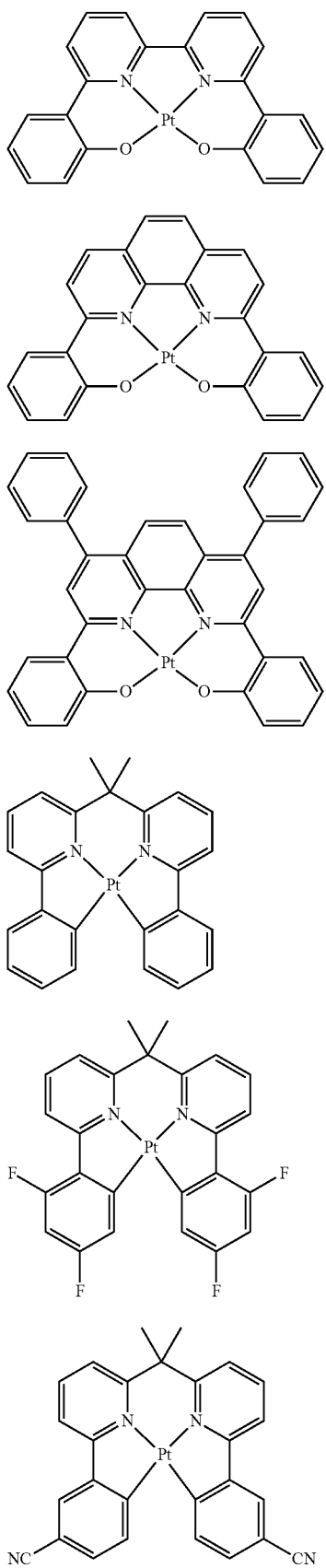
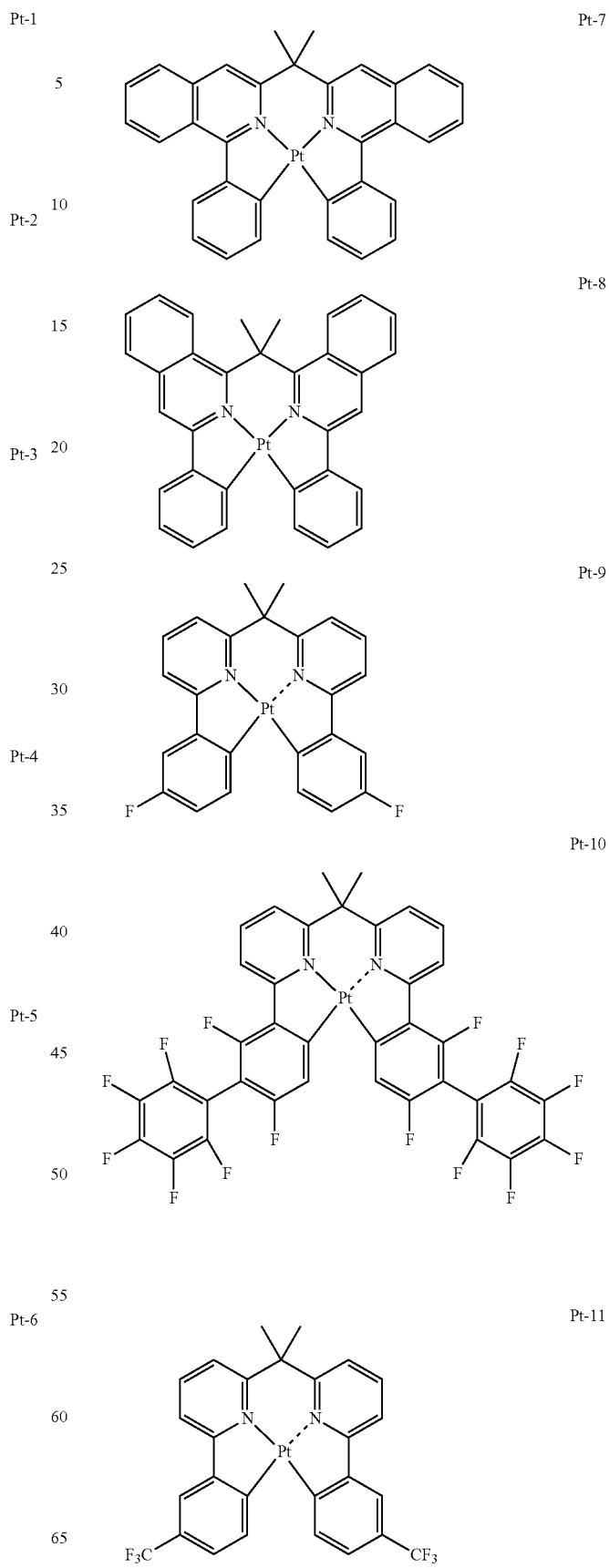

Pt-12
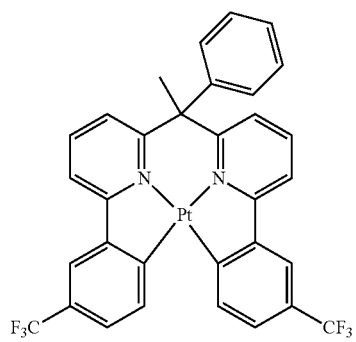
Pt-13
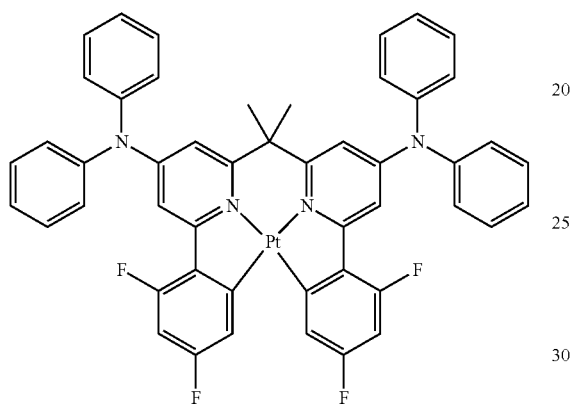
Pt-14
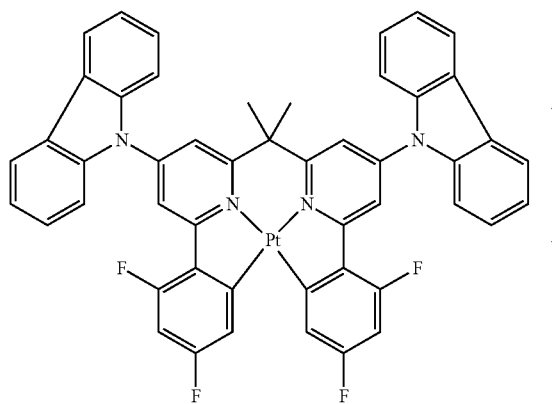
Pt-15
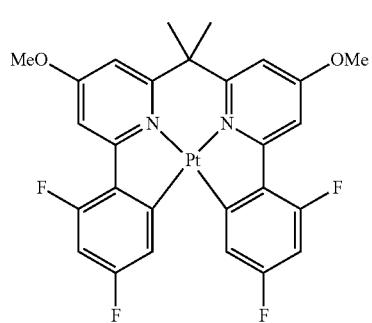
Pt-16
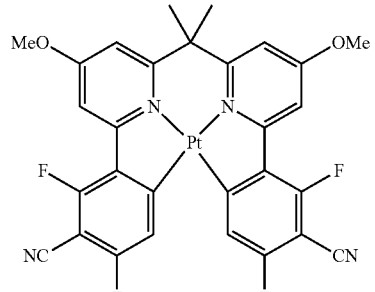
Pt-17
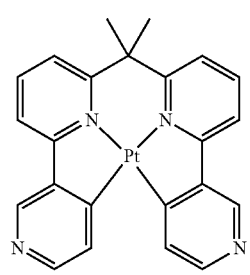
Pt-18
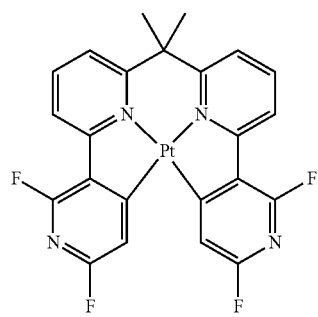
Pt-19
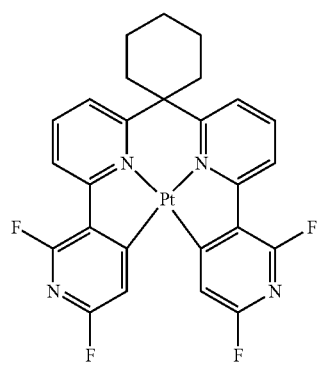
Pt-20
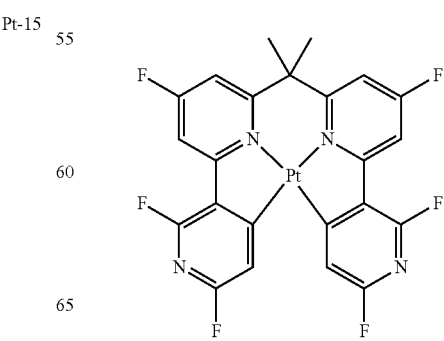

Pt-21
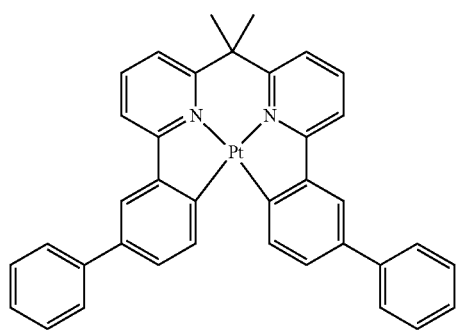
Pt-22
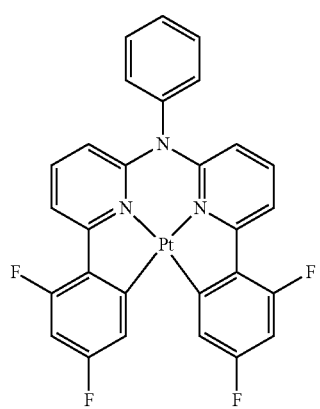
Pt-23
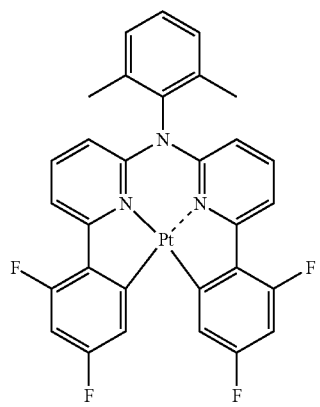
Pt-24
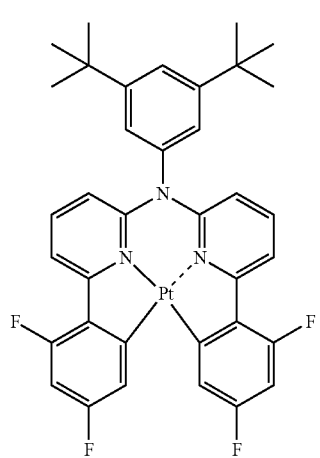
Pt-25
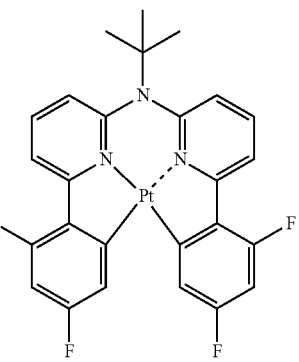
Pt-26
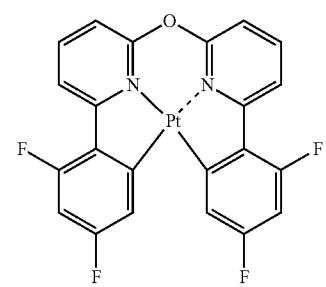
Pt-27
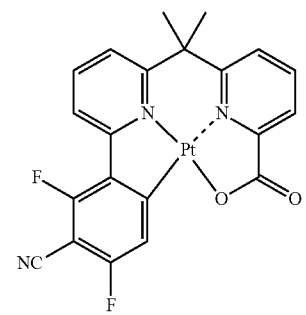
Pt-28
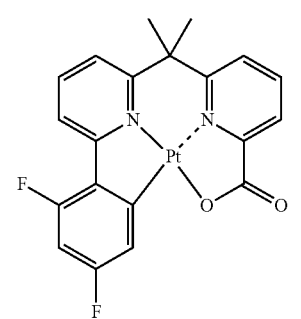
Pt-29
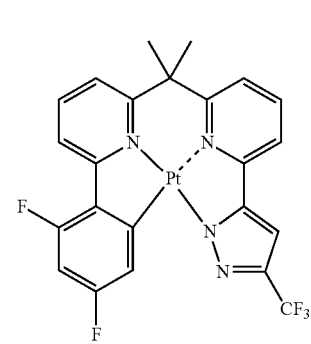

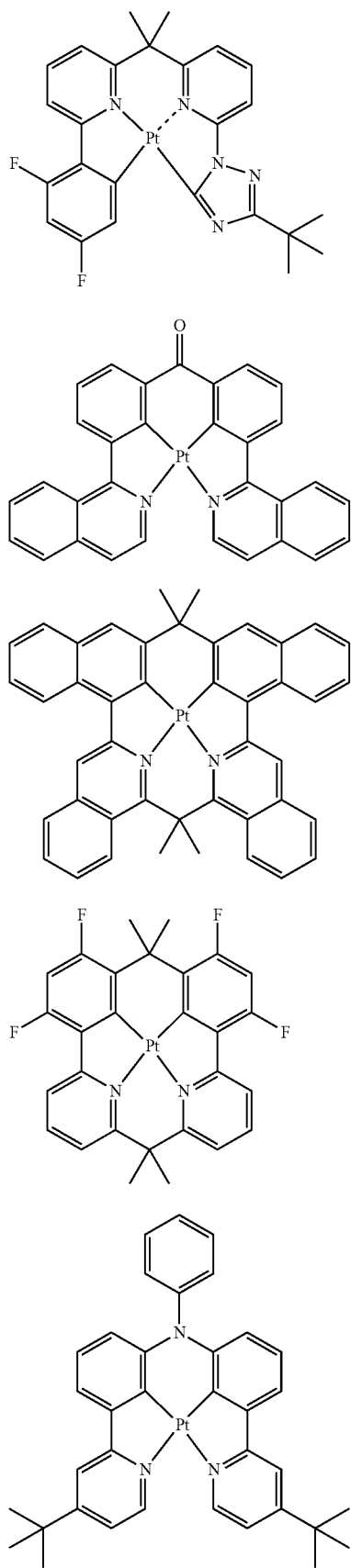
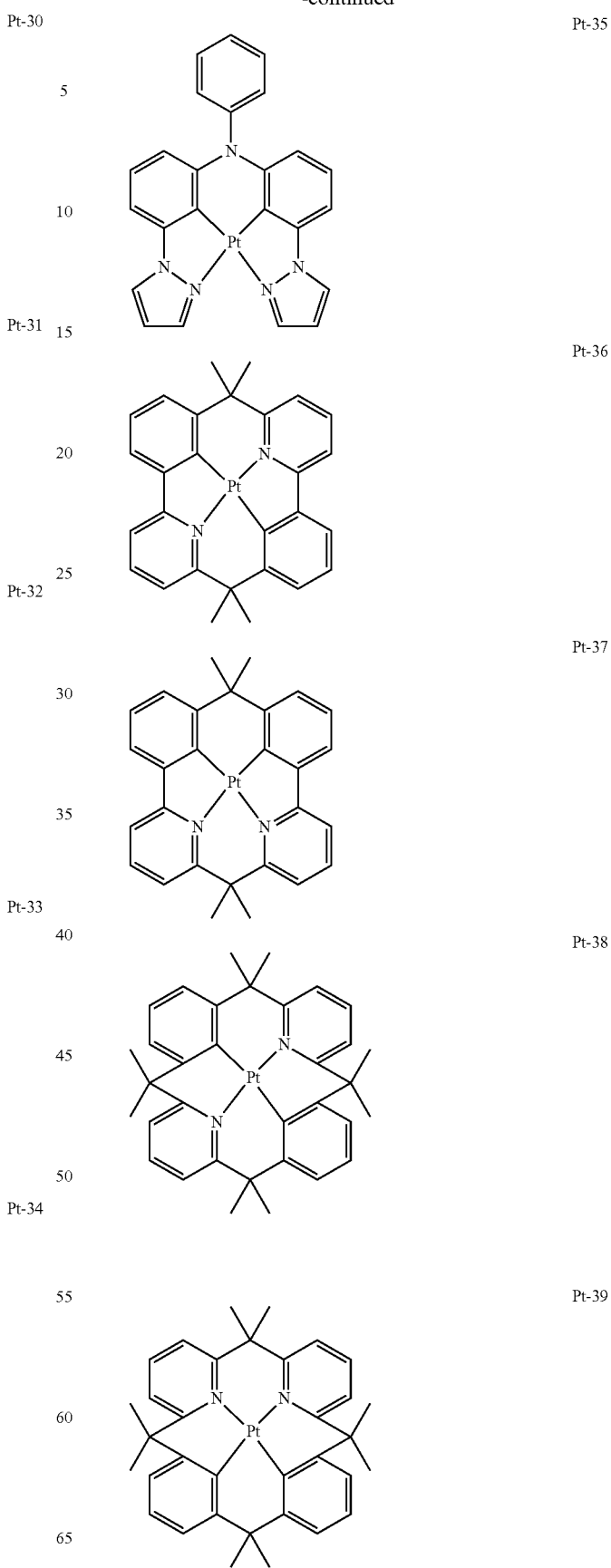

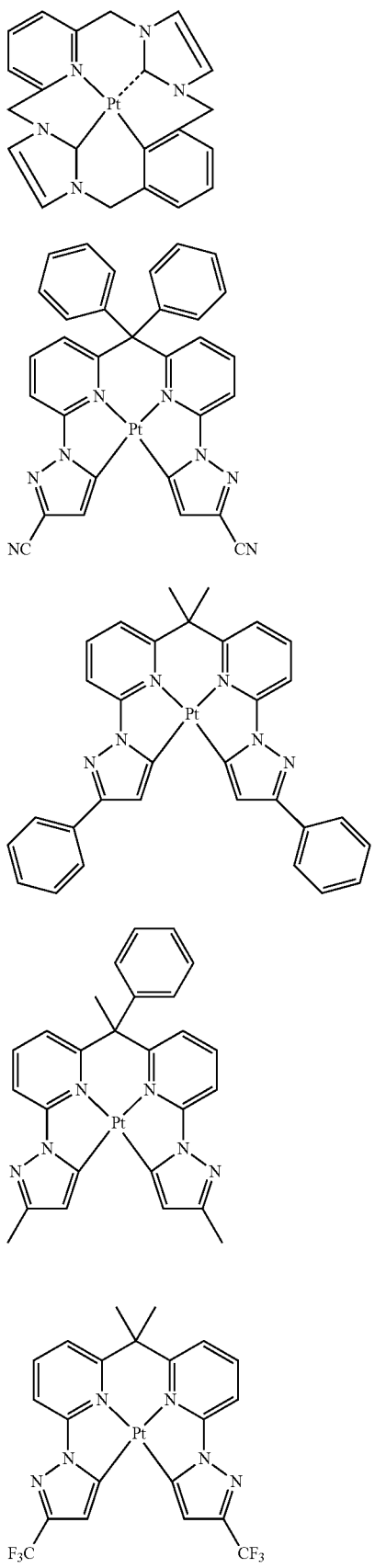
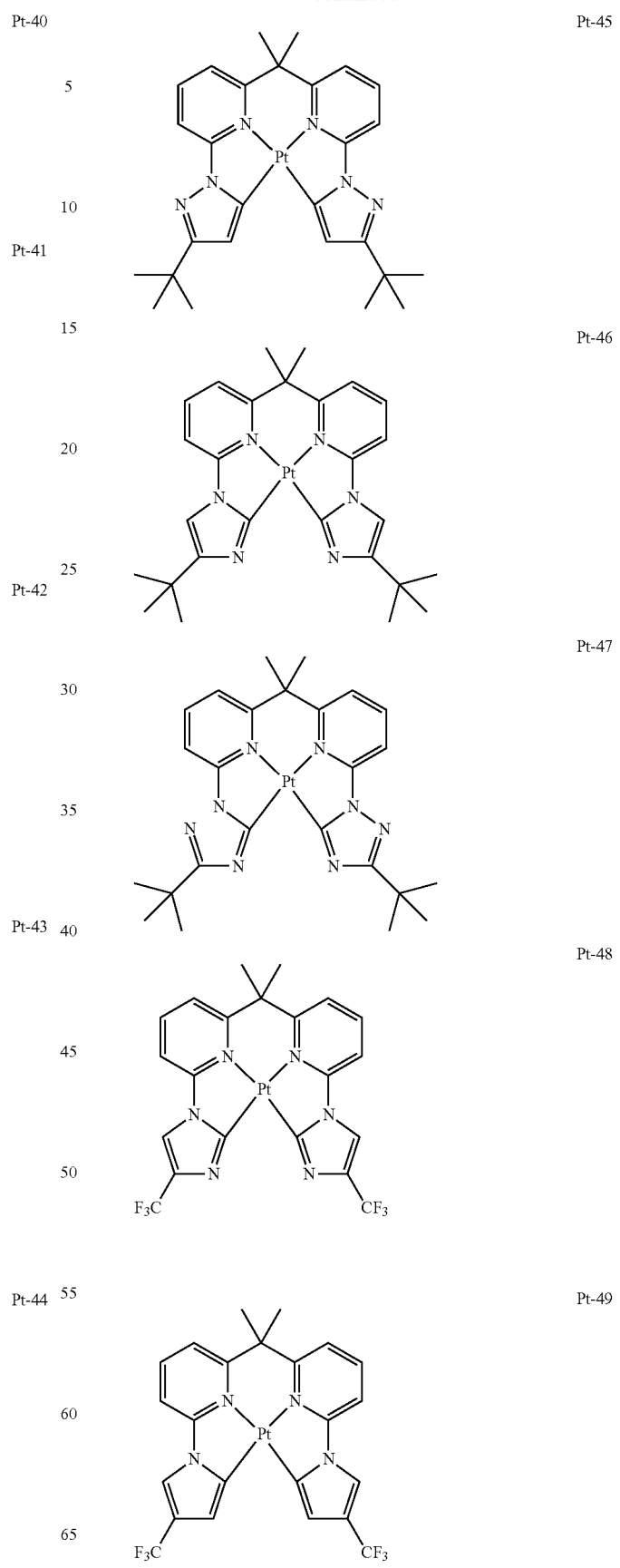

Pt-50
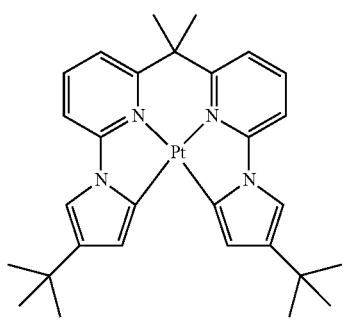
Pt-51
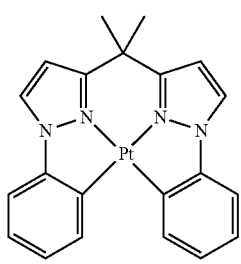
Pt-52
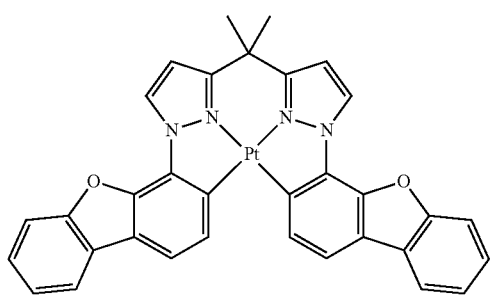
Pt-53
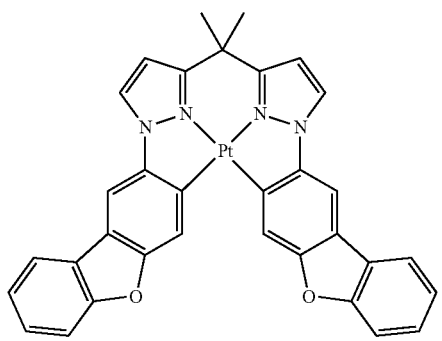
Pt-54
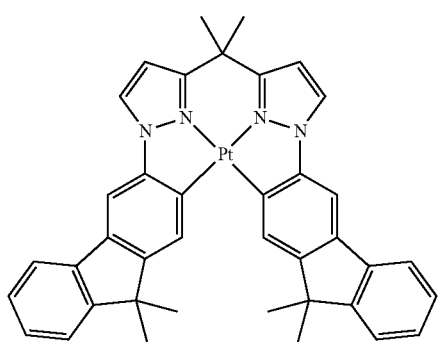
Pt-55
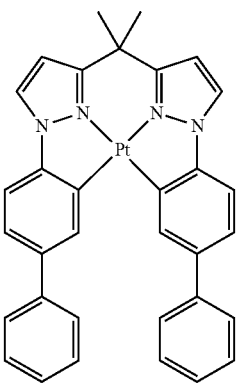
Pt-56
Pt-57
Pt-58
Pt-59

Pt-60 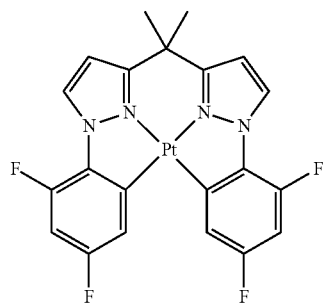
Pt-61 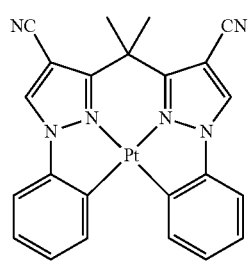
Pt-62 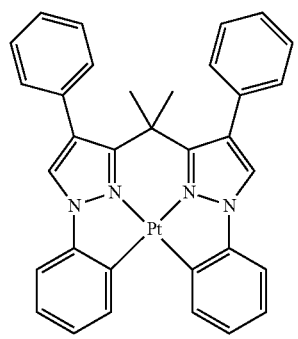
Pt-63 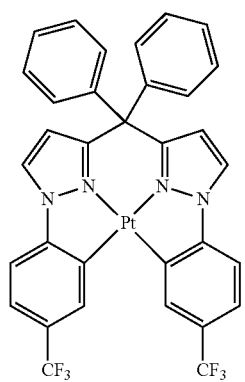
Pt-64 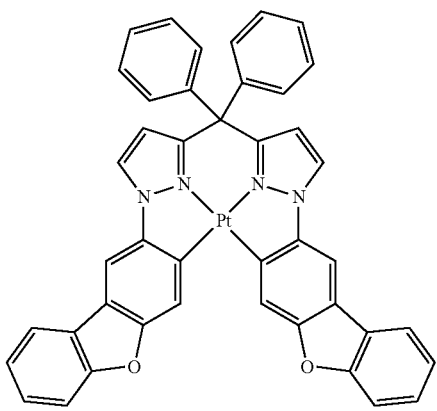
Pt-65 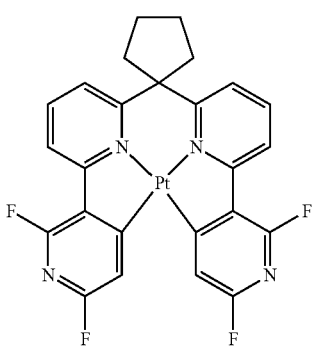
Pt-66 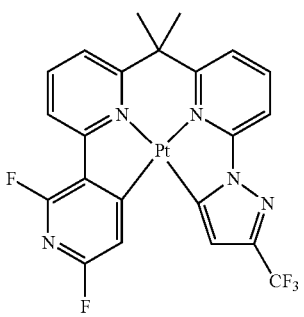
Pt-67 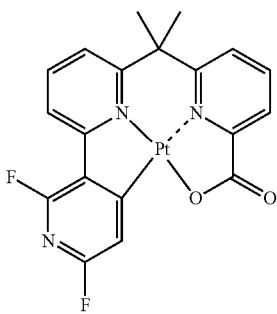

Pt-68

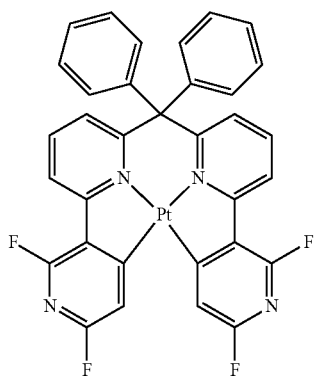

Pt-69

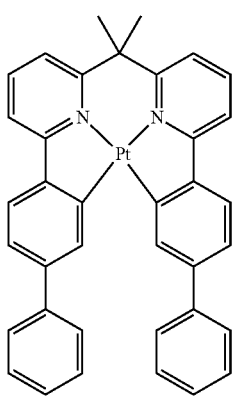

The platinum complex compound represented by the general formula (C-1) can be synthesized by various techniques, for example, a method described at page 789, left-hand column, line 53 to right-hand column, line 7, a method described at page 790, left-hand column lines 18 to 38, a method described page 790, right-hand, lines 19 to 30, and a combination thereof in *Journal of Organic Chemistry*, 53, 786 (1988), G. R. Newkome, et al.; a method described at page 2752, lines 26 to 35 in *Chemische Berichte*, 113, 2749 (1980), H. Lexy, et al.; and the like.

For example, the platinum complex compound represented by the general formula (C-1) can be obtained by treating a ligand or a dissociation material thereof and a metal compound in the presence or absence of a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, water, etc.) and in the presence or absence of a base (various inorganic or organic bases, for example, sodium methoxide, t-butoxy potassium, triethylamine, potassium carbonate, etc.) at room temperature or a lower temperature or by heating (in addition to usual heating, a technique for achieving heating by microwaves is also effective).

The content of the compound represented by the general formula (C-1) in the light emitting layer of the present invention is preferably from 1 to 30% by mass, more preferably from 3 to 25% by mass, and still more preferably from 5 to 20% by mass in the light emitting layer.

Such a phosphorescent light emitting metal complex compound is preferably contained together with the compound represented by the general formula (1) in the light emitting layer.

(III) Other Host Material:

Examples of other host material than the compound represented by the general formula (1), which can be used in the light emitting layer, include compounds having the following partial structure, for example:

Conductive high-molecular oligomers such as aromatic hydrocarbons, pyrrole, indole, carbazole, azaindole, indolocarbazole, azacarbazole, triazole, oxazole, oxadiazole, pyrazole, imidazole, thiophene, polyarylalkanes, pyrazoline, pyrazolone, phenylenediamine, arylamines, amino-substituted chalcone, styrylanthracene, hydrazone, stilbene, silazane, aromatic tertiary amine compounds, styrylamine compounds, porphyrin-based compounds, polysilane-based compounds, poly(N-vinylcarbazole), aniline-based copolymers, thiophene oligomers, and polythiophene, organic silanes, carbon films, pyridine, pyrimidine, triazine, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring).

(Other Layers)

The organic electroluminescent element according to the present invention may include layers other than the light emitting layer.

Examples of the organic layer other than the light emitting layer which may be included in the organic layer include a hole injecting layer, a hole transporting layer, a blocking layer (e.g., a hole blocking layer, an electron blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode Anode/hole injecting layer/hole transporting layer/blocking layer/light emitting layer/blocking layer/electron transporting layer/electron injecting layer/cathode The organic electroluminescent element according to the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element according to the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred embodiments of the organic electroluminescent element according to the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

These layers other than the light emitting layer which the organic electroluminescent element according to the present invention may have are hereunder described.

(A) Organic Layer Preferably Disposed Between Anode and Light Emitting Layer:

First, (A) the organic layer preferably disposed between the anode and the light emitting layer is described.

(A-1) Hole Injecting Layer and Hole Transporting Layer

Each of the hole injecting layer and the hole transporting layer is a layer having a function of accepting holes from the anode or the anode side to transport them into the cathode side. A hole injecting material and a hole transporting material used in these layers may be any of a low-molecular compound or a high-molecular compound.

With respect to the hole injecting layer and the hole transporting, the detailed descriptions in paragraphs [0165] to [0167] of JP-A-2008-270736 can be applied to the present invention.

In the organic electroluminescent element according to the present invention, each of the following compounds is preferably contained in the organic layer between the light emitting layer and the anode, and more preferably contained in the hole injecting layer.

Specifically, compounds having the following structures are preferable.

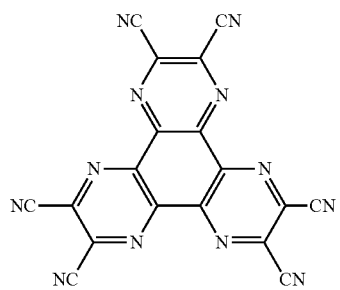

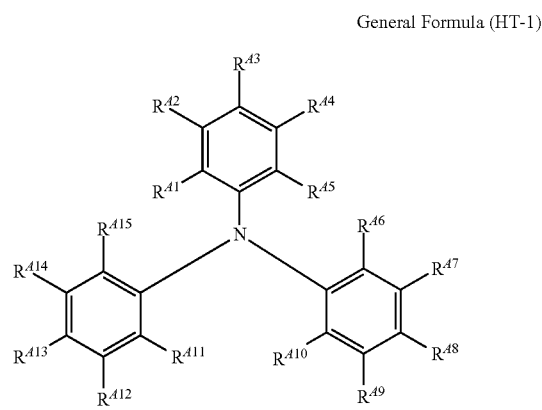

In the organic electroluminescent element according to the present invention, at least one of compounds represented by the following general formula (HT-1) is preferably contained in the organic layer between the light emitting layer and the anode, and more preferably contained in the hole transporting layer.

Examples of the hole transporting material include triarylamine compounds represented by the following general formula (HT-1).

General Formula (HT-1)

In the general formula (HT-1), $R^{A1}$ to $R^{A15}$ each represent a hydrogen atom or a substituent.

Examples of the substituent represented by $R^{A1}$ to $R^{A15}$ include the substituents exemplified as the Substituent Group A. The adjacent substituents may be bounded to each other via a single bond or a connecting group. From the viewpoints of heat resistance and durability, at least one of $R^{A1}$ to $R^{A5}$ and at least one of $R^{A6}$ to $R^{A10}$ are preferably an aryl group.

Specific examples of the compound represented by the general formula (HT-1) are shown below, but it should not be construed that the present invention is limited thereto.

(HTL-1) 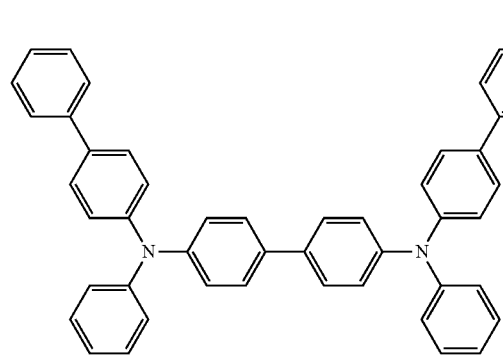
(HTL-2) 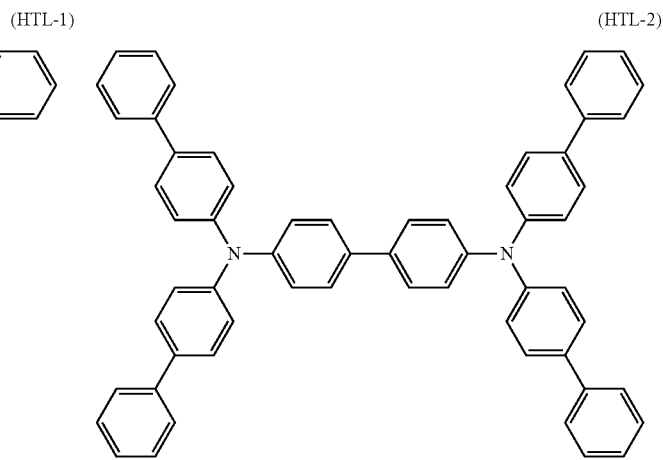
(HTL-3) 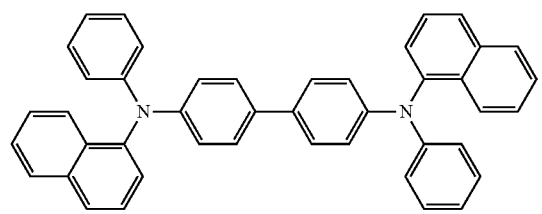
(HTL-4) 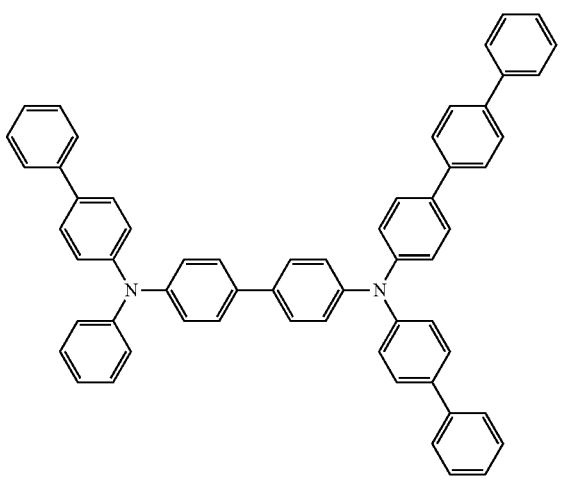
(HTL-5) 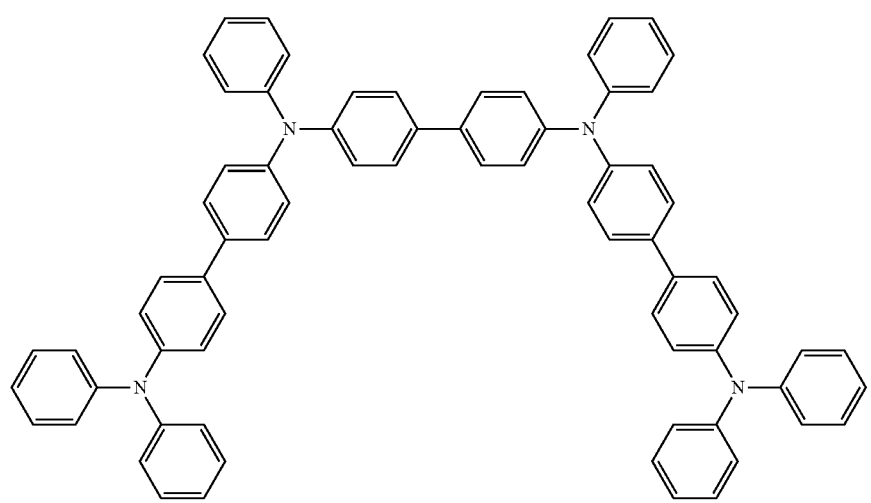

-continued
(HTL-6)
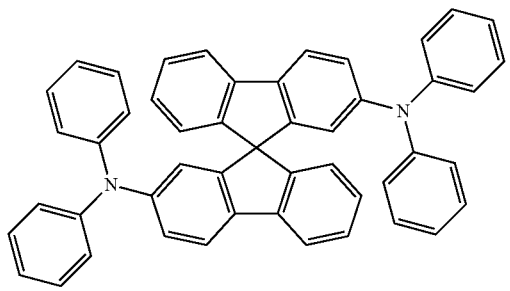
(HTL-7)
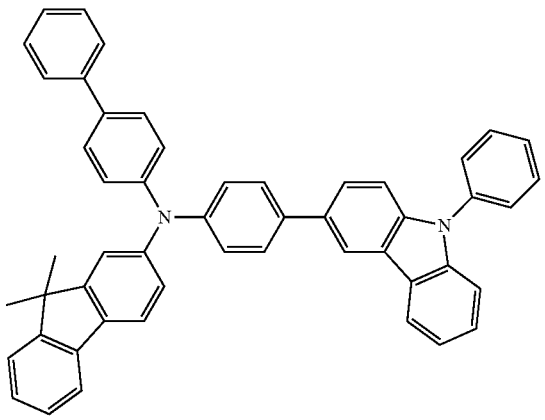
(HTL-8)
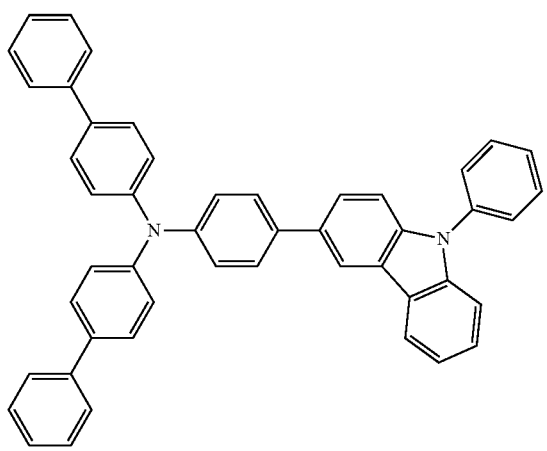
(HTL-9)
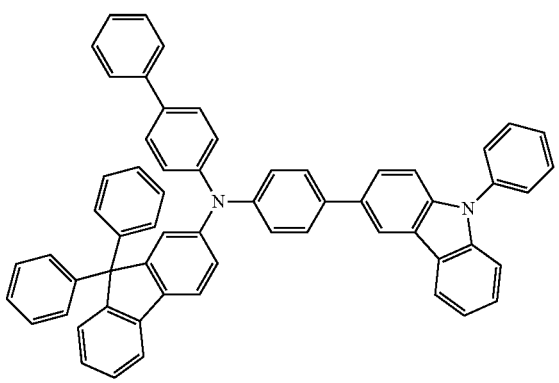
(HTL-10)
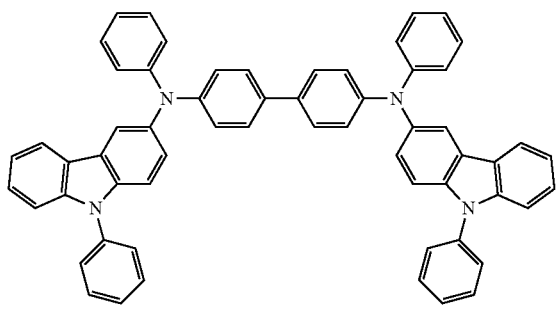
(HTL-11)
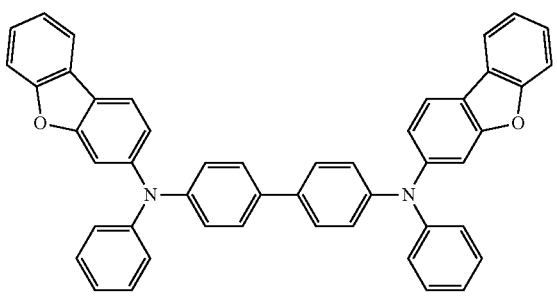
(HTL-12)
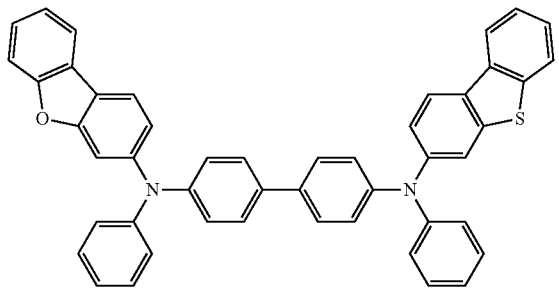
(HTL-13)
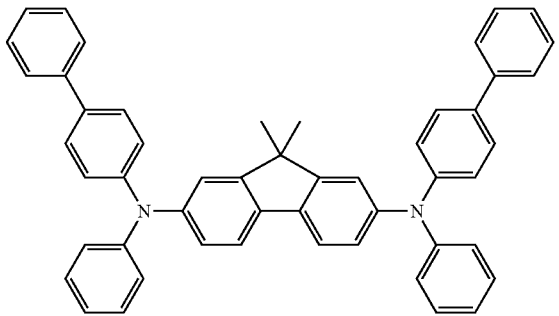

(HTL-14)

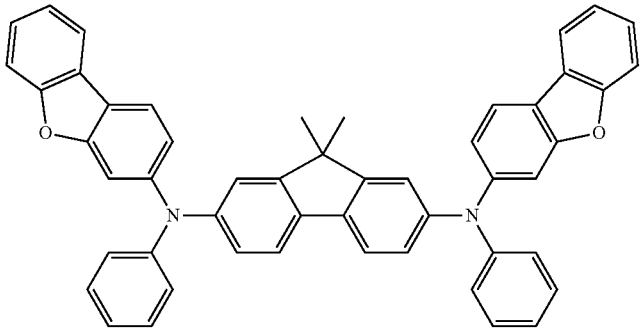

In the case of using the compound represented by the general formula (HT-1) in the hole transporting layer, the compound represented by the general formula (HT-1) is contained in an amount of preferably from 50 to 100% by mass, more preferably from 80 to 100% by mass, and especially preferably from 95 to 100% by mass.

In addition, in the case of using the compound represented by the general formula (HT-1) in plural organic layers, it is preferable that the compound represented by the general formula (HT-1) is contained in an amount falling within the foregoing range in each of the layers.

Only one kind of the compound represented by the general formula (HT-1) may be contained, or a plurality of the compounds represented by the general formula (HT-1) may be contained in an arbitrary combination, in any one of the organic layers.

The thickness of the hole transporting layer containing the compound represented by the general formula (HT-1) is preferably from 1 nm to 500 nm, more preferably from 3 nm to 200 nm, and still more preferably from 5 nm to 100 nm. In addition, the hole transporting layer is preferably provided in a contact state with the light emitting layer.

The hole transporting layer may have either a single layer structure composed of one or two or more kinds of the above-described materials or may be of a multilayer structure composed of a plurality of layers of the same composition or different compositions.

The lowest excited triplet ($T_1$) energy of the compound represented by the general formula (HT-1) in a thin film state is preferably 2.52 eV (58 kcal/moles) or more and not more than 3.47 eV (80 kcal/mole), more preferably eV (57 kcal/moles) or more and not more than 3.25 eV (75 kcal/mole), and still more preferably 2.52 eV (58 kcal/moles) or more and not more than 3.04 eV (70 kcal/mole).

The hydrogen atom constituting the general formula (HT-1) also includes isotopes (a deuterium atom and the like). In that case, all of the hydrogen atoms in the compound may be substituted with a hydrogen isotope, or a part thereof may be a mixture of a compound containing a hydrogen isotope.

The compound represented by the general formula (HT-1) can be synthesized by a combination of various known synthesis methods. Most generally, concerning the carbazole compounds, synthesis by dehydrogenation aromatization after the Aza-Cope arrangement of the condensation product of an aryl hydrazine and a cyclohexane derivative (L. F. Tieze and Th. Eicher, translated by Takano and Ogasawara, *Precision Organic Syntheses*, page 339, published by Nanko-Do) is exemplified. In addition, concerning the coupling reaction of the obtained compound and an aryl halide compound using a palladium catalyst, the methods described in *Tetrahedron Letters*, Vol. 39, page 617 (1998), ibid., Vol. 39, page 2367 (1998), and ibid., Vol. 40, page 6393 (1999) are exemplified. The reaction temperature and the reaction time are not particularly limited, and the conditions in the above-described documents are applicable.

As for the compound represented by the general formula (HT-1) in the present invention, though it is preferable to form a thin layer by a vacuum deposition process, a wet process such as solution coating can also be suitably adopted. From the viewpoints of deposition adaptability and solubility, the molecular weight of the compound is preferably not more than 2,000, more preferably not more than 1,200, and especially preferably not more than 800. In addition, from the viewpoint of deposition adaptability, when the molecular weight is too low, the vapor pressure becomes low, and a change from the vapor phase to the solid phase does not occur, so that it becomes difficult to form the organic layer. Thus, the molecular weight of the compound is preferably 250 or more, and especially preferably 300 or more.

(A-2) Electron Blocking Layer:

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 200 nm, and still more preferably from 5 nm to 100 nm.

The electron blocking layer may have either a single layer structure composed of one or two or more kinds of materials selected from the above-exemplified materials or a multilayer structure composed of a plurality of layers having the same composition or different compositions.

In order to prevent the energy movement of excitons produced in the light emitting layer and not lower the luminous efficiency, the $T_1$ energy of the organic compound constituting the electron blocking layer in a film state is preferably higher than the $T_1$ energy of the light emitting material is preferable.

(B) Organic Layer Preferably Disposed Between Cathode and Light Emitting Layer:

Next, the (B) organic layer preferably disposed between the cathode and the light emitting layer is described.

(B-1) Electron Injecting Layer and Electron Transporting Layer:

The electron injecting layer and the electron transporting layer are a layer having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As other electron transporting materials, any one of compounds selected from aromatic ring tetracarboxylic acid anhydrides such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof; organic silane derivatives typified by silole; hydrocarbon compounds with fused rings, such as naphthalene, anthracene, phenanthrene, triphenylene, and pyrene is preferable. Any one of compounds selected from pyridine derivatives, benzimidazole derivatives, imidazopyridine derivatives, metal complexes, and hydrocarbon compounds with fused rings are more preferable.

From the viewpoint of decreasing the driving voltage, the thickness of each of the electron injecting layer and the electron transporting layer is preferably not more than 500 nm.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials selected or a multilayer structure composed of a plurality of layers having the same composition or different compositions.

The electron injecting layer can contains an electron donating dopant. By incorporating the electron donating dopant into the electron injecting layer, for example, there are brought such effects that the electron injecting properties are enhanced; that the driving voltage is lowered; and that the efficiency is enhanced. The electron donating dopant may be any one of organic materials and inorganic materials as long as it is capable of giving electrons to the material to be doped and generating radical anions. Examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass relative to the total mass of the compounds forming the electron injecting layer.

(B-2) Hole Blocking Layer:

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order to prevent the energy movement of excitons produced in the light emitting layer and not lower the luminous efficiency, the $T_1$ energy of the organic compound constituting the hole blocking layer in a film state is preferably higher than the $T_1$ energy of the light emitting material is preferable.

As an example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum(III) tris-8-dydroxyquinoline (abbreviated as "Alq"), aluminum(III) bis(2-methyl-8-quinolinato) 4-phenylphenolate (abbreviated as "BAlq"), triazole derivatives, and phenanthroline derivatives such as 2,9-dimethyl-4,7-diphenyl-1,10-phenanthroline (abbreviated as "BCP"). In the present invention, the hole blocking layer is not limited to the function to actually block holes, and it may have a function to not diffuse the excitons of the light emitting layer into the electron transporting layer, or to block the energy movement extinction. The compound represented by the general formula (1) can also be applied to the hole blocking layer.

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material which is used in the hole blocking layer preferably has higher $T_1$ energy than that of the light emitting material in view of color purity, luminous efficiency, and driving durability.

(B-3) Material Especially Preferably Used in Organic Layer, which is Preferably Disposed Between Cathode and Light Emitting Layer:

For the organic electroluminescent element according to the present invention, examples of the material which is especially preferably used in the materials for an organic layer, preferably disposed between the (B) cathode and the light emitting layer include the compound represented by the general formula (1) and an aromatic hydrocarbon compound (in particular, compounds represented by the following general formula (Tp-1) and the following general formula (O-1).

The aromatic hydrocarbon compound and the compound represented by the general formula (O-1) are hereunder described.

[Aromatic Hydrocarbon Compound]

The aromatic hydrocarbon compound is more preferably contained in the organic layer which is located between the light emitting layer and the cathode and adjacent to the light emitting layer. However, the aromatic hydrocarbon compound is not limited with respect to an application thereof and may further be contained in any layer in the organic layers. As for the layer into which the aromatic hydrocarbon compound is introduced, the aromatic hydrocarbon compound can be contained in any one or plural layers of the light emitting layer, the hole injecting layer, the hole transporting layer, the electron transporting layer, the electron injecting layer, the exciton blocking layer, and the charge blocking layer.

The organic layer in which the aromatic hydrocarbon compound is contained, and which is located between the light emitting layer and the cathode and adjacent to the light emitting layer, is preferably the blocking layer (the hole blocking layer or the exciton blocking layer) or the electron transporting layer, and more preferably the electron transporting layer.

In the case of containing the aromatic hydrocarbon compound in other layer than the light emitting layer, it is contained in an amount of preferably from 70 to 100% by mass, and more preferably from 85 to 100% by mass. In the case of containing the aromatic hydrocarbon compound in the light emitting layer, it is contained in an amount of preferably from 0.1 to 99% by mass, more preferably from 1 to 95% by mass, and still more preferably from 10 to 95% by mass relative to the total mass of the light emitting layer.

As the aromatic hydrocarbon compound, it is preferable to use a hydrocarbon compound having a molecular weight falling within the range of from 400 to 1,200 and having a fused polycyclic skeleton having from 13 to 22 carbon atoms in total. The fused polycyclic skeleton having from 13 to 22 carbon atoms in total is preferably any one of fluorene, anthracene, phenanthrene, tetracene, chrysene, pentacene, pyrene, perylene, and triphenylene. From the viewpoint of $T_1$, fluorene, triphenylene, and phenanthrene are more preferable, and from the viewpoints of stability and charge injecting or transporting properties of the compound, the compound represented by the following general formula (Tp-1) is especially preferable.

The aromatic hydrocarbon compound represented by the general formula (Tp-1) has a molecular weight in the range of preferably from 400 to 1,200, more preferably from 400 to 1,100, and still more preferably from 400 to 1,000. So far as the molecular weight is 400 or more, an amorphous thin film with good quality can be formed, whereas what the molecular weight is not more than 1,200 is preferable in view of solubility in a solvent and sublimation and deposition adaptabilities.

The aromatic hydrocarbon compound represented by the general formula (Tp-1) is not limited with respect to an application thereof and may be contained in not only the organic layer adjacent to the light emitting layer but any layer in the organic layers.

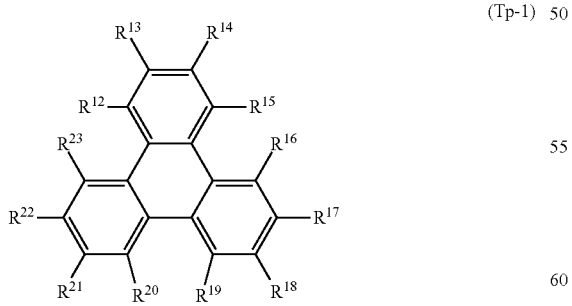

(Tp-1)

In the general formula (Tp-1), $R^{12}$ to $R^{23}$ each independently represent a hydrogen atom, an alkyl group, a phenyl group, a fluorenyl group, a naphthyl group, or a triphenylenyl group (each of which may be further substituted with an alkyl group, a phenyl group, a fluorenyl group, a naphthyl group, or a triphenylenyl group). However, all of $R^{12}$ to $R^{23}$ are not a hydrogen atom at the same time.

Examples of the alkyl group represented by $R^{12}$ to $R^{23}$ include substituted or unsubstituted alkyl groups such as a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group. Of these, a methyl group, an ethyl group, an isopropyl group, a tert-butyl group, and a cyclohexyl group are preferable, and a methyl group, an ethyl group, and a tert-butyl group are more preferable.

$R^{12}$ to $R^{23}$ are preferably an alkyl group having from 1 to 4 carbon atoms, a phenyl group, a fluorenyl group, a naphthyl group, or a triphenylenyl group (each of which may be further substituted with an alkyl group, a phenyl group, a fluorenyl group, a naphthyl group, or a triphenylenyl group), and more preferably a phenyl group, a fluorenyl group, a naphthyl group, or a triphenylenyl group.

$R^{12}$ to $R^{23}$ are especially preferably a benzene ring which may be substituted with a phenyl group, a fluorenyl group, a naphthyl group, or a triphenylenyl group (each of which may be further substituted with an alkyl group, a phenyl group, a fluorenyl group, a naphthyl group, or a triphenylenyl group).

The total number of the aryl rings in the general formula (Tp-1) is preferably from 2 to 8, and more preferably from 3 to 5. When the total number of the aryl rings in the general formula (Tp-1) is allowed to fall within this range, an amorphous thin film with good quality can be formed, and the solubility in a solvent and the sublimation and deposition adaptabilities become good.

$R^{12}$ to $R^{23}$ each independently have the total carbon number of preferably from 20 to 50, and more preferably from 20 to 36. When the total carbon number is allowed to fall within this range, an amorphous thin film with good quality can be formed, and the solubility in a solvent and the sublimation and deposition adaptabilities become good.

The hydrocarbon compound represented by the general formula (Tp-1) is also preferably a compound represented by the following general formula (Tp-3).

General Formula (Tp-3)

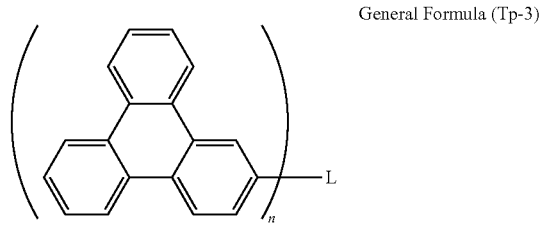

In the general formula (Tp-3), L represents an n-valent connecting group composed of an alkyl group, a phenyl group, a fluorenyl group, a naphthyl group, or a triphenylenyl group (each of which may be further substituted with an alkyl group, a phenyl group, a fluorenyl group, a naphthyl group, or a triphenylenyl group), or a combination thereof. n represents an integer of from 2 to 6.

The alkyl group, the phenyl group, the fluorenyl group, the naphthyl group, and the triphenylenyl group, each of which forms the n-valent connecting group represented by L, are synonymous with those exemplified for $R^{12}$ to $R^{23}$.

L is preferably an n-valent connecting group composed of an alkyl group, or a benzene ring or a fluorene ring, each of which may be substituted with a benzene ring, or a combination thereof.

Preferred specific examples of L are enumerated below, but it should not be construed that the present invention is limited thereto.

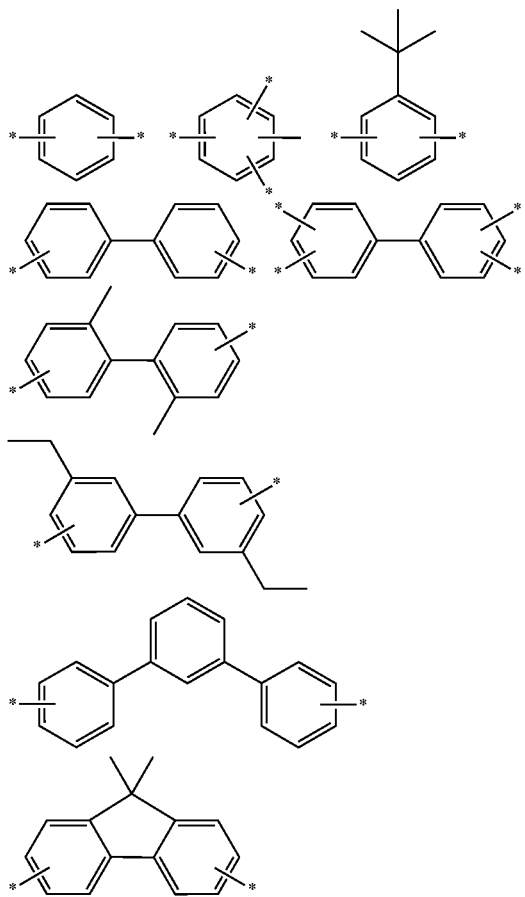

n is preferably from 2 to 5, and more preferably from 2 to 4.

The compound represented by the general formula (Tp-1) is preferably a compound represented by the following general formula (Tp-4).

General Formula (Tp-4)

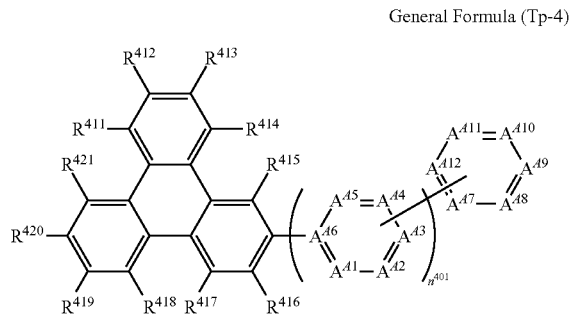

In the general formula (Tp-4), $A^{41}$ to $A^{412}$ each independently represent $CR^{400}$ or a nitrogen atom; and $n^{401}$ represents an integer of from 0 to 8. In the case where $n^{401}$ is 0, the ring represented by $A^{41}$ to $A^{46}$ represents a single bond between the triphenylene ring and the ring represented by $A^{47}$ to $A^{412}$. In the case where $n^{401}$ is from 2 to 6, plurally existing rings represented by $A^{41}$ to $A^{46}$ may vary at every appearance, and a connecting mode between plurally existing rings to each other may vary at every appearance.

Incidentally, in the present invention, the hydrogen atom in the description of the general formula (Tp-4) also includes isotopes (a deuterium atom and the like), and the atoms constituting the substituent are also intended to include isotopes of the atoms.

In the general formula (Tp-4), $R^{41}$ to $R^{42}$ each independently represent a hydrogen atom, an alkyl group, a phenyl group, a fluorenyl group, a naphthyl group, or a triphenylenyl group (each of which may be further substituted with an alkyl group, a phenyl group, a fluorenyl group, a naphthyl group, or a triphenylenyl group).

$R^{411}$ to $R^{421}$ are preferably a hydrogen atom, an alkyl group having from 1 to 4 carbon atoms, a phenyl group, a fluorenyl group, a naphthyl group, or a triphenylenyl group (each of which may be further substituted with an alkyl group, a phenyl group, a fluorenyl group, a naphthyl group, or a triphenylenyl group), more preferably a hydrogen atom or a phenyl group (the phenyl group may be substituted with an alkyl group, a phenyl group, a fluorenyl group, a naphthyl group, or a triphenylenyl group), and especially preferably a hydrogen atom.

$A^{41}$ to $A^{412}$ are preferably $CR^{400}$.

In the general formula (Tp-4), the substituent represented by $R^{400}$ represents a hydrogen atom, an alkyl group having from 1 to 4 carbon atoms, a phenyl group, a fluorenyl group, a naphthyl group, or a triphenylenyl group (each of which may be further substituted with an alkyl group, a phenyl group, a fluorenyl group, a naphthyl group, or a triphenylenyl group) Plurally existing $R^{400}$s may be different from each other.

$R^{400}$ is preferably a hydrogen atom, an alkyl group having from 1 to 4 carbon atoms, a phenyl group, a fluorenyl group, a naphthyl group, or a triphenylenyl group (each of which may be further substituted with an alkyl group, a phenyl group, a fluorenyl group, a naphthyl group, or a triphenylenyl group), more preferably a hydrogen atom, an alkyl group having from 1 to 4 carbon atoms, or a phenyl group (each of which may be substituted with an alkyl group, a phenyl group, a fluorenyl group, a naphthyl group, or a triphenylenyl group), and especially preferably a hydrogen atom, an alkyl group having from 1 to 4 carbon atoms, or a phenyl group (each of which may be substituted with an alkyl group, a phenyl group, a fluorenyl group, a naphthyl group, or a triphenylenyl group).

$n^{401}$ is preferably an integer of from 0 to 5, more preferably an integer of from 1 to 5, and especially preferably an integer of from 2 to 4.

In the case where $n^{401}$ is an integer of 1 or more, and the connecting position to the ring represented by $A^{47}$ to $A^{412}$ is $A^{43}$, from the viewpoint of luminous efficiency, the substituent represented by $A^{44}$ or $A^{45}$ is $CR^{400}$, and $R^{400}$ is preferably an alkyl group having from 1 to 4 carbon atoms or a phenyl group, more preferably an alkyl group having from 1 to 4 carbon atoms, and especially preferably a methyl group.

In the general formula (Tp-4), among the respective 6-membered aromatic rings constituted of $A^{41}$ to $A^{412}$, the number of rings containing a nitrogen atom is preferably not more than 1, and more preferably 0. In the general formula (Tp-4), though the connection of the respective 6-membered aromatic rings constituted of $A^{41}$ to $A^{412}$ is not limited, the connection at the meta-position or para-position is preferable. Furthermore, in the compound represented by the general formula (Tp-4), the number of aromatic rings continuously connecting at the para-position to each other including a phenyl ring that is a partial structure of the fused ring constituting the triphenylene ring is preferably not more than 3.

In the case of using the hydrocarbon compound represented by the general formula (Tp-1) in the host material of the light emitting layer of the organic electroluminescent element or the charge transporting material of the layer adjacent to the light emitting layer, when an energy gap in a thinner film state than the light emitting material (lowest excited triplet ($T_1$) energy in a thin film state in the case where the light emitting material as described later is a phosphorescent material) is large, quenching of the light emission can be prevented from occurring, and such is advantageous for enhancing the efficiency. On the other hand, from the viewpoint of chemical stability of the compound, it is preferable that the energy gap and the $T_1$ energy are not excessively large. The $T_1$ energy of the compound represented by the general formula (Tp-1) in a thin film state is preferably 1.77 eV (40 kcal/moles) or more and not more than 3.51 eV (81 kcal/mole), and more preferably 2.39 eV (55 kcal/moles) or more and not more than 3.25 eV (75 kcal/mole). From the viewpoint of luminous efficiency, it is preferable that in the organic electroluminescent element according to the present invention, the $T_1$ energy of the compound represented by the general formula (Tp-1) is higher than the $T_1$ energy of the phosphorescent material. In particular, in the case where a luminous color from the organic electroluminescent element is green (emission peak wavelength: 490 to 580 nm), from the viewpoint of luminous efficiency, the $T_1$ energy is still more preferably 2.39 eV (55 kcal/mole) or more and not more than 2.82 eV (65 kcal/mole).

The $T_1$ energy of the hydrocarbon compound represented by the general formula (Tp-1) can be determined by the same method as that in the description of the general formula (1).

From the viewpoint of stably operating the organic electroluminescent element against the heat generation at the time of high-temperature driving or during the element driving, the glass transition temperature (Tg) of the hydrocarbon compound according to the present invention is preferably 80° C. or higher and not higher than 400° C., more preferably 100° C. or higher and not higher than 400° C., and still more preferably 120° C. or higher and not higher than 400° C.

Specific examples of the hydrocarbon compound represented by the general formula (Tp-1) are exemplified below, but it should not be construed that the hydrocarbon compound used in the present invention is limited thereto.

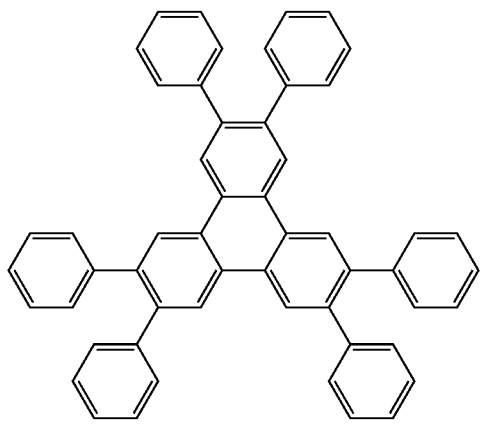

TpH-1

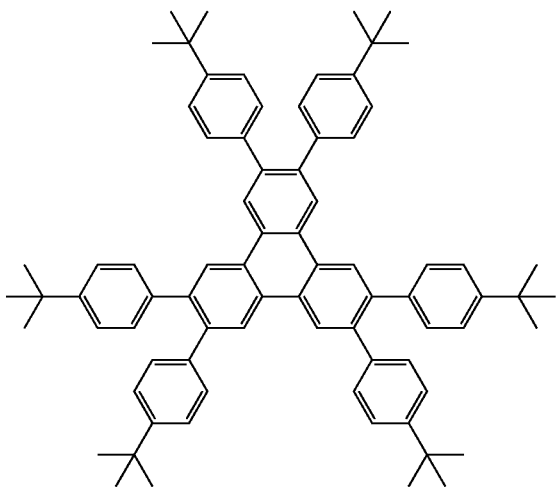

TpH-2

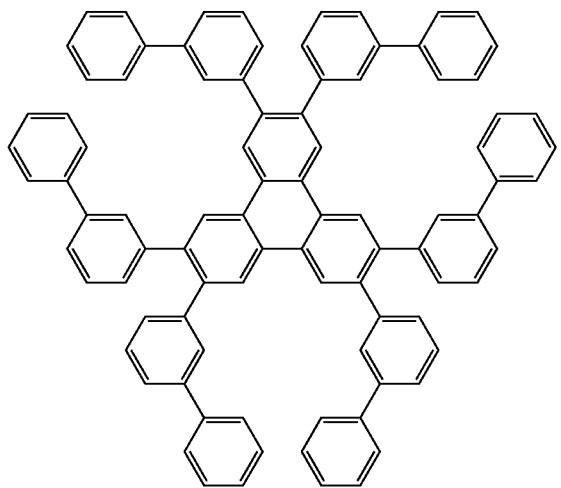

TpH-3

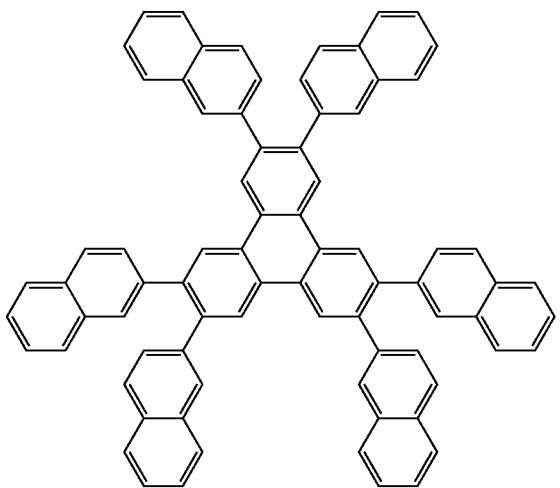

TpH-4

TpH-5
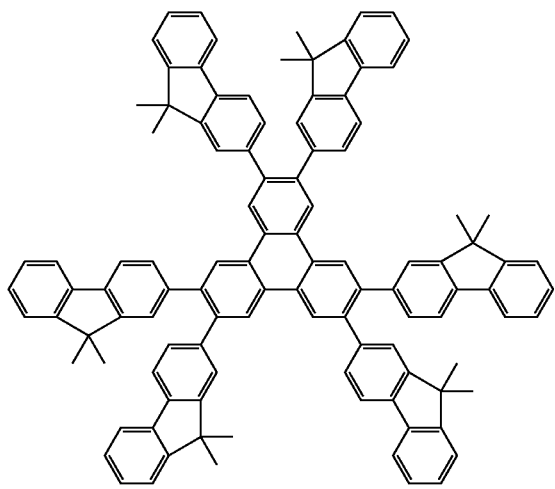
TpH-6
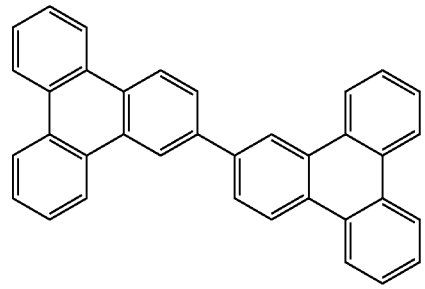
TpH-7
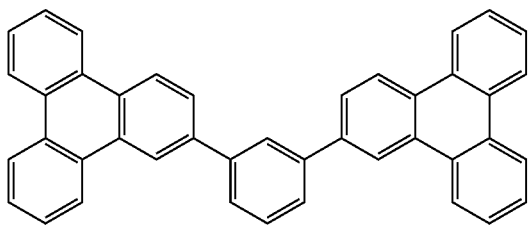
TpH-8
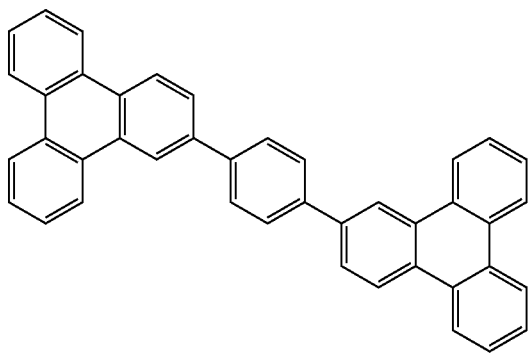
TpH-9
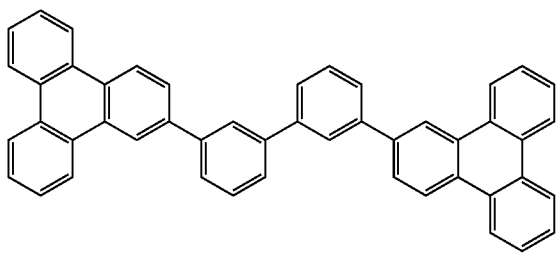
TpH-10
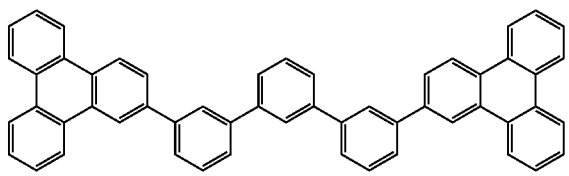

-continued
TpH-11
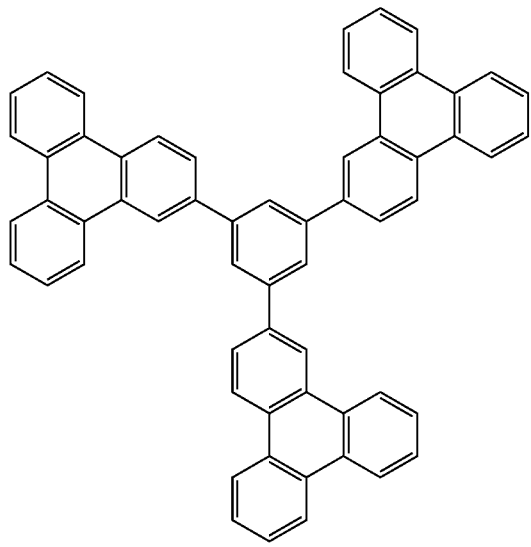
TpH-12
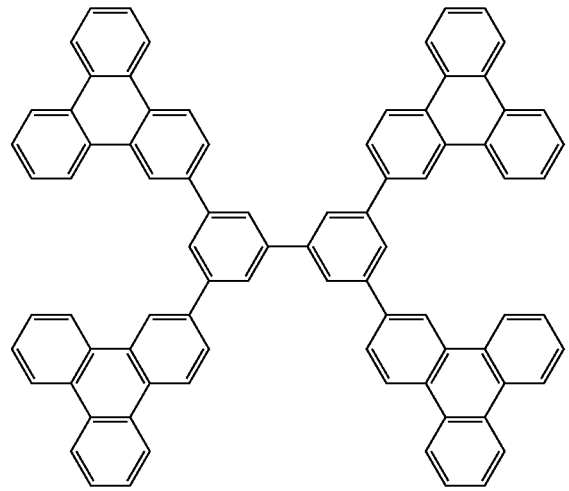
TpH-13
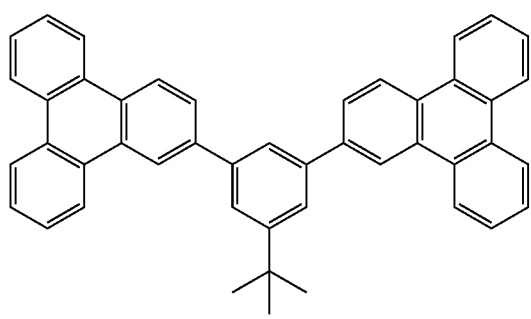
TpH-14
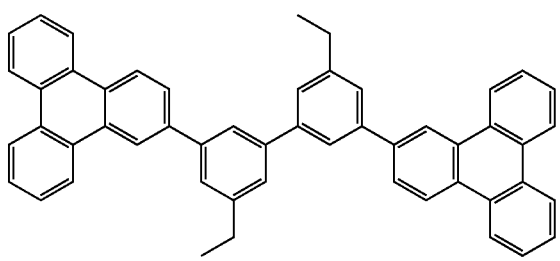
TpH-15
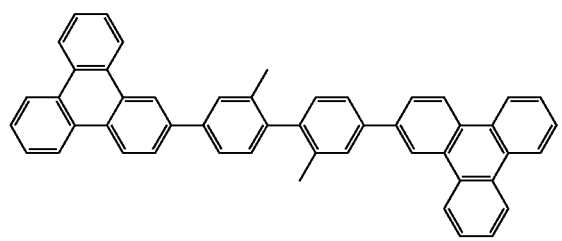
TpH-16
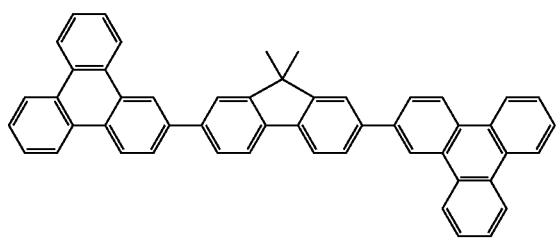

-continued
TpH-17
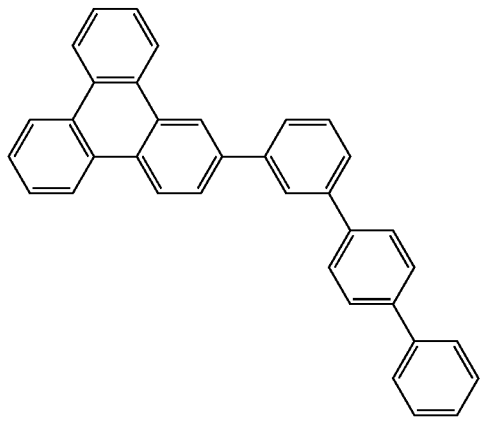
TpH-18
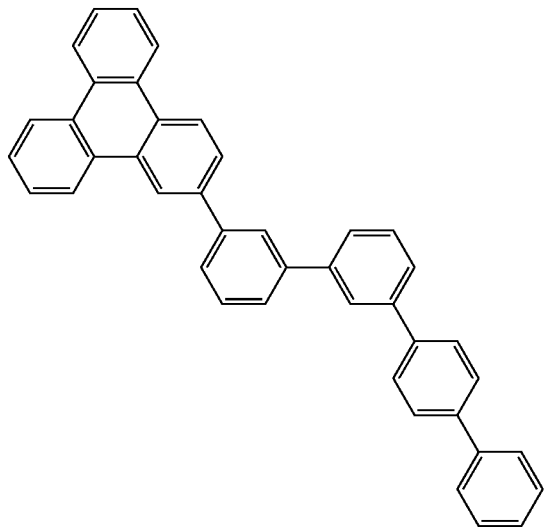
TpH-19
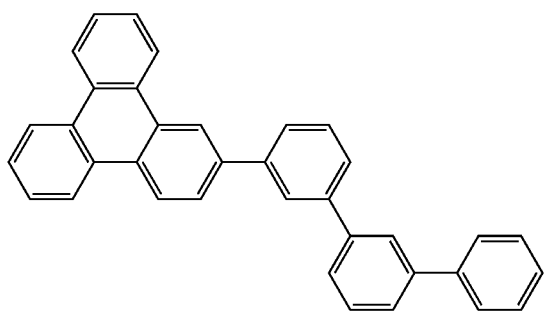
TpH-20
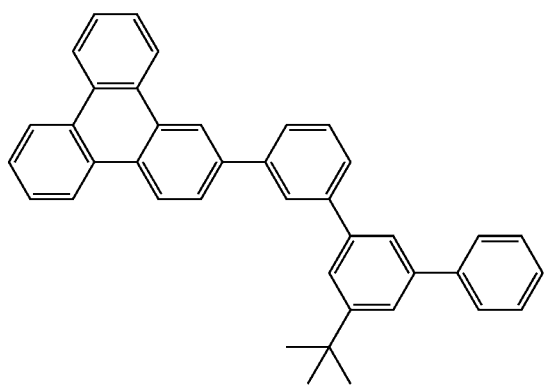
TpH-21
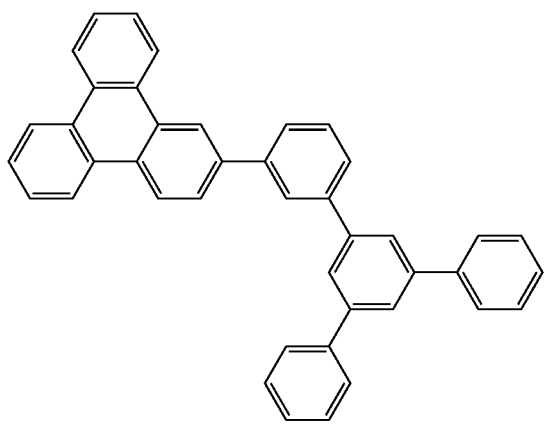
TpH-22
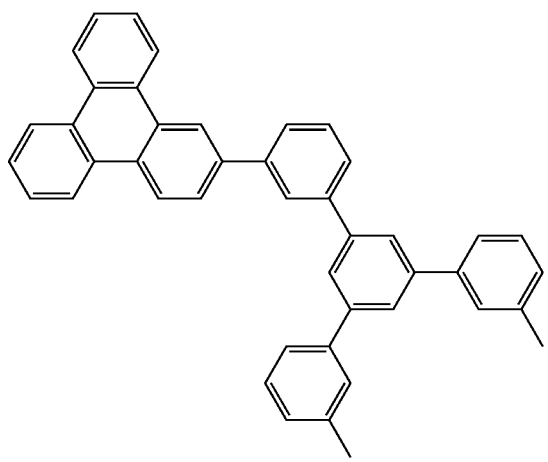

TpH-23

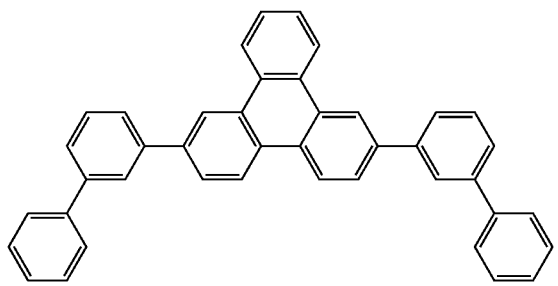

TpH-24

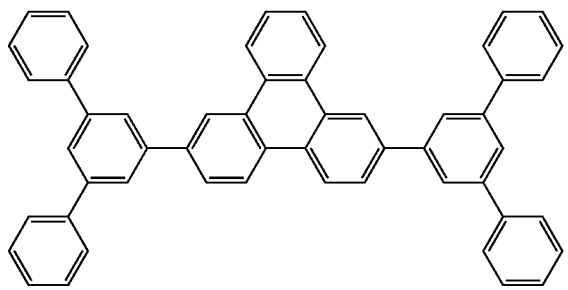

TpH-25

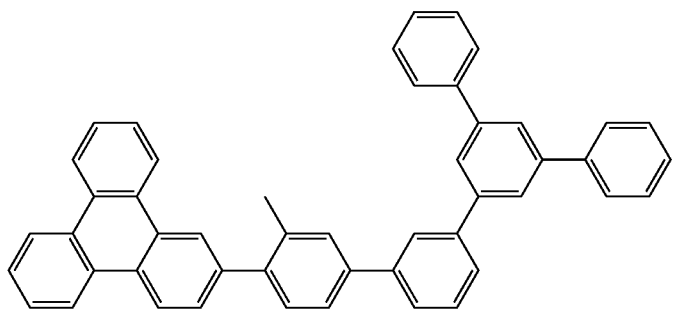

TpH-26

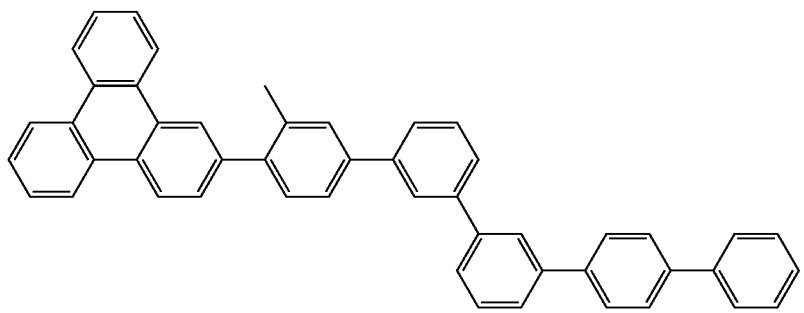

The compounds exemplified as the hydrocarbon compound represented by the general formula (Tp-1) can be synthesized by methods described in WO05/013388, WO06/130598, WO09/021107, US2009/0009065, WO09/008311, and WO04/018587.

It is preferable that after the synthesis, the product is purified by means of column chromatography, recrystallization, or the like and then purified by means of sublimation purification. By the sublimation purification, not only organic impurities can be separated, but inorganic salts, a residual solvent, and the like can be effectively removed.

[Compound Represented by the General Formula (O-1)]

From the viewpoints of efficiency and driving voltage of the organic electroluminescent element, it is preferable to use a compound represented by the following general formula (O-1) as a material which is especially preferably used for the material of the organic material preferably disposed between the (B) cathode and the light emitting material. The general formula (O-1) is hereunder described.

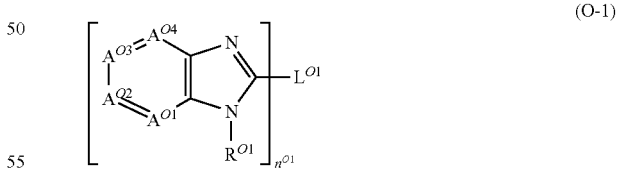

(O-1)

In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^A$s may be the same as or different from each other. $L^{O1}$ represents any of divalent to hexavalent linking groups composed of an aryl ring or a heteroaryl ring. $n^{O1}$ represents an integer of 2 to 6.

In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^4$s may be the same as or different from each other. $L^{O1}$ represents any of divalent to hexavalent linking groups composed of an aryl ring or a heteroaryl ring. $n^{O1}$ represents an integer of 2 to 6.

$R^{O1}$ represents an alkyl group (preferably having from 1 to 8 carbon atoms), an aryl group (preferably having from 6 to 30 carbon atoms), or a heteroaryl group (preferably having from 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group. Of these, an alkyl group and an aryl group are more preferable, with an aryl group being still more preferable. In the case where the aryl group of $R^{O1}$ has plural substituents, the plural substituents may be bonded to each other to form a 5- or 6-membered ring. The aryl group of $R^{O1}$ is preferably a phenyl group which may have a substituent selected from the Substituent Group A, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^4$ or a nitrogen atom. It is preferable that from 0 to 2 of $A^{O1}$ to $A^{O4}$ are a nitrogen atom; and it is more preferable that 0 or 1 of $A^{O1}$ to $A^{O4}$ is a nitrogen atom. It is preferable that all of $A^{O1}$ to $A^{O4}$ are C—$R^4$, or $A^{O1}$ is a nitrogen atom, and $A^{O2}$ to $A^{O4}$ are C—$R^4$; it is more preferable that $A^{O1}$ is a nitrogen atom, and $A^{O2}$ to $A^{O4}$ are C—$R^4$; and it is still more preferable that $A^{O1}$ is a nitrogen atom, $A^{O2}$ to $A^{O4}$ are C—$R^4$, and $R^4$s are all a hydrogen atom.

$R^4$ represents a hydrogen atom, an alkyl group (preferably having from 1 to 8 carbon atoms), an aryl group (preferably having from 6 to 30 carbon atoms), or a heteroaryl group (preferably having from 4 to 12 carbon atoms), and may have a substituent selected from the above-described Substituent Group A. In addition, plural $R^4$s may be the same as or different from each other. $R^4$ is preferably a hydrogen atom or an alkyl group, and more preferably a hydrogen atom.

$L^{O1}$ represents a divalent to hexavalent linking group composed of an aryl ring (preferably having from 6 to 30 carbon atoms) or a heteroaryl ring (preferably having from 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^1$ may have a substituent selected from the above-described Substituent Group A, and in the case where $L^{O1}$ has a substituent, the substituent is preferably an alkyl group, an aryl group, or a cyano group. Specific examples of $L^{O1}$ include the following.

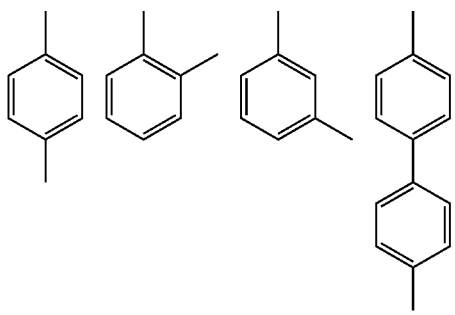

-continued

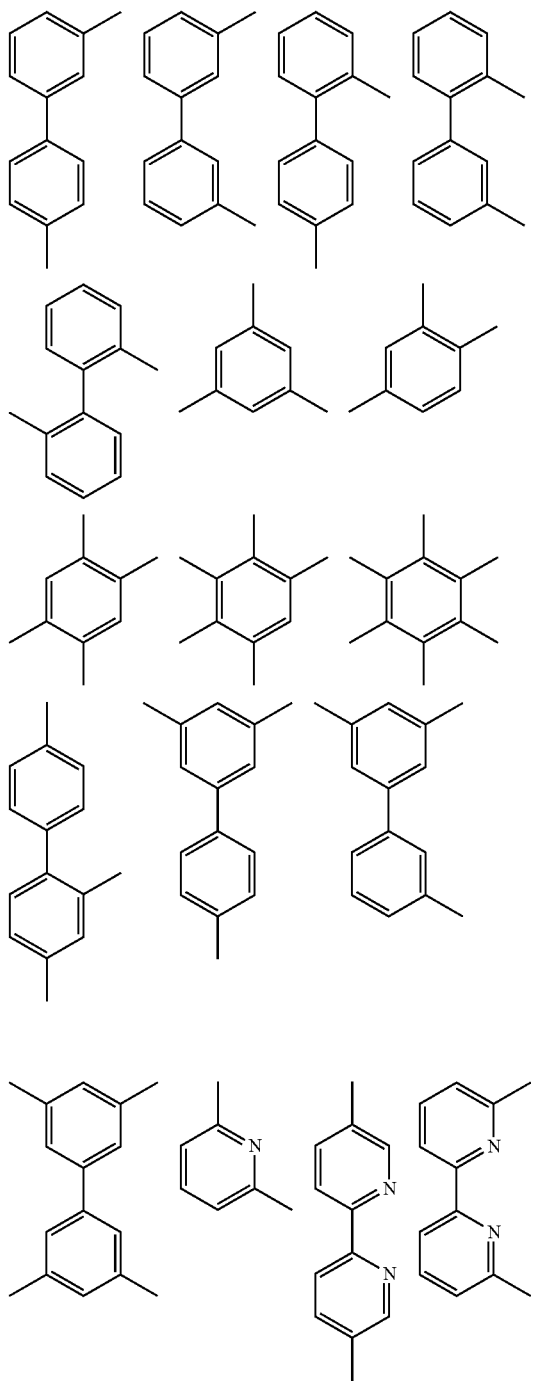

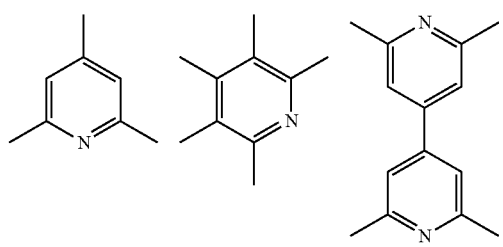

-continued

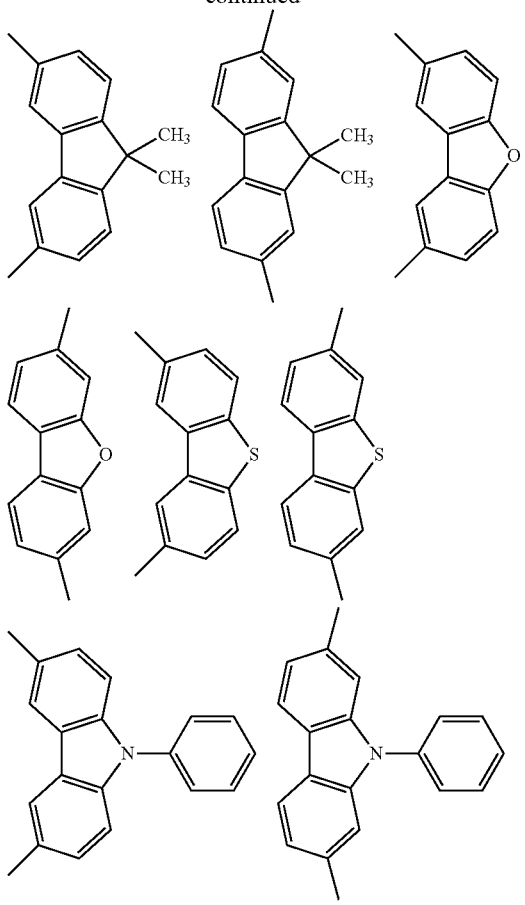

$n^{O1}$ represents an integer of from 2 to 6, preferably an integer of from 2 to 4, and more preferably 2 or 3. $n^{O1}$ is most preferably 3 from the viewpoint of efficiency of the organic electroluminescent element, or $n^{O1}$ is most preferably 2 from the viewpoint of durability of the organic electroluminescent element.

The compound represented by the general formula (O-1) is more preferably a compound represented by the following general formula (O-2).

(O-2)

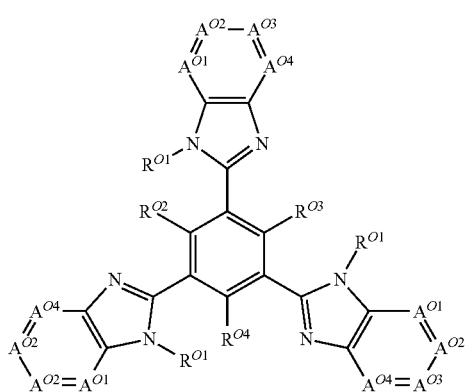

In the general formula (O-2), $R^{O1}$ represents an alkyl group, an aryl group, or a heteroaryl group. $R^{O2}$ to $R^{O4}$ each independently represents a hydrogen atom, an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^A$s may be the same as or different from each other.

$R^{O1}$ and $A^{O1}$ to $A^{O4}$ are synonymous with $R^{O1}$ and $A^{O1}$ to $A^{O4}$ in the general formula (O-1), respectively, and preferred examples thereof are also the same.

$R^{O2}$ to $R^{O4}$ each independently represent a hydrogen atom, an alkyl group (preferably having from 1 to 8 carbon atoms), an aryl group (preferably having from 6 to 30 carbon atoms), or a heteroaryl group (preferably having from 4 to 12 carbon atoms), and may have a substituent selected from the above-described Substituent Group A. $R^{O2}$ to $R^{O4}$ are preferably a hydrogen atom, an alkyl group, or an aryl group, more preferably a hydrogen atom or an aryl group, and most preferably a hydrogen atom.

The glass transition temperature (Tg) of the compound represented by the general formula (O-1) is preferably from 100° C. to 400° C., more preferably from 120° C. to 400° C., and still more preferably from 140° C. to 400° C. from the viewpoint of stability at the time of storage at a high temperature, or stable operation during driving at a high temperature or against heat generation during driving.

Specific examples of the compound represented by the general formula (O-1) are shown below, but it should not be construed that the compound which is used in the present invention is limited thereto.

OM-1

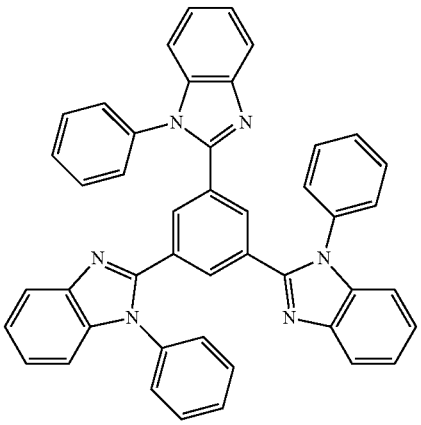

OM-2

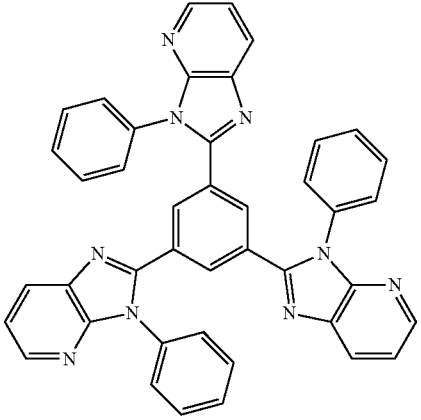

OM-3
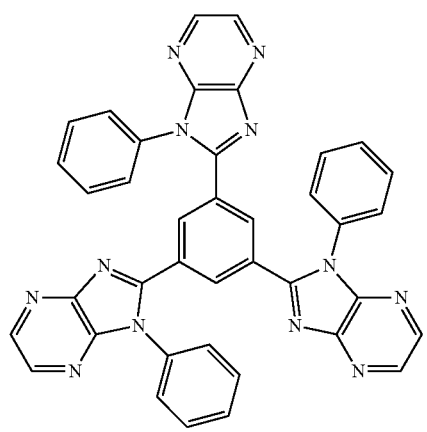
OM-6
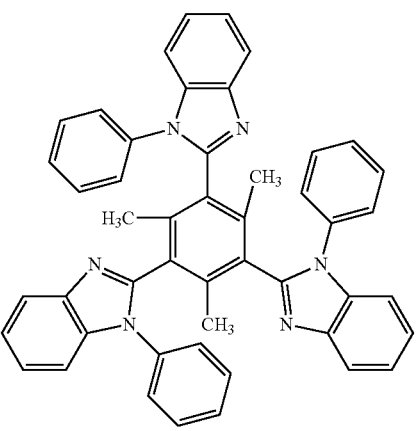
OM-4
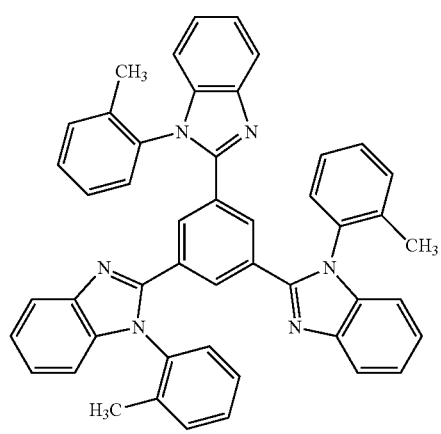
OM-7
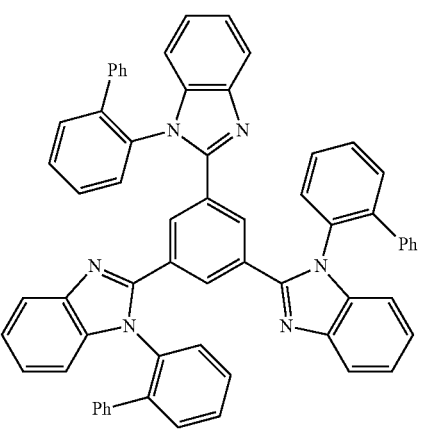
OM-5
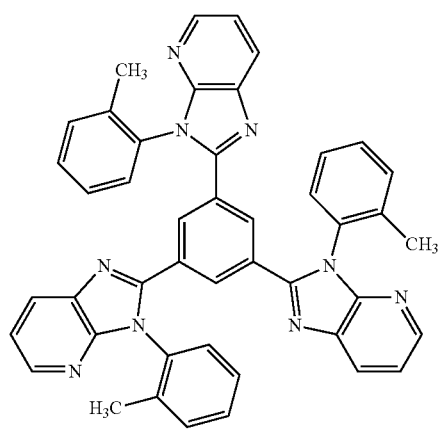
OM-8
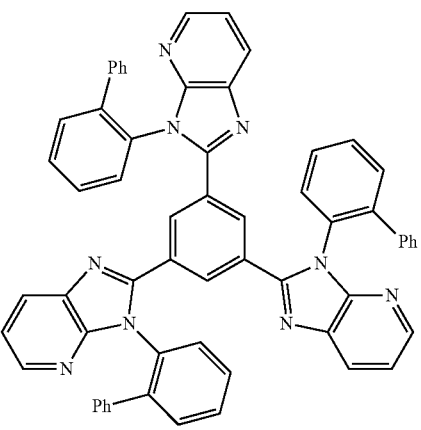

OM-9
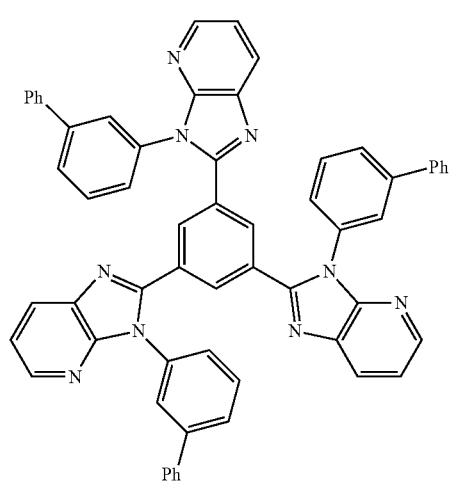
OM-10
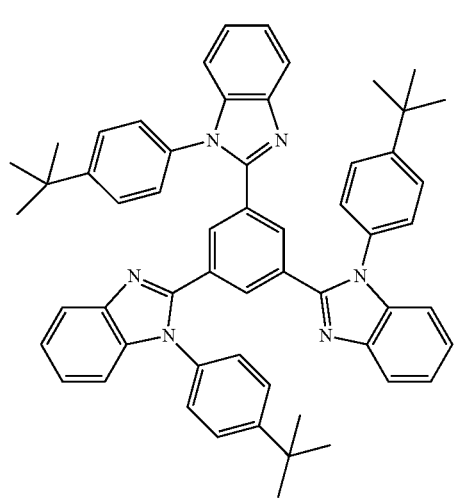
OM-11
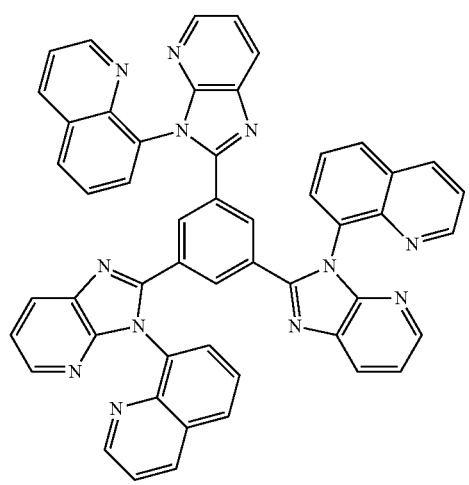
OM-12
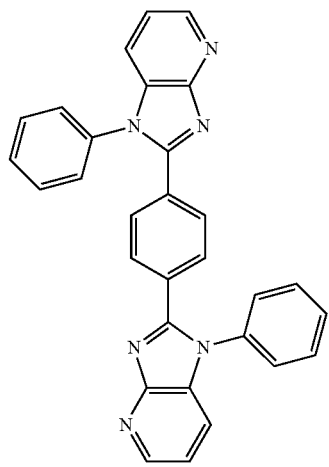
OM-13
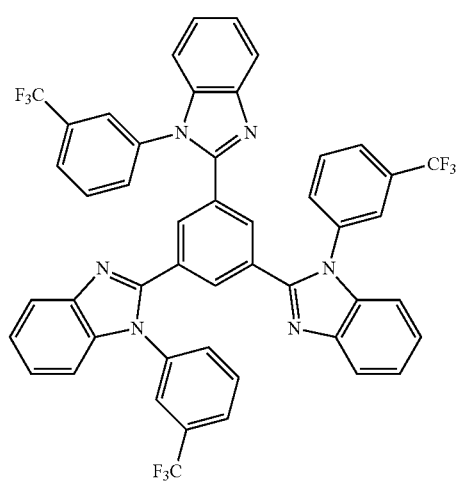
OM-14
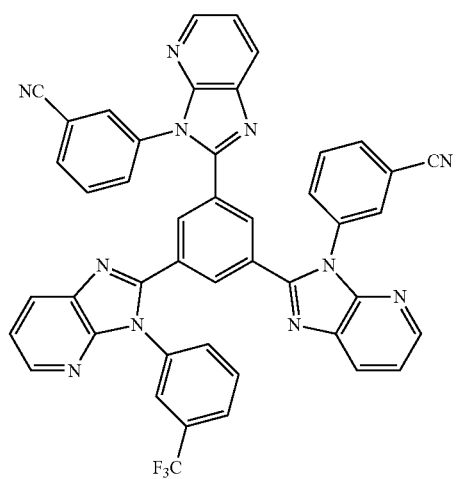

OM-15

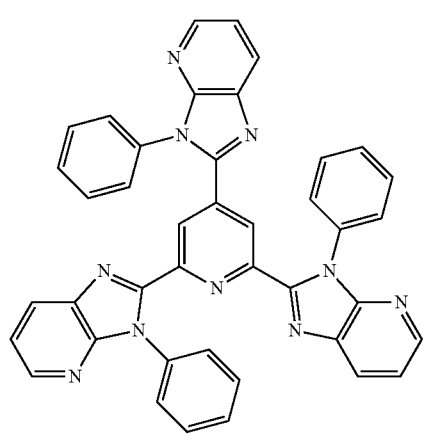

OM-16

OM-17

OM-18

OM-19

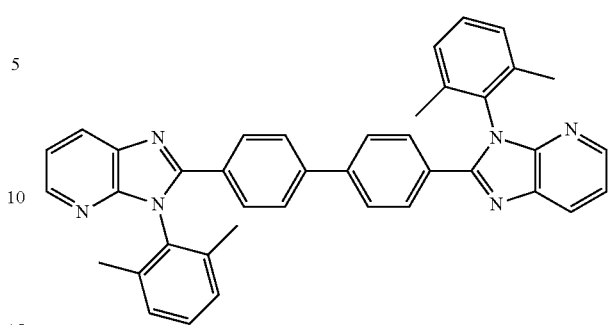

OM-20

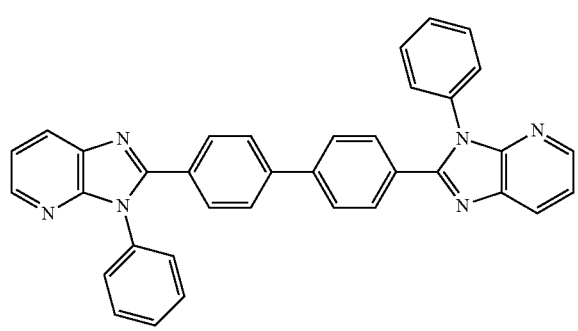

OM-21

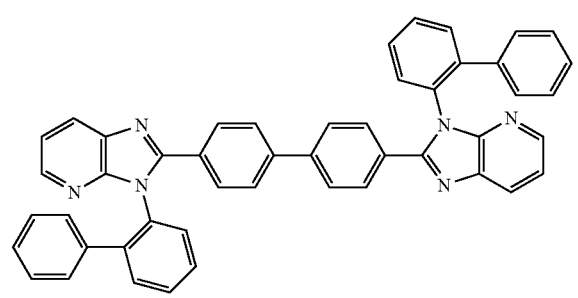

OM-22

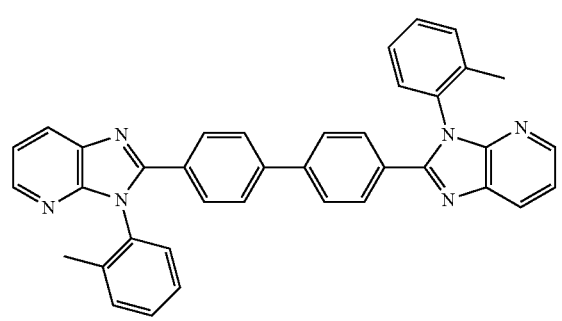

The compound represented by the general formula (O-1) can be synthesized by the method described in JP-A-2001-335776. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the organic electroluminescent element according to the present invention, though the compound represented by the general formula (O-1) is preferably contained in the organic layer between the light emitting layer and the cathode, it is more preferably contained in the layer on the cathode side adjacent to the light emitting layer.

<Protective Layer>

In the present invention, the entirety of the organic electroluminescent element may be protected by a protective layer.

For the protective layer, the detailed description in paragraphs [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph [0171] of JP-A-2008-270736 can be applied to the present invention.

<Driving Method>

The organic electroluminescent element according to the present invention can emit light by applying a direct current (it may include an alternate current component, if desired) voltage (usually from 2 volts to 15 volts) or a direct current between the anode and the cathode.

As a driving method of the organic electroluminescent element according to the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element according to the present invention is preferably 7% or more, and more preferably 10% or more. As for the numerical value of the external quantum efficiency, a maximum value of the external quantum efficiency obtained when the organic electroluminescent element is driven at 20° C., or a value of the external quantum efficiency in the vicinity of from 300 to 400 cd/m$^2$ obtained when the element is driven at 20° C. can be employed.

The internal quantum efficiency of the organic electroluminescent element according to the present invention is preferably 30% or more, more preferably 50% or more, and still more preferably 70% or more. The internal quantum efficiency of the element is calculated by dividing the external quantum efficiency by the light extraction efficiency. Though the light extraction efficiency in usual organic EL elements is about 20%, by taking into consideration the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element according to the present invention, its light emitting wavelength is not limited. For example, the organic electroluminescent element according to the present invention may be used for red light emission, may be used for green light emission, or may be used for blue light emission among the three primary colors of light. Above all, from the viewpoint of luminous efficiency taking into consideration the lowest excited triplet ($T_1$) energy of the compound represented by the general formula (1), the organic electroluminescent element according to the present invention preferably has an emission peak wavelength of from 400 to 700 nm.

Specifically, in the organic electroluminescent element according to the present invention, in the case of using the compound represented by the general formula (1) as the host material of the light emitting layer or the electron transporting material of the electron transporting layer or the hole blocking layer, the emission peak wavelength of a guest material is preferably from 400 to 700 nm, more preferably from 450 to 650 nm, and especially preferably from 480 to 550 nm.

<Use of Organic Electroluminescent Element According to the Present Invention>

The organic electroluminescent element according to the present invention can be suitably used for display elements, displays, backlights, electrophotography, illumination light sources, recording light sources, exposure light sources, readout light sources, signs, billboards, interior decorations, optical communications, and the like. In particular, it is preferably used for devices to be driven in a region of high-intensity luminescence, such as a light emitting device, an illumination device, and a display device.

[Light Emitting Device]

The light emitting device according to the present invention comprises the organic electroluminescent element according to the present invention.

Next, the light emitting device according to the present invention is described with reference to FIG. 2.

FIG. 2 is a cross-sectional view schematically showing one example of the light emitting device according to the present invention. A light emitting device 20 in FIG. 2 is constituted of a transparent substrate 2 (supporting substrate), an organic electroluminescent element 10, a sealing enclosure 16, and the like.

The organic electroluminescent element 10 is constituted by laminating an anode 3 (first electrode), an organic layer 11, and a cathode 9 (second electrode) in this order on the substrate 2. In addition, a protective layer 12 is laminated on the cathode 9, and a sealing enclosure 16 is further provided on the protective layer 12 via an adhesive layer 14. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet can also be used as the adhesive layer 14.

The light emitting device according to the present invention is not particularly limited in its use, and it can be used as not only an illumination device but a display device of a television set, a personal computer, a mobile phone, electronic paper, or the like.

[Illumination Device]

The illumination device according to the present invention comprises the organic electroluminescent element according to the present invention.

Next, the illumination device according to the present invention is described with reference to FIG. 3.

FIG. 3 is a cross-sectional view schematically showing one example of the illumination device according to the present invention. As shown in FIG. 3, an illumination device 40 according to the present invention is provided with the above-described organic EL element 10 and a light scattering member 30. More specifically, the illumination device 40 is configured in such a manner that the substrate 2 of the organic EL element 10 and the light scattering member 30 are brought in contact with each other.

Though the light scattering member 30 is not particularly limited so far as it is able to scatter light, a member obtained by dispersing fine particles 32 in a transparent substrate 31 is used in FIG. 3. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is made incident onto a light incident surface 30A of the scattering member 30, the incident light is scattered by the light scattering member 30, and the scattered light is outputted as illuminating light from a light outputting surface 30B.

[Display Device]

The display device according to the present invention comprises the organic electroluminescent element according to the present invention.

The display device according to the present invention can be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

Synthesis Example 1

(Synthesis of Compound 3)

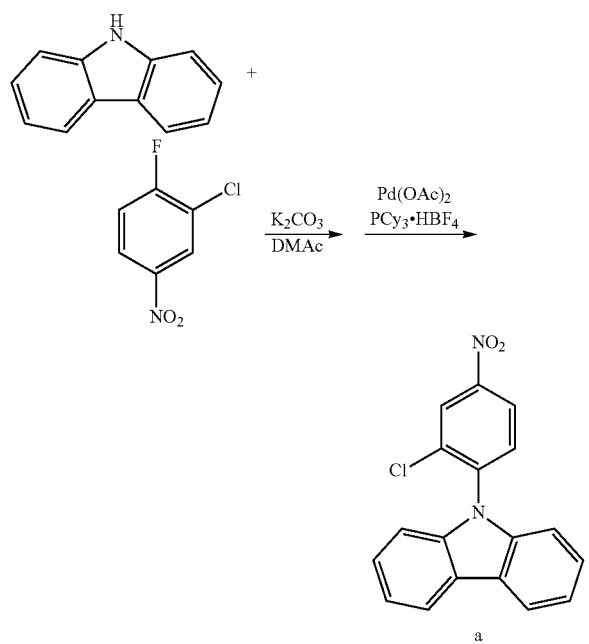

9H-Carbazole (23.81 g, 142.4 mmoles, 1.0 equivalent) and 3-chloro-4-fluoronitrobenzene (25.00 g, 142.4 mmoles, 1.0 equivalent) were dissolved in N,N-dimethylacetamide (450 mL), to which was then added potassium carbonate (59.05 g, 427.2 mmoles, 3.0 equivalents), and the mixture was heated in a nitrogen gas stream at 150° C. for 3.5 hours. After allowing the reaction solution to stand for cooling, palladium acetate (1.60 g, 7.13 mmoles, 0.05 equivalents) and tricyclohexyl phosphine tetrafluoroborate (5.24 g, 14.23 mmoles, 0.1 equivalents) was added thereto, followed by heating at 170° C. for one hour. After allowing the reaction solution to stand for cooling, water (3 L) was added thereto, the mixture was stirred, and the thus obtained precipitate was filtered off. A solid collected by means of filtration was dissolved in toluene, dried, and then concentrated, followed by reprecipitation with methanol. A solid was collected by means of filtration to obtain 33.20 g (81.4%) of Compound a as a brown powder.

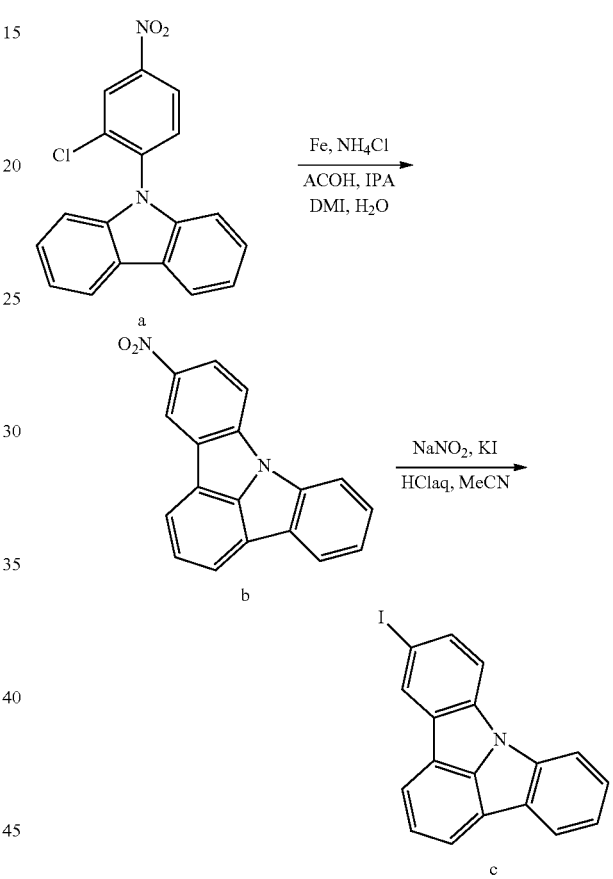

Ammonium chloride (1.01 g, 18.88 mmoles, 0.2 equivalents), reduced iron (21.07 g, 377.3 mmoles, 4.0 equivalents), and water (94.5 mL) were heated at 160° C. for one hour. Thereafter, isopropanol (855 mL), acetic acid (13.5 mL), and N,N'-dimethylimidazolidinone (40.5 mL) were added. Compound a (27.00 g, 94.31 mmoles, 1.0 equivalent) was added to the reaction solution, followed by heating at 90° C. for 1.5 hours. After allowing the reaction solution to stand for cooling, the resultant was filtered with Celite and extracted with ethyl acetate, followed by drying. The resulting solution was concentrated to obtain Compound b as a dark brown solid.

Acetonitrile (270 mL) and hydrochloric acid (1.5 M aqueous solution, 136 mL) were added to Compound b, and after cooling with ice to −5° C., an aqueous solution (34 mL) of sodium nitrite (7.8 g, 113.04 mmoles, 1.2 equivalents) was added dropwise thereto. After stirring the mixture for one hour while cooling with ice, an aqueous solution (54 mL) of potassium iodide (39.12 g, 235.60 mmoles, 2.5 equivalents) was added dropwise thereto, and the mixture was stirred for 4 hours while gradually elevating the temperature to 80° C. After allowing the reaction solution to stand for cooling, 900 mL was added thereto, and an extracted organic layer was washed with a sodium sulfite aqueous solution. A concentrated residue was subjected to column purification (eluant: hexane/toluene=2/1), thereby obtaining 35 g of Compound c as a white crystal. Yield: 48.8% (two steps)

in toluene, the resultant was allowed to stand for cooling, and a deposited crystal was collected by means of filtration, thereby obtaining 840 mg of Illustrative Compound 3. Yield: 77.0%

The result obtained by the H NMR measurement of the obtained Illustrative Compound 3 is shown in FIG. 4.

In addition, other compounds used as the host material were also synthesized in the same manner as that in Synthesis Example 1.

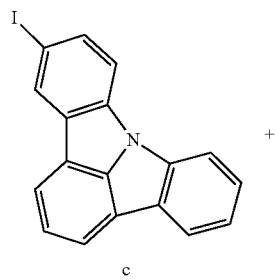
c

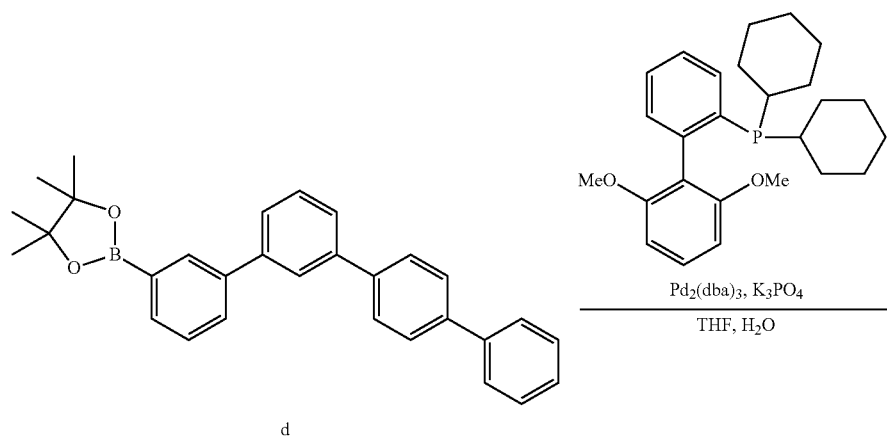
d

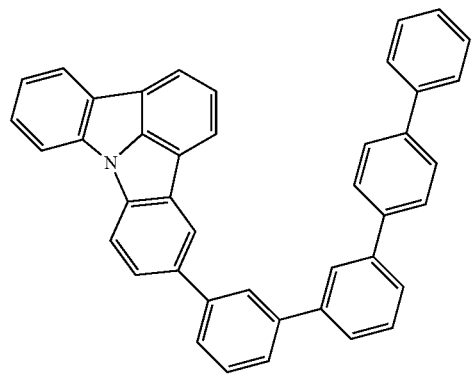
Illustrative Compound 3

Compound c (734 mg, 2.0 mmoles, 1.0 equivalent), Compound d (951 mg, 2.2 mmoles, 1.1 equivalents), tripotassium phosphate (1.27 g, 6.0 mmoles, 3.0 equivalents), tris(dibenzilideneacetone)palladium (55 mg, 0.06 mmoles, 0.03 equivalents), 2-dicyclohexylphosphino-2',6'-dimethoxybiphenyl (98 mg, 0.24 mmoles, 0.12 equivalents), THF (20 mL), and water (10 mL) were stirred in a nitrogen gas stream for 4 hours under heat-refluxing condition. The reaction solution was allowed to stand for cooling to room temperature, ethanol was added, and a deposited crystal was then filtered. The obtained solid was heated for dissolution <Fabrication and Evaluation of Organic Electroluminescent Element>

It was confirmed that all of the materials used in the fabrication of the organic electroluminescent element were subjected to sublimation purification, and the purity (absorption intensity area ratio at 254 nm) was confirmed to be 99.9% or more by using a high performance liquid chromatograph (TSKgel ODS-100Z, manufactured by Tosoh Corporation).

Example 1

(Fabrication of Organic EL Element by Means of Deposition))

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method.

First layer: HAT-CN: Film thickness: 10 nm

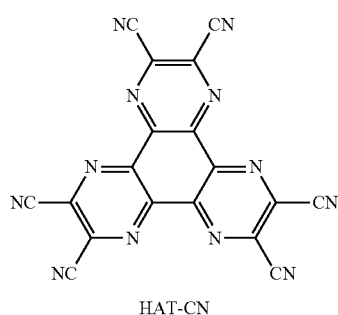 [SMILES: N#Cc1nc2c3nc(C#N)c(C#N)nc3c3nc(C#N)c(C#N)nc3c2nc1C#N]

HAT-CN

Second layer: NPD: Film thickness: 30 nm

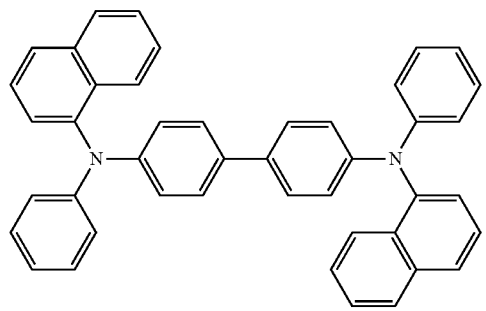

NPD

Third layer: Light Emitting Material 1 descried below and host material shown in the following Table 1 (mass ratio=85/15): Film thickness: 30 nm Light Emitting Material 1

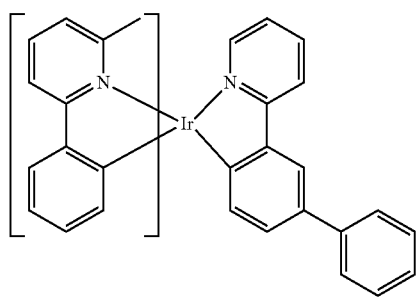

Light Emitting Material 2

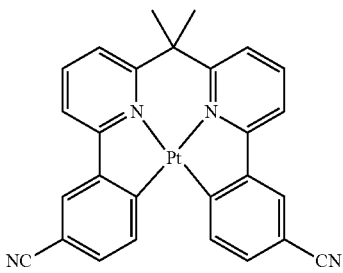

Host Material of Third Layer (Light Emitting Layer):

Comparative Compound ref-1: Compound HTM1 described in WO02007/031165

Comparative Compound ref-2: Compound 48 described in WO2010/050778

Compound 1

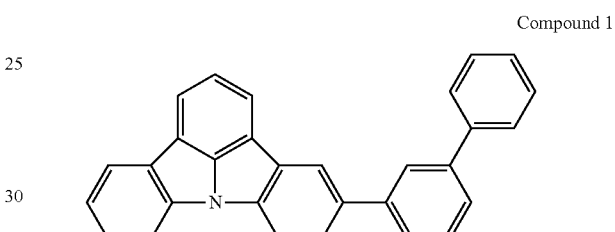

Compound 2

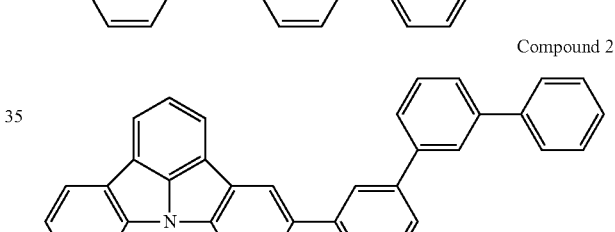

Compound 3

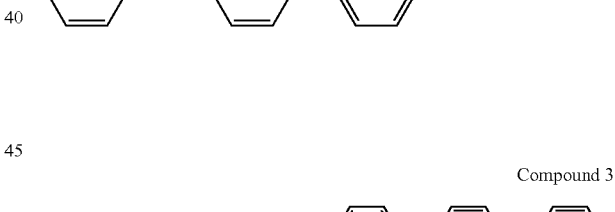

Compound 4

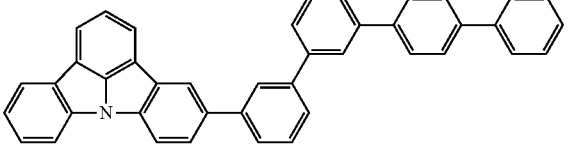

-continued

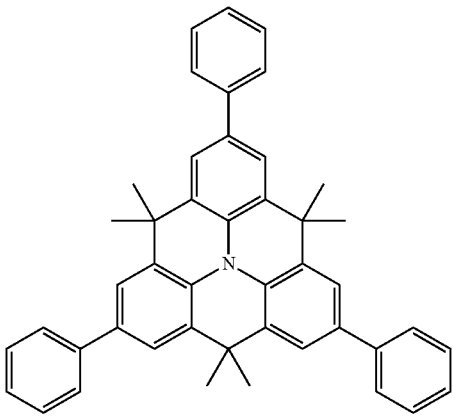

ref-1

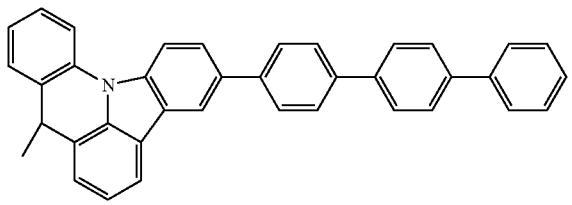

ref-2

Fourth layer: TpH-18: Film thickness: 10 nm

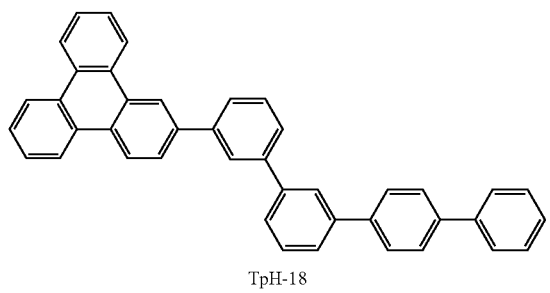 [SMILES: c1ccc(-c2ccc(-c3cccc(-c4cccc(-c5ccc6c7ccccc7c7ccccc7c6c5)c4)c3)cc2)cc1]

TpH-18

Fifth layer: Alq: Film thickness: 40 nm

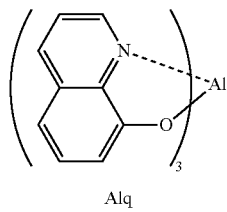

Alq 1 nm of lithium fluoride and 100 nm of metallic aluminum were deposited in this order thereon, thereby forming a cathode. At that time, a patterned mask (mask having a light emitting area of 2 mm×2 mm) was placed on the layer of lithium fluoride, and the metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-CIBA Ltd.), thereby obtaining the organic electroluminescent element of Example 1.

Examples 2 to 5 and Comparative Examples 1 and 2

Organic electroluminescent elements of Examples 2 to 5 and Comparative Examples 1 and 2 were produced in the same manner as that in Example 1, except that the host material and the light emitting material of the third layer (light emitting layer) were changed as shown in the following Table 1.

Incidentally, as a result of allowing the organic electroluminescent element of each of the Examples and Comparative Examples to emit light, light emission originating in the light emitting material was obtained in each of the organic electroluminescent elements.

In addition, in the elements of this configuration, the case of using, as the host material, the compound represented by the general formula (1) shown in the following Table 1 was excellent in both the time to half luminance and the time to reach 95% luminance as compared with the case of using, as the host material, Compound 1 of JP-A-2010-87496, Compound 26 of the same patent document, or Compound 48 of the same patent document.

<Evaluation of Element>

Each of the elements was measured for each of the time to half luminance (LT1) and the time to reach 95% luminance (LT2) when light was emitted such that the luminance reached 5,000 cd/m$^2$. The obtained results are shown in the following Table 1 in terms of a relative value while defining each of the evaluation results of the organic electroluminescent element of Comparative Example 1 as 1.

TABLE 1

| | Element configuration (light emitting layer) | | Evaluation results | |
|---|---|---|---|---|
| | Host material | Light emitting material | Time to half luminance LT1 | Time to reach 95% luminance LT2 |
| Comparative Example 1 | ref-1 | Light Emitting Material 1 | 1 | 1 |
| Comparative Example 2 | ref-2 | Light Emitting Material 1 | 1.3 | 2.2 |
| Example 1 | Compound 1 | Light Emitting Material 1 | 8.4 | 3.5 |
| Example 2 | Compound 2 | Light Emitting Material 1 | 9.9 | 4.8 |
| Example 3 | Compound 3 | Light Emitting Material 1 | 16.5 | 6.4 |
| Example 4 | Compound 4 | Light Emitting Material 1 | 7.5 | 3.8 |
| Example 5 | Compound 1 | Light Emitting Material 2 | 7.5 | 3.6 |

Examples 11 to 14

(Fabrication (Coating) of Organic EL Element)
—Preparation of Coating Solution for Forming Light Emitting Layer—

Light Emitting Material 1 (0.25% by mass) and Compound 1 (5% by mass) as the host material were mixed with toluene (94.75% by mass) to obtain Coating Solution 1 for forming a light emitting layer.

Coating Solutions 2 to 4 for forming a light emitting layer were prepared in the same manner as that in the preparation of the Coating Solution 1 for forming a light emitting layer, except that the Compound 1 as the host material was changed to Compounds 2 and 4, respectively.

—Fabrication of Organic Electroluminescent Element—

ITO was deposited in a thickness of 150 nm on a glass substrate at 25 mm×25 mm×0.7 mm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the electronics industry use (manufactured by Kanto Chemical Co., Inc.) and spin coated in a thickness of about 40 nm (at 2,000 rpm for 20 seconds). Thereafter, the coated ITO glass substrate was dried at 120° C. for 30 minutes and subjected to an annealing treatment at 160° C. for 10 minutes, thereby forming a hole injecting layer.

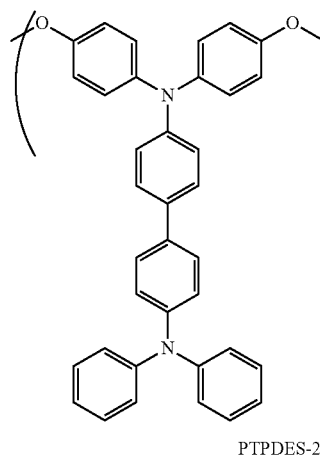

PTPDES-2

Each of the Coating Solutions 1 to 4 for forming a light emitting layer was spin coated in a thickness of about 40 nm on this hole injecting layer (at 1,300 rpm, 30 seconds), thereby obtaining a light emitting layer.

Subsequently, BAlq (bis-(2-methyl-8-quinolato)-4-(phenyl-phenolate)-aluminum(III)) was formed in a thickness of 40 nm as an electron transporting layer on the light emitting layer by a vacuum deposition method.

Lithium fluoride (LiF) was formed in a thickness of 1 nm as an electron injecting layer on the electron transporting layer by a vacuum deposition method. Metallic aluminum was further deposited in a thickness of 70 nm thereon, thereby forming a cathode.

The thus-fabricated laminate was put in a globe box purged with an argon gas and then sealed with a sealing can made of stainless steel and an ultraviolet ray-curable adhesive (XNR5516HV, manufactured by Nagase-CIBA Ltd.), thereby fabricating organic electroluminescent elements of Examples 11 to 14.

It was confirmed that in all of the obtained organic electroluminescent elements of Examples 11 to 14, good light emission was obtained.

Example 101

<Fabrication and Evaluation of Element>: Use as Host Material of Light Emitting Layer in Green Phosphorescent Element It was confirmed that all of the materials used in the element fabrication were subjected to sublimation purification, and the purity (absorption intensity area ratio at 254 nm) was confirmed to be 99.1% or more by using a high performance liquid chromatograph (TSKgel ODS-100Z, manufactured by Tosoh Corporation).

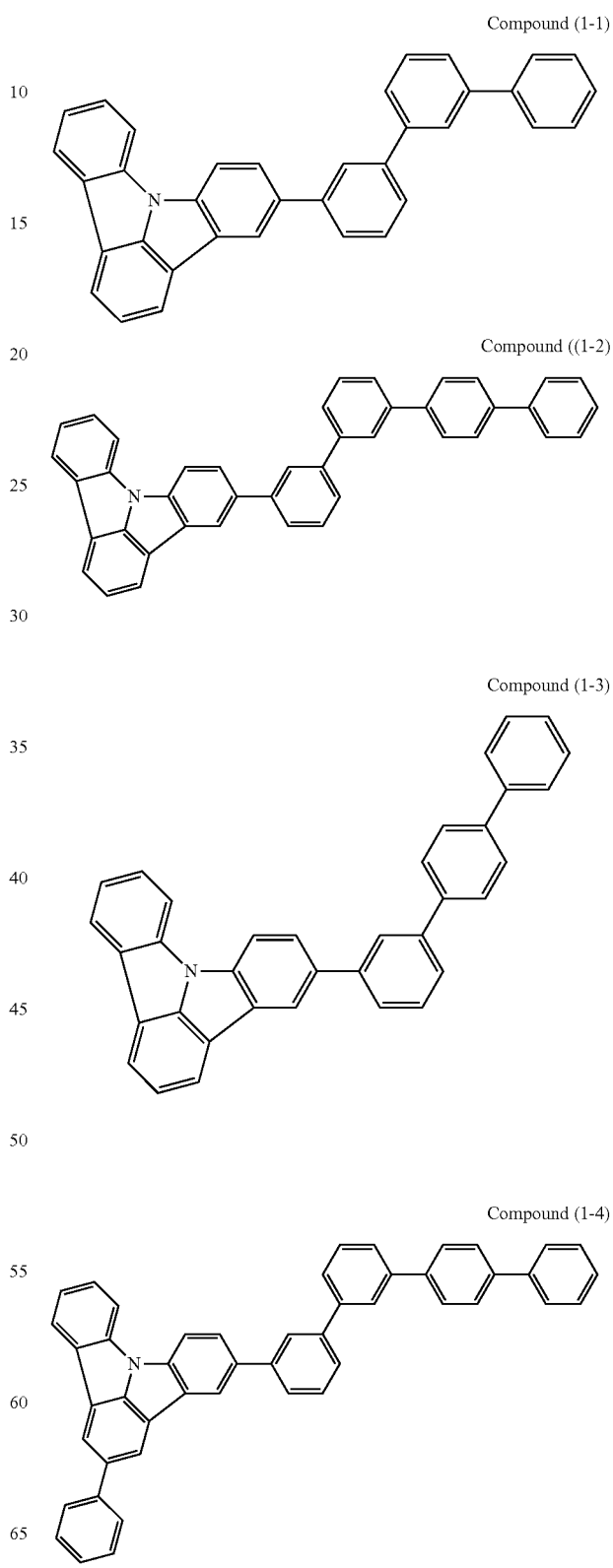

Compound (1-5)

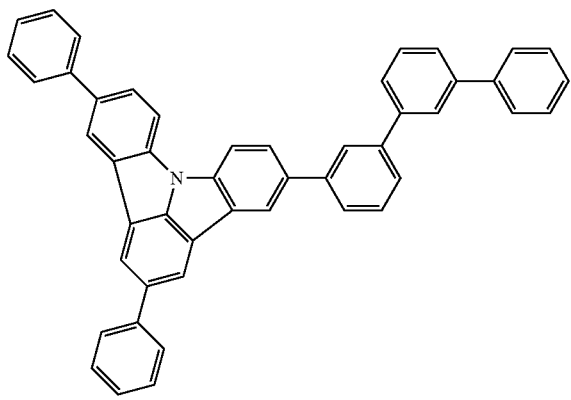

Compound (1-6)

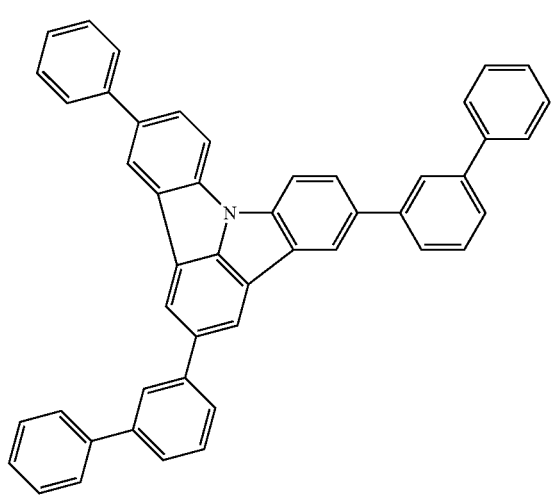

Compound (1-7)

Compound (1-8)

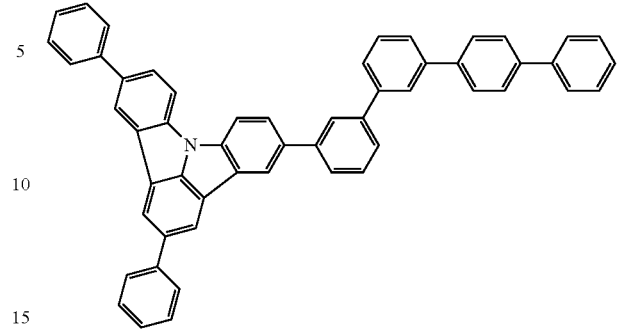

Compound (1-9)

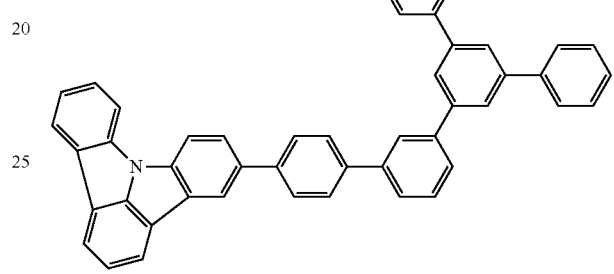

Compound (1-10)

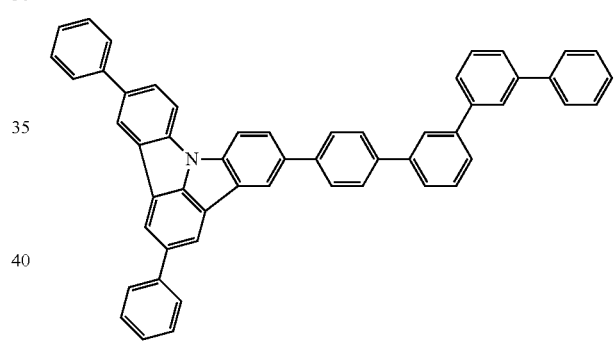

Compound (1-11)

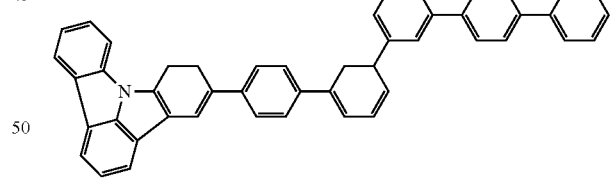

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method.

First layer: Compound (A) described below: Film thickness: 10 nm

Second layer: HTL-1: Film thickness: 30 nm

Third layer: Compound (1-1) and GD-1 (mass ratio: 85/15): Film thickness: 40 nm

Fourth layer: ETL-1: Film thickness: 40 nm 1 nm of lithium fluoride and 100 nm of metallic aluminum were deposited in this order thereon, thereby forming a cathode.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-CIBA Ltd.), thereby obtaining the organic electroluminescent element of Example 101.

Material of Hole Injecting Layer (First Layer):

Compound (A): HAT-CN

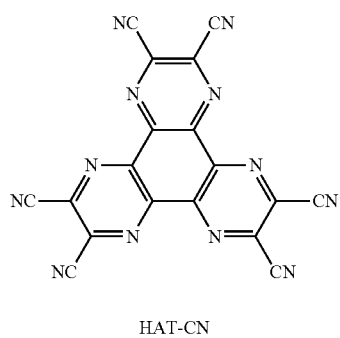

Compound (A)

HAT-CN

Hole Transporting Material (Second Layer):

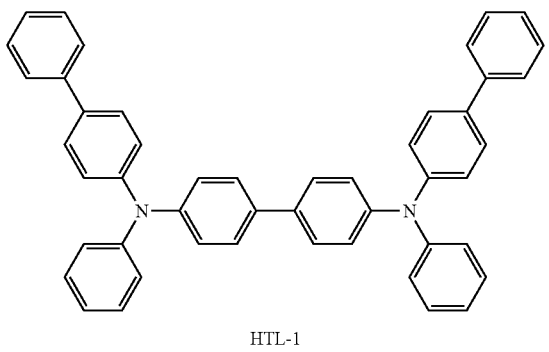 [SMILES: c1ccc(-c2ccc(N(c3ccccc3)c3ccc(-c4ccc(N(c5ccccc5)c5ccc(-c6ccccc6)cc5)cc4)cc3)cc2)cc1]

HTL-1

Material of Light Emitting Layer (Third Layer):

Host material: Compound (1-1)

Light emitting material: GD-1

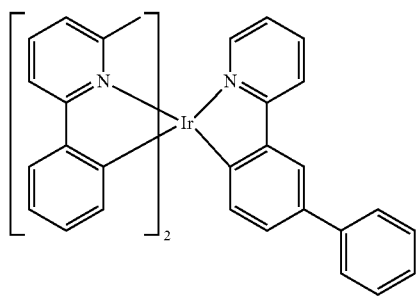

Electron Transporting Material (Fourth Layer):

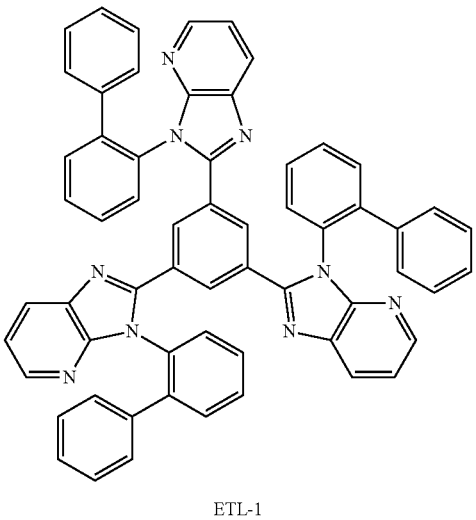 [SMILES: c1ccc(-c2ccccc2-n2c(-c3cc(-c4nc5cccnc5n4-c4ccccc4-c4ccccc4)cc(-c4nc5cccnc5n4-c4ccccc4-c4ccccc4)c3)nc3cccnc32)cc1]

ETL-1

Examples 102 to 111 and Comparative Examples 101 and 102

Organic electroluminescent elements of Examples 102 to 111 and Comparative Examples 101 and 102 were obtained in the same manner as that in Example 101, except that in the preparation of the organic electroluminescent element of Example 101, the Compound (1-1) of the third layer was replaced by Compounds (1-2) to (1-11) and the above-described Comparative Compounds ref-1 and ref-2, respectively, as shown in the following Table 2.

These elements were evaluated from the viewpoints of driving voltage, external quantum efficiency (luminous efficiency), and durability. The obtained results are shown in the following Table 2.

(Driving Voltage)

A direct voltage was applied to each of the elements to emit light such that the luminance reached 1,000 cd/m$^2$. The applied voltage at that time was defined as an index of driving voltage evaluation. The results are shown in the following Table 2, in which the case where the driving voltage is less than 5 V is designated as "⦾"; the case where the driving voltage is 5 V or more and less than 5.5 V is designated as "○○"; the case where the driving voltage is 5.5 V or more and less than 6 V is designated as "○"; the case where the driving voltage is 6 V or more and less than 7 V is designated as "Δ"; and the case where the driving voltage is 7 V or more is designated as "x".

(External Quantum Efficiency)

A direct current voltage was applied to each of the elements by using a source measure unit 2400, manufactured by Toyo Corporation to allow the organic electroluminescent element to emit light. The luminance was measured by a luminance meter BM-8, manufactured by Topcon Corporation. The luminous spectrum and the emission peak wavelength were measured by a spectrum analyzer PMA-11, manufactured by Hamamatsu Photonics K.K. On the basis of these values, the external quantum efficiency at a luminance in the vicinity of 1,000 cd/m$^2$ was calculated by a luminance conversion method.

The results are shown in the following Table 2, in which the case where the external quantum efficiency is 15% or more is designated as "⦾"; the case where the external quantum efficiency is 10% or more and less than 15% is designated as "○"; the case where the external quantum efficiency is 8% or more and less than 10% is designated as "Δ"; and the case where the external quantum efficiency is less than 8% is designated as "x".

(Durability)

A direct voltage was applied at room temperature (20° C.) to each of the elements to continuously emit light such that the luminance reached 5,000 cd/m², and a time required until the luminance reached 4,000 cd/m² (time to reach 80% luminance, LT0) was defined as an index of durability. The results are shown in the following Table 2, in which the case where the time is 600 hours or more is designated as "◉"; the case where the time is 400 hours or more and less than 600 hours is designated as "○○"; the case where the time is 200 hours or more and less than 400 hours is designated as "○"; the case where the time is 100 hours or more and less than 200 hours is designated as "Δ"; and the case where the time is less than 100 hours is designated as "x".

Similarly, when each of the elements was allowed to emit light such that the luminance reached 5,000 cd/m², the time to half luminance (LT1) was measured. The results are shown in the following Table 2, in which the case where the time is 600 hours or more is designated as "◉"; the case where the time is 400 hours or more and less than 600 hours is designated as "○○"; the case where the time is 200 hours or more and less than 400 hours is designated as "○"; the case where the time is 100 hours or more and less than 200 hours is designated as "Δ"; and the case where the time is less than 100 hours is designated as "x".

Similarly, when each of the elements was allowed to emit light such that the luminance reached 5,000 cd/m², the time to reach 95% luminance (LT2) was measured. The results are shown in the following Table 2, in which the case where the time is 600 hours or more is designated as "◉"; the case where the time is 400 hours or more and less than 600 hours is designated as "○○"; the case where the time is 200 hours or more and less than 400 hours is designated as "○"; the case where the time is 100 hours or more and less than 200 hours is designated as "Δ"; and the case where the time is less than 100 hours is designated as "x"

TABLE 2

| | Host material | Driving voltage | External quantum efficiency | Durability | | |
|---|---|---|---|---|---|---|
| | | | | LT0 | LT1 | Lt2 |
| Example 101 | Compound (1-1) | ◉ | ◉ | ○○ | ◉ | Δ |
| Example 102 | Compound (1-2) | ◉ | ◉ | ◉ | ◉ | Δ |
| Example 103 | Compound (1-3) | ◉ | ◉ | ○○ | ◉ | Δ |
| Example 104 | Compound (1-4) | ◉ | ◉ | ◉ | ◉ | Δ |
| Example 105 | Compound (1-5) | ◉ | ◉ | ○○ | ◉ | Δ |
| Example 106 | Compound (1-6) | ○○ | ◉ | ○○ | ◉ | Δ |
| Example 107 | Compound (1-7) | ◉ | ◉ | ○ | ◉ | Δ |
| Example 108 | Compound (1-8) | ◉ | ◉ | ◉ | ◉ | Δ |
| Example 109 | Compound (1-9) | ○○ | ◉ | ○○ | ◉ | Δ |
| Example 110 | Compound (1-10) | ◉ | ◉ | ○○ | ◉ | Δ |
| Example 111 | Compound (1-11) | ◉ | ◉ | ◉ | ◉ | Δ |
| Comparative Example 101 | Comparative Compound ref-1 | ◉ | ○ | x | x | x |
| Comparative Example 102 | Comparative Compound ref-2 | ◉ | ○ | x | Δ | x |

It was noted from the above-described Table 2 that by using the compound represented by the general formula (1) as the host material (charge transporting material) of the light emitting layer of the green phosphorescent element, an organic electroluminescent element having a slow luminance deterioration rate at the initial stage of lighting and excellent long-term durability.

Incidentally, it was noted that the organic electroluminescent element fabricated in each of the Examples has an emission peak wavelength of from 510 to 530 nm, low driving voltage, good luminous efficiency, and good durability against the luminance reduction to 80%.

On the other hand, it was noted that when each of Comparative Compounds ref-1 and ref-2 is used as the host material of the light of the green phosphorescent element, the luminance deterioration rate at the initial stage of lighting and the long-term durability are poor.

In addition, in the elements of this configuration, the case of using, as the host material, the compound represented by the general formula (1) in the above-described Table 2 was excellent in both the time to half luminance and the time to reach 95% luminance as compared with the case of using, as the host material, Compound 1 of JP-A-2010-87496, Compound 26 of the same patent document, or Compound 48 of the same patent document.

Examples 201 to 211 and Comparative Examples 201 and 202

Organic electroluminescent elements of Examples 201 to 211 and Comparative Examples 201 and 202 were obtained in the same manner as that in Examples 101 to 111 and Comparative Examples 101 and 102, respectively, except that in the preparation of the organic electroluminescent elements of Examples 101 to 111 and Comparative Examples 101 and 102, the light emitting material GD-1 of the third layer was replaced by the following compound.

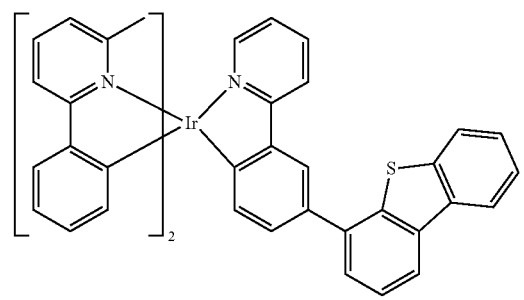

The thus obtained elements were evaluated in the same methods as those in the organic electroluminescent elements of Examples 101 to 111 and Comparative Examples 101 and 102. The results are shown in the following Table 3.

TABLE 3

| | Host material | Driving voltage | External quantum efficiency | Durability LT0 | LT1 | Lt2 |
|---|---|---|---|---|---|---|
| Example 201 | Compound (1-1) | ◉ | ○ | ○○ | ◉ | △ |
| Example 202 | Compound (1-2) | ◉ | ○ | ◉ | ◉ | ○ |
| Example 203 | Compound (1-3) | ◉ | ○ | ○○ | ◉ | △ |
| Example 204 | Compound (1-4) | ◉ | ○ | ◉ | ◉ | △ |
| Example 205 | Compound (1-5) | ◉ | ○ | ○○ | ◉ | △ |
| Example 206 | Compound (1-6) | ◉ | ○ | ◉ | ◉ | △ |
| Example 207 | Compound (1-7) | ◉ | ○ | ○○ | ◉ | △ |
| Example 208 | Compound (1-8) | ◉ | ○ | ◉ | ◉ | △ |
| Example 209 | Compound (1-9) | ◉ | ○ | ◉ | ◉ | △ |
| Example 210 | Compound (1-10) | ◉ | ○ | ◉ | ◉ | △ |
| Example 211 | Compound (1-11) | ◉ | ○ | ◉ | ◉ | △ |
| Comparative Example 201 | Comparative Compound ref-1 | ◉ | ○ | × | × | × |
| Comparative Example 202 | Comparative Compound ref-2 | ◉ | ○ | × | △ | × |

It was noted from the above-described Table 3 that by using the compound represented by the general formula (1) as the host material (charge transporting material) of the light emitting layer of the green phosphorescent element, an organic electroluminescent element having a slow luminance deterioration rate at the initial stage of lighting and excellent long-term durability.

Incidentally, it was noted that the organic electroluminescent element fabricated in each of the Examples has an emission peak wavelength of from 510 to 530 nm, low driving voltage, good luminous efficiency, and good durability against the luminance reduction to 80%.

On the other hand, it was noted that when each of Comparative Compounds ref-1 and ref-2 is used as the host material of the light of the green phosphorescent element, the luminance deterioration rate at the initial stage of lighting and the long-term durability are poor.

In addition, in the elements of this configuration, the case of using, as the host material, the compound represented by the general formula (1) in the above-described Table 3 was excellent in both the time to half luminance and the time to reach 95% luminance as compared with the case of using, as the host material, Compound 1 of JP-A-2010-87496, Compound 26 of the same patent document, or Compound 48 of the same patent document.

DESCRIPTION OF REFERENCE NUMERALS AND SIGNS

2: Substrate
3: Anode
4: Hole injecting layer
5: Hole transporting layer
6: Light emitting layer
7: Hole blocking layer
8: Electron transporting layer
9: Cathode
10: Organic electroluminescent element (organic EL element)
11: Organic layer
12: Protective layer
14: Adhesive layer
16: Sealing enclosure
20: Light emitting device
30: Light scattering member
30A: Light incident surface
30B: Light outputting surface
31: Transparent substrate
32: Fine particle
40: Illumination device

What is claimed:

1. An organic electroluminescent element comprising a substrate; a pair of electrodes including an anode and a cathode, disposed on the substrate; and at least one organic layer including a light emitting layer, disposed between the electrodes, wherein the light emitting layer includes a compound represented by the following general formula (3):

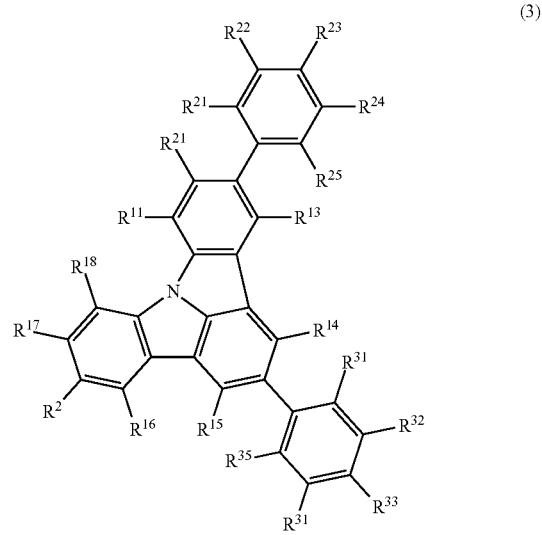

(3)

wherein: $R^2$ represents a hydrogen atom, a phenyl group, a monovalent oligoaryl hydrocarbon group having the number of rings of from 2 to 10, or a monovalent fused polycyclic aromatic hydrocarbon group having the number of rings of from 2 to 6, provided that the phenyl group, the monovalent oligoaryl hydrocarbon group having the number of rings of from 2 to 10, and the monovalent fused polycyclic aromatic hydrocarbon group having the number of rings of from 2 to 6 do not have an amino group as a substituent; and $R^{11}$ to $R^{18}$, $R^{21}$ to $R^{25}$, and $R^{31}$ to $R^{35}$ each independently represent a hydrogen atom or a substituent, provided that at least one of the following conditions (i)-(iii) is met:

(i) $R^2$ represents a monovalent oligoaryl group having the number of rings of from 2 to 10 or a monovalent fused polycyclic aromatic hydrocarbon group having the number of rings from 2 to 6;

(ii) at least one of $R^{21}$ to $R^{25}$ and $R^{31}$ to $R^{35}$ represents an aryl group;

(iii) two or more of $R^{21}$ to $R^{25}$ or two or more of $R^{31}$ to $R^{35}$ are bound to each other to form a fused polycyclic aromatic hydrocarbon ring having the number of rings of from 2 to 6.

2. The organic electroluminescent element according to claim 1, wherein, in the general formula (3), the group represented by $R^2$ is a group containing only one p-phenylene group.

3. The organic electroluminescent element according to claim 1, wherein the compound represented by the general formula (3) has a $T_1$ energy of not less than 1.77 eV and not more than 3.51 eV.

4. The organic electroluminescent element according to claim 1, wherein the compound represented by the general formula (3) has a glass transition temperature of not less than 100° C. and not more than 400° C.

5. The organic electroluminescent element according to claim 1, wherein the light emitting layer further contains a phosphorescent material.

6. The organic electroluminescent element according to claim 5, wherein the phosphorescent material is an iridium complex.

7. The organic electroluminescent element according to claim 6, wherein the iridium complex is represented by the following general formula (E-1):

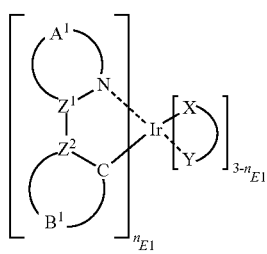

(E-1)

wherein: $Z^1$ and $Z^2$ each independently represent a carbon atom or a nitrogen atom; $A^1$ represents an atomic group for forming a 5- or 6-membered heterocyclic ring together with $Z^1$ and the nitrogen atom; $B^1$ represents an atomic group for forming a 5- or 6-membered heterocyclic ring together with $Z^2$ and the carbon atom; (X—Y) represents a monoanionic bidentate ligand; and $n_{E1}$ represents an integer of from 1 to 3.

8. The organic electroluminescent element according to claim 7, wherein the iridium complex represented by the general formula (E-1) is represented by the following general formula (E-2):

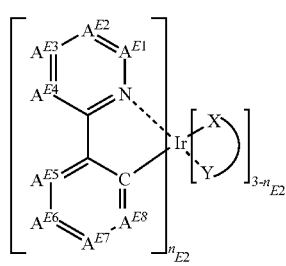

(E-2)

wherein: $A^{E1}$ to $A^{E8}$ each independently represent a nitrogen atom or C—$R^E$; $R^E$ represents a hydrogen atom or a substituent; (X—Y) represents a monoanionic bidentate ligand; and $n_{E2}$ represents an integer of from 1 to 3.

9. The organic electroluminescent element according to claim 7, wherein the iridium complex represented by the general formula (E-1) is the following compound:

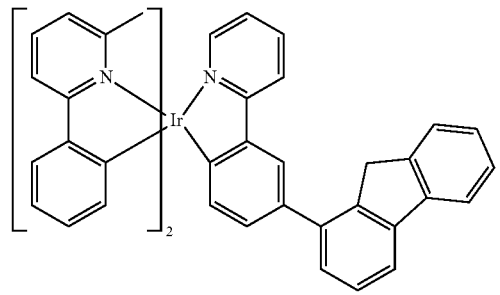

10. The organic electroluminescent element according to claim 1, wherein the compound represented by the general formula (3) has a molecular weight of not more than 800.

11. The organic electroluminescent element according to claim 1, wherein the light emitting layer is formed by a vacuum deposition process.

12. The organic electroluminescent element according to claim 1, wherein the light emitting layer is formed by a wet process.

13. A charge transporting material for an organic electroluminescent element represented by the following general formula (3):

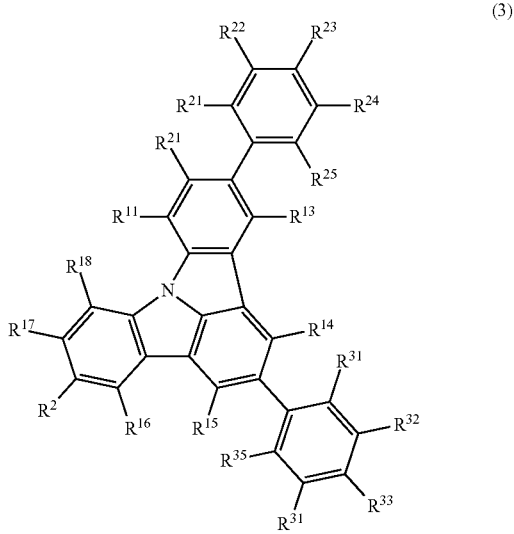

(3)

wherein: $R^2$ represents a hydrogen atom, a phenyl group, a monovalent oligoaryl hydrocarbon group having the number of rings of from 2 to 10, or a monovalent fused polycyclic aromatic hydrocarbon group having the number of rings of from 2 to 6, provided that the phenyl group, the monovalent oligoaryl hydrocarbon group having the number of rings of from 2 to 10, and the monovalent fused polycyclic aromatic hydrocarbon group having the number of rings of from 2 to 6 do not have an amino group as a substituent; and $R^{11}$ to $R^{18}$, $R^{21}$ to $R^{25}$, and $R^{31}$ to $R^{35}$ each independently represent a hydrogen atom or a substituent, provided that at least one of the following conditions (i)-(iii) is met:

(i) $R^2$ represents a monovalent oligoaryl group having the number of rings of from 2 to 10 or a monovalent fused polycyclic aromatic hydrocarbon group having the number of rings from 2 to 6;

(ii) at least one of $R^{21}$ to $R^{25}$ and $R^{31}$ to $R^{35}$ represents an aryl group;

(iii) two or more of $R^{21}$ to $R^{25}$ or two or more of $R^{31}$ to $R^{35}$ are bound to each other to form a fused polycyclic aromatic hydrocarbon ring having the number of rings of from 2 to 6.

14. The charge transporting material according to claim 13, wherein, in the general formula (3), the group represented $R^2$ is a group containing only one p-phenylene group.

15. The charge transporting material according to claim 13, wherein the charge transporting material represented by the general formula (3) has a $T_1$ energy of not less than 1.77 eV and not more than 3.51 eV.

16. The charge transporting material according to claim 13, wherein the charge transporting material represented by the general formula (3) has a glass transition temperature of not less than 100° C. and not more than 400° C.

17. The charge transporting material for an organic electroluminescent element according to claim 13, wherein the charge transporting material represented by the general formula (3) has a molecular weight of not more than 800.

18. A light emitting device using the organic electroluminescent element of claim 1.

19. A display device using the organic electroluminescent element of claim 1.

20. An illumination device using the organic electroluminescent element of claim 1.

* * * * *